United States Patent
Maruyama et al.

(10) Patent No.: US 8,541,585 B2
(45) Date of Patent: Sep. 24, 2013

(54) N-ACYL CYCLIC AMINE DERIVATIVE OR PHARMACEUTICALLY ACCEPTABLE SALT THEREOF

(75) Inventors: Megumi Maruyama, Osaka (JP); Naoya Kinomura, Suita (JP); Satoshi Nojima, Osaka (JP); Masahiro Takamura, Osaka (JP); Keisuke Kakiguchi, Osaka (JP); Hiroto Tatamidani, Suita (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 13/505,161

(22) PCT Filed: Mar. 11, 2011

(86) PCT No.: PCT/JP2011/056497
§ 371 (c)(1),
(2), (4) Date: Apr. 30, 2012

(87) PCT Pub. No.: WO2011/111875
PCT Pub. Date: Sep. 15, 2011

(65) Prior Publication Data
US 2012/0214790 A1    Aug. 23, 2012

(30) Foreign Application Priority Data

Mar. 11, 2010 (JP) ................. 2010-054177
Dec. 22, 2010 (JP) ................. 2010-285844

(51) Int. Cl.
*C07D 401/00* (2006.01)
*A61K 31/44* (2006.01)

(52) U.S. Cl.
USPC ......................................... 546/201; 514/300

(58) Field of Classification Search
USPC .......................................................... 546/201
See application file for complete search history.

(56) References Cited

U.S. PATENT DOCUMENTS

| | | | |
|---|---|---|---|
| 3,133,061 A | | 5/1964 | Kirchner |
| 4,029,790 A | | 6/1977 | Mauvernay et al. |
| 5,641,777 A | | 6/1997 | Emonds-Alt et al. |
| 6,166,037 A | * | 12/2000 | Budhu et al. .................. 514/326 |
| 6,221,879 B1 | | 4/2001 | Marabout et al. |

FOREIGN PATENT DOCUMENTS

| | | |
|---|---|---|
| EP | 1 386 920 | 2/2004 |
| JP | 51-76281 | 7/1976 |
| JP | 8-502474 | 3/1996 |
| JP | 2005-518378 | 6/2005 |
| JP | 2007-517014 | 6/2007 |
| WO | 94/07496 | 4/1994 |
| WO | 96/23787 | 8/1996 |
| WO | 99/19325 | 4/1999 |
| WO | 02/085890 | 10/2002 |
| WO | 03/051869 | 6/2003 |
| WO | 2005/066165 | 7/2005 |
| WO | 2007/061741 | 5/2007 |

OTHER PUBLICATIONS

Rasmussen et al American Journal of Psychiatry 2006, 163, 507-511.*
International Search Report issued Jun. 7, 2011 in International (PCT) Application No. PCT/JP2011/056497 along with theWritten Opinion.
S. Leucht et al., "Second-Generation Versus First-Generation Antipsychotic Drugs for Schizophrenia: A Meta-Analysis", The Lancet, vol. 373, pp. 31-41, Jan. 3, 2009.
O. Agid et al., "Emerging Drugs for Schizophrenia", Expert Opin. Emerging Drugs, vol. 13, No. 3, pp. 479-495, 2008.

* cited by examiner

*Primary Examiner* — John Mabry
(74) *Attorney, Agent, or Firm* — Wenderoth, Lind & Ponack, L.L.P.

(57) ABSTRACT

The present invention provides compounds which show high effectiveness against positive symptoms, negative symptoms and cognitive dysfunction in schizophrenia and reduce conventional side-effect risks as well as have remarkable effects for central neurological diseases associated with cognitive dysfunction other than schizophrenia. N-Acyl cyclic amine derivatives of formula (1): wherein $Ar^1$ and $Ar^2$ are aryl or heteroaryl; V is nitrogen, or $CR^3$; $W^1$ is a single bond, —C(O)—, etc.; $W^2$ is C1-alkylene; $W^3$ is a single bond, methylene, —NH—, —$CR^4$=$CR^5$—, etc.; Ring Q is a group of formula (a) in which n is 0 or 1; m is 0 to 2; k is 1 to 3; Z is a single bond, methylene, oxygen, etc.; $R^{1a}$, $R^{1b}$ and $R^{1c}$ are each, same or different, hydrogen, hydroxyl, halogen, cyano, $C_{1-6}$ alkyl, etc.; or pharmaceutically acceptable salts thereof are provided.

(1)

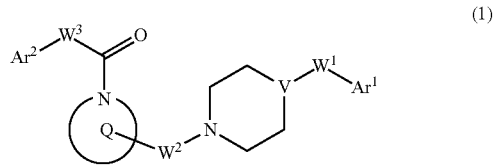

(a)

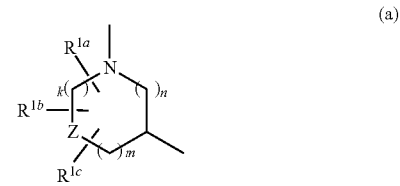

23 Claims, No Drawings

N-ACYL CYCLIC AMINE DERIVATIVE OR PHARMACEUTICALLY ACCEPTABLE SALT THEREOF

This application is a U.S. national stage of International Application No. PCT/JP2011/056497 filed Mar. 11, 2011.

TECHNICAL FIELD

The present invention relates to N-acyl cyclic amine derivatives or pharmaceutically acceptable salts thereof. The present compound is particularly useful as a therapeutic agent for mental disorders including schizophrenia, bipolar disorder, mania, major depression, mood disorder, anxiety disorder, eating disorder, attention-deficit hyperactivity disorder. Additionally, the present compound is also useful as a therapeutic agent for Alzheimer's disease, Parkinson disease, Huntington disease, epilepsy, drug dependence, drug abuse, type 2 diabetes, obesity.

BACKGROUND ART

Compounds disclosed in Patent Document 1, Patent Document 2, Patent Document 3 and Patent Document 4 have been known as N-acyl cyclic amine derivatives having a psychotropic activity. However, these compounds have different chemical structures from the derivatives of the present invention.

Schizophrenia is a mental disorder with positive symptoms (e.g., hallucination, delusion), negative symptoms (e.g., apathy, social withdrawal), and cognitive dysfunction (e.g., disorders of working memory, attentional function and vigilance, verbal memory, visual learning and memory, movement velocity, abilities for executive function and business solution, sociocoginitive abilities, etc.) as a prominent symptom.

First-generation therapeutic agents for schizophrenia such as haloperidol show high therapeutic activities against positive symptoms, while they have not much effect on negative symptoms and cognitive dysfunction. Further, it has been known that said agents often cause side effects including extrapyramidal symptoms, hyperprolactinemia and oversedation. On the other hand, second-generation therapeutic agents for schizophrenia (e.g., olanzapine, risperidone), which have a current central role in drug therapy, improve positive symptoms as well as have effect on negative symptoms, and it has been said that said agents have low risks for onset of extrapyramidal side effects. However, it has not been said that even second-generation therapeutic agents for schizophrenia have enough therapeutic effects on negative symptoms and cognitive dysfunction. Moreover, new side effects including weight gain, sugar metabolic abnormality have become a problem in second-generation therapeutic agents for schizophrenia [Nonpatent Documents 1 to 2].

As such, compounds which show high efficacies in negative symptoms and cognitive dysfunction on which conventional therapeutic agents for schizophrenia have not had enough therapeutic effects, and those which reduce the risks for side effects in conventional therapeutic agents for schizophrenia are expected to be an agent which meets unmet needs in such fields. Further, compounds having high effects on improvement in cognition function are also effective in treatment of central neurological diseases associated with similar cognitive dysfunction including Alzheimer's disease, Parkinson disease, Huntington disease as well as cognitive dysfunction in schizophrenia.

CITATION LIST

Patent Document

[Patent Document 1] WO96/023787 pamphlet
[Patent Document 2] WO99/019325 pamphlet
[Patent Document 3] WO2002/085890 pamphlet
[Patent Document 4] WO2007/061741 pamphlet Nonpatent Document

[Nonpatent Document 1] S. Leucht et al., The Lancet, 2009, Vol 373, p 31-41
[Nonpatent Document 2] O. Agid et al., Expert Opinion on Emerging Drugs, 2008, Vol 13(3), p 479-495

DISCLOSURE OF INVENTION

Technical Problem

The problem to be resolved by the present invention is to provide novel compounds having high efficacies on positive symptoms, negative symptoms and cognitive dysfunction in schizophrenia to reduce the risk of side effects of the conventional therapeutic agents for schizophrenia as well as showing advantageous effects on central neurological diseases associated with cognitive dysfunction other than schizophrenia.

Solution to Problem

According to extensive studies, the inventors of the present invention have found that a compound of the following formula (1) or a pharmaceutically acceptable salt thereof, also referred to as the present compound hereinafter, has the desired pharmacological activity, and have achieved the present invention.

Specifically, the present invention is as follows.
Section 1: A compound of the following formula (1):

[Chemical Formula 1]

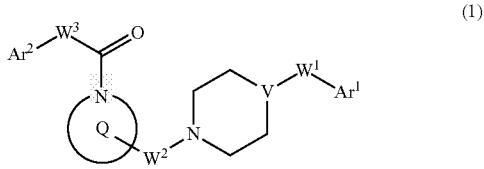

(1)

wherein $Ar^1$ and $Ar^2$ are each independently optionally substituted $C_{6-10}$ aryl or optionally substituted heteroaryl;

V is nitrogen, or $CR^3$, in which $R^3$ is hydrogen, hydroxyl, halogen, cyano, or optionally substituted $C_{1-6}$ alkyl;

when V is nitrogen, $W^1$ is a single bond or —C(O)—, when V is $CR^3$, $W^1$ is a single bond, oxygen, sulfur, —C(O)— or —$NR^2$—, in which $R^2$ is hydrogen or optionally substituted $C_{1-6}$ alkyl, piperazine ring in case that V is nitrogen and piperidine ring in case that V is $CR^3$ may be each independently optionally substituted by one or more and same or different groups selected from the group consisting of hydroxyl, halogen, cyano, $C_{1-6}$ alkyl and $C_{1-6}$ alkoxy on any substituent positions;

$W^2$ is optionally substituted $C_{1-3}$ alkylene;

$W^3$ is a single bond, oxygen, sulfur, —NH—, optionally substituted methylene, optionally substituted ethylene, or —$CR^4$=$CR^5$—, in which $R^4$ and $R^5$ are each independently hydrogen, halogen or optionally substituted $C_{1-6}$ alkyl;

Ring Q is a group of the following formula (a):

[Chemical Formula 2]

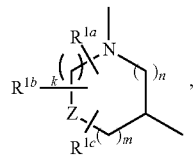

(a)

in which n is 0 or 1;

m is 0, 1 or 2;

k is 1, 2 or 3;

Z is a single bond, methylene, oxygen, sulfur, —S(O)—, —S(O)$_2$— or —$NR^{21}$—, in which $R^{21}$ is hydrogen or optionally substituted $C_{1-6}$ alkyl;

$R^{1a}$, $R^{1b}$ and $R^{1c}$ are each, same or different, hydrogen, hydroxyl, halogen, cyano, carboxyl, optionally substituted amino, optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkoxy, optionally substituted $C_{3-7}$ cycloalkoxy, optionally substituted $C_{6-10}$ aryloxy, optionally substituted heteroaryloxy, optionally substituted saturated heterocyclic oxy, optionally substituted $C_{7-14}$ aralkyloxy, optionally substituted $C_{1-6}$ alkylcarbonylamino, optionally substituted $C_{3-7}$ cycloalkylcarbonylamino, optionally substituted $C_{6-10}$ arylcarbonylamino, optionally substituted saturated heterocyclic carbonylamino, optionally substituted heteroarylcarbonylamino, optionally substituted $C_{1-6}$ alkylcarbonyloxy, optionally substituted aminocarbonyloxy, optionally substituted $C_{1-6}$ alkoxycarbonylamino, optionally substituted $C_{3-7}$ cycloalkoxycarbonylamino, optionally substituted saturated heterocyclic oxycarbonylamino, optionally substituted aminocarbonylamino, optionally substituted aminosulfonylamino, optionally substituted $C_{1-6}$ alkylsulfonylamino, optionally substituted $C_{3-7}$ cycloalkylsulfonylamino, optionally substituted $C_{6-10}$ arylsulfonylamino, optionally substituted saturated heterocyclic sulfonylamino, or optionally substituted heteroarylsulfonylamino, alternatively, $R^{1a}$ and $R^{1b}$ may combine each other together with the carbon atom to which they bind to form $C_{3-7}$ cycloalkyl ring, or saturated heterocycle, in which the $C_{3-7}$ cycloalkyl ring and the saturated heterocycle may be optionally substituted by one or more and same or different groups selected from the group consisting of hydroxyl, halogen, cyano, $C_{1-6}$ alkyl, $C_{1-6}$ alkoxy, $C_{6-10}$ aryl, heteroaryl and 4- to 7-membered saturated heterocycle; or a pharmaceutically acceptable salt thereof.

Section 2: The compound of either one of Section 1 or 30, wherein $W^2$ is ethylene; n is 0; or a pharmaceutically acceptable salt thereof.

Section 3: The compound of any one of Section 1, 2 or 30, represented by the following formula (2):

[Chemical Formula 3]

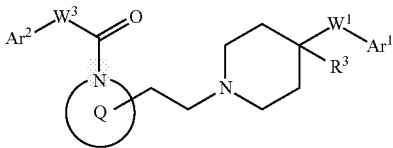

(2)

wherein $Ar^1$ and $Ar^2$ are each independently optionally substituted $C_{6-10}$ aryl or optionally substituted heteroaryl;

$W^1$ is a single bond or —C(O)—;

$W^3$ is a single bond, optionally substituted methylene, optionally substituted ethylene, or —$CR^4$=$CR^5$—, in which $R^4$ and $R^5$ are each independently hydrogen, halogen or optionally substituted $C_{1-6}$ alkyl;

$R^3$ is hydrogen, hydroxyl, halogen or cyano;

Ring Q is a group of the following formula (a-1):

[Chemical Formula 4]

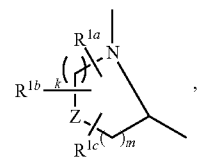

(a-1)

in which m is 0, 1 or 2;

k is 1, 2 or 3;

Z is a single bond, methylene, oxygen, or —$NR^{21}$—, in which $R^{21}$ is hydrogen or optionally substituted $C_{1-6}$ alkyl;

$R^{1a}$, $R^{1b}$, and $R^{1c}$ have the same meanings as defined in Section 1; or a pharmaceutically acceptable salt thereof.

Section 4: The compound of any one of Sections 1 to 3 and 30, wherein $Ar^1$ is any one of groups of the following formulae (b-1) to (b-17):

[Chemical Formula 5]

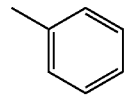

(b-1)

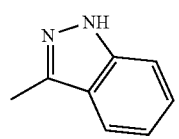

(b-2)

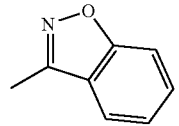

(b-3)

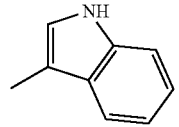

(b-4)

(b-5) 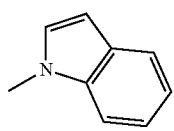

(b-6) 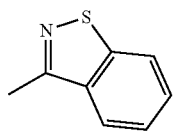

(b-7) 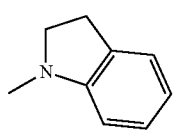

(b-8) 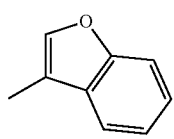

(b-9) 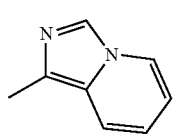

(b-10) 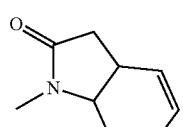

(b-11) 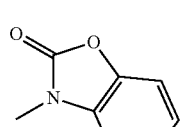

(b-12) 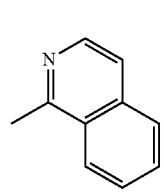

(b-13) 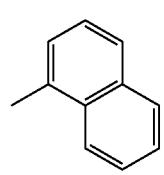

(b-14) 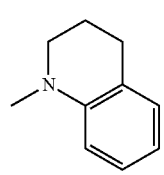

(b-15) 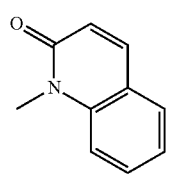

(b-16) 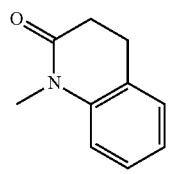

(b-17) 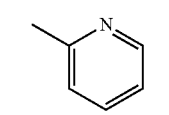

in which carbon atoms in the groups of the formulae (b-1) to (b-17) may be optionally substituted by one or more and same or different groups selected from the group consisting of halogen, hydroxyl, cyano, $C_{1-6}$ alkyl and $C_{1-6}$ alkoxy; or a pharmaceutically acceptable salt thereof.

Section 5: The compound of any one of Sections 1 to 4 and 30, wherein $Ar^2$ is any one of groups of the following formulae (c-1) to (c-19):

[Chemical Formula 6]

(c-1) 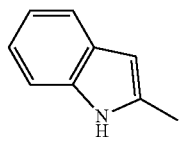

(c-2) 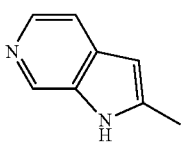

(c-3) 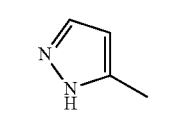

(c-4) 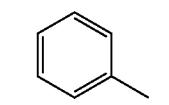

(c-5) 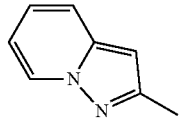

(c-6) 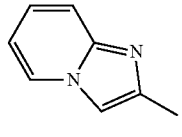

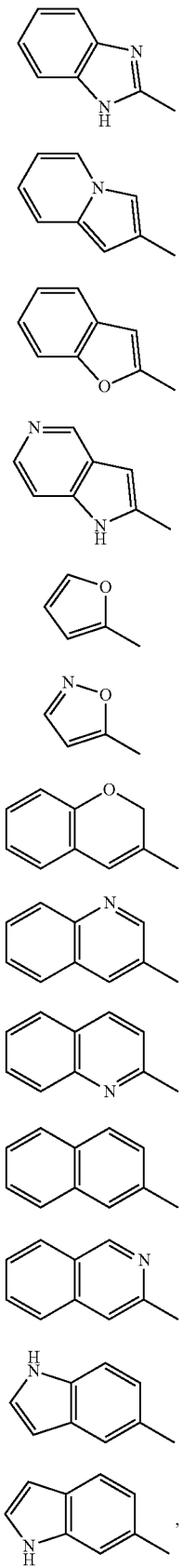

in which carbon atoms in the groups of the formulae (c-1) to (c-19) may be optionally substituted by one or more and same or different groups selected from the group consisting of hydroxyl, halogen, cyano, carboxyl, optionally substituted amino, optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkoxy, optionally substituted $C_{1-6}$ alkylthio, optionally substituted $C_{3-7}$ cycloalkoxy, optionally substituted $C_{6-10}$ aryloxy, optionally substituted heteroaryloxy, optionally substituted saturated heterocyclic oxy, optionally substituted $C_{1-6}$ alkylcarbonylamino, optionally substituted $C_{3-7}$ cycloalkylcarbonylamino, optionally substituted $C_{6-10}$ arylcarbonylamino, optionally substituted heteroarylcarbonylamino, optionally substituted saturated heterocyclic carbonylamino, optionally substituted $C_{1-6}$ alkoxycarbonylamino, optionally substituted $C_{3-7}$ cycloalkoxycarbonylamino, optionally substituted saturated heterocyclic oxycarbonylamino, optionally substituted aminocarbonylamino, optionally substituted aminosulfonylamino, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{6-10}$ arylcarbonyl, optionally substituted heteroarylcarbonyl, optionally substituted saturated heterocyclic carbonyl, optionally substituted $C_{1-6}$ alkoxycarbonyl, optionally substituted $C_{3-7}$ cycloalkoxycarbonyl, optionally substituted saturated heterocyclic oxycarbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl;

NH in the groups of the formulae (c-1) to (c-19) may be optionally substituted by one or more and same or different groups selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{1-6}$ alkoxycarbonyl, optionally substituted $C_{3-7}$ cycloalkoxycarbonyl, optionally substituted saturated heterocyclic oxycarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl; or a pharmaceutically acceptable salt thereof.

Section 6: The compound of Section 5, wherein carbon atoms in the groups of the formulae (c-1) to (c-19) may be optionally substituted by one or more and same or different groups selected from the group consisting of hydroxyl, halogen, cyano, optionally substituted $C_{1-6}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{1-6}$ alkoxy, optionally substituted $C_{1-6}$ alkylthio, optionally substituted saturated heterocyclic oxy, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl;

NH in the groups of the formulae (c-1) to (c-19) may be optionally substituted by one or more and same or, different groups selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{1-6}$ alkoxycarbonyl, optionally substituted $C_{3-7}$ cycloalkoxycarbonyl, optionally substituted saturated heterocyclic oxycarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl; or a pharmaceutically acceptable salt thereof.

Section 7: The compound of any one of Sections 1 to 6 and 30, wherein $R^{1a}$, $R^{1b}$ and $R^{1c}$ are each, same or different, hydrogen, hydroxyl, halogen, cyano, optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkoxy, optionally substituted $C_{3-7}$ cycloalkoxy, optionally substituted $C_{6-10}$ aryloxy, optionally substituted heteroaryloxy, optionally substituted saturated heterocyclic oxy, optionally substituted $C_{7-14}$ aralkyloxy, optionally substituted $C_{1-6}$ alkylcarbonyloxy, or optionally substituted aminocarbonyloxy, alternatively, $R^{1a}$ and $R^{1b}$ may combine each other together with the carbon atom to which they bind to form $C_{3-7}$ cycloalkyl ring, or saturated heterocycle, in which the $C_{3-7}$ cycloalkyl ring and the saturated heterocycle may be optionally substituted by one or more and same or different groups selected from the group consisting of hydroxyl, halogen and cyano; or a pharmaceutically acceptable salt thereof.

Section 8: The compound of Sections 1 to 7 and 30, wherein Ring Q is any one of rings of the following formulae (a-2) to (a-7):

[Chemical Formula 7]

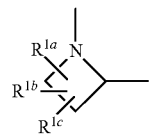
(a-2)

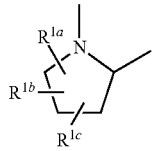
(a-3)

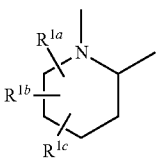
(a-4)

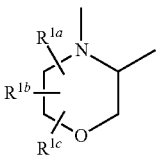
(a-5)

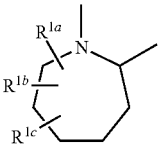
(a-6)

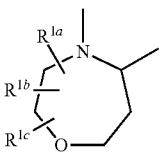
(a-7)

in which $R^{1a}$, $R^{1b}$ and $R^{1c}$ have the same meanings as defined in Section 7; or a pharmaceutically acceptable salt thereof.

Section 9: The compound of any one of Sections 1 to 8 and 30, wherein $Ar^1$ is any one of groups of the following formulae (b-1) to (b-4):

[Chemical Formula 8]

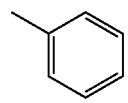
(b-1)

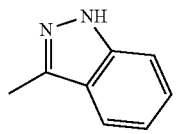
(b-2)

(b-3)

[structure: 1,2-benzisoxazole with methyl]

(b-4)

[structure: 3-methylindole]

in which carbon atoms in the groups of the formulae may be optionally substituted by one or more and same or different groups selected from halogen, hydroxyl, cyano, $C_{1-6}$ alkyl or $C_{1-6}$ alkoxy; or a pharmaceutically acceptable salt thereof.

Section 10: The compound of any one of Sections 1 to 9 and 30, wherein $Ar^2$ is any one of groups of the following formulae (c-1) to (c-3):

[Chemical Formula 9]

(c-1)

[structure: 2-methylindole]

(c-2)

[structure: 2-methyl-6-azaindole]

(c-3)

[structure: 3-methylpyrazole]

in which carbon atoms and NH in the groups of the formulae may be each optionally substituted by a substituent defined in Section 6; or a pharmaceutically acceptable salt thereof.

Section 11: The compound of any one of Sections 1 to 10 and 30, wherein Ring Q is a group of formula (a-3) of Section 8; or a pharmaceutically acceptable salt thereof.

Section 12: The compound of any one of Sections 1 to 11 and 30, wherein $W^3$ is a single bond, and V is CH; or a pharmaceutically acceptable salt thereof.

Section 13: The compound of any one of Sections 1 to 12 and 30, represented by the following formula (3):

[Chemical Formula 10]

(3)

[structure showing indole with $R^{11}$–$R^{16}$ substituents, carbonyl linker to N of ring with $R^{1a}$, $R^{1b}$, $R^{1c}$, ethyl tether to piperidine with $W^1$–$Ar^1$]

wherein $Ar^1$ is any one of groups of the following formulae (b-1'), (b-2'), (b-3') or (b-4'):

[Chemical Formula 11]

(b-1')

[structure: phenyl with $R^{17}$]

(b-2')

[structure: indazole with methyl and $R^{17}$]

(b-3')

[structure: benzisoxazole with methyl and $R^{17}$]

(b-4')

[structure: indole with methyl and $R^{17}$]

in which $R^{17}$ is hydrogen or halogen;

$W^1$ is a single bond or —C(O)—;

$R^{1a}$, $R^{1b}$ and $R^{1c}$ have the same meanings as defined in Section 7;

$R^{11}$ has the same meaning as defined for substituents of NH in the group of formula (c-1) of Section 6, $R^{12}$, $R^{13}$, $R^{14}$, $R^{15}$ and $R^{16}$ have the same meanings as defined for substituents of carbon atoms in the group of formula (c-1) of Section 6; or a pharmaceutically acceptable salt thereof.

Section 14: The compound of any one of Sections 1 to 12 and 30, represented by the following formula (4):

[Chemical Formula 12]

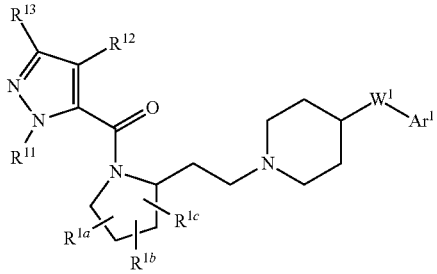

(4)

wherein $Ar^1$ is any one of groups of formula (b-1'), (b-2'), (b-3') or (b-4') of Section 13;

$W^1$ is a single bond or —C(O)—;

$R^{1a}$, $R^{1b}$ and $R^{1c}$ have the same meanings as defined in Section 7;

$R^{11}$ has the same meaning as defined for substituents of NH in the group of formula (c-3) of Section 6, $R^{12}$ and $R^{13}$ have the same meanings as defined for substituents of carbon atoms in the group of formula (c-3) of Section 6; or a pharmaceutically acceptable salt thereof.

Section 15: The compound of any one of Sections 1 to 12 and 30, represented by the following formulae (5):

[Chemical Formula 13]

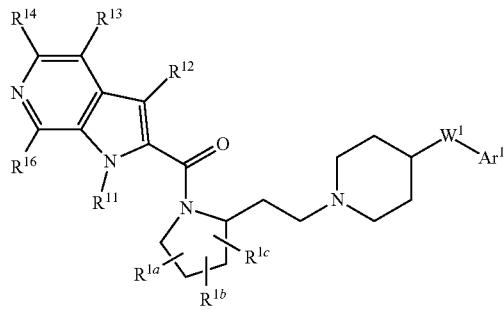

(5)

wherein $Ar^1$ is any one of groups of formula (b-1'), (b-2'), (b-3') or (b-4') of Section 13;

$W^1$ is a single bond or —C(O)—;

$R^{1a}$, $R^{1b}$ and $R^{1c}$ have the same meanings as defined in Section 7;

$R^{11}$ has the same meaning as defined for substituents of NH in the group of formula (c-2), $R^{12}$, $R^{13}$, $R^{14}$, and $R^{16}$ have the same meanings as defined for substituents of carbon atoms in the group of formula (c-2) of Section 6; or a pharmaceutically acceptable salt thereof.

Section 16: The compound of Section 1, wherein $W^2$ is methylene; n is 1; or a pharmaceutically acceptable salt thereof.

Section 17: The compound of either one of Section 1 or 16, represented by the following formula (6):

[Chemical Formula 14]

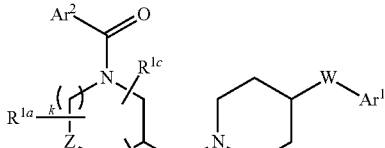

(6)

wherein $Ar^1$ is any one of groups of formula (b-1), (b-2), (b-3) or (b-4) of Section 9, in which carbon atoms in the groups of the formulae may be optionally substituted by one or more and same or different groups selected from the group consisting of halogen, hydroxyl, cyano, $C_{1-6}$ alkyl and $C_{1-6}$ alkoxy;

$Ar^2$ is any one of groups of formula (c-1), (c-2) or (c-3) of Section 10, in which carbon atoms and NH in the groups of the formulae may be each optionally substituted by a substituent defined in Section 6;

$W^1$ is a single bond or —C(O)—;

m, k, Z, $R^{1a}$, $R^{1b}$ and $R^{1c}$ have the same meanings as defined in Section 1; or a pharmaceutically acceptable salt thereof.

Section 18: The compound of any one of Section 1, 16 or 17, represented by the following formula (7):

[Chemical Formula 15]

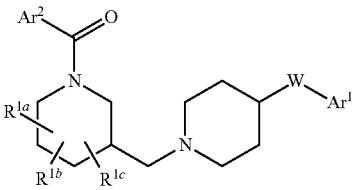

(7)

wherein $Ar^1$ is any one of groups of formula (b-1), (b-2), (b-3) or (b-4) of Section 9, in which carbon atoms in the groups of the formulae may be optionally substituted by one or more and same or different groups selected from the group consisting of halogen, hydroxyl, cyano, $C_{1-6}$ alkyl and $C_{1-6}$ alkoxy;

$Ar^2$ is any one of groups of formula (c-1), (c-2) or (c-3) of Section 10, in which carbon atoms and NH in the groups of the formulae may be each optionally substituted by a substituent defined in Section 6;

$R^{1a}$, $R^{1b}$ and $R^{1c}$ have the same meanings as defined in Section 7; or a pharmaceutically acceptable salt thereof.

Section 19: The compound of any one of Section 16, 17 or 18, wherein $Ar^1$ is a group of formula (b-4) of Section 9, in which carbon atoms in the group of the formula may be optionally substituted by one or more and same or different groups selected from the group consisting of halogen, hydroxyl, cyano, $C_{1-6}$ alkyl and $C_{1-6}$ alkoxy;

$Ar^2$ is a group of formula (c-1) of Section 10, in which carbon atoms and NH in the group of the formula may be each optionally substituted by a substituent defined in Section 6;

$W^1$ is a single bond; or a pharmaceutically acceptable salt thereof

Section 20: The compound of Section 13, wherein $R^{1a}$, $R^{1b}$ and $R^{1c}$ are each, same or different, hydrogen, hydroxyl, halogen, cyano, $C_{1-6}$ alkyl (in which the group may be optionally substituted by one or more same or different groups selected from hydroxyl, cyano, and halogen), $C_{1-6}$ alkoxy (in which the group may be optionally substituted by one or more and same or different groups selected from hydroxyl, cyano, and halogen), heteroaryl (in which the group may be optionally substituted by one or more and same or different groups selected from hydroxyl, cyano, halogen, and $C_{1-6}$ alkyl), or saturated heterocycle (in which the group may be optionally substituted by one or more and same or different groups selected from hydroxyl, cyano, halogen, $C_{1-6}$ alkyl, or $C_{1-6}$ alkylcarbonyl), alternatively, $R^{1a}$ and $R^{1b}$ may combine each other together with the carbon atom to which they bind to form $C_{3-7}$ cycloalkyl ring, or saturated heterocycle;

$R^{11}$ is a group selected from the group consisting of hydrogen, $C_{1-6}$ alkyl (in which the group may be optionally substituted by one or more and same or different groups selected from hydroxyl, cyano, and halogen), $C_{3-7}$ cycloalkyl (in which the group may be optionally substituted by one or more and same or different groups selected from hydroxyl, cyano, halogen, and $C_{1-6}$ alkyl), $C_{6-10}$ aryl (in which the group may be optionally substituted by one or more and same or different groups selected from hydroxyl, cyano, halogen, and $C_{1-6}$ alkyl), heteroaryl (in which the group may be optionally substituted by one or more and same or different groups selected from hydroxyl, cyano, halogen, and $C_{1-6}$ alkyl), saturated heterocycle (in which the group may be optionally substituted by one or more and same or different groups selected from hydroxyl, cyano, halogen, $C_{1-6}$ alkyl, $C_{1-6}$ alkylcarbonyl, and $C_{1-6}$ alkylsulfonyl), $C_{1-6}$ alkylcarbonyl (in which the group may be optionally substituted by one or more and same or different groups selected from hydroxyl, cyano, and halogen), $C_{1-6}$ alkylsulfonyl (in which the group may be optionally substituted by one or more and same or different groups selected from hydroxyl, cyano, and halogen), and $C_{6-10}$ arylsulfonyl (in which the group may be optionally substituted by one or more and same or different groups selected from hydroxyl, cyano, halogen, and $C_{1-6}$ alkyl);

$R^{12}$, $R^{13}$, $R^{14}$, $R^{15}$ and $R^{16}$ are each, same or different, a group selected from the group consisting of hydrogen, hydroxyl, halogen, cyano, $C_{1-6}$ alkyl (in which the group may be optionally substituted by one or more and same or different groups selected from hydroxyl, cyano, and halogen), $C_{1-6}$ alkoxy (in which the group may be optionally substituted by one or more and same or different groups selected from hydroxyl, cyano, halogen, and $C_{1-6}$ alkyl), $C_{1-6}$ alkylthio (in which the group may be optionally substituted by one or more and same or different groups selected from hydroxyl, cyano, halogen, and $C_{1-6}$ alkyl), $C_{6-10}$ aryl (in which the group may be optionally substituted by one or more and same or different groups selected from hydroxyl, cyano, halogen, and $C_{1-6}$ alkyl), heteroaryl (in which the group may be optionally substituted by one or more and same or different groups selected from hydroxyl, cyano, halogen, and $C_{1-6}$ alkyl), and saturated heterocycle (in which the group may be optionally substituted by one or more and same or different groups selected from hydroxyl, cyano, halogen, $C_{1-6}$ alkyl, $C_{1-6}$ alkylcarbonyl, and $C_{1-6}$ alkylsulfonyl); or a pharmaceutically acceptable salt thereof.

Section 21: The compound of Section 14, wherein $R^{1a}$, $R^{1b}$ and $R^{1c}$ are each, same or different, hydrogen, hydroxyl, halogen, cyano, $C_{1-6}$ alkyl (in which the group may be optionally substituted by one or more and same or different groups selected from hydroxyl, cyano, and halogen), $C_{1-6}$ alkoxy (in which the group may be optionally substituted by one or more and same or different groups selected from hydroxyl, cyano, and halogen), heteroaryl (in which the group may be optionally substituted by one or more and same or different groups selected from hydroxyl, cyano, halogen, and $C_{1-6}$ alkyl), or saturated heterocycle (in which the group may be optionally substituted by one or more and same or different groups selected from hydroxyl, cyano, halogen, $C_{1-6}$ alkyl, or $C_{1-6}$ alkylcarbonyl), alternatively, $R^{1a}$ and $R^{1b}$ may combine each other together with the carbon atom to which they bind to form $C_{3-7}$ cycloalkyl ring, or saturated heterocycle;

$R^{11}$ is a group selected from the group consisting of hydrogen, $C_{1-6}$ alkyl (in which the group may be optionally substituted by one or more and same or different groups selected from hydroxyl, cyano, and halogen), $C_{3-7}$ cycloalkyl (in which the group may be optionally substituted by one or more and same or different groups selected from hydroxyl, cyano, halogen, and $C_{1-6}$ alkyl), $C_{6-10}$ aryl (in which the group may be optionally substituted by one or more and same or different groups selected from hydroxyl, cyano, halogen, and $C_{1-6}$ alkyl), heteroaryl (in which the group may be optionally substituted by one or more and same or different groups selected from hydroxyl, cyano, halogen, and $C_{1-6}$ alkyl), saturated heterocycle (in which the group may be optionally substituted by one or more and same or different groups selected from hydroxyl, cyano, halogen, $C_{1-6}$ alkyl, $C_{1-6}$ alkylcarbonyl, and $C_{1-6}$ alkylsulfonyl), $C_{1-6}$ alkylcarbonyl (in which the group may be optionally substituted by one or more and same or different groups selected from hydroxyl, cyano, and halogen), $C_{1-6}$ alkylsulfonyl (in which the group may be optionally substituted by one or more and same or different groups selected from hydroxyl, cyano, and halogen), and $C_{6-10}$ arylsulfonyl (in which the group may be optionally substituted by one or more and same or different groups selected from hydroxyl, cyano, halogen, and $C_{1-6}$ alkyl);

$R^{12}$ and $R^{13}$ are each, same or different, a group selected from the group consisting of hydrogen, hydroxyl, halogen, cyano, $C_{1-6}$ alkyl (in which the group may be optionally substituted by one or more and same or different groups selected from hydroxyl, cyano, and halogen), $C_{1-6}$ alkoxy (in which the group may be optionally substituted by one or more and same or different groups selected from hydroxyl, cyano, halogen, and $C_{1-6}$ alkyl), $C_{1-6}$ alkylthio (in which the group may be optionally substituted by one or more and same or different groups selected from hydroxyl, cyano, halogen, and $C_{1-6}$ alkyl), $C_{6-10}$ aryl (in which the group may be optionally substituted by one or more and same or different groups selected from hydroxyl, cyano, halogen, and $C_{1-6}$ alkyl), heteroaryl (in which the group may be optionally substituted by one or more and same or different groups selected from hydroxyl, cyano, halogen, and $C_{1-6}$ alkyl), and saturated heterocycle (in which the group may be optionally substituted by one or more and same or different groups selected from hydroxyl, cyano, halogen, $C_{1-6}$ alkyl, $C_{1-6}$ alkylcarbonyl, and $C_{1-6}$ alkylsulfonyl); or a pharmaceutically acceptable salt thereof.

Section 22: The compound of Section 15, wherein $R^{1a}$, $R^{1b}$ and $R^{1c}$ are each, same or different, hydrogen, hydroxyl, halogen, cyano, $C_{1-6}$ alkyl (in which the group may be optionally substituted by one or more and same or different groups selected from hydroxyl, cyano, and halogen), $C_{1-6}$ alkoxy (in which the group may be optionally substituted by one or more and same or different groups selected from hydroxyl, cyano, and halogen), heteroaryl (in which the group may be optionally substituted by one or more and same or different groups selected from hydroxyl, cyano, halogen, and $C_{1-6}$ alkyl), or saturated heterocycle (in which the group may be optionally substituted by one or more and same or different groups selected from hydroxyl, cyano, halogen, $C_{1-6}$ alkyl, $C_{1-6}$ alkylcarbonyl), alternatively, $R^{1a}$ and $R^{1b}$ may combine each other together with the carbon atom to which they bind to form $C_{3-7}$ cycloalkyl ring, or saturated heterocycle;

$R^{11}$ is a group selected from the group consisting of hydrogen, $C_{1-6}$ alkyl (in which the group may be optionally substituted by one or more and same or different groups selected from hydroxyl, cyano, and halogen), $C_{3-7}$ cycloalkyl (in which the group may be optionally substituted by one or more and same or different groups selected from hydroxyl, cyano, halogen, and $C_{1-6}$ alkyl), $C_{6-10}$ aryl (in which the group may be optionally substituted by one or more and same or different groups selected from hydroxyl, cyano, halogen, and $C_{1-6}$ alkyl), heteroaryl (in which the group may be optionally substituted by one or more and same or different groups selected from hydroxyl, cyano, halogen, and $C_{1-6}$ alkyl), saturated heterocycle (in which the group may be optionally substituted by one or more and same or different groups selected from hydroxyl, cyano, halogen, $C_{1-6}$ alkyl, $C_{1-6}$ alkylcarbonyl, and $C_{1-6}$ alkylsulfonyl), $C_{1-6}$ alkylcarbonyl (in which the group may be optionally substituted by one or more and same or different groups selected from hydroxyl, cyano, and halogen), $C_{1-6}$ alkylsulfonyl (in which the group may be optionally substituted by one or more and same or different groups selected from hydroxyl, cyano, and halogen), and $C_{6-10}$ arylsulfonyl (in which the group may be optionally substituted by one or more and same or different groups selected from hydroxyl, cyano, halogen, and $C_{1-6}$ alkyl);

$R^{12}$, $R^{13}$, $R^{14}$, and $R^{16}$ are each, same or different, a group selected from the group consisting of hydrogen, hydroxyl, halogen, cyano, $C_{1-6}$ alkyl (in which the group may be optionally substituted by one or more and same or different groups selected from hydroxyl, cyano, and halogen), $C_{1-6}$ alkoxy (in which the group may be optionally substituted by one or more and same or different groups selected from hydroxyl, cyano, halogen, and $C_{1-6}$ alkyl), $C_{1-6}$ alkylthio (in which the group may be optionally substituted by one or more and same or different groups selected from hydroxyl, cyano, halogen, and $C_{1-6}$ alkyl), $C_{6-10}$ aryl (in which the group may be optionally substituted by one or more and same or different groups selected from hydroxyl, cyano, halogen, and $C_{1-6}$ alkyl), heteroaryl (in which the group may be optionally substituted by one or more and same or different groups selected from hydroxyl, cyano, halogen, and $C_{1-6}$ alkyl), and saturated heterocycle (in which the group may be optionally substituted by one or more and same or different groups selected from hydroxyl, cyano, halogen, $C_{1-6}$ alkyl, $C_{1-6}$ alkylcarbonyl, and $C_{1-6}$ alkylsulfonyl); or a pharmaceutically acceptable salt thereof.

Section 23: The compound of any one of Section 16, 17 or 18, wherein $R^{1a}$, $R^{1b}$ and $R^{1c}$ are each, same or different, hydrogen, hydroxyl, halogen, cyano, $C_{1-6}$ alkyl (in which the group may be optionally substituted by one or more and same or different groups selected from hydroxyl, cyano, and halogen), $C_{1-6}$ alkoxy (in which the group may be optionally substituted by one or more and same or different groups selected from hydroxyl, cyano, and halogen), heteroaryl (in which the group may be optionally substituted by one or more and same or different groups selected from hydroxyl, cyano, halogen, and $C_{1-6}$ alkyl), or saturated heterocycle (in which the group may be optionally substituted by one or more and same or different groups selected from hydroxyl, cyano, halogen, $C_{1-6}$ alkyl, $C_{1-6}$ alkylcarbonyl), alternatively, $R^{1a}$ and $R^{1b}$ may combine each other together with the carbon atom to which they bind to form $C_{3-7}$ cycloalkyl ring, or saturated heterocycle;

$Ar^2$ is a group of any one of groups of formula (c-1), (c-2) or (c-3) of Section 10, in which carbon atoms of the groups of the formulae may be optionally substituted by one or more and same or different groups selected from the group consisting of hydroxyl, halogen, cyano, $C_{1-6}$ alkyl (in which the group may be optionally substituted by one or more and same or different groups selected from hydroxyl, cyano, and halogen), $C_{1-6}$ alkoxy (in which the group may be optionally substituted by one or more and same or different groups selected from hydroxyl, cyano, halogen, and $C_{1-6}$ alkyl), $C_{1-6}$ alkylthio (in which the group may be optionally substituted by one or more and same or different groups selected from hydroxyl, cyano, halogen, and $C_{1-6}$ alkyl), $C_{6-10}$ aryl (in which the group may be optionally substituted by one or more and same or different groups selected from hydroxyl, cyano, halogen, and $C_{1-6}$ alkyl), heteroaryl (in which the group may be optionally substituted by one or more and same or different groups selected from hydroxyl, cyano, halogen, and $C_{1-6}$ alkyl), and saturated heterocycle (in which the group may be optionally substituted by one or more and same or different groups selected from hydroxyl, cyano, halogen, $C_{1-6}$ alkyl, $C_{1-6}$ alkylcarbonyl, and $C_{1-6}$ alkylsulfonyl);

NH of the groups of the formulae may be optionally substituted by a group selected from the group consisting of $C_{1-6}$ alkyl (in which the group may be optionally substituted by one or more and same or different groups selected from hydroxyl, cyano, and halogen), $C_{3-7}$ cycloalkyl (in which the group may be optionally substituted by one or more and same or different groups selected from hydroxyl, cyano, halogen, and $C_{1-6}$ alkyl), $C_{6-10}$ aryl (in which the group may be optionally substituted by one or more and same or different groups selected from hydroxyl, cyano, halogen, and $C_{1-6}$ alkyl), heteroaryl (in which the group may be optionally substituted by one or more and same or different groups selected from hydroxyl, cyano, halogen, and $C_{1-6}$ alkyl), saturated heterocycle (in which the group may be optionally substituted by one or more and same or different groups selected from hydroxyl, cyano, halogen, $C_{1-6}$ alkyl, $C_{1-6}$ alkylcarbonyl, and $C_{1-6}$ alkylsulfonyl), $C_{1-6}$ alkylcarbonyl (in which the group may be optionally substituted by one or more and same or different groups selected from hydroxyl, cyano, and halogen), $C_{1-6}$ alkylsulfonyl (in which the group may be optionally substituted by one or more and same or different groups selected from hydroxyl, cyano, and halogen), and $C_{6-10}$ arylsulfonyl (in which the group may be optionally substituted by one or more and same or different groups selected from hydroxyl, cyano, halogen, and $C_{1-6}$ alkyl); or a pharmaceutically acceptable salt thereof.

Section 24: The compound of Section 1, wherein $Ar^1$ and $Ar^2$ are each independently $C_{6-10}$ aryl or heteroaryl (in which the $C_{6-10}$ aryl and the heteroaryl may be optionally substituted by one or more and same or different groups selected from the group consisting of hydroxyl, halogen, cyano, $C_{1-6}$ alkyl, trifluoromethyl, trifluoromethoxy, trifluoromethylthio, $C_{6-10}$ aryl, $C_{1-6}$ alkoxy, $C_{1-6}$ alkylthio, $C_{1-6}$ alkyl which is substituted by one or more hydroxy groups, heteroaryl, $C_{1-6}$ alkyl which is substituted by one or more cyano groups, 4- to 7-membered cyclic aminocarbonyl, $C_{1-6}$ alkylcarbonylamino, $C_{1-6}$ alkylsulfonyl, $C_{6-10}$ arylsulfonyl, $C_{1-6}$ alkylcarbonyl, $C_{1-6}$ alkylcarbonylamino and $C_{1-6}$ alkylaminocarbonylamino;

V is nitrogen or CH;

$W^1$ is a single bond or —C(O)—;

$W^2$ is $C_{1-3}$ alkylene;

$W^3$ is a single bond, or —$CR^4$=$CR^5$—, in which $R^4$ and $R^5$ are each independently hydrogen, or halogen;

n is 0 or 1;

m is 0, 1 or 2;

k is 1, 2 or 3;

Z is a single bond, methylene, or oxygen;

$R^{1a}$, $R^{1b}$ and $R^{1c}$ are each, same or different, hydrogen, hydroxyl, halogen, $C_{1-3}$ alkyl, $C_{1-3}$ alkoxy, $C_{1-3}$ alkoxy-$C_{1-3}$ alkoxy, mono- or di-$C_{1-3}$ alkylaminocarbonyloxy, $C_{1-3}$ alkoxycarbonylamino, mono- or di-$C_{1-3}$ alkylaminocarbonylamino, or $C_{1-3}$ alkylsulfonylamino; or a pharmaceutically acceptable salt thereof.

Section 25: The compound of Section 24, wherein Ring Q is a group of any one of formulae (a-2) to (a-7) of Section 8; or a pharmaceutically acceptable salt thereof.

Section 26: The compound of Section 1, selected from the group consisting of:
- (S)-(2-(2-(4-(4-fluorobenzoyl)piperidin-1-yl)ethyl)pyrrolidin-1-yl)(6-methyl-1H-indol-2-yl)methanone;
- (S)-(6-fluoro-1H-indol-2-yl)(2-(2-(4-(4-fluorobenzoyl)piperidin-1-yl)ethyl)pyrrolidin-1-yl)methanone;
- (S)-(2-(2-(4-(4-fluorobenzoyl)piperidin-1-yl)ethyl)pyrrolidin-1-yl)(6-(trifluoromethoxy)-1H-indol-2-yl)methanone;
- (S)-(2-(2-(4-(4-fluorobenzoyl)piperidin-1-yl)ethyl)pyrrolidin-1-yl)(6-isopropyl-1H-indol-2-yl)methanone;
- (S)-(5-fluoro-4-methoxy-1H-indol-2-yl)(2-(2-(4-(4-fluorobenzoyl)piperidin-1-yl)ethyl)-pyrrolidin-1-yl)methanone;
- (S)-(3,6-difluoro-1H-indol-2-yl)(2-(2-(4-(4-fluorobenzoyl)piperidin-1-yl)ethyl)pyrrolidin-1-yl)methanone;
- (S)-(3-fluoro-6-(trifluoromethoxy)-1H-indol-2-yl)(2-(2-(4-(4-fluorobenzoyl)piperidin-1-yl)ethyl)pyrrolidin-1-yl)methanone;
- (S)-(3-fluoro-1H-indol-2-yl)(2-(2-(4-(4-fluorobenzoyl)piperidin-1-yl)ethyl)pyrrolidin-1-yl)methanone;
- ((2S,5S)-2-(2-(4-(4-fluorobenzoyl)piperidin-1-yl)ethyl)-5-methylpyrrolidin-1-yl)(6-methyl-1H-indol-2-yl)methanone;
- ((2S,5S)-2-(2-(4-(4-fluorobenzoyl)piperidin-1-yl)ethyl)-5-methylpyrrolidin-1-yl)(6-(trifluoromethyl)-1H-indol-2-yl)methanone;
- ((2S,5S)-2-(2-(4-(4-fluorobenzoyl)piperidin-1-yl)ethyl)-5-methylpyrrolidin-1-yl)(6-(trifluoromethylthio)-1H-indol-2-yl)methanone;
- (S)-(2-(2-(4-(4-fluorobenzoyl)piperidin-1-yl)ethyl)pyrrolidin-1-yl)(1-methyl-1H-indol-5-yl)methanone; and
- (S)-(2-(2-(4-(6-fluorobenzo[d]isoxazol-3-yl)piperidin-1-yl)ethyl)pyrrolidin-1-yl)(3-phenyl-1H-pyrazol-5-yl)methanone; or a pharmaceutically acceptable salt thereof.

Section 27: A therapeutic agent for schizophrenia, comprising the compound of any one of Sections 1 to 26 and 30, or a pharmaceutically acceptable salt thereof.

Section 28: A method for treating schizophrenia, which comprises administering a therapeutically effective amount of the compound of any one of Sections 1 to 26 and 30, or a pharmaceutically acceptable salt thereof to mammals in need thereof.

Section 29: Use of the compound of any one of Sections 1 to 26 and 30, or a pharmaceutically acceptable salt thereof in the manufacture of a medicament for the treatment of schizophrenia.

Section 30: The compound of Section 1, wherein $W^2$ is optionally substituted ethylene; n is 0; or a pharmaceutically acceptable salt thereof.

Advantageous Effects of Invention

The present compound and a pharmaceutically acceptable salt thereof show affinities for dopamine receptors, serotonin receptors and adrenaline receptors. Thus, the present compound and a pharmaceutically acceptable salt thereof are expected to improve positive symptoms, negative symptoms, cognitive dysfunction, etc. in schizophrenia, and to weaken extrapyramidal side effects.

BEST MODE FOR CARRYING OUT THE INVENTION

The present invention is described in detail below.

The number of substituents in "optionally substituted" or "substituted" groups herein is one or more, but is not limited thereto if possible. Each definition for each group is applicable in case that the group is a part of other groups or a substituent thereof, unless otherwise indicated.

The "halogen" used herein includes, for example, fluorine atom, chlorine atom, bromine atom, or iodine atom, etc. Preferable one is fluorine atom, or chlorine atom.

The "$C_{1-6}$ alkyl" includes, for example, straight or branched-chain alkyl groups with 1 to 6 carbon atoms, etc. Preferable one includes straight or branched-chain alkyl with 1 to 4 carbon atoms. Particular one includes methyl, ethyl, propyl, 1-methylethyl, butyl, 2-methylpropyl, 1-methylpropyl, 1,1-dimethyl ethyl.

The "$C_{1-3}$ alkylene" used herein includes, for example, methylene, ethylene, propylene, etc. Preferable one includes methylene, ethylene. More preferable one includes ethylene.

The "$C_{3-7}$ cycloalkyl" includes, for example, 3- to 7-membered cycloalkyl, etc. Preferable one includes cycloalkyl with 3 to 6 carbon atoms. Particular one includes, for example, cyclopropyl, cyclobutyl, cyclopentyl, or cyclohexyl.

The "$C_{6-10}$ aryl" includes, for example, aryl with 6 to 10 carbon atoms, etc., particularly phenyl, 1-naphthyl or 2-naphthyl, etc.

The "$C_{6-10}$ aryl" also includes a condensed ring wherein "$C_6$ aryl" is condensed with 5- or 6-membered ring comprising same or different and one or more (e.g., 1 to 4) heteroatoms selected from nitrogen atom, sulfur atom or oxygen atom, or with 5- to 6-membered cycloalkyl ring (e.g., cyclopentane, or cyclohexane). Particular examples for the group include, for example, groups of the following formulae.

[Chemical Formula 16]

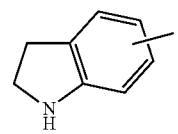
(10)

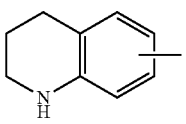
(11)

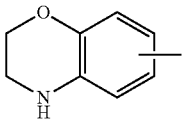
(12)

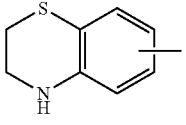
(13)

(14) 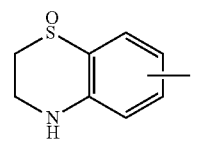
(15) 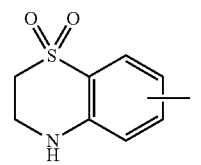
(16) 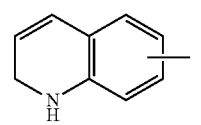
(17) 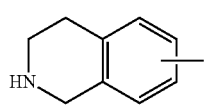
(18) 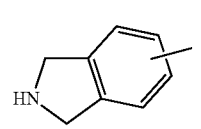
(19) 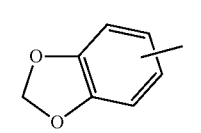
(20) 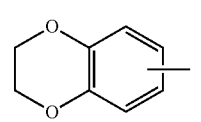
(21) 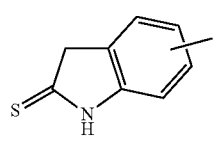
(22) 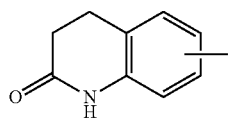
(23) 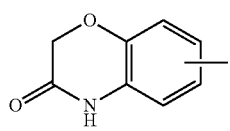
(24) 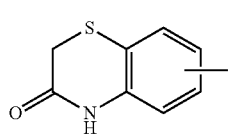
(25) 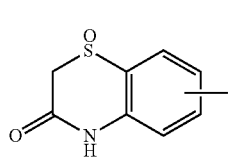
(26) 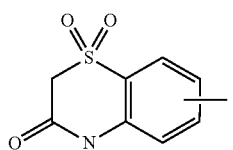
(27) 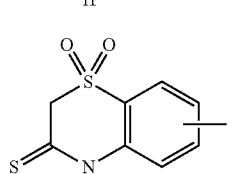
(28) 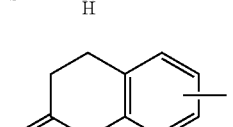
(29) 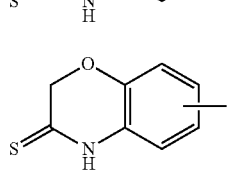
(30) 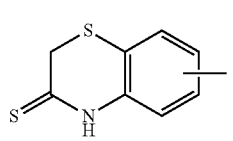
(31) 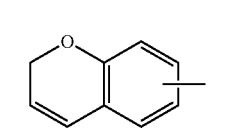
(32) 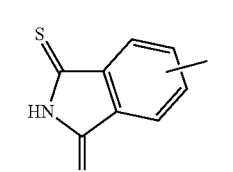
(33) 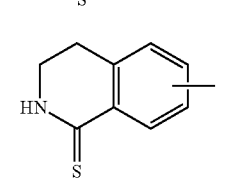
(34) 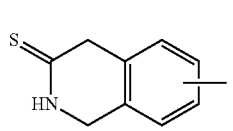
(35) 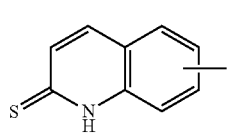
(36) 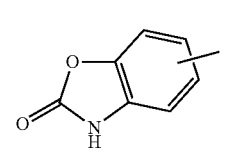

(37) 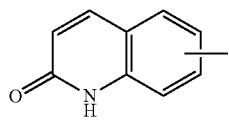

(38) 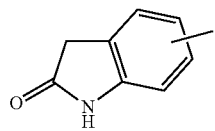

(39) 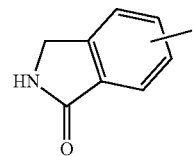

(40) 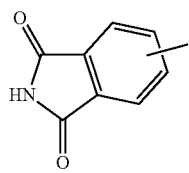

(41) 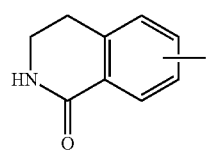

(42) 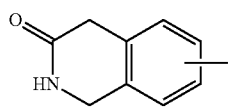

(43) 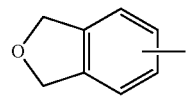

(44) 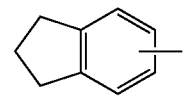

(45) 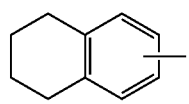

(47) 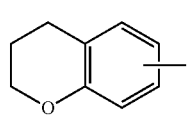

(48) 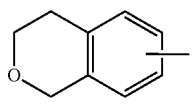

(49) 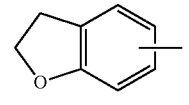

A bond across a ring in the above formulae means that a "group" attaches on any substituent positions of the ring. Particularly, the group may be substituted on any carbon or nitrogen atoms on the ring.

Preferable one includes phenyl, naphthyl, groups of formulae (10), (11), (12), (13), (16), (17), (18), (19), (20), (22), (23), (31), (36), (37), (38), (39), (40), (41), (42), (43), (44), (45), (47), (48) and (49).

The "$C_{6-10}$ aryl" in $Ar^1$ includes phenyl, naphthyl, groups of formulae (10), (11), (12), (13), (16), (17), (18), (19), (20), (22), (23), (31), (36), (37), (38), (39), (40), (41), (42), (43), (44), (45), (47), (48) and (49).

Preferable one includes phenyl, naphthyl, groups of formulae (10), (11), (22), (36), (37) and (38).

The "$C_{6-10}$ aryl" in $Ar^2$ includes phenyl, naphthyl, groups of formulae (10), (11), (12), (13), (16), (17), (18), (19), (20), (22), (23), (31), (36), (37), (38), (39), (40), (41), (42), (43), (44), (45), (47), (48) and (49).

Preferable one includes phenyl, naphthyl and a group of formula (31).

The "heteroaryl" includes, for example, 5- to 10-membered mono- or poly-cycles which comprise same or different and one or more (e.g., 1 to 4) heteroatoms selected from nitrogen atom, sulfur atom or oxygen atom. Particular examples for the "heteroaryl" include, for example, groups of the following formulae.

[Chemical Formula 17]

(50)

(51)

(52)

(53)

(54)

(55)

(56)

(57)

-continued
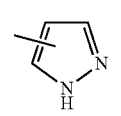 (58)
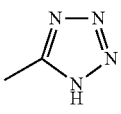 (59)
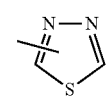 (60)
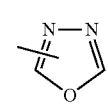 (61)
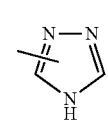 (62)
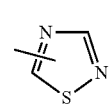 (63)
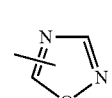 (64)
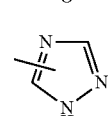 (65)
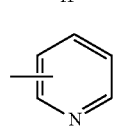 (66)
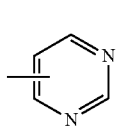 (67)
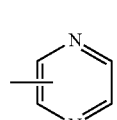 (68)
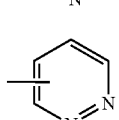 (69)
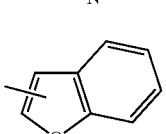 (70)
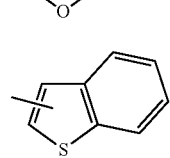 (71)
-continued
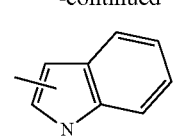 (72)
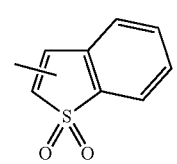 (73)
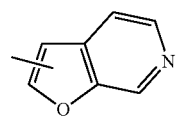 (74)
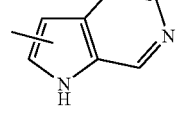 (75)
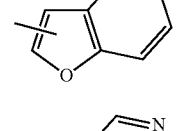 (76)
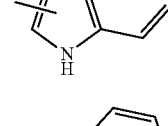 (77)
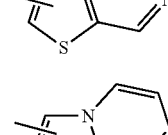 (78)
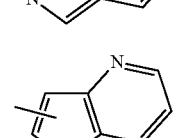 (79)
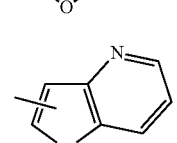 (80)
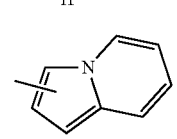 (81)
(82)
(83)

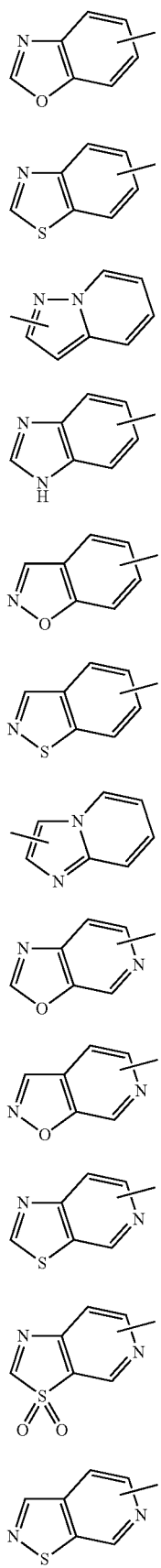
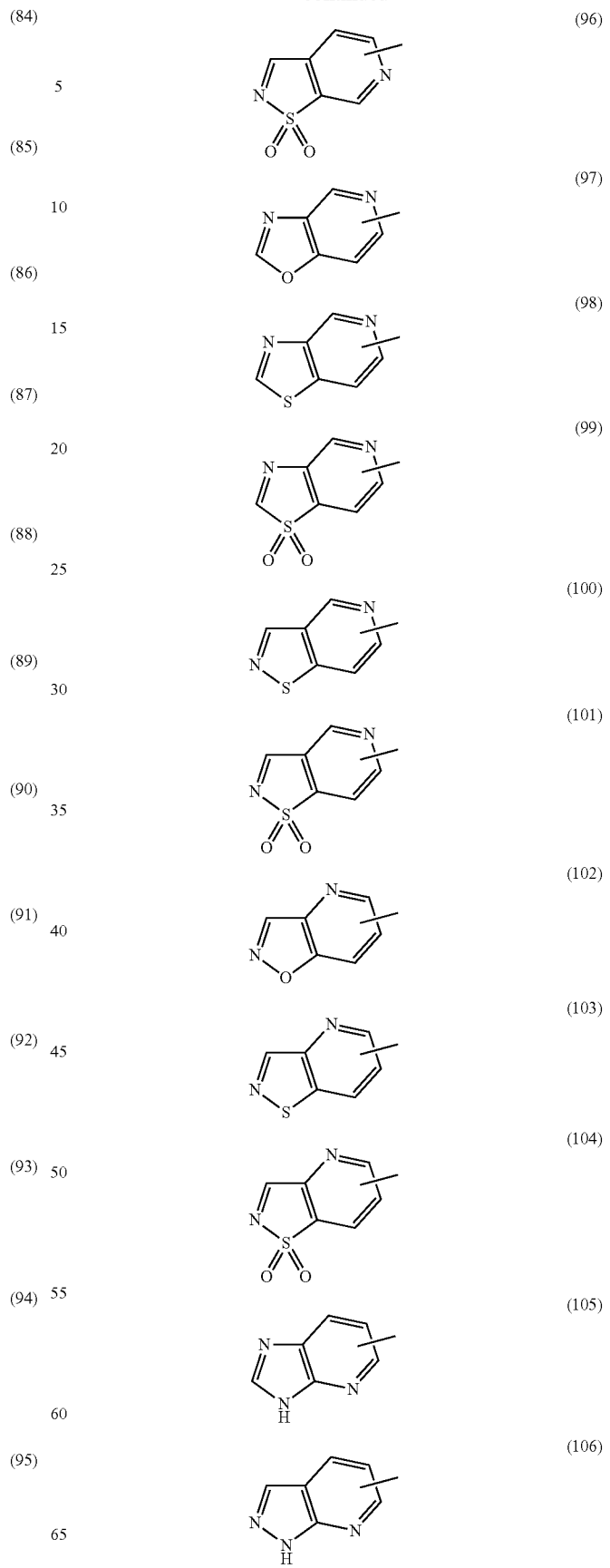

-continued (107) 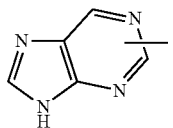

(108) 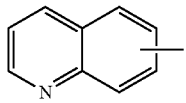

(109) 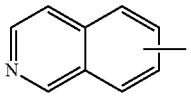

(110) 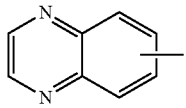

(111) 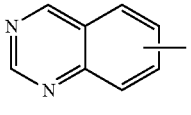

(112) 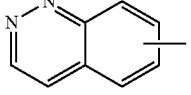

(113) 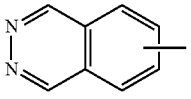

(114) 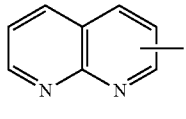

(115) 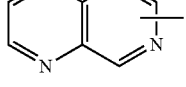

(116) 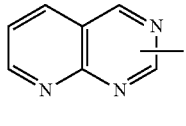

(117) 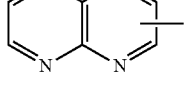

A bond across a ring in the above formulae means that a "group" attaches on any substituent positions of the ring. For example, the heteroaryl of the following formula:

[Chemical Formula 18]

(50) 

refers to 2-furyl, or 3-furyl.

The "heteroaryl" which is a polycycle and a group of the following formula:

[Chemical Formula 19]

(70) 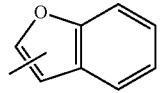

may be also, for example, 2-benzofuryl or 3-benzofuryl as well as 4-, 5-, 6- or 7-benzofuryl.

Preferable one includes groups of formulae (50), (51), (52), (53), (54), (55), (56), (57), (58), (66), (67), (68), (69), (70), (71), (72), (74), (75), (76), (77), (78), (79), (80), (81), (82), (83), (84), (85), (86), (87), (88), (89), (90), (91), (92), (93), (95), (97), (98), (100), (102), (103), (105), (106), (107), (108), (109), (110), (111), (112), (113), (114), (115), (116) and (117).

The "heteroaryl" in $Ar^1$ includes groups of formulae (66), (67), (70), (71), (72), (74), (75), (76), (77), (78), (79), (80), (81), (83), (84), (85), (87), (88), (89), (91), (92), (93), (95), (97), (98), (100), (102), (103), (105), (106), (107), (108), (109), (110), (111), (112), (113), (114), (115), (116) and (117).

Preferable one includes groups of formulae (66), (70), (72), (87), (88), (89) and (109).

More preferable one includes groups of formulae (72), (87), (88), (89).

The "heteroaryl" in $Ar^2$ includes groups of formulae (50), (52), (53), (54), (55), (56), (57), (58), (64), (65), (66), (67), (68), (69), (70), (71), (72), (74), (75), (76), (77), (78), (79), (80), (81), (82), (83), (84), (85), (86), (87), (88), (89), (90), (91), (92), (93), (95), (97), (98), (100), (102), (103), (105), (106), (108), (109), (110), (111), (112), (113), (114), (115), (116) and (117).

Preferable one includes groups of formulae (50), (57), (58), (70), (72), (75), (77), (79), (80), (81), (82), (83), (88), (89), (90), (108) and (109).

More preferable one includes groups of formulae (58), (72) and (75).

The "saturated heterocycle" includes, for example, 4- to 7-membered saturated heterocycles comprising 1 to 4 heteroatoms selected from 0 to 2 nitrogen atoms, 0 to 1 oxygen atom or 0 to 1 sulfur atom, etc. A "group" attaches on any ring carbon atoms in the heterocycle. Particular one includes, for example, azetidinyl, oxetanyl, tetrahydropyranyl, tetrahydropyridinyl, pyrrolidinyl, oxopyrrolidinyl, oxopiperidinyl, oxopiperazinyl, oxomorpholinyl, tetrahydrofuranyl, piperidinyl, piperazinyl, morpholinyl, thiomorpholinyl, dioxoimidazolidinyl, tetrahydrotriazoloazepinyl, oxodihydroacrydinyl, tetrahydrocyclopentachromenyl, oxobenzoxathiolyl, dihydroindenyl, azepanyl or oxoazepanyl, etc. Preferable one includes azetidinyl, oxetanyl, tetrahydropyranyl, tetrahydropyridinyl, pyrrolidinyl, oxopyrrolidinyl, oxopiperidinyl, oxopiperazinyl, oxomorpholinyl, tetrahydrofuranyl, piperidinyl, piperazinyl, morpholinyl, thiomorpholinyl, etc. Preferable "saturated heterocycle" in $R^{1a}$, $R^{1b}$ and $R^{1c}$ includes oxetanyl, tetrahydropyranyl, tetrahydrofuranyl. Preferable "saturated heterocycle" wherein $R^{1a}$ and $R^{1b}$ combine each other includes tetrahydropyranyl, tetrahydrofuranyl.

The "$C_{3-7}$ cycloalkyl-$C_{1-4}$ alkyl" refers to a group wherein "$C_{3-7}$ cycloalkyl" is substituted on "$C_{1-4}$ alkyl". Preferable one includes $C_{3-6}$ cycloalkyl-$C_{1-4}$ alkyl. Particular one includes, for example, cyclopropylmethyl, cyclobutylmethyl, cyclopentylmethyl, cyclohexylmethyl, cycloheptylmethyl, cyclohexylethyl, cyclohexylpropyl or cyclohexylbutyl, etc.

The "$C_{7-14}$ aralkyl" refers to a group wherein "$C_{6-10}$ aryl" is substituted on "$C_{1-4}$ alkyl". Preferable one includes $C_{7-10}$ aralkyl. Particular one includes, for example, benzyl, phenethyl, phenylpropyl or naphthylmethyl, etc.

The "heteroaryl-$C_{1-4}$ alkyl" refers to a group wherein "heteroaryl" is substituted on "$C_{1-4}$ alkyl". Preferable one is 5- or 6-membered monocyclic heteroaryl-$C_{1-4}$ alkyl. Particular one includes, for example, pyridylmethyl, pyridylethyl, imidazolylethyl, pyrrolylpropyl, etc.

The "saturated heterocyclic $C_{1-4}$ alkyl" refers to a group wherein "saturated heterocycle" is substituted on "$C_{1-4}$ alkyl". Preferable one is 4- to 7-membered saturated heterocyclic $C_{1-4}$ alkyl. Particular one includes, for example, azetidinylmethyl, pyrrolidylethyl, tetrahydrofuranylpropyl, morphonylbutyl, tetrahydropyranylmethyl, etc.

The "$C_{1-6}$ alkoxy" includes, for example, straight or branched-chain alkoxy with 1 to 6 carbon atoms. Preferable one includes $C_{1-4}$ alkoxy. Particular one includes methoxy, ethoxy, propoxy, 1-methylethoxy, butoxy, 2-methylpropoxy, 1-methylpropoxy, 1,1-dimethylethoxy.

The "$C_{1-6}$ alkylthio" includes, for example, straight or branched-chain alkylthio with 1 to 6 carbon atoms. Preferable one includes $C_{1-4}$ alkylthio. Particular one includes methylthio, ethylthio, propylthio, 1-methylethylthio, butylthio, 2-methylpropylthio, 1-methylpropylthio, 1,1-dimethylethylthio.

The "$C_{3-7}$ cycloalkyl" moiety of the "$C_{3-7}$ cycloalkoxy" is the same as the "$C_{3-7}$ cycloalkyl". Preferable one includes $C_{3-6}$ cycloalkoxy. Particular one includes, for example, cyclopropoxy, cyclobutoxy, cyclopentyloxy, or cyclohexyloxy.

The "$C_{6-10}$ aryloxy" refers to a group wherein the "$C_{6-10}$ aryl" binds to oxygen atom. Preferable one is aryloxy with 6 carbon atoms. Particular one includes phenoxy.

The "heteroaryloxy" refers to a group wherein the "heteroaryl" binds to oxygen atom. Preferable one is 5- or 6-membered monocyclic heteroaryloxy. Particular one includes, for example, pyridyloxy, imidazolyloxy, pyrrolyloxy, etc.

The "saturated heterocyclic oxy" refers to a group wherein the "saturated heterocycle" binds to oxygen atom. Preferable one is "4- to 7-membered saturated heterocyclic oxy". Particular one includes, for example, tetrahydropyranyloxy, tetrahydrofuranyloxy, pyrrolidyloxy, etc.

The "$C_{1-6}$ alkyl" moiety of the "$C_{1-6}$ alkylcarbonyl" is the same as the "$C_{1-6}$ alkyl". Preferable one includes $C_{1-4}$ alkylcarbonyl. Particular one includes, for example, methylcarbonyl, ethylcarbonyl, propylcarbonyl, 1-methylethylcarbonyl, butylcarbonyl, 2-methylpropylcarbonyl, 1-methylpropylcarbonyl or 1,1-dimethylethylcarbonyl, etc.

The "$C_{3-7}$ cycloalkyl" moiety of the "$C_{3-7}$ cycloalkylcarbonyl" is the same as the "$C_{3-7}$ cycloalkyl". Preferable one includes $C_{3-6}$ cycloalkylcarbonyl. Particular one includes, for example, cyclopropylcarbonyl, cyclobutylcarbonyl, cyclopentylcarbonyl, or cyclohexylcarbonyl.

The "$C_{6-10}$ aryl" moiety of the "$C_{6-10}$ arylcarbonyl" is the same as the "$C_{6-10}$ aryl". Preferable one is arylcarbonyl with 6 carbon atoms. Particular one includes benzoyl.

The "heteroaryl" moiety of the "heteroarylcarbonyl" is the same as the "heteroaryl". Preferable one includes 5- or 6-membered monocyclic heteroarylcarbonyl. Preferable one includes pyridinecarbonyl, pyrrolecarbonyl.

The "saturated heterocyclic" moiety of the "saturated heterocyclic carbonyl" is the same as the "saturated heterocycle". Preferable one is "4- to 7-membered saturated heterocyclic carbonyl". Particular one includes, for example, tetrahydropyrancarbonyl, tetrahydrofurancarbonyl, morpholinecarbonyl, etc.

The "$C_{1-6}$ alkyl" moiety of the "$C_{1-6}$ alkylsulfonyl" is the same as the "$C_{1-6}$ alkyl". Preferable one includes $C_{1-4}$ alkylsulfonyl. Particular one includes, for example, methanesulfonyl, ethanesulfonyl, propylsulfonyl, 1-methylethylsulfonyl, 2-methylethylsulfonyl, 1-methylpropylsulfonyl, 2-methylpropylsulfonyl, 1,1-dimethylethylsulfonyl or butylsulfonyl, etc.

The "$C_{3-7}$ cycloalkyl" moiety of the "$C_{3-7}$ cycloalkylsulfonyl" is the same as the "$C_{3-7}$ cycloalkyl". Preferable one includes $C_{3-6}$ cycloalkylsulfonyl. Particular one includes, for example, cyclopropylsulfonyl, cyclobutylsulfonyl, cyclopentylsulfonyl, or cyclohexylsulfonyl.

The "$C_{6-10}$ aryl" moiety of the "$C_{6-10}$ arylsulfonyl" is the same as the "$C_{6-10}$ aryl". Preferable one is arylsulfonyl with 6 carbon atoms. Particular one includes benzenesulfonyl.

The "heteroaryl" moiety of the "heteroarylsulfonyl" is the same as the "heteroaryl". Preferable one includes 5- or 6-membered monocyclic heteroarylsulfonyl. Particular one includes pyrrolesulfonyl, pyridinesulfonyl.

The "saturated heterocyclic" moiety of the "saturated heterocyclic sulfonyl" is the same as the "saturated heterocycle". Preferable one is "4- to 7-membered saturated heterocyclic sulfonyl". Particular one includes, for example, tetrahydropyranesulfonyl, tetrahydrofuransulfonyl, etc.

The "optionally substituted amino" includes, for example, amino, mono- or di-substituted amino, 4- to 7-membered cyclic amino.

Substituents of the "mono- or di-substituted amino" include, for example, same or different and one or two groups selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted saturated heterocycle, optionally substituted $C_{6-10}$ aryl, optionally substituted heteroaryl.

A particular example of the "mono-substituted amino" includes, for example, "$C_{1-6}$ alkylamino" (e.g., methylamino, etc.), "$C_{3-7}$ cycloalkylamino" (e.g., cyclopropylamino, etc.), "($C_{6-10}$ aryl)amino" (e.g., phenylamino, etc.), "(heteroaryl)amino" (e.g., pyrrolylamino, etc.). Preferable one includes $C_{1-4}$ alkylamino, $C_{3-6}$ cycloalkylamino, phenylamino, pyrrolylamino.

A particular example of the "di-substituted amino" includes, for example, "di-$C_{1-6}$ alkylamino" (e.g., dimethylamino, methylethylamino, etc.), "N—($C_{1-6}$ alkyl)-N—($C_{3-7}$ cycloalkyl)amino" (e.g., methylcyclopropylamino, etc.), "N—($C_{1-6}$ alkyl)-N-(5- or 6-membered saturated heterocyclic)amino" (e.g., methyltetrahydropyranylamino, etc.), etc. Preferable one includes di-$C_{1-4}$ alkylamino, N—($C_{1-4}$ alkyl)-N—($C_{3-6}$ cycloalkyl)amino.

The "4- to 7-membered cyclic amino" includes, for example, 4- to 7-membered monocyclic cyclic amino which may comprise same or different 1 to 3 heteroatoms selected from nitrogen atom, oxygen atom and sulfur atom. A "group" attaches on any ring nitrogen atoms in the cyclic amino. Particular one includes, for example, azetidino, pyrrolidino, imidazolidino, oxazolidino, thiazolidino, piperazino, piperidino, morpholino, thiomorpholino, azepano or oxoazepano, etc. Preferable one includes azetidino, pyrrolidino, imidazolidino, morpholino.

The "4- to 7-membered cyclic amino" may form a condensed ring together with 6-membered aromatic hydrocarbon, or 5- or 6-membered heterocycle. Particular one includes "groups" of the following formulae:

[Chemical Formula 20]
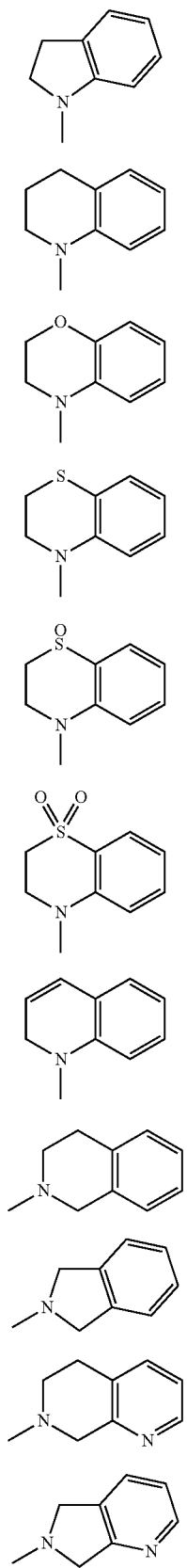
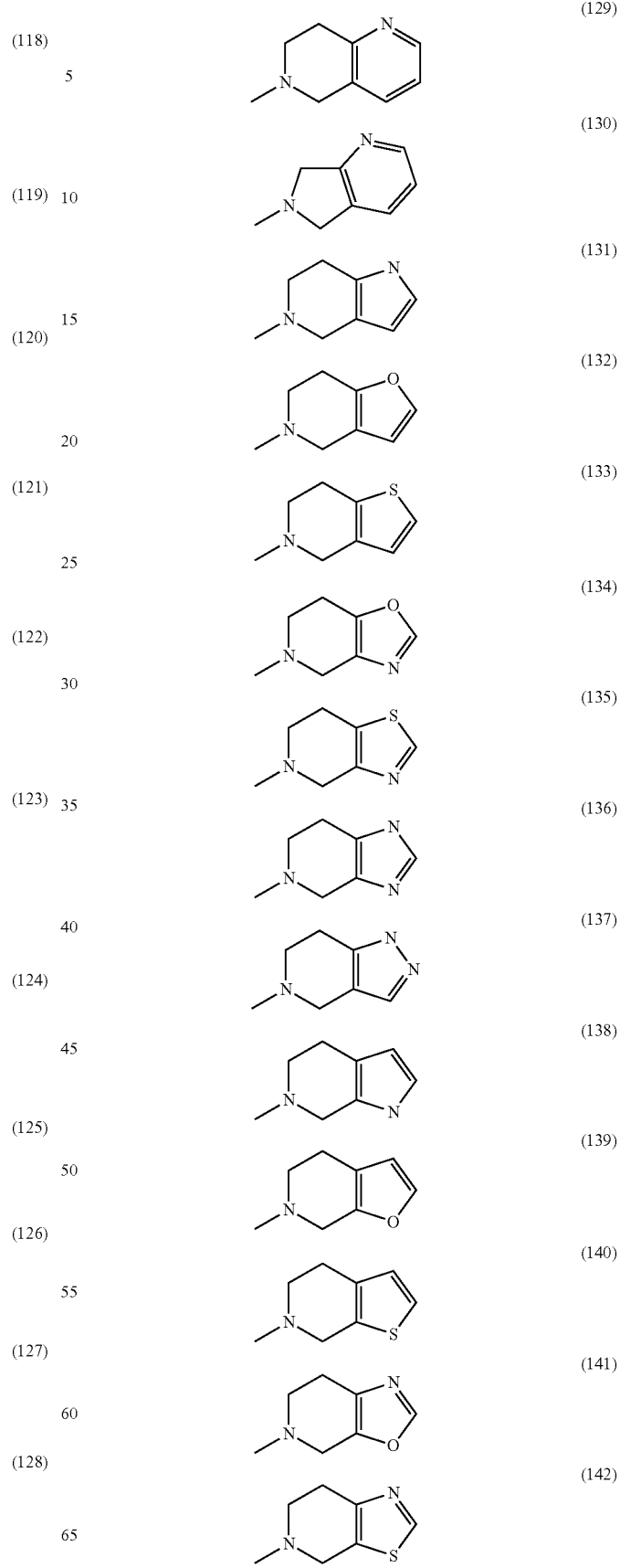

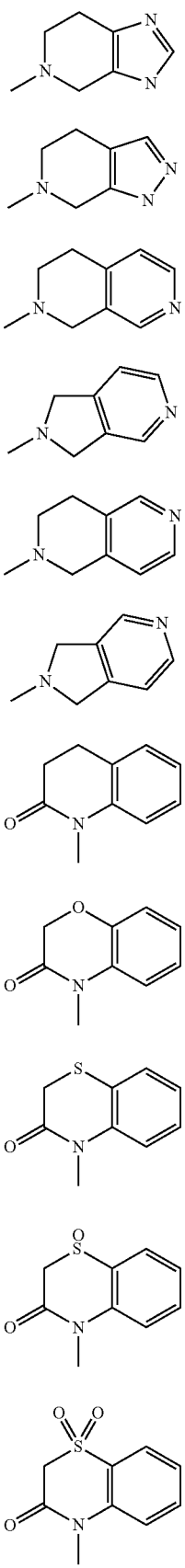

(143)
(144)
(145)
(146)
(147)
(148)
(149)
(150)
(151)
(152)
(153)

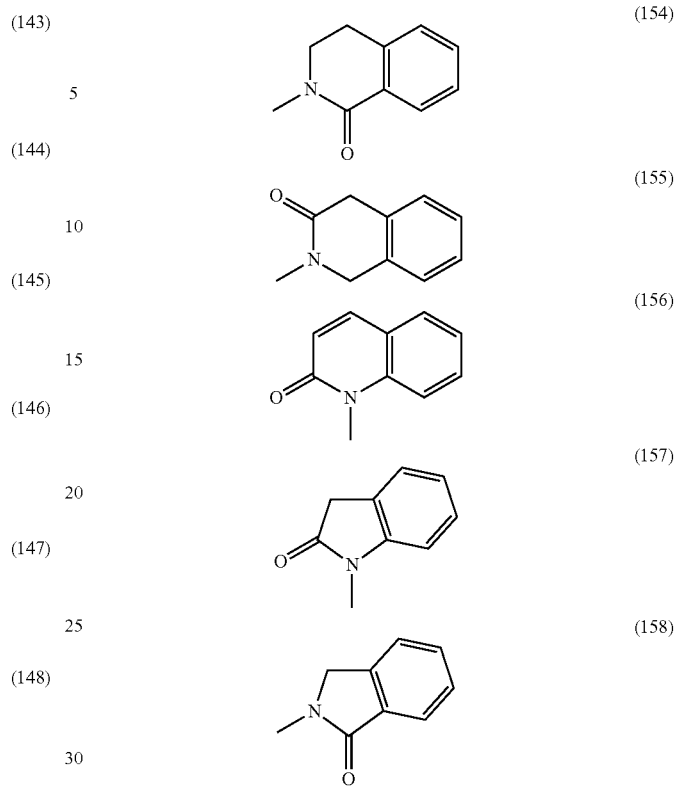

(154)
(155)
(156)
(157)
(158)

Preferable one includes groups of the formulae (120), (125), (127), (128), (129), (130), (134), (136), (137), (141), (143), (144), (145), (146), (147), (148), (149) and (150).

The "$C_{3-7}$ cycloalkyl" moiety of the "$C_{3-7}$ cycloalkyl-$C_{1-4}$ alkylcarbonyl" is the same as the "$C_{3-7}$ cycloalkyl". Preferable one is $C_{3-6}$ cycloalkyl-$C_{1-4}$ alkyl. Particular one includes, for example, cyclopropylmethylcarbonyl, cyclohexylethylcarbonyl, etc.

The "$C_{1-6}$ alkoxycarbonyl" includes straight or branched-chain alkoxycarbonyl with 1 to 6 carbon atoms. Preferable one includes $C_{1-4}$ alkoxycarbonyl. Particular one includes, for example, methoxycarbonyl, ethoxycarbonyl, propoxycarbonyl, 2-methylethoxycarbonyl, butoxycarbonyl, 2-methylpropoxycarbonyl, 1-methylpropoxycarbonyl or 1,1-dimethylethoxycarbonyl, etc.

The "$C_{3-7}$ cycloalkoxy" moiety of the "$C_{3-7}$ cycloalkoxycarbonyl" is the same as the "$C_{3-7}$ cycloalkoxy". Preferable one includes $C_{3-6}$ cycloalkoxycarbonyl. Particular one includes, for example, cyclopropoxycarbonyl, cyclobutoxycarbonyl, cyclopentyloxycarbonyl, or cyclohexyloxycarbonyl.

The "saturated heterocyclic oxy" moiety of the "saturated heterocyclic oxycarbonyl" is the same as the "saturated heterocyclic oxy". Preferable one is "5- to 7-membered saturated heterocyclic oxycarbonyl". Particular one includes, for example, tetrahydropyranyloxycarbonyl, etc.

The "optionally substituted amino" moiety of the "optionally substituted aminocarbonyl" is the same as the "optionally substituted amino". The "optionally substituted aminocarbonyl" includes, for example, aminocarbonyl, mono- or di-substituted aminocarbonyl, 4- to 7-membered cyclic aminocarbonyl.

Substituents of the "mono- or di-substituted aminocarbonyl" include, for example, same or different 1 to 2 groups selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted 4- to 7-membered saturated heterocycle, optionally substituted $C_{6-10}$ aryl and optionally substituted heteroaryl.

A particular example of the "mono-substituted aminocarbonyl" includes, for example, "$C_{1-6}$ alkylaminocarbonyl (e.g., methylaminocarbonyl, etc.)", "$C_{3-7}$ cycloalkylaminocarbonyl (e.g., cyclopropylaminocarbonyl, etc.)", "($C_{6-10}$ aryl)aminocarbonyl (e.g., phenylaminocarbonyl, etc.), "(heteroaryl)aminocarbonyl (e.g., pyrrolylaminocarbonyl, etc.)". Preferable one includes $C_{1-4}$ alkylaminocarbonyl, $C_{3-6}$ cycloalkylaminocarbonyl.

A particular example of the "di-substituted aminocarbonyl" includes, for example, "di-$C_{1-6}$ alkylaminocarbonyl (e.g., dimethylaminocarbonyl, methylethylaminocarbonyl, etc.)", "N—($C_{1-6}$ alkyl)-N—($C_{3-7}$ cycloalkyl)aminocarbonyl (e.g., methylcyclopropylaminocarbonyl, etc.)", "N—($C_{1-6}$ alkyl)-N-(5- or 6-membered saturated heterocyclic)aminocarbonyl (e.g., methyltetrahydropyranylaminocarbonyl, etc.)", etc. Preferable one includes di-$C_{1-4}$ alkylaminocarbonyl, N—($C_{1-4}$ alkyl)-N—($C_{3-6}$ cycloalkyl)aminocarbonyl.

The "4- to 7-membered cyclic aminocarbonyl" includes, for example, 4- to 7-membered monocyclic cyclic aminocarbonyl which may comprise same or different 1 to 3 heteroatoms selected from nitrogen atom, oxygen atom and sulfur atom. Particular one includes, for example, azetidinocarbonyl, pyrrolidinocarbonyl, imidazolidinocarbonyl, oxazolidinocarbonyl, thiazolidinocarbonyl, piperazinocarbonyl, piperidinocarbonyl, morpholinocarbonyl, thiomorpholinocarbonyl, azepanocarbonyl or oxoazepanocarbonyl, etc. Preferable one includes azetidinocarbonyl, morpholinocarbonyl.

The 4- to 7-membered cyclic amino moiety of the "4- to 7-membered cyclic aminocarbonyl" may form a condensed ring together with 6-membered aromatic hydrocarbon, or 5- or 6-membered heterocycle.

The "optionally substituted amino" moiety of the "optionally substituted aminosulfonyl" is the same as the "optionally substituted amino". The "optionally substituted aminosulfonyl" includes, for example, aminosulfonyl, mono- or di-substituted aminosulfonyl, 4- to 7-membered cyclic aminosulfonyl.

Substituents of the "mono- or di-substituted aminosulfonyl" include, for example, same or different 1 to 2 groups selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted 4- to 7-membered saturated heterocycle, optionally substituted $C_{6-10}$ aryl and optionally substituted heteroaryl.

A particular example of the "mono-substituted aminosulfonyl" includes, for example, "$C_{1-6}$ alkylaminosulfonyl (e.g., methylaminosulfonyl, etc.)", "$C_{3-7}$ cycloalkylaminosulfonyl (e.g., cyclopropylaminosulfonyl, etc.)", "($C_{6-10}$ aryl)aminosulfonyl (e.g., phenylaminosulfonyl, etc.)", "(heteroaryl) aminosulfonyl (e.g., pyrrolylaminosulfonyl, etc.)". Preferable one includes $C_{1-4}$ alkylaminosulfonyl, $C_{3-6}$ cycloalkylaminosulfonyl.

A particular example of the "di-substituted aminosulfonyl" includes, for example, "di-$C_{1-6}$ alkylaminosulfonyl (e.g., dimethylaminosulfonyl, methylethylaminosulfonyl, etc.)", "N—($C_{1-6}$ alkyl)-N—($C_{3-7}$ cycloalkyl)aminosulfonyl (e.g., methylcyclopropylaminosulfonyl, etc.)", "N—($C_{1-6}$ alkyl)-N-(5- or 6-membered saturated heterocyclic)aminosulfonyl (e.g., methyltetrahydropyranylaminosulfonyl, etc.)", etc. Preferable one includes di-$C_{1-4}$ alkylaminosulfonyl, N—($C_{1-4}$ alkyl)-N—($C_{3-6}$ cycloalkyl)aminosulfonyl.

The "4- to 7-membered cyclic aminosulfonyl" includes, for example, 4- to 7-membered monocyclic cyclic aminosulfonyl which may comprise same or different 1 to 3 heteroatoms selected from nitrogen atom, oxygen atom and sulfur atom. Particular one includes, for example, azetidinosulfonyl, pyrrolidinosulfonyl, imidazolidinosulfonyl, oxazolidinosulfonyl, thiazolidinosulfonyl, piperazinosulfonyl, piperidinosulfonyl, morpholinosulfonyl, thiomorpholinosulfonyl, azepanosulfonyl or oxoazepanosulfonyl, etc. Preferable one includes azetidinosulfonyl, morpholinosulfonyl.

The 4- to 7-membered cyclic amino moiety of the "4- to 7-membered cyclic aminosulfonyl" may form a condensed ring with 6-membered aromatic hydrocarbon, or 5- or 6-membered heterocycle.

The "$C_{1-6}$ alkyl" moiety of the "$C_{1-6}$ alkylcarbonylamino" is the same as the "$C_{1-6}$ alkyl". Preferable one is $C_{1-4}$ alkylcarbonylamino. Particular one includes methylcarbonylamino, etc.

The "$C_{3-7}$ cycloalkyl" moiety of the "$C_{3-7}$ cycloalkylcarbonylamino" is the same as the "$C_{3-7}$ cycloalkyl". Preferable one is $C_{3-6}$ cycloalkylcarbonylamino. Particular one includes, for example, cyclopropylcarbonylamino, etc.

The "$C_{6-10}$ aryl" moiety of the "$C_{6-10}$ arylcarbonylamino" is the same as the "$C_{6-10}$ aryl". Preferable one is arylcarbonylamino with 6 carbon atoms. Particular one includes benzoylamino.

The "heteroaryl" moiety of the "heteroarylcarbonylamino" is the same as the "heteroaryl". Preferable one is 5- or 6-membered monocyclic heteroarylcarbonylamino. Particular one includes, for example, pyrrolecarbonylamino.

The "saturated heterocyclic" moiety of the "saturated heterocyclic carbonylamino" is the same as the "saturated heterocycle". Preferable one includes 4- to 7-membered saturated heterocyclic carbonyl. Particular one includes, for example, azetidinecarbonylamino.

The "$C_{7-14}$ aralkyloxy" refers to a group wherein the "$C_{7-14}$ aralkyl" binds to oxygen atom. Preferable one is $C_{7-11}$ aralkyloxy. Particular one includes, for example, benzyloxy, phenethyloxy, phenylpropyloxy or naphthylmethyloxy, etc.

The "$C_{1-6}$ alkyl" moiety of the "$C_{1-6}$ alkylcarbonyloxy" is the same as the "$C_{1-6}$ alkyl", and the "$C_{1-6}$ alkylcarbonyloxy" includes, for example, straight or branched-chain alkylcarbonyloxy with 1 to 6 carbon atoms, etc. Preferable one is $C_{1-4}$ alkylcarbonyloxy. Particular one includes methylcarbonyloxy, etc.

The "optionally substituted amino" moiety of the "optionally substituted aminocarbonyloxy" is the same as the "optionally substituted amino", and the "optionally substituted aminocarbonyloxy" includes, for example, aminocarbonyloxy, mono- or di-substituted aminocarbonyloxy, 4- to 7-membered cyclic aminocarbonyloxy.

Substituents of the "mono- or di-substituted aminocarbonyloxy" include, for example, same or, different 1 to 2 groups selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted 4- to 7-membered saturated heterocycle, optionally substituted $C_{6-10}$ aryl, and optionally substituted heteroaryl.

A particular example of the "mono-substituted aminocarbonyloxy" includes, for example, "$C_{1-6}$ alkylaminocarbonyloxy (e.g., methylaminocarbonyloxy, etc.)", "$C_{3-7}$ cycloalkylaminocarbonyloxy (e.g., cyclopropylaminocarbonyloxy, etc.)", "($C_{6-10}$ aryl)-aminocarbonyloxy (e.g., phenylaminocarbonyloxy, etc.)", "(heteroaryl)aminocarbonyloxy (e.g., pyrrolylaminocarbonyloxy, etc.)". Preferable one includes $C_{1-4}$ alkylaminocarbonyloxy, $C_{3-6}$ cycloalkylaminocarbonyloxy.

A particular example of the "di-substituted aminocarbonyloxy" includes, for example, "di-$C_{1-6}$ alkylaminocarbonyloxy (e.g., dimethylaminocarbonyloxy, methylethylaminocarbonyloxy, etc.)", "N—($C_{1-6}$ alkyl)-N—($C_{3-7}$ cycloalkyl)aminocarbonyloxy (e.g., methylcyclopropylaminocarbonyloxy, etc.)", "N—($C_{1-6}$ alkyl)-N-(5- or 6-membered saturated heterocyclic)aminocarbonyloxy (e.g., methyltetrahydropyranylaminocarbonyloxy, etc.)", etc. Preferable one includes di-$C_{1-4}$ alkylaminocarbonyloxy, N—($C_{1-4}$ alkyl)-N—($C_{3-6}$ cycloalkyl)-aminocarbonyloxy.

The "4- to 7-membered cyclic aminocarbonyloxy" includes, for example, 4- to 7-membered monocyclic cyclic aminocarbonyloxy which may comprise same or different 1 to 3 heteroatoms selected from nitrogen atom, oxygen atom and sulfur atom. Particular one includes, for example, azetidinocarbonyloxy, pyrrolidinocarbonyloxy, imidazolidinocarbonyloxy, oxazolidinocarbonyloxy, thiazolidinocarbonyloxy, piperazinocarbonyloxy, piperidinocarbonyloxy, morpholinocarbonyloxy, thiomorpholinocarbonyloxy, azepanocarbonyloxy or oxoazepanocarbonyloxy, etc. Preferable one includes azetidinocarbonyloxy, morpholinocarbonyloxy.

The "$C_{1-6}$ alkoxy" moiety of the "$C_{1-6}$ alkoxycarbonylamino" is the same as the "$C_{1-6}$ alkoxy". Preferable one includes $C_{1-4}$ alkoxycarbonylamino. Particular one includes, for example, methoxycarbonylamino, ethoxycarbonylamino, propoxycarbonylamino, 2-methylethoxycarbonylamino, butoxycarbonylamino, 2-methylpropoxycarbonylamino, or 1-methylpropoxycarbonylamino.

The "$C_{3-7}$ cycloalkoxy" moiety of the "$C_{3-7}$ cycloalkoxycarbonylamino" is the same as the "$C_{3-7}$ cycloalkoxy". Preferable one includes $C_{3-6}$ cycloalkoxycarbonylamino. Particular one includes, for example, cyclopropoxycarbonylamino, cyclobutoxycarbonylamino, cyclopentyloxycarbonylamino, or cyclohexyloxycarbonylamino.

The "saturated heterocyclic oxy" moiety of the "saturated heterocyclic oxycarbonylamino" is the same as the "saturated heterocyclic oxy". Preferable one is "5- to 7-membered saturated heterocyclic oxycarbonylamino". Particular one includes, for example, tetrahydropyranyloxycarbonylamino, etc.

The "optionally substituted amino" moiety of the "optionally substituted aminocarbonylamino" is the same as the "optionally substituted amino", and the "optionally substituted aminocarbonylamino" includes, for example, aminocarbonylamino, mono- or di-substituted aminocarbonylamino, 4- to 7-membered cyclic aminocarbonylamino.

Substituents of the "mono- or di-substituted aminocarbonylamino" include, for example, same or different 1 to 2 groups selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted 4- to 7-membered saturated heterocycle, optionally substituted $C_{6-10}$ aryl, and optionally substituted heteroaryl.

A particular example of the "mono-substituted aminocarbonylamino" includes, for example, "$C_{1-6}$ alkylaminocarbonylamino (e.g., methylaminocarbonylamino, etc.)", "$C_{3-7}$ cycloalkylaminocarbonylamino (e.g., cyclopropylaminocarbonylamino, etc.)", "($C_{6-10}$ aryl)-aminocarbonylamino (e.g., phenylaminocarbonylamino, etc.)", "(heteroaryl)aminocarbonylamino (e.g., pyrrolylaminocarbonylamino, etc.)". Preferable one includes $C_{1-4}$ alkylaminocarbonylamino, $C_{3-6}$ cycloalkylaminocarbonylamino.

A particular example of the "di-substituted aminocarbonylamino" includes, for example, "di-$C_{1-6}$ alkyl aminocarbonylamino (e.g., dimethylaminocarbonylamino, methylethylaminocarbonylamino, etc.)", "N—($C_{1-6}$ alkyl)-N—($C_{3-7}$ cycloalkyl)-aminocarbonylamino (e.g., methylcyclopropylaminocarbonylamino, etc.)", "N—($C_{1-6}$ alkyl)-N-(5- or 6-membered saturated heterocyclic)aminocarbonylamino (e.g., methyltetrahydropyranylaminocarbonylamino, etc.)", etc. Preferable one includes di-$C_{1-4}$ alkylaminocarbonylamino, N—($C_{1-4}$ alkyl)-N—($C_{3-6}$ cycloalkyl)aminocarbonylamino.

The "4- to 7-membered cyclic aminocarbonylamino" includes, for example, 4- to 7-membered monocyclic cyclic aminocarbonylamino which may comprise same or different 1 to 3 heteroatoms selected from nitrogen atom, oxygen atom and sulfur atom. Particular one includes, for example, azetidinocarbonylamino, pyrrolidinocarbonylamino, imidazolidinocarbonylamino, oxazolidinocarbonylamino, thiazolidinocarbonylamino, piperazinocarbonylamino, piperidinocarbonylamino, morpholinocarbonylamino, thiomorpholinocarbonylamino, azepanocarbonylamino or oxoazepanocarbonylamino, etc. Preferable one includes azetidinocarbonylamino, morpholinocarbonylamino.

The "$C_{1-6}$ alkyl" moiety of the "$C_{1-6}$ alkylsulfonylamino" is the same as the "$C_{1-6}$ alkyl". Preferable one includes $C_{1-4}$ alkylsulfonylamino. Particular one includes, for example, methanesulfonylamino, ethanesulfonylamino, propylsulfonylamino, 1-methylethylsulfonylamino, 2-methylethylsulfonylamino, 1-methylpropylsulfonylamino, 2-methylpropylsulfonylamino, 1,1-dimethylethylsulfonylamino or butylsulfonylamino, etc.

The "$C_{3-7}$ cycloalkyl" moiety of the "$C_{3-7}$ cycloalkylsulfonylamino" is the same as the "$C_{3-7}$ cycloalkyl". Preferable one includes $C_{3-6}$ cycloalkylsulfonylamino. Particular one includes, for example, cyclopropylsulfonylamino, cyclobutylsulfonylamino, cyclopentylsulfonylamino, or cyclohexylsulfonylamino.

The "$C_{6-10}$ aryl" moiety of the "$C_{6-10}$ arylsulfonylamino" is the same as the "$C_{6-10}$ aryl". Preferable one includes arylsulfonylamino with 6 carbon atoms. Particular one includes benzenesulfonylamino.

The "heteroaryl" moiety of the "heteroarylsulfonylamino" is the same as the "heteroaryl". Preferable one includes 5- or 6-membered monocyclic heteroarylsulfonylamino. Particular one includes pyrrolesulfonylamino, pyridinesulfonylamino.

The "saturated heterocyclic" moiety of the "saturated heterocyclic sulfonylamino" is the same as the "saturated heterocycle". Preferable one includes "4- to 7-membered saturated heterocyclic sulfonylamino". Particular one includes, for example, tetrahydropyransulfonylamino, tetrahydrofuransulfonylamino, etc.

The "optionally substituted amino" moiety of the "optionally substituted aminosulfonylamino" is the same as the "optionally substituted amino", and the "optionally substituted aminosulfonylamino" includes, for example, aminosulfonylamino, mono- or di-substituted aminosulfonylamino, 4- to 7-membered cyclic aminosulfonylamino.

Substituents of the "mono- or di-substituted aminosulfonylamino" include, for example, same or different 1 to 2 groups selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted 4- to 7-membered saturated heterocycle, optionally substituted $C_{6-10}$ aryl, and optionally substituted heteroaryl.

A particular example of the "mono-substituted aminosulfonylamino" includes, for example, "$C_{1-6}$ alkylaminosulfonylamino. Preferable one includes "$C_{1-4}$ alkylaminosulfonylamino (e.g., methylaminosulfonylamino, etc.)".

A particular example of the "di-substituted aminosulfonylamino" includes, for example, "di-$C_{1-6}$ alkylaminosulfonylamino. Preferable one includes "di-$C_{1-4}$ alkylaminosulfonylamino (e.g., dimethylaminosulfonylamino, methylethylaminosulfonylamino, etc.)".

The "4- to 7-membered cyclic aminosulfonylamino" includes, for example, 4- to 7-membered monocyclic cyclic aminosulfonylamino which may comprise same or different 1 to 3 heteroatoms selected from nitrogen atom, oxygen atom and sulfur atom. Particular one includes, for example, azetidinosulfonylamino, morpholinosulfonylamino, etc. Preferable one includes morpholinosulfonylamino.

Substituents of the "optionally substituted $C_{1-6}$ alkyl" and the "optionally substituted $C_{1-3}$ alkyl" include, for example:
(a) halogen,
(b) cyano,
(c) hydroxy,
(d) formyl,
(e) $C_{1-6}$ alkylcarbonyl,
(f) $C_{1-6}$ alkylcarbonyloxy,
(g) carboxyl,
(h) amino (in which the amino may be optionally substituted by same or different 1 to 2 groups selected from the group consisting of:
　(h1) $C_{1-6}$ alkyl (in which the alkyl may be optionally substituted by:
　　(h11) hydroxy,
　　(h12) $C_{1-6}$ alkoxy,
　　(h13) carboxyl,
　　(h14) aminocarbonyl,
　　(h15) mono- or di-$C_{1-6}$ alkylamino,
　　(h16) mono- or di-$C_{1-6}$ alkylaminocarbonyl,
　　(h17) $C_{1-6}$ alkylcarbonylamino,
　　(h18) mono- or di-$C_{1-6}$ alkylaminocarbonylamino, or
　　(h19) $C_{1-6}$ alkoxycarbonylamino),
　(h2) $C_{3-7}$ cycloalkyl (in which the cycle may be optionally substituted by $C_{1-6}$ alkyl),
　(h3) $C_{3-7}$ cycloalkyl-$C_{1-4}$ alkyl,
　(h4) 4- to 7-membered saturated heterocycle (in which the heterocycle may be optionally substituted by halogen, or $C_{1-6}$ alkyl),
　(h5) 4- to 7-membered saturated heterocyclic-$C_{1-4}$ alkyl,
　(h6) $C_{6-10}$ aryl (in which the ring may be optionally substituted by halogen, $C_{1-6}$ alkyl or $C_{1-6}$ alkoxy),
　(h7) $C_{7-14}$ aralkyl (in which the ring may be optionally substituted by halogen, $C_{1-6}$ alkyl or $C_{1-6}$ alkoxy),
　(h8) heteroaryl (in which the heteroaryl may be optionally substituted by same or different 1 to 3 groups selected from the group consisting of halogen and $C_{1-6}$ alkyl) and
　(h9) heteroaryl-$C_{1-4}$ alkyl (in which the heteroaryl may be optionally substituted by same or different 1 to 3 groups selected from the group consisting of halogen and $C_{1-6}$ alkyl)),
(i) 4- to 7-membered cyclic amino (in which the cycle may be optionally substituted by:
　(i1) halogen,
　(i2) hydroxy,
　(i3) $C_{1-6}$ alkyl (in which the group may be optionally substituted by hydroxy or $C_{1-6}$ alkoxy),
　(i4) $C_{1-6}$ alkoxy,
　(i5) amino (in which the group may be optionally substituted by 1 to 2 $C_{1-6}$ alkyl),
　(i6) cyano,
　(i7) aminocarbonyl (in which the group may be optionally substituted by 1 to 2 $C_{1-6}$ alkyl),
　(i8) $C_{1-6}$ alkylcarbonyl,
　(i9) $C_{1-6}$ alkylcarbonylamino, or
　(i10) $C_{1-6}$ alkylsulfonylamino),
(j) $C_{1-6}$ alkoxy (in which the group may be optionally substituted by:
　(j1) hydroxy,
　(j2) $C_{1-6}$ alkoxy,
　(j3) $C_{3-7}$ cycloalkyl,
　(j4) 4- to 7-membered saturated heterocycle (in which the heterocycle may be optionally substituted by halogen, or $C_{1-6}$ alkyl),
　(j5) 4- to 7-membered cyclic amino (in which the cycle may be optionally substituted by the above (i1) to (i10)),
　(j6) 4- to 7-membered cyclic aminocarbonyl (in which the cycle may be optionally substituted by the above (i1) to (i10)),
　(j7) $C_{6-10}$ aryl (in which the group may be optionally substituted by halogen, $C_{1-6}$ alkyl, or $C_{1-6}$ alkoxy),
　(j8) $C_{1-6}$ alkylcarbonylamino,
　(j9) mono- or di-$C_{1-6}$ alkylamino,
　(j10) mono- or di-$C_{1-6}$ alkylaminocarbonyl,
　(j11) halogen, or
　(j12) $C_{3-7}$ cycloalkyl),
(k) $C_{3-7}$ cycloalkoxy (in which the cycle may be optionally substituted by $C_{1-6}$ alkyl),
(l) $C_{6-10}$ aryl (in which the aryl may be optionally substituted by halogen, $C_{1-6}$ alkyl, or $C_{1-6}$ alkoxy),
(m) 4- to 7-membered saturated heterocycle (in which the heterocycle may be optionally substituted by the above (i1) to (i10)),
(n) aminocarbonyl (in which the amino moiety refers to unsubstituted amino, mono- or di-$C_{1-6}$ alkylamino, or 4- to 7-membered cyclic amino),
(o) aminosulfonyl (in which the amino moiety refers to unsubstituted amino, mono- or di-$C_{1-6}$ alkylamino, or 4- to 7-membered cyclic amino),
(p) aminocarbonyloxy (in which the amino moiety refers to unsubstituted amino, mono- or di-$C_{1-6}$ alkylamino, or 4- to 7-membered cyclic amino),
(q) $C_{6-10}$ aryloxy (in which the group may be optionally substituted by halogen, $C_{1-6}$ alkyl, or $C_{1-6}$ alkoxy),
(r) $C_{7-14}$ aralkyloxy,
(s) heteroaryloxy (in which the ring may be optionally substituted by halogen, or $C_{1-6}$ alkyl),
(t) 4- to 7-membered saturated heterocyclic oxy (in which the heterocycle may be optionally substituted by halogen, or $C_{1-6}$ alkyl),
(u) $C_{1-6}$ alkylsulfonyl,
(v) $C_{1-6}$ alkylcarbonylamino,
(w) $C_{1-6}$ alkoxycarbonyl,
(x) $C_{1-6}$ alkylsulfonylamino,
(y) $C_{1-6}$ alkoxycarbonylamino
(z) mono- or di-$C_{1-6}$ alkylaminocarbonylamino, or
(aa) mono- or di-$C_{1-6}$ alkylaminosulfonylamino, etc.
Preferable one includes:
(a) halogen,
(b) cyano,
(c) hydroxy,
(h) amino (in which the amino may be optionally substituted by same or different 1 to 2 groups selected from the group consisting of:
　(h1) $C_{1-6}$ alkyl,
　(h2) $C_{3-7}$ cycloalkyl, and
　(h8) heteroaryl (in which the ring may be optionally substituted by same or different 1 to 3 halogen atoms)),
(i) 4- to 7-membered cyclic amino (in which the cycle may be optionally substituted by:
　(i1) halogen,
　(i2) hydroxy, or
　(i6) cyano), (j) $C_{1-6}$ alkoxy (in which the group may be optionally substituted by:
  (j1) hydroxy,
  (j2) $C_{1-6}$ alkoxy,
  (j3) $C_{3-7}$ cycloalkyl, or
  (j4) 4- to 7-membered saturated heterocycle),
(k) $C_{3-7}$ cycloalkoxy,
(l) $C_{6-10}$ aryl (in which the group may be optionally substituted by halogen, or $C_{1-6}$ alkoxy),
(m) 4- to 7-membered saturated heterocycle (in which the heterocycle may be optionally substituted by the above (i1), (i2), (i6)),
(n) aminocarbonyl (in which the amino moiety refers to unsubstituted amino, mono- or di-$C_{1-6}$ alkylamino, or 4- to 7-membered cyclic amino),
(o) aminosulfonyl (in which the amino moiety refers to unsubstituted amino, mono- or di-$C_{1-6}$ alkylamino, or 4- to 7-membered cyclic amino),
(p) aminocarbonyloxy (in which the amino moiety refers to unsubstituted amino, mono- or di-$C_{1-6}$ alkylamino, or 4- to 7-membered cyclic amino),
(t) 4- to 7-membered saturated heterocyclic oxy,
(v) $C_{1-6}$ alkylcarbonylamino,
(w) $C_{1-6}$ alkoxycarbonyl,
(y) $C_{1-6}$ alkoxycarbonylamino.

Substituents of the "optionally substituted $C_{1-6}$ alkylcarbonyl", the "optionally substituted $C_{1-6}$ alkylsulfonyl", the "optionally substituted $C_{1-6}$ alkylsulfonylamino", the "optionally substituted $C_{1-6}$ alkoxy", the "optionally substituted $C_{1-6}$ alkylthio", the "optionally substituted $C_{1-6}$ alkoxycarbonyl", the "optionally substituted $C_{1-6}$ alkylcarbonylamino", the "optionally substituted $C_{1-6}$ alkylcarbonyloxy", the "optionally substituted $C_{1-6}$ alkoxycarbonylamino", the "optionally substituted $C_{1-3}$ alkylene", the "optionally substituted methylene", and the "optionally substituted ethylene" include, for example, groups selected from the above (a) to (aa), etc.

Preferable one includes:
(a) halogen,
(b) cyano,
(c) hydroxy,
(j) $C_{1-6}$ alkoxy (in which the group may be optionally substituted by:
  (j1) hydroxy,
  (j2) $C_{1-6}$ alkoxy,
  (j3) $C_{3-7}$ cycloalkyl, or
  (j4) 4- to 7-membered saturated heterocycle),
(k) $C_{3-7}$ cycloalkoxy,
(l) $C_{6-10}$ aryl (in which the group may be optionally substituted by halogen, or $C_{1-6}$ alkoxy),
(m) 4- to 7-membered saturated heterocycle (in which the group may be optionally substituted by the above (i1), (i2), (i6)).

Substituents of the "optionally substituted $C_{3-7}$ cycloalkyl", the "optionally substituted $C_{3-7}$ cycloalkyl-$C_{1-4}$ alkyl", the "optionally substituted $C_{3-7}$ cycloalkylcarbonyl", the "optionally substituted $C_{3-7}$ cycloalkylcarbonylamino", the "optionally substituted $C_{3-7}$ cycloalkylsulfonyl", the "optionally substituted $C_{3-7}$ cycloalkylsulfonylamino", the "optionally substituted $C_{3-7}$ cycloalkyl-$C_{1-4}$ alkylcarbonyl", the "optionally substituted $C_{3-7}$ cycloalkoxy", the "optionally substituted $C_{3-7}$ cycloalkoxycarbonyl", the "optionally substituted $C_{3-7}$ cycloalkylcarbonylamino", the "optionally substituted 4- to 7-membered cyclic amino", the "optionally substituted 4- to 7-membered cyclic aminocarbonyl", the "optionally substituted 4- to 7-membered cyclic aminosulfonyl", the "optionally substituted 4- to 7-membered cyclic aminocarbonyloxy", the "optionally substituted 4- to 7-membered cyclic aminocarbonylamino", the "optionally substituted 4- to 7-membered cyclic aminosulfonylamino", the "optionally substituted saturated heterocycle", the "optionally substituted saturated heterocyclic $C_{1-4}$ alkyl", the "optionally substituted saturated heterocyclic carbonyl", the "optionally substituted saturated heterocyclic sulfonyl", the "optionally substituted saturated heterocyclic sulfonylamino", the "optionally substituted saturated heterocyclic oxy", the "optionally substituted saturated heterocyclic carbonylamino", the "optionally substituted saturated heterocyclic oxycarbonyl", and the "optionally substituted saturated heterocyclic oxycarbonylamino" include, for example, groups selected from the above (a) to (aa), etc.

Preferable one includes:
(a) halogen,
(b) cyano,
(c) hydroxy,
(j) $C_{1-6}$ alkoxy.

Substituents of the "optionally substituted $C_{6-10}$ aryl" defined except in $Ar^1$ and $Ar^2$, the "optionally substituted $C_{7-14}$ aralkyl", the "optionally substituted $C_{7-14}$ aralkyloxy", the "optionally substituted $C_{6-10}$ arylcarbonyl, the "optionally substituted $C_{6-10}$ aryloxy", the "optionally substituted $C_{6-10}$ arylsulfonyl", the "optionally substituted $C_{6-10}$ arylsulfonylamino", the "optionally substituted $C_{6-10}$ arylcarbonylamino", the "optionally substituted heteroaryl" defined except in $Ar^1$ and $Ar^2$, the "optionally substituted heteroaryl-$C_{1-4}$ alkyl", the "optionally substituted heteroaryloxy", the "optionally substituted heteroarylcarbonyl", the "optionally substituted heteroarylsulfonyl", the "optionally substituted heteroarylsulfonylamino", and the "optionally substituted heteroarylcarbonylamino" include, for example:
(a2) halogen,
(b2) cyano,
(c2) $C_{1-6}$ alkyl,
(d2) $C_{1-6}$ alkylsulfonyl (in which the group may be optionally substituted by:
  (d21) halogen,
  (d22) hydroxy,
  (d23) $C_{1-6}$ alkoxy,
  (d24) $C_{3-7}$ cycloalkyl,
  (d25) $C_{3-7}$ cycloalkoxy,
  (d26) di-$C_{1-6}$ alkylamino,
  (d27) 4- to 7-membered cyclic amino, or
  (d28) saturated heterocycle),
(e2) $C_{3-7}$ cycloalkylsulfonyl (in which the group may be optionally substituted by $C_{1-6}$ alkyl),
(ee2) $C_{6-10}$ arylsulfonyl (in which the group may be optionally substituted by $C_{1-6}$ alkyl),
(f2) saturated heterocyclic sulfonyl (in which the cycle may be optionally substituted by halogen, or $C_{1-6}$ alkyl),
(ff2) heteroarylsulfonyl (in which the heteroaryl may be optionally substituted by halogen, or $C_{1-6}$ alkyl),
(g2) amino (in which the amino may be optionally substituted by same or different 1 to 2 groups selected from the group consisting of the above (h1) to (h9)),
(hh2) aminosulfonyl (in which the amino may be optionally substituted by same or different 1 to 2 $C_{1-6}$ alkyl (in which the alkyl may be optionally substituted by halogen, hydroxy, $C_{1-6}$ alkoxy, or di-$C_{1-6}$ alkylamino)),
(ii2) 4- to 7-membered cyclic amino (in which the cycle may be optionally substituted by the above (i1) to (i10)),
(jj2) aminocarbonyl (in which the amino may be optionally substituted by same or different 1 to 2 groups selected from the group consisting of the above (h1) to (h9)), (k2) 4- to 7-membered cyclic aminocarbonyl (in which the cycle may be optionally substituted by the above (i1) to (i10)),
(l2) 4- to 7-membered saturated heterocycle (in which the heterocycle may be optionally substituted by the above (i1) to (i10)),
(m2) carboxyl,
(n2) $C_{1-6}$ alkoxy (in which the group may be optionally substituted by the above (j1) to (j12)),
(o2) $C_{1-6}$ cycloalkoxy,
(p2) 4- to 7-membered saturated heterocyclic oxy (in which the heterocycle may be optionally substituted by the above (i1) to (i10)),
(q2) $C_{7-14}$ aralkyloxy,
(r2) $C_{1-6}$ alkoxycarbonyl (in which the group may be optionally substituted by the above (j1) to (j12)),
(s2) $C_{1-6}$ alkylcarbonylamino (in which the amino may be optionally substituted by $C_{1-6}$ alkyl, and the alkyl may be optionally substituted by the above (a) to (aa)),
(t2) $C_{3-7}$ cycloalkylcarbonylamino (in which the amino may be optionally substituted by $C_{1-6}$ alkyl),
(u2) $C_{3-7}$ cycloalkyl-$C_{1-4}$ alkylcarbonylamino (in which the amino may be optionally substituted by $C_{1-6}$ alkyl),
(v2) 5- or 6-membered monocyclic heteroarylcarbonylamino (in which the amino may be optionally substituted by $C_{1-6}$ alkyl),
(w2) 4- to 7-membered saturated heterocyclic carbonylamino (in which the amino may be optionally substituted by $C_{1-6}$ alkyl, and the heterocycle may be optionally substituted by the above (i1) to (i10)),
(x2) mono- or di-$C_{1-6}$ alkylaminocarbonylamino (in which the amino may be optionally substituted by $C_{1-6}$ alkyl),
(y2) $C_{1-6}$ alkoxycarbonylamino (in which the amino may be optionally substituted by $C_{1-6}$ alkyl, and the alkoxy may be optionally substituted by the above (j1) to (j12)),
(z2) $C_{6-10}$ aryl,
(aa2) 5- or 6-membered monocyclic heteroaryl, and
(aa2) $C_{1-6}$ alkylthio (in which the group may be optionally substituted by the above (j1) to (j12)), etc.
Preferable one includes:
(a2) halogen,
(b2) cyano,
(c2) $C_{1-6}$ alkyl,
(d2) $C_{1-6}$ alkylsulfonyl (in which the group may be optionally substituted by:
 (d21) halogen),
(ee2) $C_{6-10}$ arylsulfonyl (in which the group may be optionally substituted by $C_{1-6}$ alkyl),
(f2) saturated heterocyclic sulfonyl (in which the heterocycle may be optionally substituted by halogen, or $C_{1-6}$ alkyl),
(ff2) heteroarylsulfonyl (in which the ring may be optionally substituted by halogen, or $C_{1-6}$ alkyl),
(hh2) aminosulfonyl (in which the amino may be optionally substituted by same or different 1 to 2 $C_{1-6}$ alkyl),
(jj2) aminocarbonyl (in which the amino may be optionally substituted by same or different 1 to 2 groups selected from the group consisting of the above (h1) to (h9)),
(k2) 4- to 7-membered cyclic aminocarbonyl (in which the cycle may be optionally substituted by the above (i1) to (i10)),
(l2) 4- to 7-membered saturated heterocycle (in which the heterocycle may be optionally substituted by the above (i1) to (i10)),
(n2) $C_{1-6}$ alkoxy (in which the group may be optionally substituted by the above (j1) to (j12)),
(o2) $C_{1-6}$ cycloalkoxy,
(p2) 4- to 7-membered saturated heterocyclic oxy (in which the heterocycle may be optionally substituted by the above (i1) to (i10)),
(q2) $C_{7-14}$ aralkyloxy,
(z2) $C_{6-10}$ aryl,
(aa2) 5- or 6-membered monocyclic heteroaryl, and
(aa2) $C_{1-6}$ alkylthio (in which the group may be optionally substituted by the above (j1) to (j12)), etc.

The phrase "$R^{1a}$ and $R^{1b}$ may combine each other together with the carbon atom to which they bind to form $C_{3-7}$ cycloalkyl ring, or saturated heterocycle" means that Ring Q is, for example, the following formulae (a-8) to (a-15), etc.

[Chemical Formula 21]

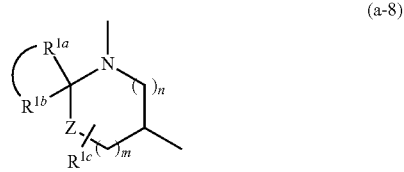
(a-8)

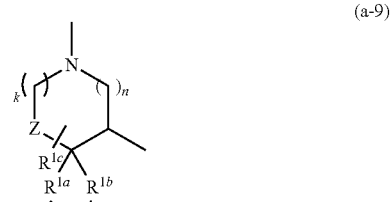
(a-9)

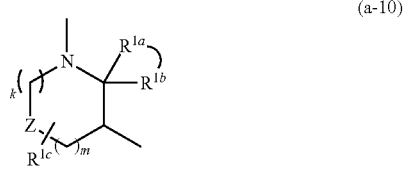
(a-10)

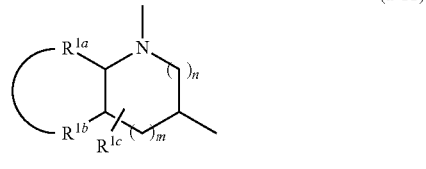
(a-11)

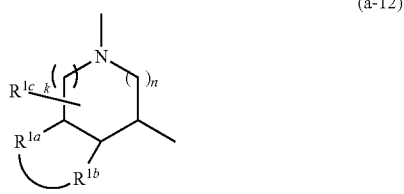
(a-12)

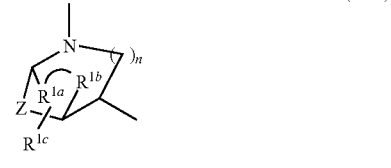
(a-13)

(a-14)

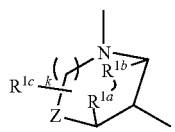
(a-15)

Preferable $R^{1a}$, $R^{1b}$ and $R^{1c}$ in the present invention each include, same or different, hydrogen, hydroxyl, halogen, cyano, $C_{1-6}$ alkyl (in which the group may be optionally substituted by one or more and same or different groups selected from hydroxyl, cyano, and halogen), $C_{6-10}$ aryl (in which the group may be optionally substituted by one or more and same or different groups selected from hydroxyl, cyano, halogen, and $C_{1-6}$ alkyl), heteroaryl (in which the group may be optionally substituted by one or more and same or different groups selected from hydroxyl, cyano, halogen, and $C_{1-6}$ alkyl), saturated heterocycle (in which the group may be optionally substituted by one or more and same or different groups selected from hydroxyl, cyano, halogen, $C_{1-6}$ alkyl, $C_{1-6}$ alkylcarbonyl, and $C_{1-6}$ alkylsulfonyl), $C_{1-6}$ alkoxy (in which the group may be optionally substituted by one or more and same or different groups selected from hydroxyl, cyano, and halogen), $C_{1-6}$ alkylcarbonyloxy (in which the group may be optionally substituted by one or more and same or different groups selected from hydroxyl, cyano, and halogen), aminocarbonyloxy (in which the group may be optionally substituted by one or two and same or different groups selected from $C_{1-6}$ alkyl), or 4- to 7-membered cyclic aminocarbonyloxy. Alternatively, $R^{1a}$ and $R^{1b}$ may combine each other together with the carbon atom to which they bind, and in that case, Ring Q is a group of formula (a-11) or (a-12).

Preferable $R^{1a}$, $R^{1b}$ and $R^{1c}$ in the present invention each include, same or different, hydrogen, hydroxyl, halogen, cyano, $C_{1-6}$ alkyl (in which the group may be optionally substituted by one or more and same or different groups selected from hydroxyl, cyano, and halogen), $C_{1-6}$ alkoxy (in which the group may be optionally substituted by one or more and same or different groups selected from hydroxyl, cyano, and halogen), heteroaryl (in which the group may be optionally substituted by one or more and same or different groups selected from hydroxyl, cyano, halogen, and $C_{1-6}$ alkyl), or saturated heterocycle (in which the group may be optionally substituted by one or more and same or different groups selected from hydroxyl, cyano, halogen, $C_{1-6}$ alkyl, $C_{1-6}$ alkylcarbonyl). Alternatively, $R^{1a}$ and $R^{1b}$ may combine each other together with the carbon atom to which they bind, and in that case, Ring Q is a group of formula (a-11) or (a-12).

When $Ar^1$ in the present invention is optionally substituted $C_{6-10}$ aryl or optionally substituted heteroaryl, substituents in the group include one or more and same or different groups selected from the group consisting of halogen atom, hydroxyl, cyano, $C_{1-6}$ alkyl and $C_{1-6}$ alkoxy.

When $Ar^2$ in the present invention is optionally substituted $C_{6-10}$ aryl or optionally substituted heteroaryl, substituents which are optionally substituted on the carbon atoms in the group include one or more and same or different groups selected from the group consisting of hydroxyl, halogen atom, cyano, carboxyl, optionally substituted amino, optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkoxy, optionally substituted $C_{1-6}$ alkylthio, optionally substituted $C_{3-7}$ cycloalkoxy, optionally substituted $C_{6-10}$ aryloxy, optionally substituted heteroaryloxy, optionally substituted saturated heterocyclic oxy, optionally substituted $C_{1-6}$ alkylcarbonylamino, optionally substituted $C_{3-7}$ cycloalkylcarbonylamino, optionally substituted $C_{6-10}$ arylcarbonylamino, optionally substituted heteroarylcarbonylamino, optionally substituted saturated heterocyclic carbonylamino, optionally substituted $C_{1-6}$ alkoxycarbonylamino, optionally substituted $C_{3-7}$ cycloalkoxycarbonylamino, optionally substituted saturated heterocyclic oxycarbonylamino, optionally substituted aminocarbonylamino, optionally substituted aminosulfonylamino, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{6-10}$ arylcarbonyl, optionally substituted heteroarylcarbonyl, optionally substituted saturated heterocyclic carbonyl, optionally substituted $C_{1-6}$ alkoxycarbonyl, optionally substituted $C_{3-7}$ cycloalkoxycarbonyl, optionally substituted saturated heterocyclic oxycarbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl, substituents which are optionally substituted on the nitrogen atoms in the group include one or more and same or different groups selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{1-6}$ alkoxycarbonyl, optionally substituted $C_{3-7}$ cycloalkoxycarbonyl, optionally substituted saturated heterocyclic oxycarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl.

When $Ar^2$ in the present invention is a group of formulae (c-1) to (c-19), preferable substituents of the carbon atoms in the group include one or more and same or different groups selected from the group consisting of hydroxyl, halogen, cyano, $C_{1-6}$ alkyl (in which the group may be optionally substituted by one or more and same or different groups selected from hydroxyl, cyano, and halogen), $C_{6-10}$ aryl (in which the group may be optionally substituted by one or more and same or different groups selected from hydroxyl, cyano, halogen, and $C_{1-6}$ alkyl), $C_{1-6}$ alkoxy (in which the group may be optionally substituted by one or more and same or different groups selected from hydroxyl, cyano, halogen, and $C_{1-6}$ alkyl), $C_{1-6}$ alkylthio (in which the group may be optionally substituted by one or more and same or different groups selected from hydroxyl, cyano, halogen, and $C_{1-6}$ alkyl), $C_{3-7}$ cycloalkyl (in which the group may be optionally substituted by one or more and same or different groups selected from hydroxyl, cyano, halogen, and $C_{1-6}$ alkyl), heteroaryl (in which the group may be optionally substituted by one or more and same or different groups selected from hydroxyl, cyano, halogen, and $C_{1-6}$ alkyl), saturated heterocycle (in which the group may be optionally substituted by one or more and same or different groups selected from hydroxyl, cyano, halogen, $C_{1-6}$ alkyl, $C_{1-6}$ alkylcarbonyl, and $C_{1-6}$ alkylsulfonyl), aminocarbonyl (in which the group may be optionally substituted by one or two and same or different groups selected from $C_{1-6}$ alkyl), 4- to 7-membered cyclic aminocarbonyl, $C_{1-6}$ alkylcarbonylamino (in which the group may be optionally substituted by one or more and same or different groups selected from hydroxyl, cyano, and halogen), $C_{1-6}$ alkylsulfonyl (in which the group may be optionally substituted by one or more and same or different groups selected from hydroxyl, cyano, and halogen), $C_{6-10}$ arylsulfonyl (in which the group may be optionally substituted by one or more and same or different groups selected from hydroxyl, cyano, halogen, and $C_{1-6}$ alkyl), $C_{1-6}$ alkylcarbonyl (in which the group may be optionally substituted by one or more and same or different groups selected from hydroxyl, cyano, and halogen), $C_{1-6}$ alkylcarbonylamino (in which the group may be optionally substituted by one or more and same or different groups selected from hydroxyl, cyano, and halogen) and $C_{1-6}$ alkylaminocarbonylamino (in which the group may be optionally substituted by one or more and same or different groups selected from hydroxyl, cyano, and halogen).

Preferable substituents of NH in the groups of formulae (c-1) to (c-19) include a group selected from the group consisting of $C_{1-6}$ alkyl (in which the group may be optionally substituted by one or more and same or different groups selected from hydroxyl, cyano, and halogen), $C_{6-10}$ aryl (in which the group may be optionally substituted by one or more and same or different groups selected from hydroxyl, cyano, halogen, and $C_{1-6}$ alkyl), $C_{3-7}$ cycloalkyl (in which the group may be optionally substituted by one or more and same or different groups selected from hydroxyl, cyano, halogen, and $C_{1-6}$ alkyl), heteroaryl (in which the group may be optionally substituted by one or more and same or different groups selected from hydroxyl, cyano, halogen, and $C_{1-6}$ alkyl), saturated heterocycle (in which the group may be optionally substituted by one or more and same or different groups selected from hydroxyl, cyano, halogen, $C_{1-6}$ alkyl, $C_{1-6}$ alkylcarbonyl, and $C_{1-6}$ alkylsulfonyl), aminocarbonyl (in which the group may be optionally substituted by one or two and same or different groups selected from $C_{1-6}$ alkyl), 4- to 7-membered cyclic aminocarbonyl, $C_{1-6}$ alkylsulfonyl (in which the group may be optionally substituted by one or more and same or different groups selected from hydroxyl, cyano, and halogen), $C_{6-10}$ arylsulfonyl (in which the group may be optionally substituted by one or more and same or different groups selected from hydroxyl, cyano, halogen, and $C_{1-6}$ alkyl), and $C_{1-6}$ alkylcarbonyl (in which the group may be optionally substituted by one or more and same or different groups selected from hydroxyl, cyano, and halogen).

When $Ar^2$ in the present invention is a group of formulae (c-1) to (c-19), preferable substituents of the carbon atoms in the group include one or more and same or different groups selected from the group consisting of hydroxyl, halogen, cyano, $C_{1-6}$ alkyl (in which the group may be optionally substituted by one or more and same or different groups selected from hydroxyl, cyano, and halogen), $C_{1-6}$ alkoxy (in which the group may be optionally substituted by one or more and same or different groups selected from hydroxyl, cyano, halogen, and $C_{1-6}$ alkyl), $C_{1-6}$ alkylthio (in which the group may be optionally substituted by one or more and same or different groups selected from hydroxyl, cyano, halogen, and $C_{1-6}$ alkyl), $C_{6-10}$ aryl (in which the group may be optionally substituted by one or more and same or different groups selected from hydroxyl, cyano, halogen, and $C_{1-6}$ alkyl), heteroaryl (in which the group may be optionally substituted by one or more and same or different groups selected from hydroxyl, cyano, halogen, and $C_{1-6}$ alkyl), and saturated heterocycle (in which the group may be optionally substituted by one or more and same or different groups selected from hydroxyl, cyano, halogen, $C_{1-6}$ alkyl, $C_{1-6}$ alkylcarbonyl, and $C_{1-6}$ alkylsulfonyl).

Preferable substituents of NH in the groups of formulae (c-1) to (c-19) include a group selected from the group consisting of $C_{1-6}$ alkyl (in which the group may be optionally substituted by one or more and same or different groups selected from hydroxyl, cyano, and halogen), $C_{3-7}$ cycloalkyl (in which the group may be optionally substituted by one or more and same or different groups selected from hydroxyl, cyano, halogen, and $C_{1-6}$ alkyl), $C_{6-10}$ aryl (in which the group may be optionally substituted by one or more and same or different groups selected from hydroxyl, cyano, halogen, and $C_{1-6}$ alkyl), heteroaryl (in which the group may be optionally substituted by one or more and same or different groups selected from hydroxyl, cyano, halogen, and $C_{1-6}$ alkyl), saturated heterocycle (in which the group may be optionally substituted by one or more and same or different groups selected from hydroxyl, cyano, halogen, $C_{1-6}$ alkyl, $C_{1-6}$ alkylcarbonyl, and $C_{1-6}$ alkylsulfonyl), $C_{1-6}$ alkylcarbonyl (in which the group may be optionally substituted by one or more and same or different groups selected from hydroxyl, cyano, and halogen), $C_{1-6}$ alkylsulfonyl (in which the group may be optionally substituted by one or more and same or different groups selected from hydroxyl, cyano, and halogen), and $C_{6-10}$ arylsulfonyl (in which the group may be optionally substituted by one or more and same or different groups selected from hydroxyl, cyano, halogen, and $C_{1-6}$ alkyl).

A pharmaceutically acceptable salt includes, for example, a salt with a mineral acid such as hydrochloric acid, hydrobromic acid, sulfuric acid, phosphoric acid; a salt with an organic carboxylic acid such as formic acid, acetic acid, fumaric acid, maleic acid, oxalic acid, citric acid, malic acid, tartaric acid, aspartic acid, glutamic acid; a salt with sulfonic acid such as methanesulfonic acid, benzenesulfonic acid, p-toluenesulfonic acid, hydroxybenzenesulfonic acid, dihydroxybenzenesulfonic acid; alkali metal salt such as sodium salt, potassium salt; alkaline-earth metal salt such as calcium salt, magnesium salt; ammonium salt; triethylamine salt, pyridine salt, picoline salt, ethanolamine salt, dicyclohexylamine salt, a salt with N,N'-dibenzylethylenediamine, etc.

Preferable one includes a salt with hydrochloric acid, hydrobromic acid, sulfuric acid, acetic acid, fumaric acid, maleic acid, oxalic acid, methanesulfonic acid, benzenesulfonic acid, p-toluenesulfonic acid.

The present compound (1) and a pharmaceutically acceptable salt thereof may be hydrate, or a solvate such as ethanolate, and the hydrate and/or the solvate are also included in the present compound.

The present compound (1) has stereoisomers, tautomers and/or optical isomers. The present invention includes a mixture of these isomers and an isolated isomer.

The present compound (1) may be synthesized from known compounds according to a combination of known synthetic methods, but for example, it may be also synthesized by Preparation a) of the following scheme.

Preparation a)

[Chemical Formula 22]

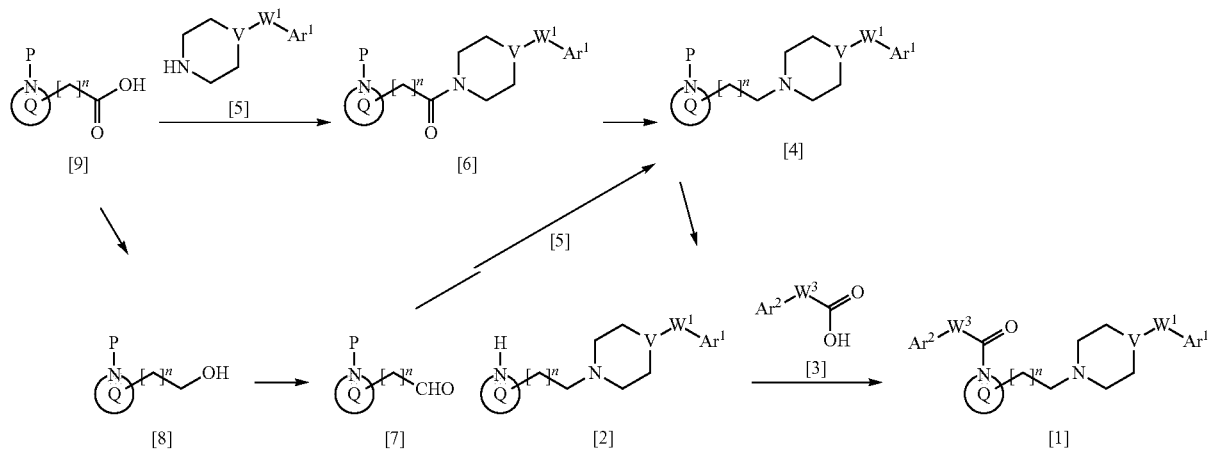

[In the scheme, $Ar^1$, $Ar^2$, Q, V, $W^1$, $W^3$ have the same meanings as defined above. P is a protective group of amino group. n is 0, 1 or 2.]

A compound of formula [1] may be prepared by reacting diamine of formula [2] with carboxylic acid of formula [3], for example in the presence of a condensing agent, in an inert solvent at room temperature or under heating, or by reacting the diamine with acid halide or acid anhydride corresponding to the carboxylic acid of formula [3] in the presence of a base in an inert solvent at room temperature or under heating.

As the condensing agent, a condensing agent such as dicyclohexylcarbodiimide (DCC), diisopropylcarbodiimide (DIPC), 1-ethyl-3-(3-dimethylaminopropyl)-carbodiimide (WSC), benzotriazol-1-yl-tris(dimethylamino)phosphonium hexafluorophosphide (BOP), diphenylphosphonyl diamide (DPPA), N,N-carbonyldiimidazole (CDI), benzotriazol-1-yl-N,N,N',N'-tetramethyluronium hexafluorophosphide (HBTU) is, for example, used, and if needed, an additive such as N-hydroxysuccinimide (HOSu), 1-hydroxybenzotriazole (HOBt), 3-hydroxy-4-oxo-3,4-dihydro-1,2,3-benzotriazine (HOOBt) may be, for example, added.

The solvent includes, for example, aromatic hydrocarbon solvent such as benzene, toluene, xylene, ether solvent such as tetrahydrofuran, 1,4-dioxane, halogenated hydrocarbon solvent such as dichloromethane, chloroform, 1,2-dichloroethane, amide solvent such as dimethylformamide, dimethylacetamide, basic solvent such as pyridine, or a mixture thereof, etc.

The base includes, for example, alkali carbonate (including cesium carbonate, potassium carbonate, sodium carbonate, potassium bicarbonate, sodium bicarbonate), alkali hydride (including sodium hydride, potassium hydride), alkali hydroxide (including potassium hydroxide, sodium hydroxide), alkali alkoxide (including sodium ethoxide, sodium tert-butoxide, potassium tert-butoxide), organic base (including N-methylmorpholine, triethylamine, diisopropylethylamine, tributylamine, 1,8-diazabicyclo[5.4.0]undec-7-ene, 1,5-diazabicyclo[4.3.0]non-5-ene, 1,4-diazabicyclo[5.4.0]undec-7-ene, pyridine), preferably potassium carbonate, potassium tert-butoxide, triethylamine, etc.

The diamine of formula [2] may be prepared by removing the protective group P on the amino group in a compound of formula [4]. As the protective group which protects the amino group, a conventional protective group used in the organic synthetic chemistry field may be used, and the protective group may be introduced and removed according to the conventional method (e.g., a method of T. W. Greene et al., Protective Groups in Organic Synthesis 3rd edition, John Wiley & Sons, Inc., 2002).

The protective group of the amino group includes, for example, tert-butyloxycarbonyl, etc. The protective group of the amino group may be removed by treating in the presence of an acid such as hydrochloric acid, trifluoroacetic acid in a solvent such as aqueous tetrahydrofuran, methylene chloride, chloroform, aqueous methanol.

A compound of formula [4] may be prepared by reacting a compound of formula [6] with a reducing agent in an inert solvent. The reducing agent includes, for example, lithium aluminum hydride, or borane complex (including borane-dimethylsulfide complex or borane-tetrahydrofuran complex), etc. The inert solvent includes, for example, tetrahydrofuran, 1,4-dioxane, or a mixture thereof, etc.

A compound of formula [6] may be prepared by reacting amine of formula [5] with carboxylic acid of formula [9] under a similar condition for, a compound of formula [1].

A compound of formula [4] may be also prepared by reacting aldehyde of formula [7] with amine of formula [5], for example in the presence of a reducing agent, in an inert solvent at room temperature or under heating in a reductive amination reaction.

As the reducing agent, a reducing agent such as a complex hydride compound including sodium triacetoxyborohydride, lithium aluminum hydride, sodium borohydride, sodium cyanoborohydride, and diborane may be used. A reduction by sodium, sodium amalgam, or zinc-acid, and an electrolytic reduction in which lead or platinum is used as an anode may be also used. The solvent includes, for example, alcohol solvent such as methanol and ethanol, ether solvent such as tetrahydrofuran, 1,4-dioxane, halogenated hydrocarbon solvent such as dichloromethane, chloroform, 1,2-dichloroethane, or a mixture thereof.

A compound of formula [7] may be prepared by treating a primary alcohol of formula [8] in an inert solvent in an oxidation reaction. The solvent includes halogen solvent (including dichloromethane, dichloroethane, chloroform), N,N-dimethylformamide, ether solvent (including diethylether, tetrahydrofuran, 1,4-dioxane), or a mixture thereof. A preferable oxidation reaction is Swern oxidation, Dess-Martin oxidation, chromic acid oxidation, activated manganese dioxide oxidation, and may be carried out according to a method of literature (e.g., R. C. Larock et al., Comprehensive Organic Transformations 2nd edition, John Wiley & Sons, Inc., 1999, or Chemical Society of Japan, Jikken Kagaku Koza 4th edition, Maruzen, 1993).

A compound of formula [8] may be prepared by reacting carboxylic acid of formula [9] with a reducing agent in an inert solvent. The reducing agent includes, for example, lithium aluminum hydride, or borane complex (including borane-dimethyl sulfide complex or borane-tetrahydrofuran complex), etc. The inert solvent includes, for example, tetrahydrofuran, 1,4-dioxane, or a mixture thereof, etc.

The carboxylic acid of formula [3] and the amine of formula [5] are known compound, or may be synthesized from known compounds by a combination of known synthetic methods.

A starting compound of formula [9] is known compound, or may be synthesized from known compounds by a combination of known synthetic methods. For example, it may be also synthesized by a method wherein the number of carbon atoms of carboxylic acid moiety of N-protected proline is increased by treating with diazomethane or trimethylsilyldiazomethane (e.g., a method of Y. Yamada et al., Chemical and pharmaceutical Bulletin, 2004, vol. 52, p 1082-1085), or by a method wherein allyl group of 2-allyl-N-protected pyrrolidine is oxidatively cleaved (e.g., a method of C. Pousset et al., Tetrahedron Asymmetry, 2004, vol. 15, p 3407-3412). A starting compound of formula [9] may be also prepared by Preparation b) of the following scheme.

Preparation b)

[Chemical Formula 23]

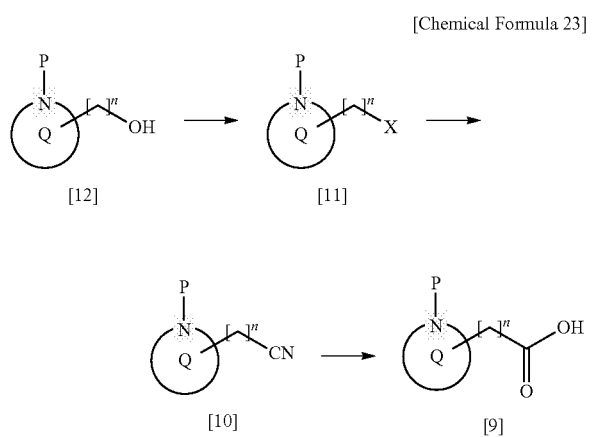

[In the scheme, Q, n, P have the same meanings as defined above. X is a leaving group.]

A compound of formula [9] may be prepared by hydrolysis of a compound of formula [10] under acidic or basic condition in an inert solvent at room temperature or under heating, for example.

The acid includes, for example, hydrochloric acid, sulfuric acid, acetic acid, etc. The base includes, for example, an inorganic base such as sodium hydroxide, potassium hydroxide. The solvent includes, for example, water, alcoholic solvent such as ethanol, methanol, ether solvent such as tetrahydrofuran, 1,4-dioxane, basic solvent such as pyridine, or a mixture thereof, etc.

A compound of formula [10] may be prepared by reacting a compound of formula [11] with cyanide in an inert solvent in the presence of an additive, if needed. The cyanide includes, for example, potassium cyanide or sodium cyanide, etc. The reaction solvent includes, for example, an inert solvent such as dimethylformamide or dimethyl sulfoxide. The additive includes potassium iodide, sodium iodide, etc.

A compound of formula [11] may be prepared by converting hydroxyl of a compound of formula [12] into a leaving group. A compound of formula [11] wherein the leaving group is halogen (e.g., chlorine atom) is obtained by reacting a compound of formula [12] with thionyl chloride in the presence of a base, if needed. The solvent includes, for example, pyridine, tetrahydrofuran, methylene chloride, etc. The base includes, for example, pyridine, etc.

A compound of formula [11] wherein the leaving group is sulfonyloxy is obtained by reacting a compound of formula [12] with sulfonyl chloride in the presence of a base, if needed. The solvent includes, for example, pyridine, tetrahydrofuran, methylene chloride, chloroform, etc. The base includes, for example, triethylamine, etc. The sulfonyl chloride includes, for example, alkylsulfonyl chloride such as methanesulfonyl chloride, arylsulfonyl chloride such as tosyl chloride, benzenesulfonyl chloride, etc.

A starting compound of formula [12] is known compound, or may be synthesized from known compounds by a combination of known synthetic methods. For example, it may be also prepared according to a synthetic reaction of cyclic amine via ring closure reaction (e.g., a method of H. Takahata et al., Tetrahedron Asymmetry, 1991, vol. 2, p 351-352, or A. I. Meyers et al., The Journal of Organic Chemistry, 1996, vol. 61, p 2586-2587).

A starting compound of formula [3] of Preparation a) is known compound, or may be synthesized from known compounds by a combination of known synthetic methods. For example, indole-2-carboxylic acid and azaindolecarboxylic acid, and an ester which can be easily converted into the carboxylic acid may be synthesized according to Fisher method or Reissert method which are known as a general synthetic method of indoles (e.g., a method of JP-A-7-10839, JP-A-8-208602, or F. D. Marsh et al., Journal of the American Chemical Society, 1965, vol. 87, p 3530-3531). 2H-Pyrazole-5-carboxylic acid and an ester which can be easily converted into the carboxylic acid may be also synthesized according to a method of X. Qi et al., Angewandte Chemie International Edition, 2007, vol. 46, p 3242-3244, A. F. C. Flores et al., Synthesis, 2005, vol. 16, p 2744-2750, or WO2006/33943, for example.

In the present compound or an intermediate thereof having a functional group including amino, carboxy, hydroxyl, or oxo, any technique for protection and deprotection may be used, if needed. A preferable protective group, protection technique and deprotection technique are described in the above Protective Groups in Organic Synthesis 3rd edition, etc., in detail.

A compound of formula [1] of the present invention, or an intermediate for preparing the same may be purified by known methods. For example, it may be purified by column chromatography (e.g., silica gel column chromatography, or ion-exchange column chromatography), or recrystallization, etc. For example, as a solvent for the recrystallization, alcohol solvent such as methanol, ethanol or 2-propanol, ether solvent such as diethylether, ester solvent such as ethyl acetate, aromatic hydrocarbon solvent such as benzene or toluene, ketone solvent such as acetone, hydrocarbon solvent such as hexane, aprotic solvent such as dimethylformamide or acetonitrile, water, or a mixture thereof may be used. Other purification methods include a method of Jikken Kagaku Koza (Chemical Society of Japan, Maruzen Co., Ltd.) vol. 1, etc.

A compound of formula [1] of the present invention having one or more asymmetric centers may be prepared by using starting compounds having asymmetric centers or by introducing asymmetric centers in midstream according to the conventional method. For example, optical isomers may be obtained by using optically active starting compounds, or by an optical resolution in an appropriate step of preparation. The optical resolution may be carried out by a diastereomer method in which a compound of formula [1] or an intermediate thereof forms a salt with an optically active acid (e.g., monocarboxylic acid such as mandelic acid, N-benzyloxyalanine, or lactic acid, dicarboxylic acid such as tartaric acid, diisopropylidenetartaric acid or malic acid, or sulfonic acid such as camphorsulfonic acid or bromocamphorsulfonic acid) in an inert solvent (e.g., alcoholic solvent such as methanol, ethanol, or 2-propanol, ether solvent such as diethylether, ester solvent such as ethyl acetate, hydrocarbon solvent such as toluene, or aprotic solvent such as acetonitrile, and a mixture thereof), for example.

A compound of formula [1] or an intermediate thereof having acidic functional groups such as carboxy may be prepared by forming a salt with optically active amine (e.g., organic amines such as α-phenethylamine, kinin, quinidine, cinchonidine, cinchonine, strychnine).

The temperature to form a salt is selected from the range of room temperature to a boiling point of a solvent. It is desired that a temperature is once raised around a boiling point of a solvent in order to improve an optical purity. Yields of filtration of a precipitated salt may be improved by cooling, if needed. A usage of an optically active acid or amine is in the range of about 0.5 to about 2.0 equivalents to a substrate, and preferably, around 1 equivalent is appropriate. A crystal may be also recrystallized in an inert solvent (e.g., alcoholic solvent such as methanol, ethanol, 2-propanol, ether solvent such as diethylether, ester solvent such as ethyl acetate, hydrocarbon solvent such as toluene, aprotic solvent such as acetonitrile, and a mixture thereof) to give an optically active salt in a high purity, if needed. An optically resolved salt may be also treated by an acid or a base in a conventional manner to give a free body thereof, if needed.

The present compound may be orally or parenterally administered for use as a pharmaceutical. Specifically, it may be orally administered in a conventional dosage form, for example, in the form of powder, granule, tablet, capsule, syrup, suspension, or it may be parenterally administered by injection, for example, in the form of solution, emulsion, suspension. It may be also transdermally administered in the form of tape, or rectally administered in the form of suppository. It may be also administered by intravesical instillation in the form of solution. The appropriate dosage forms may be prepared by combining the present compound and a conventional acceptable carrier, excipient, binder, stabilizer, diluent, for example. In the injectable form, an acceptable buffer, solubilizing agent, isotonic agent may be also added, for example. Dosage amounts and number of doses vary depending on target diseases, conditions, ages or weights of subjects, dosage forms, for example, and the present compound may be usually administered 0.1 to 2000 mg, preferably 1 to 200 mg, per a day to an adult in a single dose or several divided doses (e.g., 2 to 4 times).

The present compound has a high binding affinity to one or more receptor subtypes among dopamine receptors such as dopamine $D_1$, dopamine $D_2$, dopamine $D_3$, dopamine $D_4$, serotonin receptors such as serotonin $5\text{-}HT_{1A}$, serotonin $5\text{-}HT_2$, serotonin $5\text{-}HT_6$, serotonin $5\text{-}HT_7$, adrenergic receptors such as $\alpha_1$, $\alpha_2$.

It has been already well known that there is a strong correlation between antagonistic activities of $D_2$ receptor among dopamine receptor subtypes and activities for schizophrenia (see P. Seeman, pharmacological Reviews, 1980, vol. 32, p 229). $D_2$ Receptor antagonistic activities can particularly control positive symptoms of schizophrenia (e.g., hallucination, delusion). It has been reported that serotonin $5\text{-}HT_2$ receptor antagonistic activities are desirable to activities for schizophrenia (see P. A. Janssen et al., The Journal of pharmacology and Experimental Therapeutics, 1988, vol. 244, p 685). $5\text{-}HT_2$ Receptor antagonistic activities may contribute to an improvement for negative symptoms of schizophrenia (e.g., apathy, social withdrawal), and can reduce extrapyramidal symptoms which have been well known as side effects of a therapeutic agent for schizophrenia.

Moreover, $5\text{-}HT_6$ receptor antagonistic agent has been considered to be useful as a therapeutic agent for, particularly, cognitive dysfunction in schizophrenia and Alzheimer's disease, and depression or anxiety disorder (see E. S. Mitchell et al., pharmacology & Therapeutics, 2005, vol. 108, p 320-333, etc.), as well as for obesity and metabolic diseases (see D. J. Heal et al., pharmacology & Therapeutics, 2008, vol. 117, p 207-231). Thus, compounds having high binding affinities to these receptors are expected to show high effectiveness against positive symptoms and negative symptoms as well as cognitive dysfunction of schizophrenia. On the other hand, adrenaline $\alpha_1$ receptor antagonistic activities are considered to be involved in side-effects expression in a conventional therapeutic agent for schizophrenia including oversedation and orthostatic hypotension, and dissociation of said activities may be expected to reduce side effects via $\alpha_1$ receptor antagonistic activities.

Therefore, the present compound has, for example, therapeutic activities for schizophrenia, improvement activities of cognition function, antidepressant activities, antianxiety effects, etc., and particularly, is useful as a therapeutic agent for schizophrenia, bipolar disorder, mania, major depression, mood disorder, anxiety disorder, eating disorder, attention-deficit hyperactivity disorder, dementia and associated symptoms thereof, etc.

EXAMPLES
Mass spectrometry data of Examples 1-8 are shown in Table 1.
TABLE 1
| Ex. No. | STRUCTURE | M + 1 (% Intensity) |
|---|---|---|
| 1 | 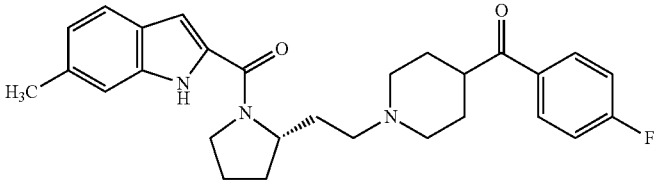 [SMILES: Cc1ccc2cc(C(=O)N3CCC[C@H]3CCN3CCC(C(=O)c4ccc(F)cc4)CC3)[nH]c2c1] | 462 100% |
| 2 | 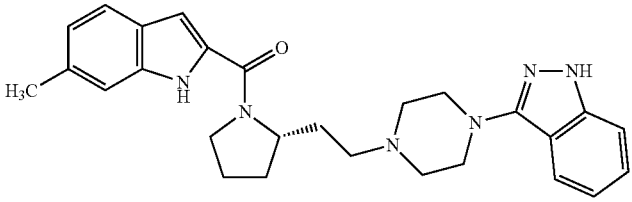 [SMILES: Cc1ccc2cc(C(=O)N3CCC[C@H]3CCN3CCN(c4n[nH]c5ccccc45)CC3)[nH]c2c1] | 457 100% |
| 3 | 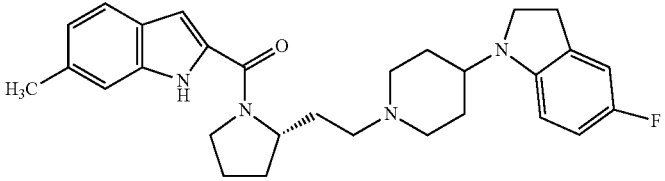 | 475 100% |
| 4 | 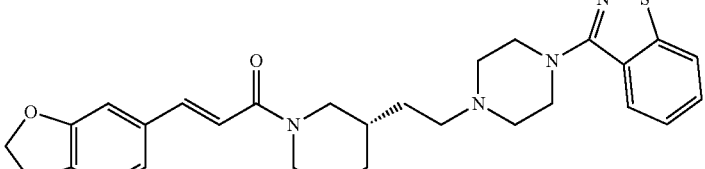 | 500 100% |
| 5 | 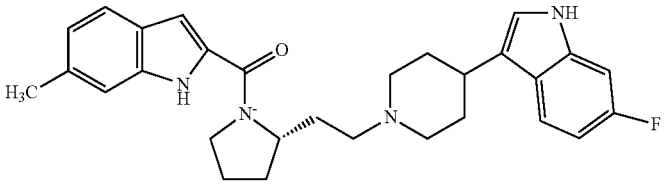 | 472 100% |
| 6 | 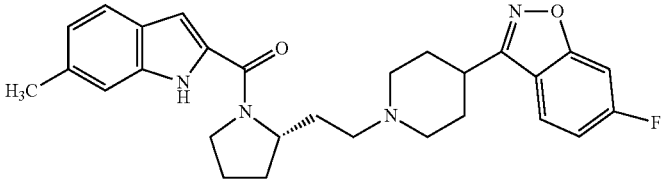 [SMILES: Cc1ccc2cc(C(=O)N3CCC[C@H]3CCN3CCC(c4noc5cc(F)ccc45)CC3)[nH]c2c1] | 475 100% |
| 7 | 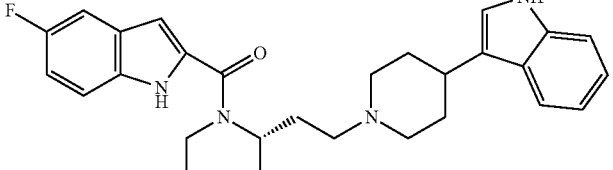 | 475 100% |

TABLE 1-continued

| Ex. No. | STRUCTURE | M + 1 (% Intensity) |
|---|---|---|
| 8 | 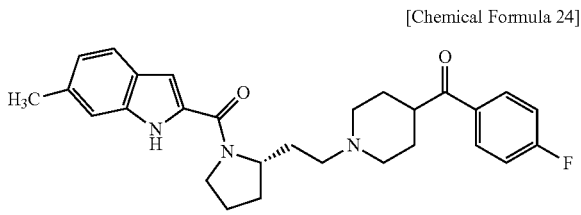 [SMILES: Cc1ccc2cc(C(=O)N3CCC[C@H]3CCN3CCC(C(=O)c4ccc(F)cc4)CC3)[nH]c2c1] | 456 100% |

Synthetic procedures are as follows.

Example 1

(S)-(2-(2-(4-(4-Fluorobenzoyl)piperidin-1-yl)ethyl)pyrrolidin-1-yl)(6-methyl-1H-indol-2-yl)methanone

[Chemical Formula 24]

To a solution of intermediate 1 (0.45 g, 1.20 mmol) and 6-methylindole-2-carboxylic acid (0.21 g, 1.20 mmol) in dimethylformamide (4.00 mL) were added triethylamine (0.85 mL, 1.32 mmol) and HBTU (0.50 g, 1.32 mmol). After stirring for 15 hours at room temperature, to the mixture were added water and ethyl acetate, and the aqueous layer was extracted with ethyl acetate. The organic layer was washed with water and brine, and then dried over sodium sulfate, and concentrated under reduced pressure. The obtained residue was purified with silica gel column (chloroform/methanol=98/2 to 85/15) to give the title compound (0.37 g, 0.80 mmol, 67%).

MS (ESI+) 462 (M$^+$+1, 100%)

$^1$H-NMR (300 MHz, CDCl$_3$) δ 9.18 (brs, 1H), 7.99-7.94 (m, 2H), 7.54 (d, 1H, J=7.8 Hz), 7.21 (brs, 1H), 7.21 (t, 2H, J=6.7 Hz), 6.97 (d, 1H, J=8.0 Hz), 6.84 (brs, 1H), 4.41 (brs, 1H), 3.86-4.00 (m, 2H), 3.18-3.34 (m, 1H), 3.04-3.17 (m, 2H), 2.47-2.68 (m, 2H), 2.46 (s, 3H), 2.38-1.78 (m, 10H).

Example 2

(S)-(2-(2-(4-(1H-Indazol-3-yl)piperazin-1-yl)ethyl)pyrrolidin-1-yl)(6-methyl-1H-indol-2-yl)methanone

[Chemical Formula 25]

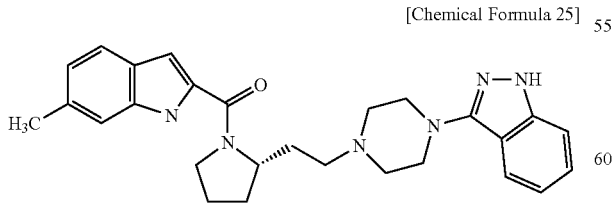

The title compound was obtained by a similar procedure to Example 1 using intermediate 8.

MS (ESI+) 457 (M$^+$+1, 100%)

$^1$H-NMR (300 MHz, CDCl$_3$) δ 9.29 (brs, 1H), 7.61-7.84 (m, 2H), 7.22 (brs, 1H), 7.04 (m, 3H), 6.84 (brs, 1H), 4.53-4.39 (m, 1H), 3.99-3.70 (m, 2H), 3.25-3.05 (m, 1H), 3.08-2.96 (m, 2H), 2.52 (s, 3H), 2.65-2.40 (m, 2H), 2.36-1.62 (m, 12H).

Example 3

(S)-(2-(2-(4-(5-Fluoroindolin-1-yl)ethyl)pyrrolidin-1-yl)(6-methyl-1H-indol-2-yl)methanone

[Chemical Formula 26]

The title compound was obtained by the same procedure as Example 1 using intermediate 9.

MS (ESI+) 475 (M$^+$+1, 100%)

$^1$H-NMR (300 MHz, CDCl$_3$) δ 9.29 (brs, 1H), 7.84-7.61 (m, 2H), 7.22 (brs, 1H), 7.04 (m, 3H), 6.95-6.88 (t, 1H, J=6.0 Hz), 6.23 (ddd, 1H, J=12.0, 9.0, 3.0 Hz), 3.78-3.68 (brs, 1H), 3.43 (d, 2H, J=9.0 Hz), 3.20-3.17 (m, 3H), 3.05-2.97 (m, 2H), 2.89 (t, 2H, J=9.0 Hz), 2.80 (s, 3H), 2.37 (brs, 2H), 2.04-1.82 (m, 12H).

Example 4

(S,E)-3-(Benzo[d][1,3]-5-dioxolyl)-1-(3-(2-(4-(benzo[d]isothiazo-3-yl)piperazin-1-yl)ethyl)piperidin-1-yl)-2-propen-1-one

[Chemical Formula 27]

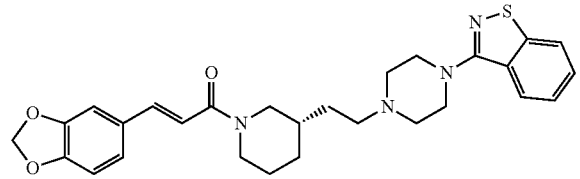

The title compound was obtained by the same procedure as Example 1 using intermediate 11.

MS (ESI+) 505 (M$^+$+1, 100%)

$^1$H-NMR (300 MHz, CDCl$_3$) δ 7.77-7.50 (m, 2H), 7.08-6.98 (m, 5H), 6.95-6.85 (m, 2H), 6.00 (brs, 2H), 3.96-3.89 (m, 4H), 3.50-3.35 (m, 4H), 3.05-2.86 (m, 6H), 2.20-1.58 (m, 11H).

Example 5

(S)-(2-(2-(4-(6-Fluoro-1H-indol-3-yl)piperidin-1-yl)ethyl)piperidin-1-yl)(6-methyl-1H-indol-2-yl)methanone

[Chemical Formula 28]

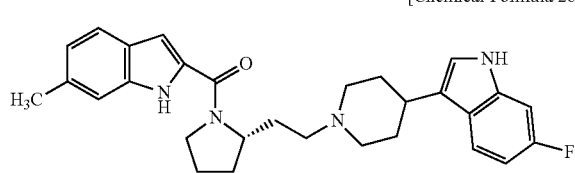

The title compound was obtained by the same procedure as Example 1 using intermediate 12.
MS (ESI+) 473 (M$^+$+1, 100%)
$^1$H-NMR (300 MHz, CDCl$_3$) δ 9.24 (brs, 1H), 8.07 (brs, 1H), 7.59-7.50 (m, 2H), 7.22 (s, 1H), 7.05-6.83 (m, 2H), 4.51-4.39 (m, 1H), 4.00-3.72 (m, 2H), 3.27-3.00 (m, 2H), 2.88-2.75 (m, 1H), 2.70-2.52 (m, 2H), 2.47 (s, 3H), 2.40-1.65 (m, 12H).

Example 6

(S)-(2-(2-(4-(6-Fluorobenzo[d]isoxazol-3-yl)piperidin-1-yl)ethyl)pyrrolidin-1-yl)(6-methyl-1H-indol-2-yl)methanone

[Chemical Formula 29]

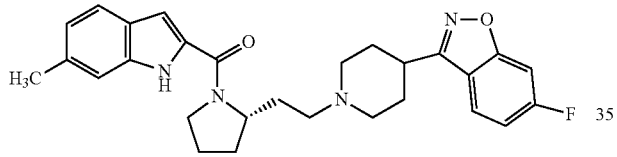

The title compound was obtained by the same procedure as Example 1 using intermediate 13.
MS (ESI+) 475 (M$^+$+1, 100%)
$^1$H-NMR (300 MHz, CDCl$_3$) δ 9.25 (brs, 1H), 7.66-7.71 (m, 1H), 7.55 (d, 1H, J=9.0 Hz), 7.22 (s, 1H), 7.04 (m, 3H), 6.84 (s, 1H), 4.53-4.39 (m, 1H), 4.02-3.70 (m, 2H), 3.25-2.98 (m, 3H), 2.47 (s, 3H), 2.65-2.40 (m, 2H), 2.36-1.92 (m, 10H), 1.90-1.59 (m, 2H).

Example 7

(R)-(3-(2-(4-(1H-Indol-3-yl)piperidin-1-yl)ethyl)morpholino)(5-fluoro-1H-indol-2-yl)methanone

[Chemical Formula 30]

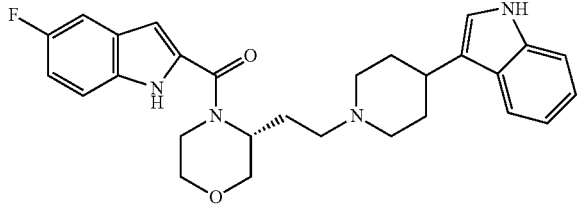

The title compound was obtained by the same procedure as Example 1 using intermediate 59.
MS (ESI+) 475 (M$^+$+1, 100%)
$^1$H-NMR (300 MHz, CDCl$_3$) δ 9.24 (brs, 1H), 8.10 (brs, 1H), 7.44-7.33 (m, 2H), 7.29-7.00 (m, 2H), 7.10-6.77 (m, 2H), 4.44-4.32 (m, 1H), 4.05-3.55 (m, 2H), 3.29-3.00 (m, 2H), 2.74-2.55 (m, 1H), 2.66-2.52 (m, 2H), 2.47 (s, 3H), 2.30-2.11 (m, 4H), 2.05-1.88 (m, 4H), 1.70-1.35 (m, 4H).

Example 8

(S)-(2-(2-(4-(Benzofuran-3-yl)piperidin-1-yl)ethyl)pyrrolidin-1-yl)(5-methyl-1H-indol-2-yl)methanone

[Chemical Formula 31]

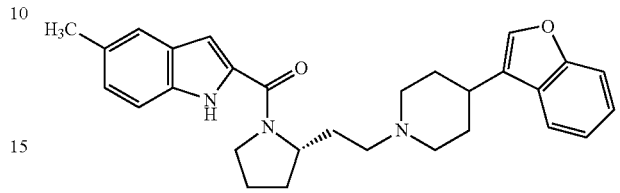

The title compound was obtained by the same procedure as Example 1 using intermediate 14.
MS (ESI+) 456 (M$^+$+1, 100%)
$^1$H-NMR (300 MHz, CDCl$_3$) δ 9.08 (brs, 1H), 7.77-7.39 (m, 2H), 7.25 (s, 1H), 7.15 (brs, 1H), 7.22-6.88 (m, 2H), 4.47 (brs, 1H), 4.11-3.54 (m, 2H), 3.21-2.88 (m, 2H), 2.70-2.44 (m, 4H), 2.48 (s, 3H), 2.27-2.10 (m, 4H), 1.98-1.80 (m, 2H), 1.73-1.60 (m, 2H), 1.50-1.32 (m, 4H).

Reference Example

Intermediate 1

(S)-(4-Fluorophenyl)(1-(2-(pyrrolidin-2-yl)ethyl)piperidin-4-yl)methanone hydrochloride

[Chemical Formula 32]

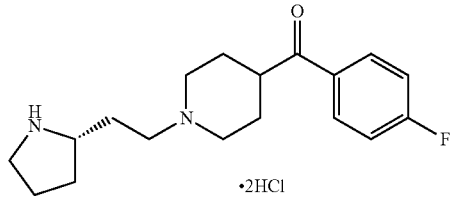

To a solution of intermediate 2 (10.4 g, 248 mmol) and 4-(4-fluorobenzoyl)-piperidine hydrochloride (12.4 g, 51.2 mmol) in tetrahydrofuran (200 mL) was added sodium triacetoxyborohydride (11.3 g, 53.6 mmol). After stirring for 3 hours at room temperature, to the mixture were added saturated sodium bicarbonate water and ethyl acetate, and the aqueous layer was extracted with ethyl acetate. The organic layer was washed with water and brine, and then dried over sodium sulfate, and concentrated under reduced pressure. The obtained residue was purified with silica gel column (chloroform/methanol=98/2 to 90/10) to give a Boc derivative of the title compound (19.7 g, 48.6 mmol, 99%).
MS (ESI+) 405 (M$^+$+1, 100%)

To a solution of the obtained Boc derivative (19.7 g, 48.6 mmol) in methanol (200 mL) was added hydrochloric acid-dioxane solution (4N, 25.0 mL). The mixture was stirred for 2 hours at 80° C. After concentrated under reduced pressure, to the mixture were added ethyl acetate and water. The aqueous layer was adjusted to pH=8-9 with aqueous sodium hydroxide solution, and extracted with ethyl acetate. To the organic layer was added 4N-hydrochloric acid-dioxane solution (24 mL), and the mixture was concentrated under reduced pressure to give the title compound (16.1 g, 42.8 mmol, 88%).
MS (ESI+) 305 (M$^+$+1, 100%)

Intermediate 2

(S)-tert-Butyl 2-(2-oxoethyl)pyrrolidine-1-carboxylate

[Chemical Formula 33]

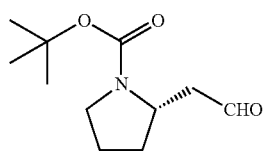

To a solution of oxalyl chloride (0.33 mL, 3.80 mmol) in dichloromethane (10.0 mL) was added a solution of dimethylsulfoxide (0.43 mL, 6.0 mmol) in dichloromethane (2.0 mL) dropwise at −78° C. After stirring for 30 minutes, to the mixture was added a solution of intermediate 3 (0.53 g, 2.5 mmol) in dichloromethane (2.0 mL) dropwise, and after additional 30 minutes, to the mixture was added triethylamine (1.8 mL, 13.0 mmol) dropwise. After stirring for 2 hours at 0° C., to the mixture was added water, and the aqueous layer was extracted with chloroform. The organic layer was washed with water and brine, and then dried over sodium sulfate, and concentrated under reduced pressure. The obtained residue was purified with silica gel column (chloroform/methanol=98/2 to 90/10) to give the title compound (0.50 g, 2.30 mmol, 93%).

MS (ESI+) 214 ($M^+$+1, 100%)

Intermediate 3

(S)-tert-Butyl 2-(2-hydroxyethyl)pyrrolidine-1-carboxylate

[Chemical Formula 34]

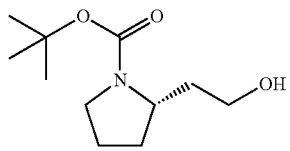

To a solution of intermediate 4 (0.57 g, 2.50 mmol) in tetrahydrofuran (10 mL) was added borane-tetrahydrofuran-complex (1.0 M, 7.5 mL). After stirring for 17 hours at room temperature, to the mixture was added methanol, and concentrated under reduced pressure. To the residue were added water and chloroform, and the aqueous layer was extracted with chloroform. The organic layer was washed with water and brine, and then dried over sodium sulfate, and concentrated under reduced pressure to give the title compound (0.53 g, 2.50 mmol, quant.).

MS (ESI+) 230 ($M^+$+1, 100%)

Intermediate 4

(S)-2-(1-(tert-Butoxycarbonyl)pyrrolidin-2-yl)acetic acid

[Chemical Formula 35]

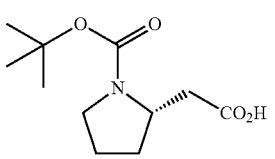

To a solution of intermediate 5 (35.2 g, 167 mmol) in methanol (167 mL) was added aqueous sodium hydroxide solution (30% w/v, 167 mL), and heated to 100° C. After stirring for 3 hours, the reaction solution was concentrated under reduced pressure. To the obtained residue was added aqueous hydrochloric acid solution to adjust pH 4-5, and the aqueous layer was extracted with ethyl acetate. The organic layer was washed with water and brine, and then dried over sodium sulfate, and concentrated under reduced pressure to give the title compound (28.8 g, 125 mmol, 75%).

MS (ESI+) 230 ($M^+$+1, 100%)

Intermediate 5

(S)-tert-Butyl 2-(cyanomethyl)pyrrolidine-1-carboxylate

[Chemical Formula 36]

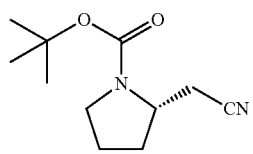

To a solution of intermediate 6 (90.4 g, 255 mmol) in dimethylsulfoxide (255 mL) was added sodium cyanide (16.2 g, 331 mmol), and heated to 100° C. After stirring for 4 hours, to the mixture was added water, and the aqueous layer was extracted with ethyl acetate. The organic layer was washed with water and brine, and then dried over sodium sulfate, and concentrated under reduced pressure. The obtained residue was purified with silica gel column (hexane/ethyl acetate=70/30 to 30/70) to give the title compound (35.2 g, 168 mmol, 66%).

MS (ESI+) 211 ($M^+$+1, 100%)

Intermediate 6

(S)-tert-Butyl 2-(tosyloxymethyl)pyrrolidine-1-carboxylate

[Chemical Formula 37]

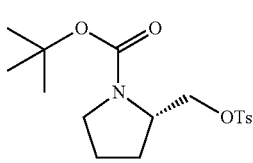

A solution of N-Boc-L-prolinol (51.2 g, 254 mmol) in dichloromethane (250 mL) was cooled to 0° C., and thereto were added p-toluenesulfonylchloride (53.4 g, 280 mmol), triethylamine (30.9 g, 42.6 mL, 305 mmol), and 4-dimethylaminopyridine (5.00 g, 40.9 mmol). After stirring overnight at room temperature, to the mixture was added water, and the aqueous layer was extracted with ethyl acetate. The organic layer was washed with water and brine, and then dried over sodium sulfate, and concentrated under reduced pressure. The obtained residue was purified with silica gel column (hexane/ethyl acetate=70/30 to 30/70) to give the title compound (89.7 g, 250 mmol, 99%).

MS (ESI+) 356 ($M^+$+1, 100%)

Intermediate 7

(S)-tert-Butyl 2-(2-oxoethyl)piperidine-1-carboxylate

[Chemical Formula 38]

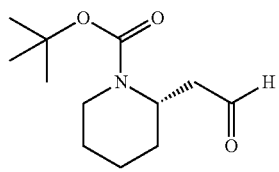

The title compound was synthesized by a similar procedure to intermediate 2.

Intermediate 8

(S)-3-(4-2-(Pyrrolidin-2-yl)piperazin-1-yl)-1H-indazole

[Chemical Formula 39]

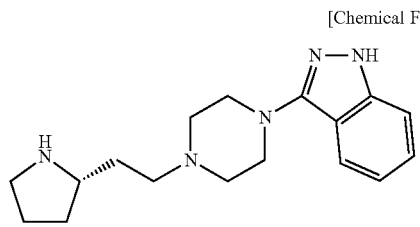

The title compound was obtained by a similar procedure to intermediate 1 using 3-(piperazin-1-yl)-1H-indazole.
MS (ESI+) 300 (M$^+$+1, 100%)

Intermediate 9

(S)-5-Fluoro-1-(1-(2-(pyrrolidin-2-yl)ethyl)piperidin-4-yl)indoline

[Chemical Formula 40]

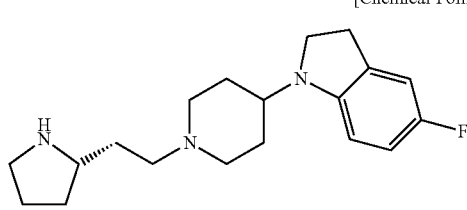

The title compound was obtained by a similar procedure to intermediate 1 using intermediate 10.
MS (ESI+) 318 (M$^+$+1, 100%)

Intermediate 10

5-Fluoro-1-(piperidin-4-yl)indoline

[Chemical Formula 41]

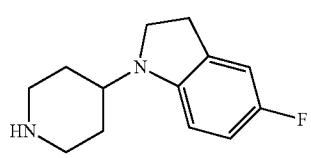

To a solution of 5-fluoroindoline (1.0 g, 7.30 mmol) and N-Boc-4-piperidone (1.60 g, 7.50 mmol) in tetrahydrofuran (10.0 mL) was added sodium triacetoxyborohydride (1.80 g, 7.50 mmol). After stirring for 3 hours at room temperature, to the mixture were added saturated sodium bicarbonate water and ethyl acetate, and the aqueous layer was extracted with ethyl acetate. The organic layer was washed with water and brine, and then dried over sodium sulfate, and concentrated under reduced pressure. The obtained residue was purified with silica gel column (chloroform/methanol=98/2 to 90/10) to give a Boc derivative of the title compound. MS (ESI+) 321 (M$^+$+1, 100%)

To a solution of the obtained Boc derivative in methanol (10.0 mL) was added hydrochloric acid-dioxane solution (4N, 3.0 mL). After stirring for 2 hours at 70° C., the mixture was concentrated under reduced pressure, and ethyl acetate and water were added. The aqueous layer was adjusted to pH=8-9 with aqueous sodium hydroxide solution, extracted with ethyl acetate, and concentrated under reduced pressure to give the title compound (1.50 g, 6.81 mmol, 93%).
MS (ESI+) 221 (M$^+$+1, 100%)

Intermediate 11

(S)-3-(4-(2-(Piperidin-3-yl)ethyl)piperazin-1-yl)benzo[d]isothiazole

[Chemical Formula 42]

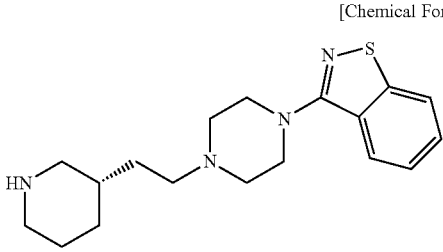

The title compound was obtained by a similar procedure to intermediate 18 using intermediate 55.
MS (ESI+) 331 (M$^+$+1, 100%)

Intermediate 12

(S)-3-(1-(2-(Piperidin-2-yl)ethyl)piperidin-4-yl)-1H-indole

[Chemical Formula 43]

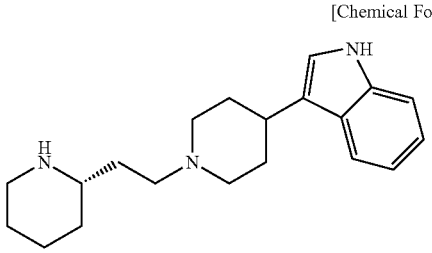

The title compound was obtained by a similar procedure to intermediate 1 using intermediate 7.
MS (ESI+) 312 (M$^+$+1, 100%)

Intermediate 13

(S)-5-Fluoro-3-(1-(2-(pyrrolidin-2-yl)ethyl)piperidin-4-yl)benzo[d]isoxazole

[Chemical Formula 44]

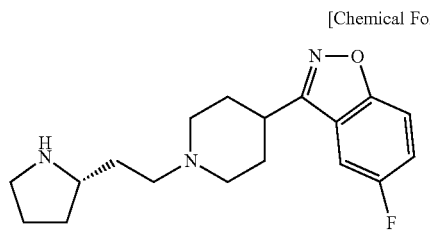

The title compound was obtained by a similar procedure to intermediate 1.

MS (ESI+) 318 (M$^+$+1, 100%)

Intermediate 14

(S)-4-(Benzofuran-3-yl)-1-(2-(pyrrolidin-2-yl)ethyl)piperidine

[Chemical Formula 45]

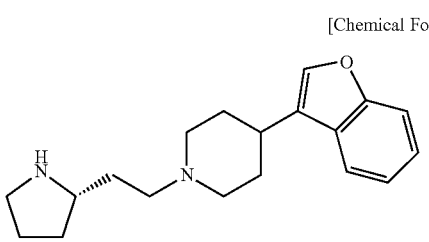

The title compound was obtained by a similar procedure to intermediate 1.

MS (ESI+) 299 (M$^+$+1, 100%)

Intermediate 15

(S)-6-Fluoro-3-(1-(2-(pyrrolidin-2-yl)ethyl)piperidin-4-yl)-1H-indazole

[Chemical Formula 46]

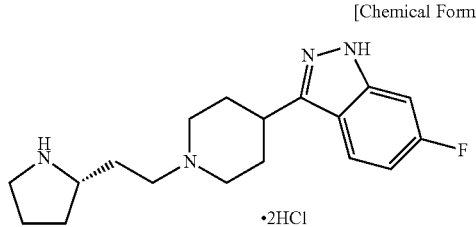

The title compound was synthesized by a similar procedure to intermediate 1.

MS (ESI+) 317 (M$^+$+1, 100%)

Intermediate 16

(S)-6-Fluoro-3-(1-(2-(pyrrolidin-2-yl)ethyl)piperidin-4-yl)benzo[d]isoxazole

[Chemical Formula 47]

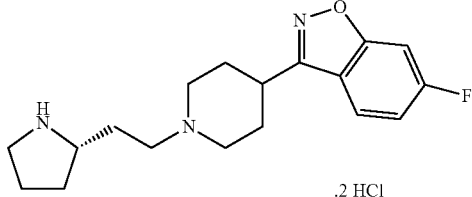

The title compound was synthesized by a similar procedure to intermediate 1.

MS (ESI+) 318 (M$^+$+1, 100%)

Intermediate 17

(S)-6-Fluoro-3-(1-(2-(pyrrolidin-2-yl)ethyl)piperidin-4-yl)-1H-indole hydrochloride

[Chemical Formula 48]

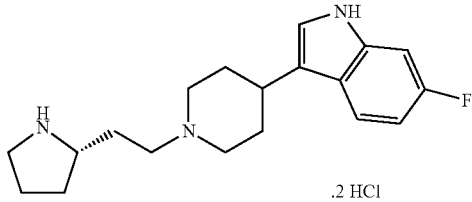

The title compound was synthesized by a similar procedure to intermediate 1.

MS (ESI+) 316 (M$^+$+1, 100%)

Intermediate 18

(S)-3-(1-(2-(Pyrrolidin-2-yl)ethyl)piperidin-4-yl)-1H-indole

[Chemical Formula 49]

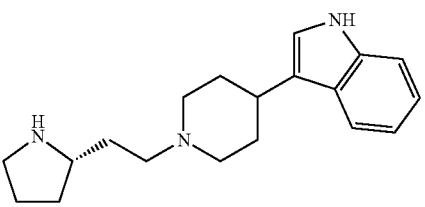

To a solution of intermediate 19 (500 mg, 1.30 mmol) in chloroform (10.0 mL) were added methanol (10.0 mL) and 4N hydrochloric acid-dioxane solution (10.0 mL). After stirring for 5 hours at room temperature, the mixture was concentrated under reduced pressure to give the title compound (501 mg, 1.30 mmol, 86%).

MS (ESI+) 298 (M$^+$+1, 100%), $^1$H-NMR (300 MHz, DMSO-d$_6$) δ 10.8-9.2 (brm, 2H), 7.68 (d, 1H, J=7.5 Hz), 7.34 (d, 1H, J=8.1 Hz), 7.30-7.10 (m, 3H), 3.30-2.90 (m, 6H), 2.40-1.70 (m, 9H), 1.70-0.30 (m, 5H).

Intermediate 19

(S)-tert-Butyl 2-(2-(4-(1H-indol-3-yl)piperidin-1-yl)ethyl)pyrrolidine-1-carboxylate

[Chemical Formula 50]

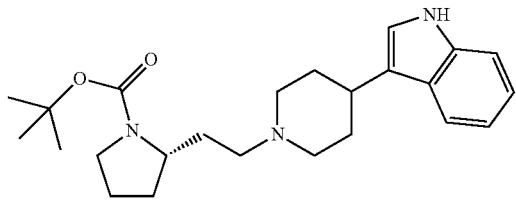

To a solution of intermediate 20 (0.60 g, 1.50 mmol) in tetrahydrofuran (10.0 mL) was added borane-tetrahydrofuran solution (8.10 mL of 0.90 mol/L solution, 7.30 mmol) dropwise for about 5 minutes. After stirring for a day at room temperature, the reaction solution was ice-cooled and methanol (10.0 mL) was added dropwise. After warmed to room temperature, the mixture was heated to reflux for additional 4 hours. After the reaction solvent was evaporated under reduced pressure, to the obtained residue was added saturated aqueous solution of sodium carbonate, and separated with ethyl acetate. The extracted organic layer was washed with brine, and then dried over sodium sulfate, and concentrated under reduced pressure. The obtained residue was purified with silica gel column (chloroform/methanol=100/0 to 80/20) to give the title compound (0.50 g, 1.30 mmol, 86%).

MS (ESI+) 398 ($M^+$+1, 60%)

$^1$H-NMR (300 MHz, CDCl$_3$) δ 7.99 (brs, 1H), 7.63 (d, 1H, J=7.5 Hz), 7.34 (d, 1H, J=7.8 Hz), 7.20-7.05 (m, 2H), 6.96 (m, 1H), 3.90-2.70 (m, 6H), 2.50-2.30 (m, 2H), 2.20-1.30 (m, 21H).

Intermediate 20

(S)-tert-Butyl 2-(2-(4-(1H-indol-3-yl)piperidin-1-yl)-2-oxoethyl)pyrrolidine-1-carboxylate

[Chemical Formula 51]

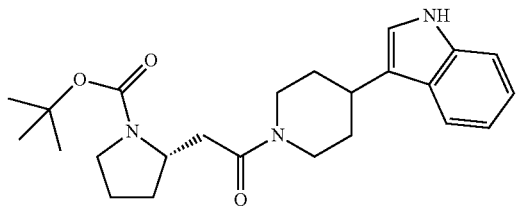

To a solution of intermediate 4 (0.30 g, 1.30 mmol) and 3-piperidin-4-yl-1H-indole (0.31 g, 1.30 mmol) in dimethylformamide (10.0 mL) were added triethylamine (0.55 mL, 3.90 mmol) and HBTU (0.54 g, 1.40 mmol). After stirring for a day at room temperature, to the mixture were added water and ethyl acetate, and the aqueous layer was extracted with ethyl acetate. The organic layer was washed with water and brine, and then dried over sodium sulfate, and concentrated under reduced pressure. The obtained residue was purified with silica gel column (hexane/ethyl acetate=50/50 to 10/90) to give the title compound (0.60 g, 1.30 mmol, 99%).

MS (ESI+) 412 ($M^+$+1, 25%)

$^1$H-NMR (300 MHz, CDCl$_3$) δ 8.14 (brs, 1H), 7.59 (d, 1H, J=7.5 Hz), 7.35 (d, 1H, J=8.1 Hz), 7.30-7.00 (m, 2H), 6.93 (m, 1H), 4.85-4.60 (m, 1H), 4.30-3.90 (m, 2H), 3.50-2.50 (m, 6H), 2.40-1.30 (m, 18H).

Intermediate 21

3-(1-(2-((2R,4R)-4-Methoxypyrrolidin-2-yl)ethyl)piperidin-4-yl)1H-indole

[Chemical Formula 52]

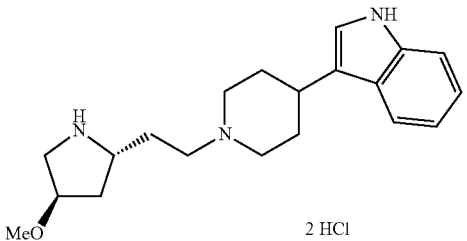

2 HCl

To a solution of intermediate 22 (40.0 mg, 0.07 mmol) in tetrahydrofuran (1.0 mL) was added borane-tetrahydrofuran-complex (1.0 M, 0.17 mL). After stirring for 2 hours at room temperature, to the mixture was added methanol, and stirred for 4 hours at 70° C. To the mixture were added saturated sodium bicarbonate water and ethyl acetate, and the aqueous layer was extracted with ethyl acetate. The organic layer was washed with water and brine, and then dried over sodium sulfate, and concentrated under reduced pressure. The obtained residue was purified with silica gel column (hexane/ethyl acetate=80/20 to 20/80) to give a Boc derivative of the title compound (26.0 mg, 0.05 mmol, 67%).

MS (ESI+) 528 ($M^+$+1, 100%)

To a solution of the obtained Boc derivative (25.0 mg, 47.0 μmol) in methanol (1 mL) was added hydrochloric acid-dioxane solution (4N, 0.20 mL). The mixture was stirred for 6 hours at 40° C. and concentrated under reduced pressure to give the title compound.

MS (ESI+) 328 ($M^+$+1, 100%)

Intermediate 22 tert-Butyl 3-(1-(2-((2S,4R)-1-(tert-butoxycarbonyl)-4-methoxypyrrolidin-2-yl)acetyl)piperidin-4-yl)-1H-indole-1-carboxylate

[Chemical Formula 53]

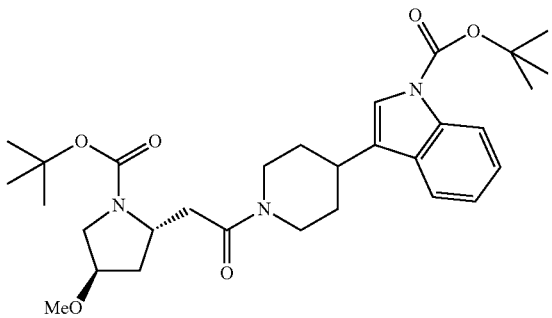

To a solution of intermediate 23 (85.0 mg, 0.16 mmol) in dimethylformamide (1.0 mL) were added sodium hydride (13.0 mg, 0.32 mmol) and methyl iodide (20 μL, 0.32 mmol). After stirring for 30 minutes at room temperature, to the mixture were added saturated aqueous solution of ammonium chloride and ethyl acetate, and the aqueous layer was extracted with ethyl acetate. The organic layer was washed with water and brine, and then dried over sodium sulfate, and concentrated under reduced pressure. The obtained residue was purified with silica gel column (hexane/ethyl acetate=80/20 to 40/60) to give the title compound (40.0 mg, 0.07 mmol, 46%).

MS (ESI+) 542 (M++1, 100%)

Intermediate 23 tert-Butyl 3-(1-(2-((2S,4R)-1-(tert-butoxycarbonyl)-4-hydroxypyrrolidin-2-yl)acetyl)-piperidin-4-yl)-1H-indole-1-carboxylate

[Chemical Formula 54]

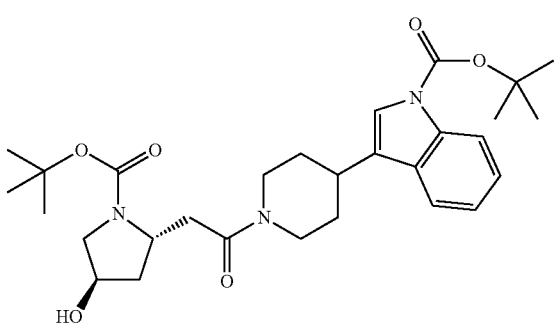

To a solution of intermediate 24 (1.90 g, 3.60 mmol) in acetonitrile (20.0 mL) were added di-tert-dibutylcarbonate (0.96 g, 4.40 mmol) and dimethylaminopyridine (45.0 mg, 0.36 mmol). After stirring for 80 minutes at 60° C., the mixture was concentrated under reduced pressure. The obtained residue was purified with silica gel column (hexane/ethyl acetate=80/20 to 30/70) to give a benzyl derivative of the title compound (2.14 g, 3.46 mmol, 94%).

To a solution of the obtained benzyl derivative (2.14 g, 3.46 mmol) in ethanol (30.0 mL) was added palladium hydroxide (0.49 g, 0.68 mmol). The mixture was stirred for 2 hours at room temperature under hydrogen atmosphere. The palladium catalyst was filtered off by Celite, and washed with ethyl acetate. The organic layer was concentrated under reduced pressure, and the obtained residue was purified with silica gel column (hexane/ethyl acetate=80/20 to 10/90) to give the title compound (0.6 g, 1.14 mmol, 33%).

MS (ESI+) 528 (M++1, 100%)

Intermediate 24

(2S,4R)-tert-Butyl 2-(2-(4-(1H-indol-3-yl)piperidin-1-yl)-2-oxoethyl)-4-(benzyloxy)-pyrrolidine-1-carboxylate

[Chemical Formula 55]

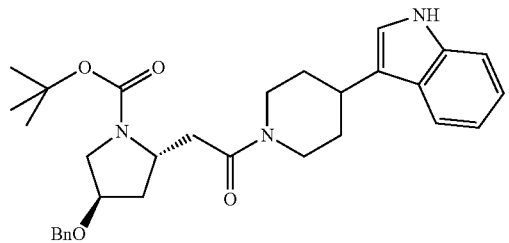

The title compound was synthesized by a similar procedure to intermediate 20 using 2-((2S,4R)-4-(benzyloxy)-1-(tert-butoxycarbonyl)pyrrolidin-2-yl)acetic acid.

MS (ESI+) 518 (M++1, 100%)

Intermediate 25

1-(4-(1H-Indol-3-yl)piperidin-1-yl)-2-((2S,4R)-4-(2-ethoxyethoxy)pyrrolidin-2-yl)ethanone

[Chemical Formula 56]

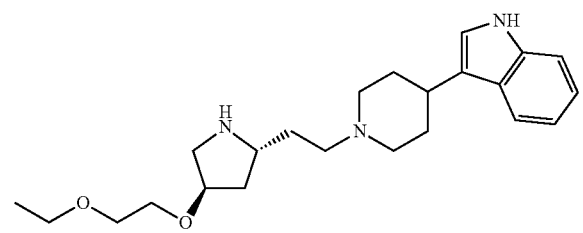

The title compound was synthesized by a similar procedure to intermediate 18 using intermediate 26.

MS (ESI+) 386 (M++1, 100%)

Intermediate 26 tert-Butyl 3-(1-(2-((2S,4R)-1-(tert-butoxycarbonyl)-4-(2-ethoxyethoxy)pyrrolidin-2-yl)-acetyl)piperidin-4-yl)-1H-indole-1-carboxylate

[Chemical Formula 57]

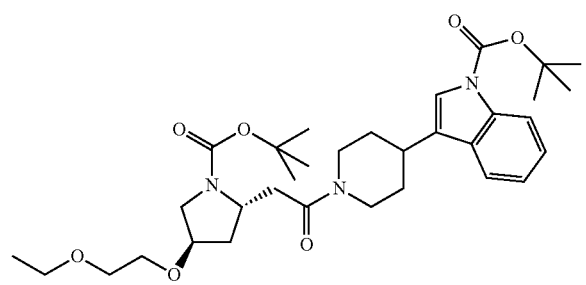

The title compound was synthesized by a similar procedure to intermediate 22 using intermediate 23.

MS (ESI+) 600 (M++1, 100%)

Intermediate 27

(3R,5R)-5-(2-(4-(1H-Indol-3-yl)piperidin-1-yl)ethyl)pyrrolidin-3-ylethyl carbamate

[Chemical Formula 58]

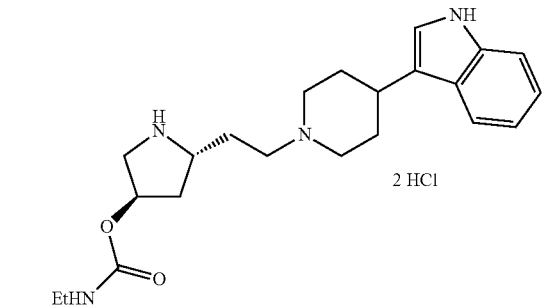

The title compound was synthesized by a similar procedure to intermediate 18 using intermediate 28.
MS (ESI+) 385 (M⁺+1, 100%)

Intermediate 28 tert-Butyl 3-(1-(2-((2S,4R)-1-(tert-butoxycarbonyl)-4-(ethylcarbamoyloxy)pyrrolidin-2-yl)-acetyl)piperidin-4-yl)-1H-indole-1-carboxylate

[Chemical Formula 59]

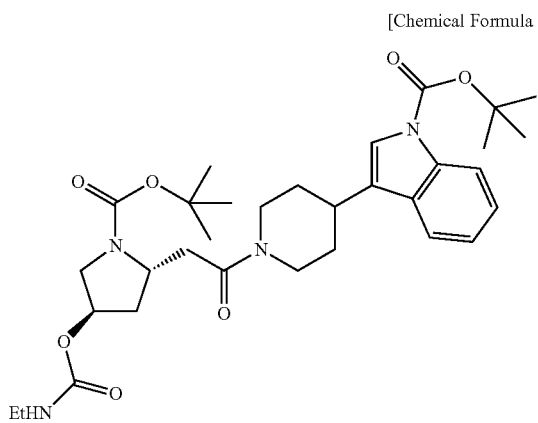

The title compound was synthesized by a similar procedure to intermediate 22 using intermediate 23.
MS (ESI+) 599 (M⁺+1, 100%)

Intermediate 29

(3R,4R)-5-(2-(4-(1H-Indol-3-yl)piperidin-1-yl)ethyl)pyrrolidin-3-ol

[Chemical Formula 60]

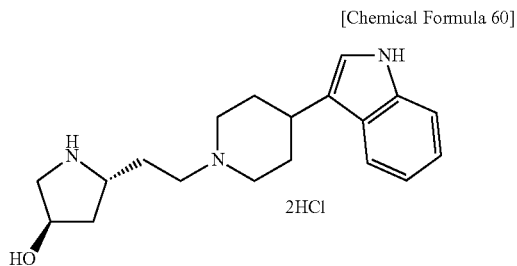 [SMILES: O[C@H]1CN[C@H](CCN2CCC(c3c[nH]c4ccccc34)CC2)C1]

Intermediate 24 (0.70 g, 1.40 mmol) was reduced by a similar procedure to intermediate 19, and subsequently, to a solution of the obtained benzyl derivative in ethanol (30.0 mL) was added palladium hydroxide (0.50 g, 0.70 mmol). The mixture was stirred for 8 hours at 40° C. under hydrogen atmosphere. The palladium catalyst was filtered off by Celite, and washed with ethyl acetate. The organic layer was concentrated under reduced pressure, and the obtained residue was purified with silica gel column (chloroform/methanol=100/0 to 88/12) to give a de-benzyl derivative of the title compound (0.16 g, 0.39 mmol, 27% in 2 processes).
MS (ESI+) 414 (M⁺+1, 100%)

To a solution of the obtained de-benzyl derivative (0.16 g, 0.39 mmol) in methanol (5 mL) was added hydrochloric acid-dioxane solution (4N, 0.58 mL). The mixture was stirred for 3 hours at room temperature, and then concentrated under reduced pressure to give the title compound (0.17 g, 0.39 mmol, 99%).
MS (ESI+) 313 (M⁺+1, 100%)

Intermediate 30

3-(1-((2S,5R)-5-(Pyridin-3-yl)pyrrolidin-2-yl)ethyl)piperidin-4-yl)-1H-indole

[Chemical Formula 61]

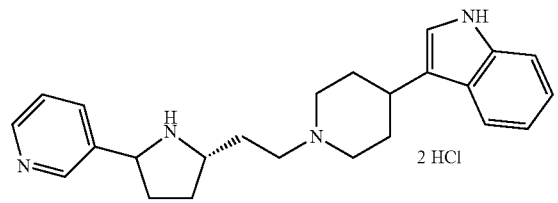

A solution of intermediate 31 (0.15 g, 0.50 mmol), 3-piperidin-4-yl-1H-indole (0.10 g, 0.50 mmol), HBTU (0.23 g, 0.60 mmol) and triethylamine (0.2 mL, 1.50 mmol) in dimethylformamide (3.0 mL) was stirred overnight at room temperature. To the mixture was added brine, and extracted 3 times with ethyl acetate. The organic layer was washed with brine, dried over sodium sulfate, concentrated under reduced pressure, and purified with silica gel column chromatography (chloroform/methanol=20/1) to give a precursor of the title compound (0.24 g, 0.50 mmol, 100%).
MS (ESI+) 489 (M⁺+1, 58%)

The obtained precursor was dissolved in THF (1.5 mL), and a solution of borane-tetrahydrofuran-complex in THF (1.0 M, 2.0 mL) was added. The mixture was stirred for 4 hours at 80° C., cooled to room temperature, and then methanol was added. After heated to 80° C. again, the mixture was stirred for 1 hour. To the mixture was added 4N-hydrochloric acid-dioxane solution (1 mL), and stirred for 1 hour at 80° C. After cooled to room temperature, the mixture was concentrated under reduced pressure to give the title compound (0.19 g, 0.44 mmol, 87%).
MS (ESI+) 375 (M⁺+1, 100%)

Intermediate 31

2-((2S,5R)-1-(tert-Butoxycarbonyl)-5-(pyridin-3-yl)pyrrolidin-2-yl)acetic acid

[Chemical Formula 62]

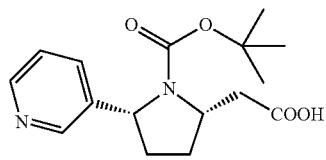

The title compound was synthesized (1.40 g, 4.70 mmol, 89%) by a similar procedure to intermediate 4 using intermediate 32.
MS (ESI+) 308 (M⁺+1, 86%)

Intermediate 32

(2S,5R)-tert-Butyl 2-(cyanomethyl)-5-(pyridin-3-yl)pyrrolidine-1-carboxylate

[Chemical Formula 63]

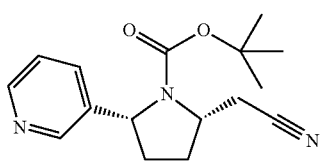

The title compound was synthesized (1.50 g, 5.30 mmol, 88%) by a similar procedure to intermediate 5 using intermediate 33.

$^1$H-NMR (CDCl$_3$) δ 1.19 (br, 9H), 1.94-2.03 (m, 1H), 2.03-2.12 (m, 1H), 2.22-2.31 (m, 1H), 2.33-2.41 (m, 1H), 2.94 (br, 2H), 4.19-4.25 (m, 1H), 4.70-4.80 (m, 1H), 7.28 (dd, J=8.3 Hz, 5.1 Hz, 1H), 7.66 (br, 1H), 8.500 (s, 1H), 8.504 (dd, J=4.9 Hz, J=1.5 Hz, 1H)

Intermediate 33

(2R,5S)-tert-Butyl 2-(pyridin-3-yl)-5-(tosyloxymethyl)pyrrolidine-1-carboxylate

[Chemical Formula 64]

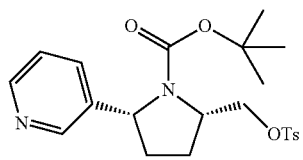

Intermediate 34 was dissolved in THF (100 mL), and triethylamine (2.10 mL, 15.0 mmol) was added. To the mixture was added di-tert-butylcarbonate (2.60 g, 12.0 mmol), and stirred for 2 hours at room temperature. After concentrated under reduced pressure, the residue was dissolved in ethyl acetate, washed with brine, dried over sodium sulfate, concentrated under reduced pressure, and purified with silica gel column chromatography (chloroform/ethyl acetate=4/1). The obtained compound was dissolved in ethanol (250 mL), and cooled to 0° C. After calcium chloride (1.80 g, 16.0 mmol) was added and dissolved in the solution, sodium borohydride (1.2 g, 33 mmol) was added. After warmed to room temperature, the mixture was stirred overnight. To the mixture was added aqueous potassium carbonate solution (2 M, 65 mL), and concentrated under reduced pressure. The residue was dissolved in water, and extracted with ethyl acetate. The organic layer was washed with brine, dried over sodium sulfate, concentrated under reduced pressure, and then purified with silica gel column chromatography. The obtained compound was dissolved in methylene chloride (40.0 mL), and triethylamine (2.4 mL, 17.0 mmol) was added. To the mixture was added p-toluenesulfonyl chloride (1.60 g, 8.40 mmol) at 0° C., and stirred for 15 hours at room temperature. To the mixture was added water, and extracted with chloroform. The organic layer was washed with brine, dried over sodium sulfate, and concentrated under reduced pressure. The obtained residue was purified with silica gel column chromatography (hexane/ethyl acetate=1/3) to give the title compound (2.60 g, 6.00 mmol, 73% in 2 processes).

MS (ESI+) 433 (M$^+$+1, 86%)

Intermediate 34

(2S,5R)-Ethyl 5-(pyridin-3-yl)pyrrolidine-2-carboxylate

[Chemical Formula 65]

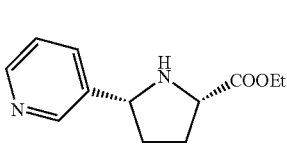

Intermediate 35 was dissolved in dioxane (20.0 mL), and 4N-hydrochloric acid-dioxane solution (31.0 mL) was added, and the mixture was stirred overnight at room temperature. After concentrated under reduced pressure, the residue was dissolved in water, and ethyl acetate was added. After then, to the mixture was added saturated sodium bicarbonate water, and the aqueous layer was adjusted to pH 10. The aqueous layer was extracted with ethyl acetate, and the organic layer was washed with brine, dried over sodium sulfate, and concentrated under reduced pressure. The residue was dissolved in isopropyl alcohol (30.0 mL), and palladium/carbon (250 mg, 10%, 50% wet) was added, and the mixture was stirred for 15 hours under hydrogen atmosphere. The insoluble matter was removed by filtration using Celite, and the filtrate was concentrated under reduced pressure to give the title compound (2.20 g, 9.80 mmol, 82%).

MS (ESI+) 221 (M$^+$+1, 100%)

Intermediate 35

(S)-Ethyl-2-(tert-butoxycarbonylamino)-5-oxo-5-(pyridin-3-yl)pentanate

[Chemical Formula 66]

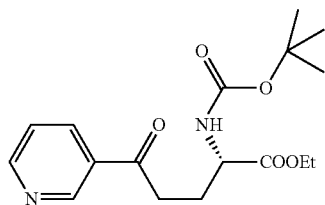

To a diethyl ether (75.0 mL) was added a solution of butyllithium in hexane (1.6 M, 21.0 mL, 33.0 mmol), and a solution of 3-bromopyridine (5.20 g, 33.0 mmol) in diethyl ether (25.0 mL) was added dropwise for 20 minutes at −78° C., and the mixture was stirred for 1 hour. Then, to the mixture was added a solution of N-Boc-(S)-ethyl pyroglutamate (5.60 g, 22.0 mmol) in diethyl ether (15.0 mL) dropwise at −78° C., stirred for 2 hours at −78° C., and stirred for 2 hours at room temperature. The solution was cooled to 0° C., saturated aqueous solution of ammonium chloride was added dropwise, and the aqueous layer was extracted with ethyl acetate. The organic layer was washed with brine, dried over sodium sulfate, concentrated under reduced pressure, and purified with silica gel column chromatography (hexane/ethyl acetate=1/1) to give the title compound (3.80 g, 11.2 mmol, 51%).

MS (ESI+) 337 (M$^+$+1, 100%)

Intermediate 36

3-(1-(2-(Azepan-2-yl)ethyl)piperidin-4-yl)-1H-indole

[Chemical Formula 67]

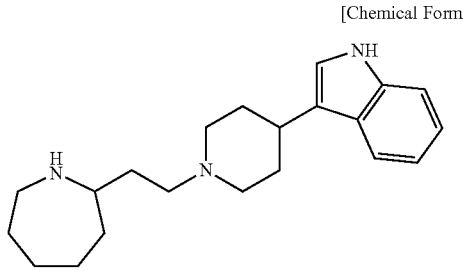

The title compound was obtained by a similar procedure to intermediate 1 using intermediate 37.

MS (ESI+) 325 (M$^+$+1, 100%)

Intermediate 37 tert-Butyl 2-(2-(4-(1H-indol-3-yl)piperidin-1-yl)ethyl)azepane-1-carboxylate

[Chemical Formula 68]

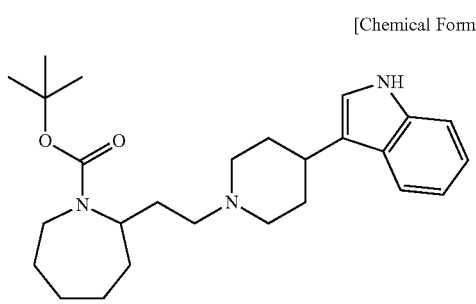

To a solution of intermediate 38 in tetrahydrofuran (15.0 mL) was added borane-tetrahydrofuran-complex (1.0 M, 12.0 mL). After the mixture was stirred for 17 hours at room temperature, methanol was added, heated to 60° C., stirred for 5 hours, and then concentrated under reduced pressure. To a solution of the obtained residue in tetrahydrofuran (10.0 mL) were added di-tert-butylcarbonate (1.75 g, 8.00 mmol) and triethylamine (0.85 mL, 5.90 mmol). After stirring for 16 hours at room temperature, the mixture was concentrated under reduced pressure. To the obtained residue were added water and ethyl acetate, and the aqueous layer was extracted with ethyl acetate. The organic layer was washed with water and brine, and then dried over sodium sulfate, and concentrated under reduced pressure. The obtained residue was purified with silica gel column (chloroform/methanol=100/0 to 90/10) to give the title compound (0.47 g, 1.12 mmol, 56%).

MS (ESI+) 426 (M$^+$+1, 100%)

Intermediate 38

7-(2-(4-(1H-Indol-3-yl)piperidin-1-yl)-2-oxoethyl)azepan-2-one

[Chemical Formula 69]

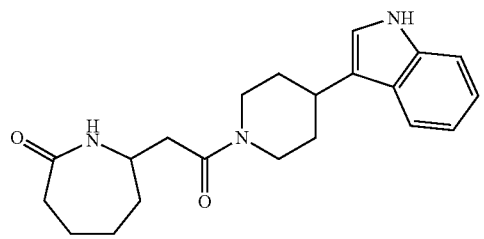

The title compound was synthesized by a similar procedure to intermediate 20 using intermediate 39.

MS (ESI+) 354 (M$^+$+1, 100%)

Intermediate 39

2-(7-Oxazepan-2-yl)acetic acid

[Chemical Formula 70]

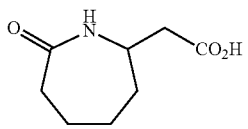

To a solution of intermediate 40 (0.66 g, 2.52 mmol) in methanol (30.0 mL) was added palladium/carbon (0.30 g). The mixture was stirred for 18 hours at room temperature under hydrogen atmosphere. The palladium catalyst was filtered off by Celite, and washed with ethyl acetate. The organic layer was concentrated under reduced pressure to give the title compound (0.39 g, 2.27 mmol, 90%).

MS (ESI+) 173 (M$^+$+1, 100%)

Intermediate 40

Benzyl 2-(7-oxazepan-2-yl)acetate

[Chemical Formula 71]

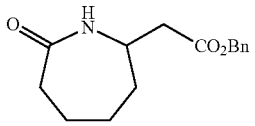

To a solution of intermediate 41 (3.12 g, 7.89 mmol) in methanol (50.0 mL) were added palladium/carbon (1.50 g) and ammonium formate (5.00 g, 79.0 mmol). The mixture was stirred for 4 hours at 80° C. The palladium catalyst was filtered off by Celite, and washed with ethyl acetate. The organic layer was concentrated under reduced pressure, and to the obtained residue was added water, and then the aqueous layer was extracted with ethyl acetate. The organic layer was washed with water and brine, and then dried over sodium sulfate, and concentrated under reduced pressure. The obtained residue was purified with silica gel column (chloroform/methanol=100/0 to 90/10) to give the title compound (0.66 g, 2.52 mmol, 32%).

MS (ESI+) 262 (M$^+$+1, 100%)

Intermediate 41

Dibenzyl 2-(7-oxazepan-2-yl)malonate

[Chemical Formula 72]

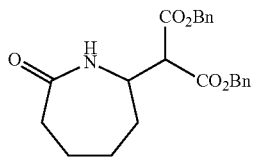

To a solution of azepan-2-one (4.05 g, 35.8 mmol) and HMPA (25.0 mL) in tetrahydrofuran (120 mL) was added N-butyllithium (30.0 mL, 47.4 mmol) dropwise at −78° C. After stirring for 15 minutes, to the mixture was added a solution of N-tert-butyl benzenesulfinimidoyl chloride (10.0 g, 46.3 mmol) in tetrahydrofuran (50.0 mL) dropwise, stirred for additional 30 minutes, and then dibenzylmalonate (15.3 g, 53.7 mmol) was added dropwise. After stirring for 15 hours at room temperature, the mixture was concentrated under reduced pressure. To the obtained residue was added water, and the aqueous layer was extracted with ethyl acetate. The organic layer was washed with water and brine, and then dried over sodium sulfate, and concentrated under reduced pressure. The obtained residue was purified with silica gel column (hexane/ethyl acetate=90/10 to 30/70) to give the title compound (5.86 g, 14.8 mmol, 41%).

Intermediate 42

5-(2-(4-(1H-Indol-3-yl)piperidin-1-yl)ethyl)-1,4-oxazepane

[Chemical Formula 73]

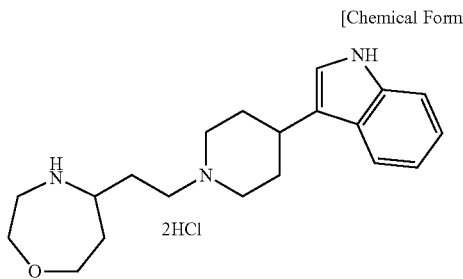

The title compound was obtained by a similar procedure to intermediate 1 using intermediate 43.
MS (ESI+) 402 (M$^+$+1, 100%)

Intermediate 43 tert-Butyl 5-(2-(4-(1H-indol-3-yl)piperidin-1-yl)ethyl)-1,4-oxazepane-4-carboxylate

[Chemical Formula 74]

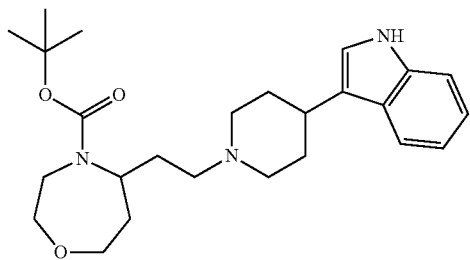

The title compound was synthesized by a similar procedure to intermediate 1 using intermediate 44.
MS (ESI+) 428 (M$^+$+1, 100%)

Intermediate 44 tert-Butyl 5-(2-oxoethyl)-1,4-oxazepane-4-carboxylate

[Chemical Formula 75]

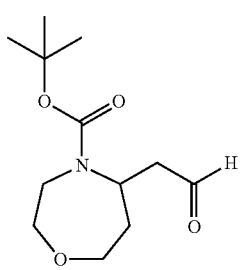

To a solution of intermediate 45 (0.27 g, 1.13 mmol) in methanol (10.0 mL) were added water (5.0 mL) and osmium tetroxide (2.5% tert-butanol solution, 85.0 µL). After stirring for 30 minutes at room temperature, to the mixture was added sodium periodate (0.72 g, 3.50 mmol), and stirred for 2 hours at room temperature. After filtration using Celite, to the mixture was added aqueous sodium thiosulfate solution, and the aqueous layer was extracted with ethyl acetate. The organic layer was washed with brine, dried over sodium sulfate, and concentrated under reduced pressure to give the title compound (0.27 g, 1.13 mmol, quant.).
MS (ESI+) 244 (M$^+$+1, 100%)

Intermediate 45 tert-Butyl 5-allyl-1,4-oxazepane-4-carboxylate

[Chemical Formula 76]

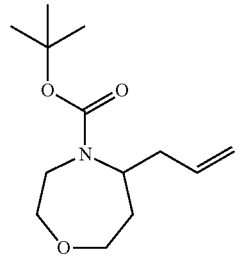

To a solution of trifluoroborane/diethyl ether (0.55 mL, 4.40 mmol) in dichloromethane (8.0 mL) was added a solution of intermediate 38 (1.15 g, 3.97 mmol) in dichloromethane (5.0 mL) dropwise at −78° C. under nitrogen atmosphere. After stirring for 10 minutes, to the mixture was added a solution of allyltrimethylsilane (0.8 mL, 5.0 mmol) in dichloromethane (5.0 mL) dropwise. After stirring for 4 hours at 0° C., to the mixture was added brine. The aqueous layer was extracted with chloroform, and the organic layer was washed with water and brine, and then dried over sodium sulfate, and concentrated under reduced pressure. The obtained residue was purified with silica gel column (chloroform/methanol=100/0 to 90/10) to give the title compound (96.0 mg) and a desilylated derivative thereof. To a solution of the desilylated derivative in tetrahydrofuran (5.0 mL) were added di-tert-butylcarbonate (0.87 g, 4.0 mmol) and triethylamine (0.56 mL, 4.0 mmol). The mixture was stirred for 12 hours at room temperature, and to the mixture was added water, and the aqueous layer was extracted with chloroform. The organic layer was washed with saturated aqueous solution of ammonium chloride and brine, and then dried over sodium sulfate, and concentrated under reduced pressure. The obtained residue was purified with silica gel column (chloroform/methanol=100/0 to 90/10) to give the combined title compound (0.17 g, 1.23 mmol, 28%).

MS (ESI+) 242 (M$^+$+1, 100%)

Intermediate 46 tert-Butyl 5-(trimethylsilyloxy)-1,4-oxazepane-4-carboxylate

[Chemical Formula 77]

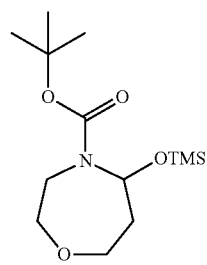

To a solution of intermediate 47 (2.15 g, 10.0 mmol) in dichloromethane (50.0 mL) was added diisobutylaluminum hydride (1.0 M, 14.0 mL) dropwise at −78° C. After stirring for 15 minutes, to the mixture were added pyridine (2.4 mL, 3.00 mmol) and trimethylsilyl triflate (4.5 mL, 2.50 mmol) dropwise. After stirring for 3 hours, to the mixture was added an aqueous solution of 15% potassium sodium tartrate. The aqueous layer was extracted with chloroform, and the organic layer was washed with water and brine, and then dried over sodium sulfate, and concentrated under reduced pressure. The obtained residue was purified with silica gel column (hexane/ethyl acetate=90/10 to 30/70) to give the title compound (1.50 g, 5.20 mmol, 52%).

MS (ESI+) 290 (M$^+$+1, 100%)

Intermediate 47 tert-Butyl 5-oxo-1,4-oxazepane-4-carboxylate

[Chemical Formula 78]

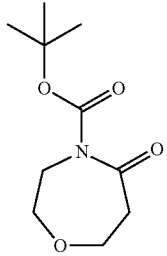

To a solution of 1,4-oxazepan-5-one (6.9 g, 60.0 mmol) in dichloromethane (120.0 mL) were added di-tert-butylcarbonate (1.75 g, 8.00 mmol) and dimethylaminopyridine (7.90 g, 65.0 mmol), and triethylamine (12.5 mL, 90.0 mmol) was added dropwise. After stirring for 16 hours at room temperature, to the mixture was added water, and the aqueous layer was extracted with chloroform. The organic layer was washed with saturated aqueous solution of ammonium chloride and brine, and then dried over sodium sulfate, and concentrated under reduced pressure. The obtained residue was purified with silica gel column (hexane/ethyl acetate=90/10 to 0/100) to give the title compound (7.30 g, 37.2 mmol, 62%).

MS (ESI+) 216 (M$^+$+1, 100%)

Intermediate 48

(S)-3-(1-(2-(Azetidin-2-yl)ethyl)piperidin-4-yl)-6-fluorobenzo[d]isoxazole

[Chemical Formula 79]

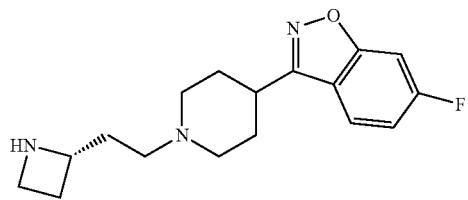

The title compound was synthesized by a similar procedure to intermediate 18 using intermediate 49.

$^1$H-NMR (CDCl$_3$) δ 5.76 (1H, s), 4.49-4.60 (1H, m), 3.71-3.94 (2H, m), 2.36-2.53 (1H, m), 2.16-2.33 (1H, m), 1.41 (9H, s)

Intermediate 49

(S)-tert-Butyl 2-(2-(4-(6-fluorobenzo[d]isoxazol-3-yl)piperidin-1-yl)-2-oxoethyl)azetidine-1-carboxylate

[Chemical Formula 80]

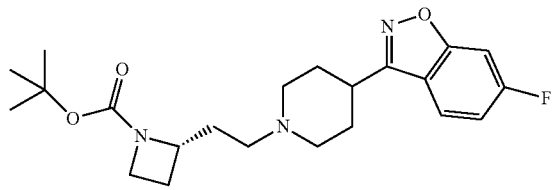

The title compound was synthesized by a similar procedure to intermediate 20 using intermediate 50.

MS (ESI+) 418 (M$^+$+1, 100%)

Intermediate 50

(S)-2-(1-(tert-Butoxycarbonyl)azetidin-2-yl)acetic acid

[Chemical Formula 81]

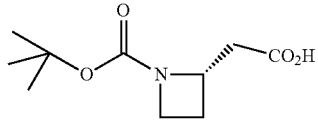

The title compound was synthesized by a similar procedure to intermediate 4 using intermediate 51.

MS (ESI+) 216 (M$^+$+1, 100%)

Intermediate 51

(S)-tert-Butyl 2-(2-methoxy-2-oxoethyl)azetidine-1-carboxylate

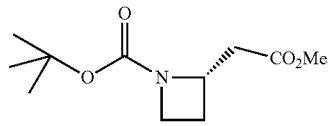
[Chemical Formula 82]

To a solution of intermediate 52 (1.40 g, 6.22 mmol) in methanol (60.0 mL) were added benzoic acid silver (0.13 g, 0.60 mmol) and triethylamine (2.60 mL, 18.7 mmol). After stirring for 1 day at 60° C., the mixture was filtered using Celite. To the mixture were added brine and ethyl acetate, and the aqueous layer was extracted with ethyl acetate, and the organic layer was washed with water and brine, and then dried over sodium sulfate, and concentrated under reduced pressure. The obtained residue was purified with silica gel column (hexane/ethyl acetate=90/10 to 75/25) to give the title compound (0.53 g, 2.30 mmol, 37%).

MS (ESI+) 130 (M$^+$+1, 100%)

Intermediate 52

(S)-tert-Butyl 2-(2-diazoacetyl)azetidine-1-carboxylate

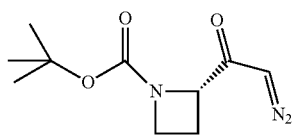
[Chemical Formula 83]

A solution of (S)-1-(tert-butoxycarbonyl)azetidine-2-carboxylic acid (1.80 g, 8.95 mmol) in tetrahydrofuran (90.0 mL) was cooled to 0° C., and isobutyl chloroformate (1.30 mL, 9.85 mmol) and triethylamine (1.50 mL, 10.7 mmol) were added. After stirring for 1 hour at room temperature, ammonium salt was filtered off, and the filtrate was concentrated under reduced pressure. The obtained residue was dissolved in acetonitrile (90.0 mL), and trimethylsilyldiazomethane (13.5 mL, 26.8 mmol) was added. After stirring for 7 hours at room temperature, to the mixture were added saturated sodium bicarbonate water and ethyl acetate. The aqueous layer was extracted with ethyl acetate, and the organic layer was washed with water and brine, and then dried over sodium sulfate, and concentrated under reduced pressure. The obtained residue was purified with silica gel column (hexane/ethyl acetate=90/10 to 75/25) to give the title compound (1.40 g, 6.22 mmol, 69%).

MS (ESI+) 226 (M$^+$+1, 100%)

Intermediate 53

(S)-6-Fluoro-3-(1-(2-(piperidin-3-yl)ethyl)piperidin-4-yl)benzo[d]isoxazole

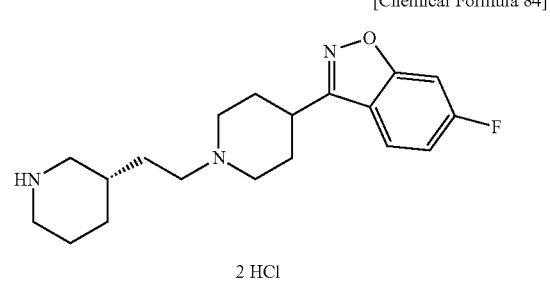
[Chemical Formula 84]

2 HCl

The title compound was synthesized by a similar procedure to intermediate 18 using intermediate 54.

MS (ESI+) 405 (M$^+$+1, 100%)

Intermediate 54

(S)-tert-Butyl 3-(2-(4-(6-fluorobenzo[d]isoxazol-3-yl)piperidin-1-yl)-2-oxoethyl)piperidine-1-carboxylate

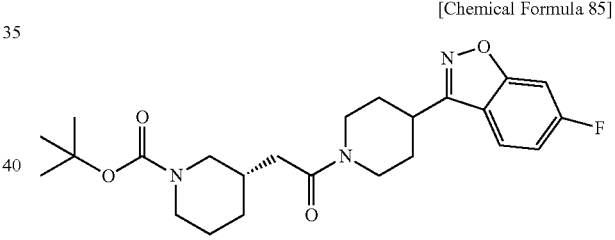
[Chemical Formula 85]

The title compound was synthesized by a similar procedure to intermediate 20 using intermediate 55.

MS (ESI+) 446 (M$^+$+1, 100%)

Intermediate 55

(S)-2-(1-(tert-Butoxycarbonyl)piperidin-3-yl)acetic acid

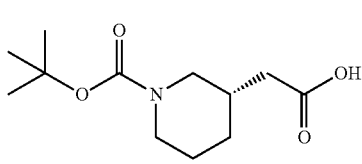
[Chemical Formula 86]

The title compound was synthesized by a similar procedure to intermediate 4 using intermediate 56.

MS (ESI+) 244 (M$^+$+1, 100%)

Intermediate 56

(S)-tert-Butyl 3-(cyanomethyl)piperidine-1-carboxylate

[Chemical Formula 87]

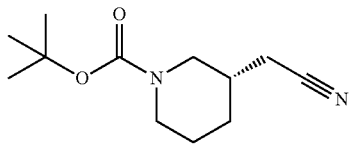

The title compound was synthesized by a similar procedure to intermediate 5 using intermediate 57.

MS (ESI+) 225 (M$^+$+1, 100%)

Intermediate 57

(R)-tert-Butyl 3-(tosyloxymethyl)piperidine-1-carboxylate

[Chemical Formula 88]

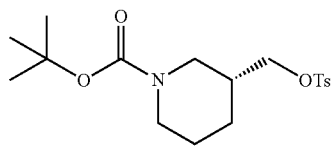

The title compound was synthesized by a similar procedure to intermediate 6 using (R)-tert-butyl 3-(hydroxymethyl)piperidine-1-carboxylate.

MS (ESI+) 370 (M$^+$+1, 100%)

Intermediate 58

(R)-3-(2-(4-(1H-Indol-3-yl)piperidin-1-yl)morpholine

[Chemical Formula 89]

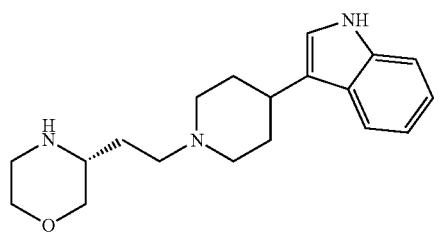

The title compound was synthesized by a similar procedure to intermediate 1 using intermediate 59.

MS (ESI+) 314 (M$^+$+1, 100%)

Intermediate 59

(R)-tert-Butyl 3-(2-oxoethyl)morpholine-4-carboxylate

[Chemical Formula 90]

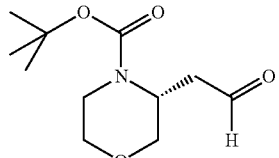

The title compound was synthesized by a similar procedure to intermediate 2 using intermediate 60.

MS (ESI+) 230 (M$^+$+1, 100%)

Intermediate 60

(R)-tert-Butyl 3-(2-hydroxyethyl)morpholine-4-carboxylate

[Chemical Formula 91]

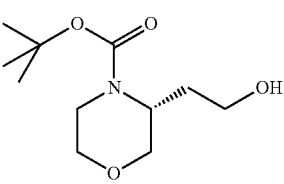

Under nitrogen atmosphere, to a solution of intermediate 59 (5.92 g, 26.8 mmol) in ethyl acetate (134 mL) were added palladium hydroxide/carbon (5.60 g, 8.03 mmol) and di-tert-butylcarbonate (7.59 g, 34.8 mmol). The mixture was stirred for 15 hours at room temperature under hydrogen atmosphere. The palladium catalyst was filtered off by Celite, and washed with ethyl acetate. The organic layer was concentrated under reduced pressure, and to the obtained residue was added water, and then the aqueous layer was extracted with ethyl acetate. The organic layer was washed with water and brine, and then dried over sodium sulfate, and concentrated under reduced pressure. The obtained residue was purified with silica gel column (hexane/ethyl acetate=90/10 to 30/70) to give the title compound (5.67 g, 24.5 mmol, 92%).

MS (ESI+) 232 (M$^+$+1, 100%)

Intermediate 61

(R)-2-(4-Benzylmorpholin-3-yl)ethanol

[Chemical Formula 92]

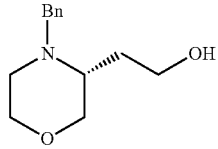

To a solution of intermediate 60 (6.44 g, 29.4 mmol) in methanol (120 mL) was added sodium borohydride (1.33 g, 35.2 mmol) at 0° C. under nitrogen atmosphere. The mixture was stirred for 30 minutes at room temperature, and ethyl acetate and water were added. The aqueous layer was extracted with ethyl acetate, and the organic layer was washed with water and brine, and then dried over sodium sulfate. The organic layer was concentrated under reduced pressure to give the title compound (6.50 g, 29.4 mmol, quant.).

MS (ESI+) 222 (M$^+$+1, 100%)

Intermediate 62

(R)-2-(4-Benzylmorpholin-3-yl)acetaldehyde

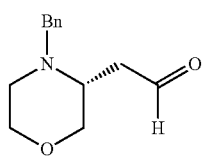

[Chemical Formula 93]

To a solution of intermediate 61 (6.90 g, 31.9 mmol) in toluene (160 mL) was added diisobutylaluminum hydride (47.4 mL, 47.9 mmol) at −78° C. under nitrogen atmosphere. After stirring for 90 minutes, to the mixture were added methanol, and additionally 2N hydrochloric acid. The aqueous layer was basified, and extracted with ethyl acetate. The organic layer was washed with water and brine, and then dried over sodium sulfate, and concentrated under reduced pressure. The obtained residue was purified with silica gel column (hexane/ethyl acetate=90/10 to 30/70) to give the title compound (7.00 g, 31.9 mmol, quant.).

MS (ESI+) 220 (M$^+$+1, 100%)

Intermediate 63

(R)-2-(4-Benzylmorpholin-3-yl)acetonitrile

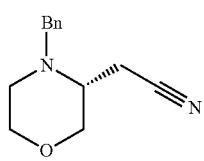

[Chemical Formula 94]

The title compound was synthesized by a similar procedure to intermediate 5 using intermediate 62.

MS (ESI+) 217 (M$^+$+1, 100%)

Intermediate 64

(S)-4-Benzyl-3-(chloromethyl)morpholine

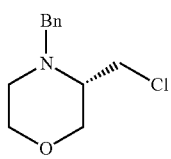

[Chemical Formula 95]

To a solution of intermediate 65 (9.60 g, 46.3 mmol) in dichloromethane (230 mL) was added thionyl chloride (60.0 mL, 69.5 mmol). After stirring for 15 hours, to the mixture was added aqueous sodium hydroxide solution. The aqueous layer was neutralized with 2N hydrochloric acid, and then extracted with dichloromethane. The organic layer was washed with water and brine, and then dried over sodium sulfate, and concentrated under reduced pressure to give the title compound (10.4 g, 46.3 mmol, quant.).

MS (ESI+) 226 (M$^+$+1, 100%)

Intermediate 65

(R)-(4-Benzylmorpholin-3-yl)methanol

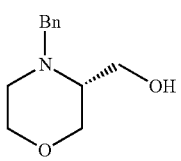

[Chemical Formula 96]

To a solution of intermediate 66 (12.6 g, 53.6 mmol) in tetrahydrofuran (200 mL) was added borane-tetrahydrofuran-complex (1.0 M, 348 mL). After stiffing for 6 hours at room temperature, to the mixture was added methanol, and after heated to 80° C., stirred for 2 hours. To the mixture were added saturated sodium bicarbonate water and ethyl acetate, and the aqueous layer was extracted with ethyl acetate. The organic layer was washed with water and brine, and then dried over sodium sulfate, and concentrated under reduced pressure. The obtained residue was purified with silica gel column (hexane/ethyl acetate=90/10 to 10/90) to give the title compound (9.60 g, 46.0 mmol, 86%).

MS (ESI+) 208 (M$^+$+1, 100%)

Intermediate 66

(S)-4-Benzyl-5-oxomorpholine-3-carboxylic acid

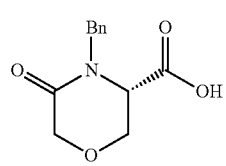

[Chemical Formula 97]

To a solution of (S)-2-(benzylamino)-3-hydroxypropanoic acid (40.0 g, 205 mmol) in tetrahydrofuran (600 mL) was added aqueous potassium carbonate solution (85.0 g, 600 mL) at 0° C. under nitrogen atmosphere, and additionally, chloroacetylchloride (29.0 mL, 369 mmol) was added. After stirring for 2 hours at room temperature, to the mixture was added 30% aqueous sodium hydroxide solution to adjust to pH 13. To the mixture was added diethyl ether, and the organic layer was separated, and then concentrated hydrochloric acid was added to adjust to pH 1, and cooled to 0° C. The precipitated crystal was collected by filtration to give the title compound (29.0 g, 123 mmol, 60%).

MS (ESI+) 236 (M$^+$+1, 100%)

Intermediate 67

3,6-Difluoro-1H-indole-2-carboxylic acid

[Chemical Formula 98]

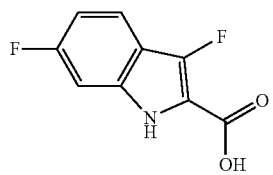

Ethyl 6-Fluoroindole-2-carboxylate (0.48 mmol, 0.10 g) was dissolved in acetonitrile (5 mL). To the solution was added magnesium oxide (0.96 mmol, 0.039 g) at room temperature. To the mixture was added Selectfluor (0.58 mmol, 0.21 g) gradually at room temperature, and stirred overnight at room temperature. The mixture was dried under reduced pressure, and purified with silica gel column chromatography (amine silica gel) (hexane/ethyl acetate=100/0→5/1) to give a 22.5 mg of white solid (yield 21%). The solid was dissolved in ethanol (1 mL). To the solution was added aqueous lithium hydroxide solution (2 M, 0.3 mmol, 0.15 mL) at room temperature, and stirred overnight at room temperature. The mixture was dried under reduced pressure, and the residuum was dissolved in water. To the solution was added aqueous hydrochloric acid solution (1 M), and the precipitated solid was collected by filtration to give the title compound (14.7 mg, yield 75%). MS (ESI+) 198 (M$^+$+1, 14%)

Intermediate 68

5-Fluoro-4-methoxy-1H-indole-2-carboxylic acid

[Chemical Formula 99]

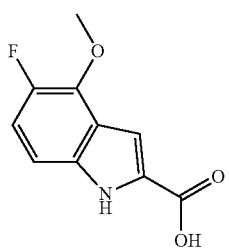

Ethyl 4-methoxyindole-2-carboxylate (1.46 mmol, 0.30 g) was dissolved in acetonitrile (15 mL). To the solution was added saturated sodium bicarbonate water (3 mL), and cooled to 0° C. To the mixture was added Selectfluor (2.2 mmol, 0.78 g) gradually, and stirred for 5 hours at room temperature. To the mixture was added water, and extracted three times with ethyl acetate. The organic layer was washed with brine, and dried over anhydrous sodium sulfate. The resultant was dried under reduced pressure, and purified with silica gel column chromatography (hexane/diethyl ether=100/0→3/1) to give a 92.1 mg of white solid (yield 28%). The solid was dissolved in methanol (2 mL). To the solution was added aqueous lithium hydroxide solution (2 M, 1.23 mmol, 0.62 mL) at room temperature, and stirred for 3 hours at 40° C. The mixture was dried under reduced pressure, and the residuum was dissolved in water. To the solution was added aqueous hydrochloric acid solution (1M), and the precipitated solid was collected by filtration to give the title compound (79.2 mg, yield 92%).

$^1$H-NMR (300 MHz, CDCl$_3$) δ 4.03 (d, J=1.2 Hz, 3H), 7.05-7.15 (m, 3H), 11.9 (s, 1H)

Intermediate 69

3-Fluoro-6-(trifluoromethoxy)-1H-indole-2-carboxylic acid

[Chemical Formula 100]

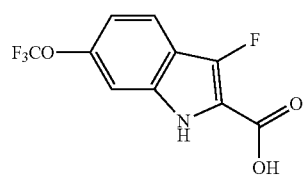

The title compound was synthesized by a similar procedure to intermediate 68.
MS (ESI+) 264 (M$^+$+1, 53%)

Intermediate 70

3-Fluoro-1H-indole-2-carboxylic acid

[Chemical Formula 101]

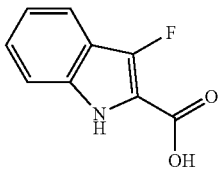

The title compound was synthesized by a similar procedure to intermediate 68.
MS (ESI+) 180 (M$^+$+1, 38%)

Intermediate 71

(4-Fluorophenyl)(1-(2-((2S,5S)-5-methylpyrrolidin-2-yl)ethyl)piperidin-4-yl)methanone hydrochloride

[Chemical Formula 102]

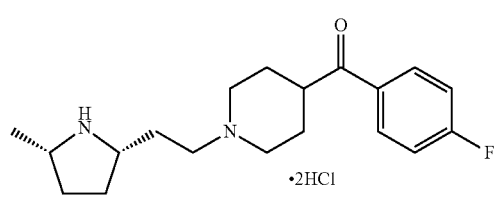

To a solution of intermediate 72 (0.62 g, 2.73 mmol) and 4-(4-fluorobenzoyl)-piperidine hydrochloride (0.66 g, 2.73 mmol) in tetrahydrofuran (10 mL) was added sodium triacetoxyborohydride (0.75 g, 3.55 mmol). After stirring for 1 hour at room temperature, to the mixture were added saturated sodium bicarbonate water and ethyl acetate, and the aqueous layer was extracted with ethyl acetate. The organic layer was washed with water and brine, and then dried over sodium sulfate, and concentrated under reduced pressure. The obtained residue was purified with silica gel column (chloroform/methanol=98/2 to 90/10) to give a Boc derivative of the title compound (1.15 g, 2.73 mmol, quant).

MS (ESI+) 419 (M$^+$+1, 100%)

To a solution of the obtained Boc derivative (1.15 g, 2.73 mmol) in methanol (150 mL) was added hydrochloric acid-dioxane solution (4N, 1.3 mL). The mixture was stirred for 2 hours at 90° C., concentrated under reduced pressure, and ethyl acetate and water were added. The aqueous layer was adjusted to pH=8-9 with aqueous sodium hydroxide solution, and extracted with ethyl acetate. To the organic layer was added 4N-hydrochloric acid-dioxane solution (24 mL), and concentrated under reduced pressure to give the title compound (0.98 g, 2.73 mmol, quant).

MS (ESI+) 432 (M$^+$+1, 100%)

Intermediate 72

(2S,5S)-tert-Butyl 2-methyl-5-(2-oxoethyl)pyrrolidine-1-carboxylate

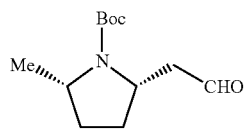

[Chemical Formula 103]

To a solution of SO$_3$/Py (1.30 g, 8.19 mmol) in chloroform (10.0 mL) were added dimethylsulfoxide (1.50 mL) and triethylamine (2.0 mL) dropwise. To the mixture was added a solution of intermediate 73 (0.63 g, 2.73 mmol) in chloroform (2.0 mL) dropwise. After stirring for 1 hour at room temperature, the mixture was cooled to 0° C., saturated sodium bicarbonate water was added, and the aqueous layer was extracted with ethyl acetate. The organic layer was washed with water and brine, and then dried over sodium sulfate, and concentrated under reduced pressure to give the title compound (0.62 g, 2.73 mmol, quant.).

MS (ESI+) 228 (M$^+$+1, 100%)

Intermediate 73

(2 S,5S)-tert-Butyl 2-(2-hydroxyethyl)-5-methylpyrrolidine-1-carboxylate

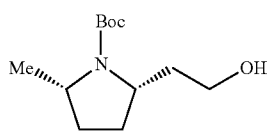

[Chemical Formula 104]

To a solution of intermediate 74 (0.80 g, 3.28 mmol) in tetrahydrofuran (15.0 mL) was added borane-tetrahydrofuran-complex (1.0 M, 10.9 mL). After stirring for 30 minutes at room temperature, to the mixture was added methanol, and stirred for 2 hours at 90° C. The mixture was concentrated under reduced pressure, and ethyl acetate and water were added. The organic layer was washed with water and brine, and then dried over sodium sulfate, and concentrated under reduced pressure. The obtained residue was purified with silica gel column (chloroform/methanol=98/2 to 90/10) to give the title compound (0.63 g, 2.73 mmol, 83%).

MS (ESI+) 230 (M$^+$+1, 100%)

Intermediate 74

2-((2S,5S)-1-(tert-Butoxycarbonyl)-5-methylpyrrolidin-2-yl)acetic acid

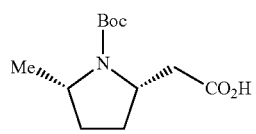

[Chemical Formula 105]

To a solution of intermediate 75 (1.43 g, 6.40 mmol) in methanol (50.0 mL) was added aqueous sodium hydroxide solution (30% w/v, 7.0 mL), and heated to 100° C. After stirring for 3 hours, the reaction solution was concentrated under reduced pressure. To the obtained residue was added aqueous hydrochloric acid solution to adjust to pH 4-5, and the aqueous layer was extracted with ethyl acetate. The organic layer was washed with water and brine, and then dried over sodium sulfate, and concentrated under reduced pressure to give the title compound (1.30 g, 5.34 mmol, 83%).

MS (ESI+) 244 (M$^+$+1, 100%)

Intermediate 75

(2S,5S)-tert-Butyl 2-(cyanomethyl)-5-methylpyrrolidine-1-carboxylate

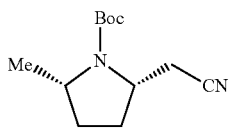

[Chemical Formula 106]

To a solution of intermediate 76 (2.63 g, 7.12 mmol) in dimethylsulfoxide (20.0 mL) was added sodium cyanide (0.38 g, 7.82 mmol), and heated to 70° C. After stirring for 3 hours, to the mixture was added water, and the aqueous layer was extracted with ethyl acetate. The organic layer was washed with water and brine, and then dried over sodium sulfate, and concentrated under reduced pressure. The obtained residue was purified with silica gel column (hexane/ethyl acetate=70/30 to 30/70) to give the title compound (1.43 g, 6.40 mmol, 90%).

MS (ESI+) 225 (M$^+$+1, 100%)

Intermediate 76

(2S,5S)-tert-Butyl 2-methyl-5-(tosyloxymethyl)pyrrolidine-1-carboxylate

[Chemical Formula 107]

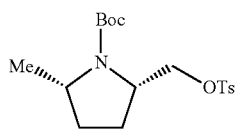

A solution of intermediate 77 (1.62 g, 7.53 mmol) in chloroform (30.0 mL) was cooled to 0° C., and p-toluenesulfonylchloride (1.90 g, 9.79 mmol), triethylamine (1.70 mL, 12.0 mmol), and 4-dimethylaminopyridine (0.16 g) were added. After stirring for 6 hours at room temperature, to the mixture was added water, and the aqueous layer was extracted with ethyl acetate. The organic layer was washed with water and brine, and then dried over sodium sulfate, and concentrated under reduced pressure. The obtained residue was purified with silica gel column (hexane/ethyl acetate=70/30 to 30/70) to give the title compound (2.63 g, 7.12 mmol, 94%).

MS (ESI+) 370 (M$^+$+1, 100%)

Intermediate 77

(2R,5S)-tert-Butyl 2-(hydroxymethyl)-5-methylpyrrolidine-1-carboxylate

[Chemical Formula 108]

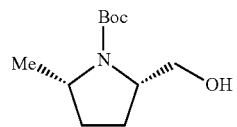

Intermediate 78 (4.15 g, 12.0 mmol) was dissolved in ethanol (130 mL), and cooled to 0° C. After calcium chloride (7.10 g, 63.6 mmol) was added and dissolved in the solution, sodium borohydride (4.53 g, 120 mmol) was added. After warmed to room temperature, the mixture was stirred overnight. To the mixture was added aqueous potassium carbonate solution (2 M, 65 mL), and concentrated under reduced pressure. The residue was dissolved in water, and extracted with ethyl acetate. The organic layer was washed with brine, dried over sodium sulfate, concentrated under reduced pressure, and then purified with silica gel column chromatography to give the title compound (1.62 g, 7.53 mmol, 63%).

MS (ESI+) 216 (M$^+$+1, 100%)

Intermediate 78

(2R,5S)-1-tert-Butyl 2-ethyl 5-methylpyrrolidine-1,2-dicarboxylate

[Chemical Formula 109]

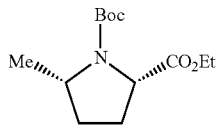

Intermediate 79 (3.10 g, 15.4 mmol) was dissolved in chloroform (40 mL), and triethylamine (5.40 mL, 38.7 mmol) was added. To the mixture was added di-tert-butylcarbonate (3.90 g, 17.8 mmol), and stirred for a day at room temperature. After concentrated under reduced pressure, the residue was dissolved in ethyl acetate, washed with brine, dried over sodium sulfate, concentrated under reduced pressure, and purified with silica gel column chromatography (chloroform/ethyl acetate=4/1) to give the title compound (4.15 g, 15.4 mmol, quant.).

MS (ESI+) 258 (M$^+$+1, 86%)

Intermediate 79

(2S,5R)-Ethyl 5-methylpyrrolidine-2-carboxylate

[Chemical Formula 110]

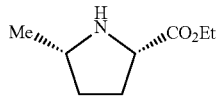

Intermediate 80 (2.32 g, 15.4 mmol) was dissolved in ethanol (160 mL), and palladium/carbon (1.10 g, 10%, 50% wet) was added, and then stirred for 2 days under hydrogen atmosphere. Insoluble matter was removed by filtration using Celite, and the filtrate was concentrated under reduced pressure to give the title compound (3.10 g, 15.4 mmol, quant.).

MS (ESI+) 158 (M$^+$+1, 100%)

Intermediate 80

(S)-Ethyl 5-methyl-3,4-dihydro-2H-pyrrole-2-carboxylate

[Chemical Formula 111]

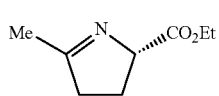

Intermediate 81 (4.30 g, 15.4 mmol) was dissolved in tetrahydrofuran (50.0 mL), and 4N-hydrochloric acid-dioxane solution (10.0 mL) was added, and then stirred overnight at 60° C. The mixture was concentrated under reduced pressure to give the title compound (2.32 g, 15.4 mmol, quant.).

MS (ESI+) 156 (M$^+$+1, 100%)

Intermediate 81

(S)-Ethyl-2-(tert-butoxycarbonylamino)-5-oxo-hexanate

[Chemical Formula 112]

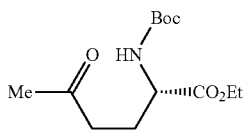

To a solution of (S)-1-tert-butyl 2-ethyl 5-oxopyrrolidine-1,2-dicarboxylate (7.00 g, 27.4 mmol) in tetrahydrofuran (100 mL) was added methyl Grignard reagent (3M in diethyl ether, 9.60 mL, 28.8 mmol) dropwise for 20 minutes at −78° C., and stirred for 1 hour. After stiffing for 2 hours at 0° C., to the mixture was added saturated sodium bicarbonate water dropwise, and the aqueous layer was extracted with ethyl acetate. The organic layer was washed with brine, dried over sodium sulfate, and concentrated under reduced pressure to give the title compound (7.60 g, 26.5 mmol, 97%).

MS (ESI+) 274 (M$^+$+1, 100%)

Data of compounds synthesized by the procedures described in Examples and Reference Examples are shown in Tables 2 to 7.
TABLE 2
| Ex. No. | STRUCTURE | M + 1 (% Intensity) |
|---|---|---|
| 9 | 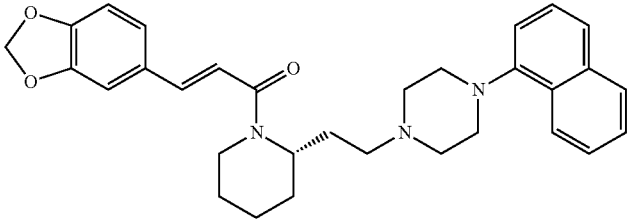 [SMILES: O=C(/C=C/c1ccc2c(c1)OCO2)N1CCCC[C@H]1CCN1CCN(c2cccc3ccccc23)CC1] | 498 100% |
| 10 | 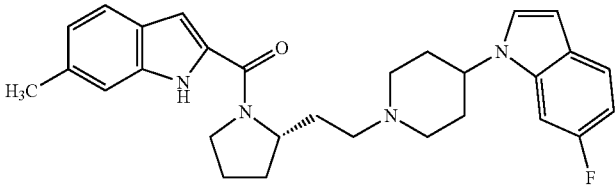 [SMILES: Cc1ccc2cc(C(=O)N3CCC[C@H]3CCN3CCC(n4ccc5ccc(F)cc54)CC3)[nH]c2c1] | 473 100% |
| 11 | 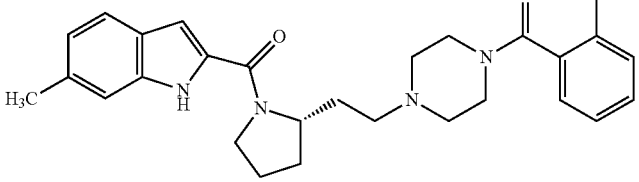 | 468 100% |
| 12 | 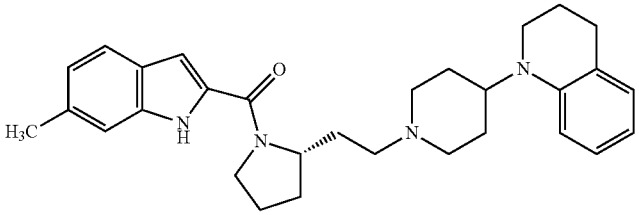 [SMILES: Cc1ccc2cc(C(=O)N3CCC[C@H]3CCN3CCC(N4CCCc5ccccc54)CC3)[nH]c2c1] | 471 100% |
| 13 | 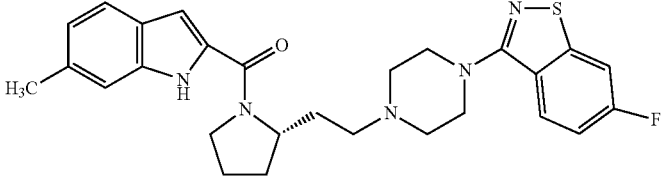 | 493 100% |
| 14 | 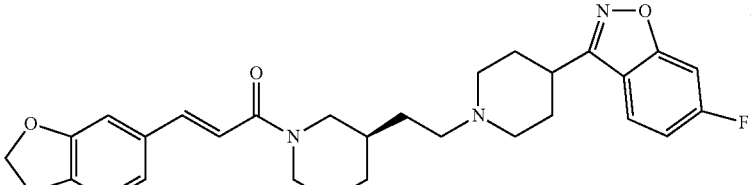 | 506 100% |

TABLE 2-continued

| Ex. No. | STRUCTURE | M + 1 (% Intensity) |
|---|---|---|
| 15 | 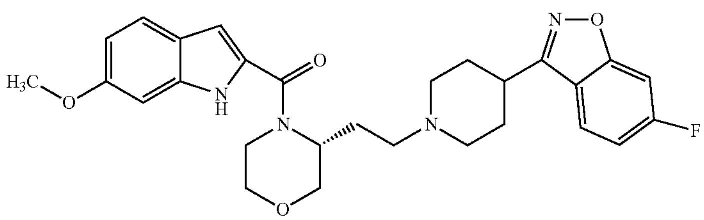 [SMILES: COc1ccc2cc(C(=O)N3CCOC[C@H]3CCN3CCC(c4noc5cc(F)ccc45)CC3)[nH]c2c1] | 507 100% |
| 16 | 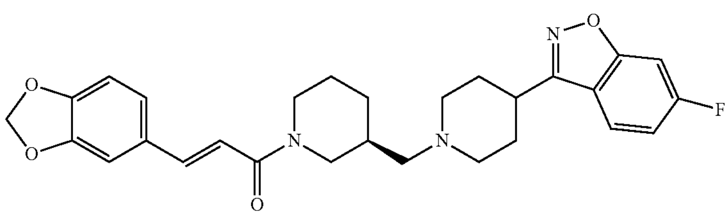 [SMILES: O=C(/C=C/c1ccc2c(c1)OCO2)N1CCC[C@@H](CN2CCC(c3noc4cc(F)ccc34)CC2)C1] | 492 100% |
| 17 | 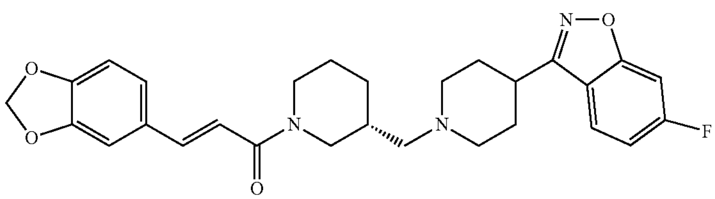 [SMILES: O=C(/C=C/c1ccc2c(c1)OCO2)N1CCC[C@H](CN2CCC(c3noc4cc(F)ccc34)CC2)C1] | 492 100% |
| 18 | 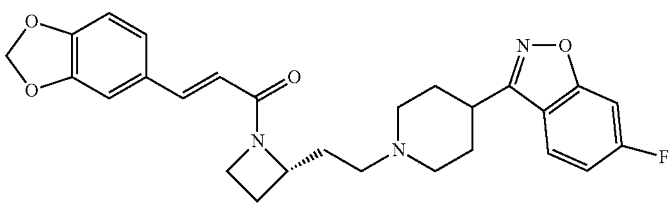 [SMILES: O=C(/C=C/c1ccc2c(c1)OCO2)N1CC[C@H]1CCN1CCC(c2noc3cc(F)ccc23)CC1] | 478 100% |
| 19 | 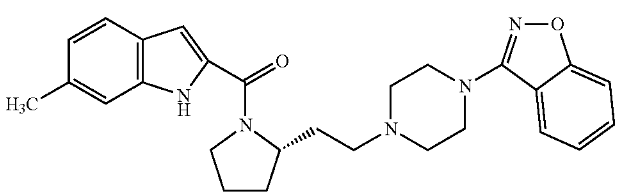 [SMILES: Cc1ccc2cc(C(=O)N3CCC[C@H]3CCN3CCN(c4noc5ccccc45)CC3)[nH]c2c1] | 475 100% |
| 20 | 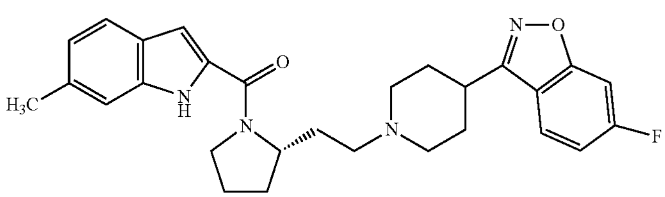 [SMILES: Cc1ccc2cc(C(=O)N3CCC[C@H]3CCN3CCC(c4noc5cc(F)ccc45)CC3)[nH]c2c1] | 475 100% |
| 21 | 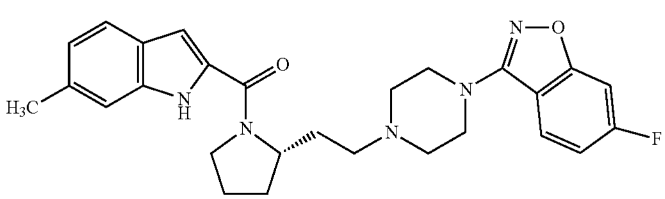 [SMILES: Cc1ccc2cc(C(=O)N3CCC[C@H]3CCN3CCN(c4noc5cc(F)ccc45)CC3)[nH]c2c1] | 476 100% |

TABLE 2-continued

| Ex. No. | STRUCTURE | M + 1 (% Intensity) |
|---|---|---|
| 22 | 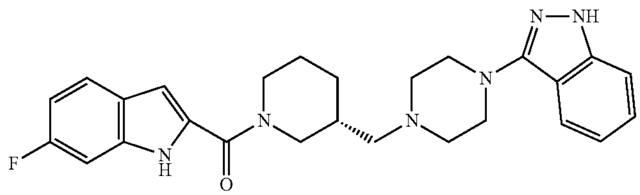 [SMILES: O=C(c1cc2ccc(F)cc2[nH]1)N1CCC[C@H](CN2CCN(c3n[nH]c4ccccc34)CC2)C1] | 461 100% |
| 23 | 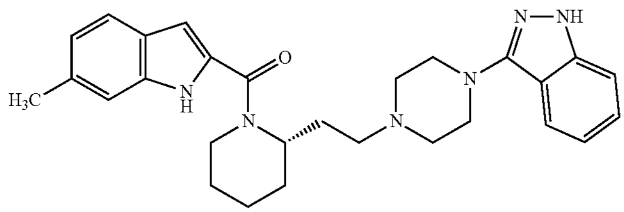 [SMILES: Cc1ccc2cc(C(=O)N3CCCC[C@H]3CCN3CCN(c4n[nH]c5ccccc45)CC3)[nH]c2c1] | 471 100% |
| 24 | 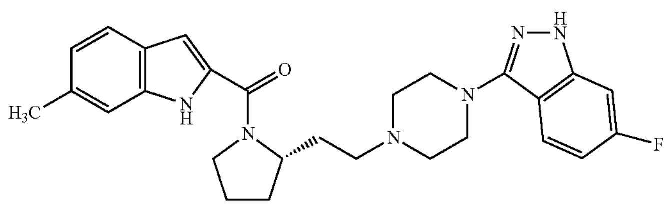 [SMILES: Cc1ccc2cc(C(=O)N3CCC[C@H]3CCN3CCN(c4n[nH]c5cc(F)ccc45)CC3)[nH]c2c1] | 475 100% |
| 25 | 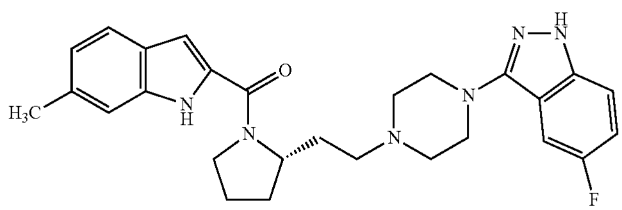 [SMILES: Cc1ccc2cc(C(=O)N3CCC[C@H]3CCN3CCN(c4n[nH]c5ccc(F)cc45)CC3)[nH]c2c1] | 475 100% |
| 26 | 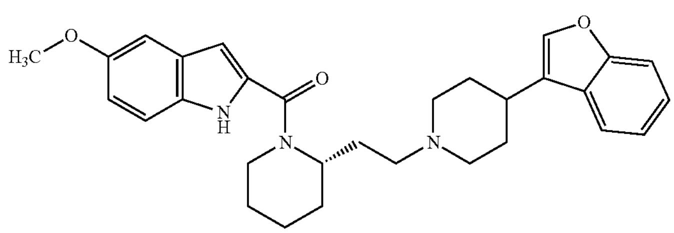 [SMILES: COc1ccc2[nH]c(C(=O)N3CCCC[C@H]3CCN3CCC(c4coc5ccccc45)CC3)cc2c1] | 486 100% |
| 27 | 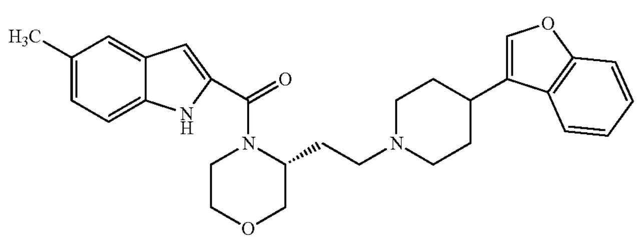 [SMILES: Cc1ccc2[nH]c(C(=O)N3CCOC[C@H]3CCN3CCC(c4coc5ccccc45)CC3)cc2c1] | 472 100% |
| 28 | 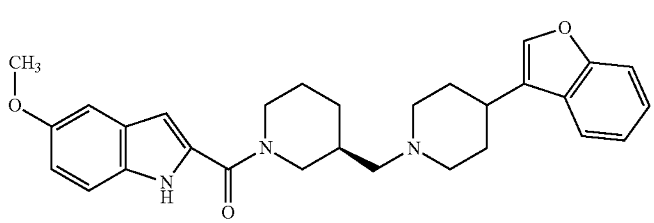 [SMILES: COc1ccc2[nH]c(C(=O)N3CCC[C@@H](CN4CCC(c5coc6ccccc56)CC4)C3)cc2c1] | 486 100% |

TABLE 2-continued

| Ex. No. | STRUCTURE | M + 1 (% Intensity) |
|---|---|---|
| 29 | 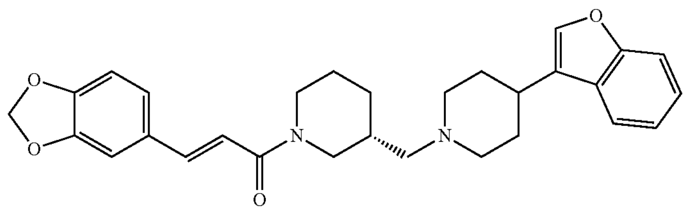 [SMILES: O=C(/C=C/c1ccc2c(c1)OCO2)N1CCC[C@H](CN2CCC(c3coc4ccccc34)CC2)C1] | 473 100% |
| 30 | 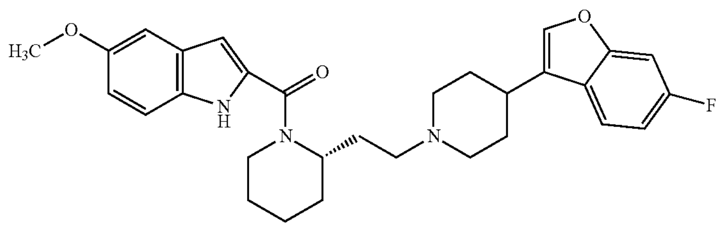 [SMILES: COc1ccc2[nH]c(C(=O)N3CCCC[C@H]3CCN3CCC(c4coc5cc(F)ccc45)CC3)cc2c1] | 504 100% |
| 31 | 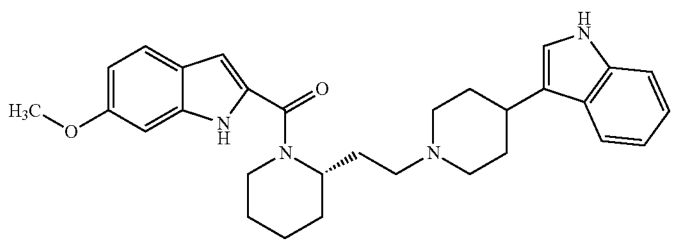 [SMILES: COc1ccc2cc(C(=O)N3CCCC[C@H]3CCN3CCC(c4c[nH]c5ccccc45)CC3)[nH]c2c1] | 485 100% |
| 32 | 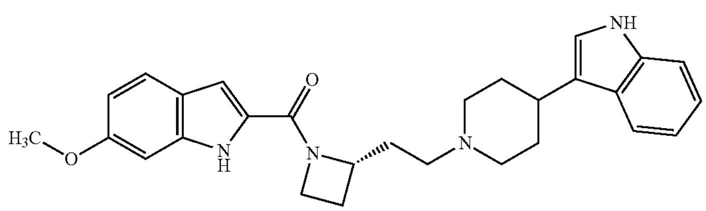 [SMILES: COc1ccc2cc(C(=O)N3CC[C@H]3CCN3CCC(c4c[nH]c5ccccc45)CC3)[nH]c2c1] | 457 100% |
| 33 | 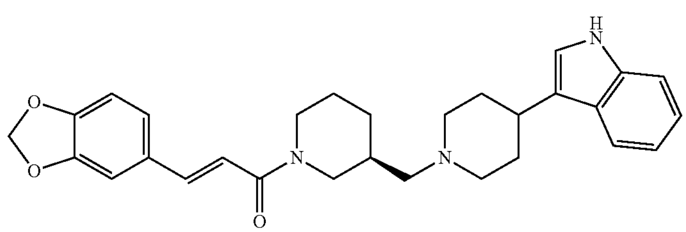 [SMILES: O=C(/C=C/c1ccc2c(c1)OCO2)N1CCC[C@@H](CN2CCC(c3c[nH]c4ccccc34)CC2)C1] | 521 100% |
| 34 | 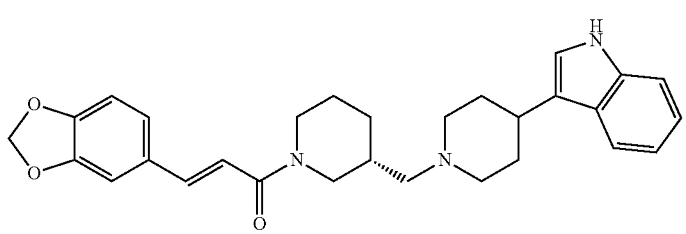 [SMILES: O=C(/C=C/c1ccc2c(c1)OCO2)N1CCC[C@H](CN2CCC(c3c[nH]c4ccccc34)CC2)C1] | 472 100% |

TABLE 3
| Ex. No. | STRUCTURE | M + 1 (% Intensity) |
|---|---|---|
| 35 | 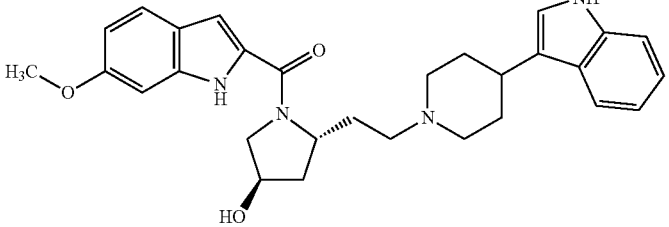 | 487 100% |
| 36 | 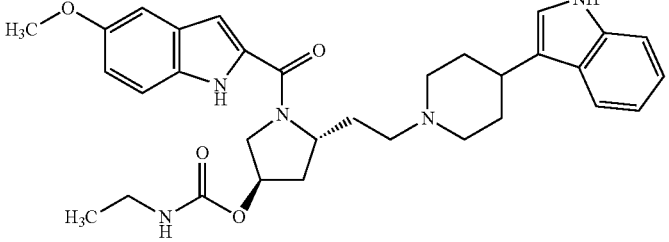 | 558 100% |
| 37 | 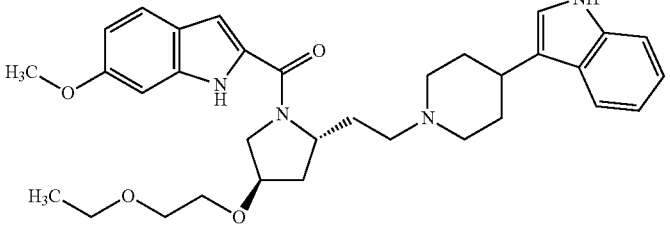 | 559 100% |
| 38 | 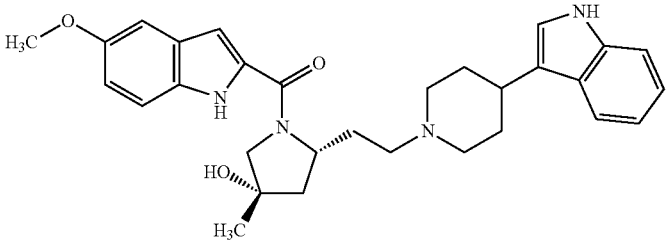 [SMILES: COc1ccc2[nH]c(C(=O)N3C[C@@](C)(O)C[C@H]3CCN3CCC(c4c[nH]c5ccccc45)CC3)cc2c1] | 501 100% |
| 39 | 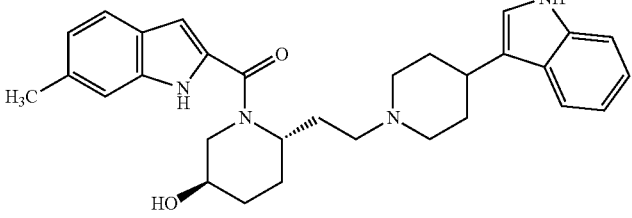 | 485 100% |
| 40 | 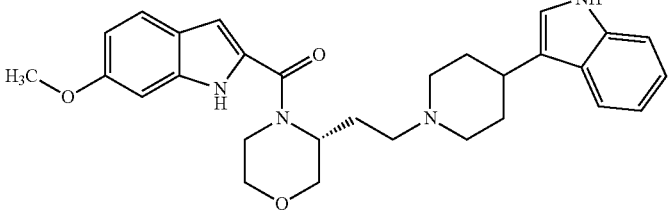 | 497 100% |

TABLE 3-continued

| Ex. No. | STRUCTURE | M + 1 (% Intensity) |
|---|---|---|
| 41 | 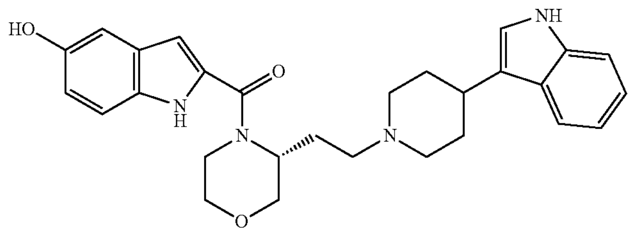 [SMILES: O=C(c1cc2cc(O)ccc2[nH]1)N1CCOC[C@H]1CCN1CCC(c2c[nH]c3ccccc23)CC1] | 473 100% |
| 42 | 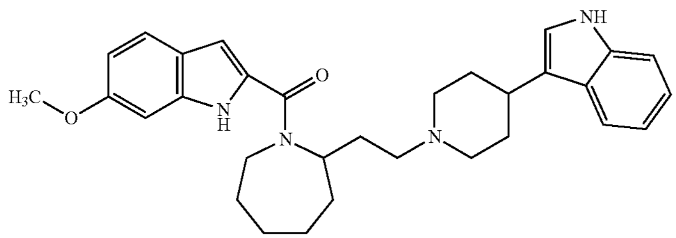 [SMILES: COc1ccc2cc(C(=O)N3CCCCCC3CCN3CCC(c4c[nH]c5ccccc45)CC3)[nH]c2c1] | 492 100% |
| 43 | 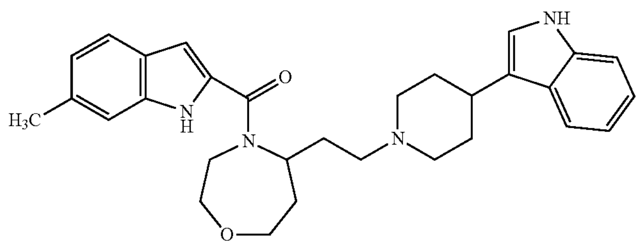 [SMILES: Cc1ccc2cc(C(=O)N3CCOCCC3CCN3CCC(c4c[nH]c5ccccc45)CC3)[nH]c2c1] | 485 100% |
| 44 | 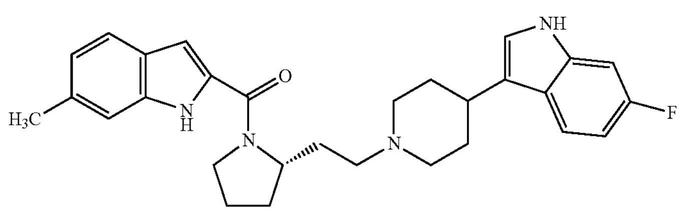 [SMILES: Cc1ccc2cc(C(=O)N3CCC[C@H]3CCN3CCC(c4c[nH]c5cc(F)ccc45)CC3)[nH]c2c1] | 469 100% |
| 45 | 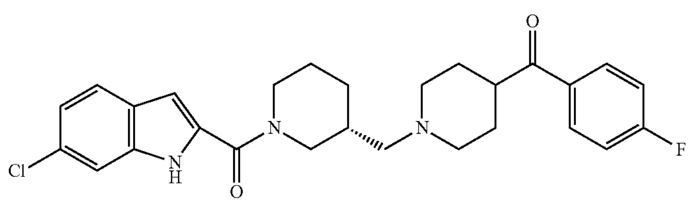 [SMILES: O=C(c1ccc(F)cc1)C1CCN(C[C@H]2CCCN(C(=O)c3cc4ccc(Cl)cc4[nH]3)C2)CC1] | 482 100% |
| 46 | 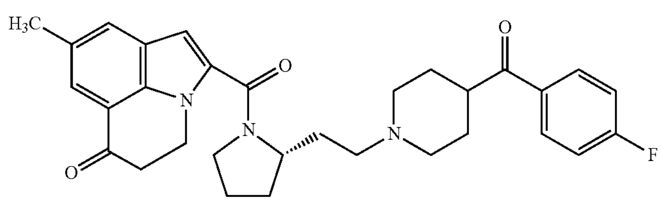 [SMILES: Cc1cc2c3c(c1)cc(C(=O)N1CCC[C@H]1CCN1CCC(C(=O)c4ccc(F)cc4)CC1)n3CCC2=O] | 516 100% |
| 47 | 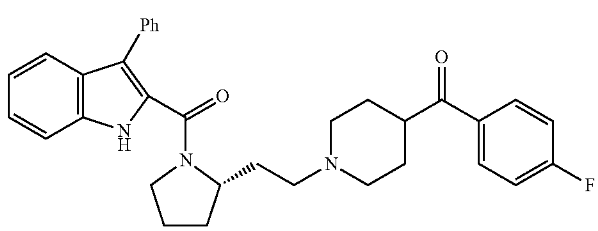 [SMILES: O=C(c1ccc(F)cc1)C1CCN(CC[C@@H]2CCCN2C(=O)c2[nH]c3ccccc3c2-c2ccccc2)CC1] | 524 100% |

TABLE 3-continued
| Ex. No. | STRUCTURE | M + 1 (% Intensity) |
|---|---|---|
| 48 | 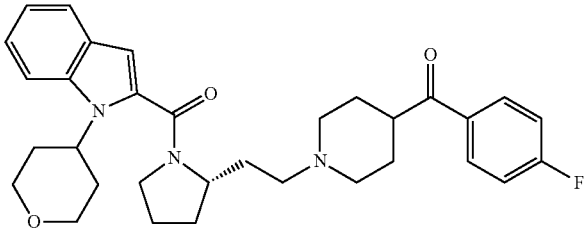 [SMILES: O=C(c1ccc(F)cc1)C1CCN(CC[C@@H]2CCCN2C(=O)c2cc3ccccc3n2C2CCOCC2)CC1] | 532 100% |
| 49 | 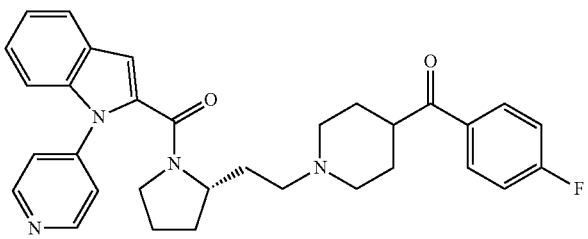 [SMILES: O=C(c1ccc(F)cc1)C1CCN(CC[C@@H]2CCCN2C(=O)c2cc3ccccc3n2-c2ccncc2)CC1] | 525 80% |
| 50 | 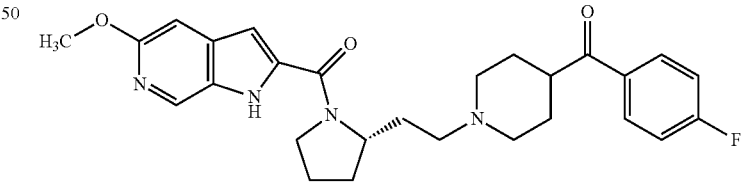 | 479 70% |
| 51 | 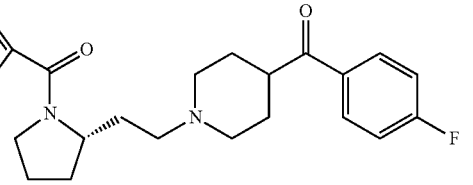 | 475 100% |
| 52 | 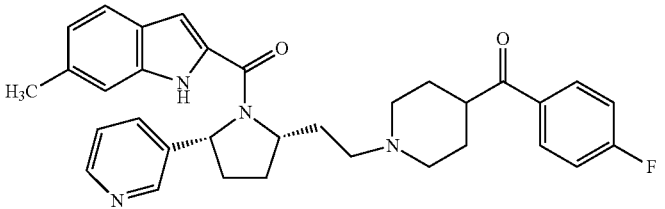 [SMILES: Cc1ccc2cc(C(=O)N3[C@H](CCN4CCC(C(=O)c5ccc(F)cc5)CC4)CC[C@@H]3c3cccnc3)[nH]c2c1] | 539 100% |
| 53 | 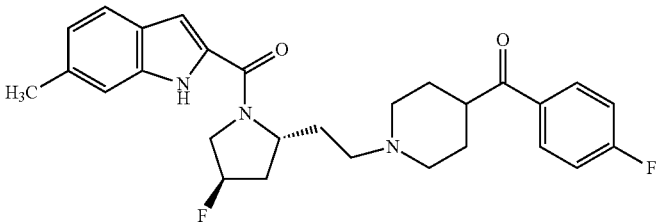 [SMILES: Cc1ccc2cc(C(=O)N3C[C@H](F)C[C@H]3CCN3CCC(C(=O)c4ccc(F)cc4)CC3)[nH]c2c1] | 480 100% |

TABLE 3-continued

| Ex. No. | STRUCTURE | M + 1 (% Intensity) |
|---|---|---|
| 54 | 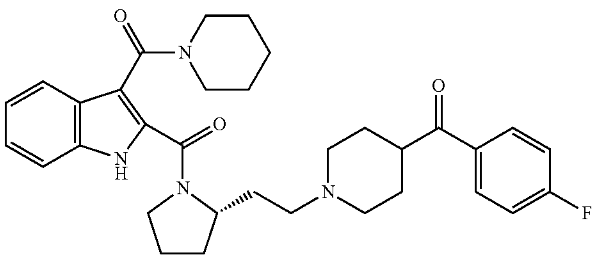 [SMILES: O=C(c1ccc(F)cc1)C1CCN(CC[C@@H]2CCCN2C(=O)c2[nH]c3ccccc3c2C(=O)N2CCCCC2)CC1] | 559 100% |
| 55 | 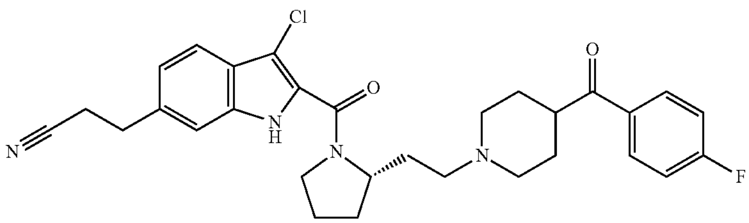 [SMILES: N#CCCc1ccc2c(Cl)c(C(=O)N3CCC[C@H]3CCN3CCC(C(=O)c4ccc(F)cc4)CC3)[nH]c2c1] | 535 100% |
| 56 | 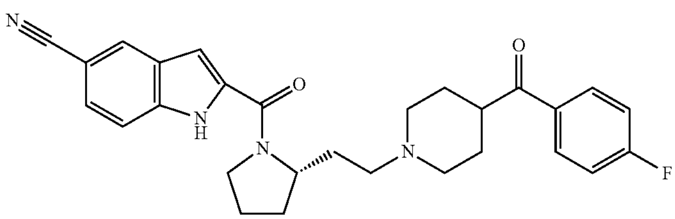 [SMILES: N#Cc1ccc2[nH]c(C(=O)N3CCC[C@H]3CCN3CCC(C(=O)c4ccc(F)cc4)CC3)cc2c1] | 473 100% |
| 57 | 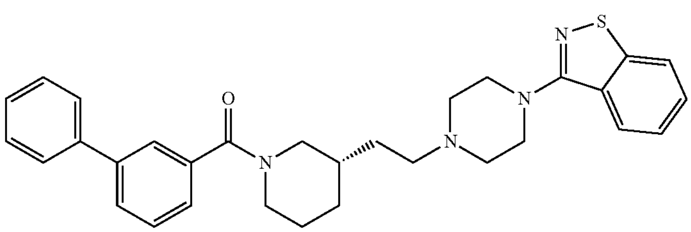 [SMILES: O=C(c1cccc(-c2ccccc2)c1)N1CCC[C@@H](CCN2CCN(c3nsc4ccccc34)CC2)C1] | 511 100% |
| 58 | 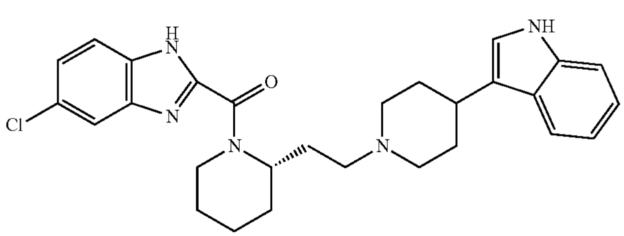 [SMILES: O=C(c1nc2cc(Cl)ccc2[nH]1)N1CCCC[C@H]1CCN1CCC(c2c[nH]c3ccccc23)CC1] | 490 100% |
| 59 | 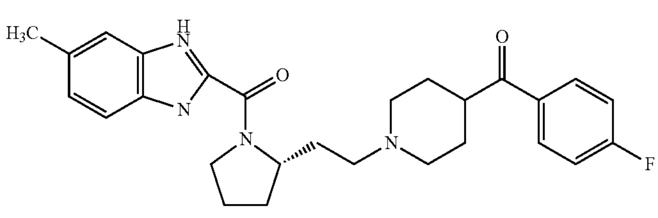 | 463 100% |

TABLE 3-continued
| Ex. No. | STRUCTURE | M + 1 (% Intensity) |
|---|---|---|
| 60 | 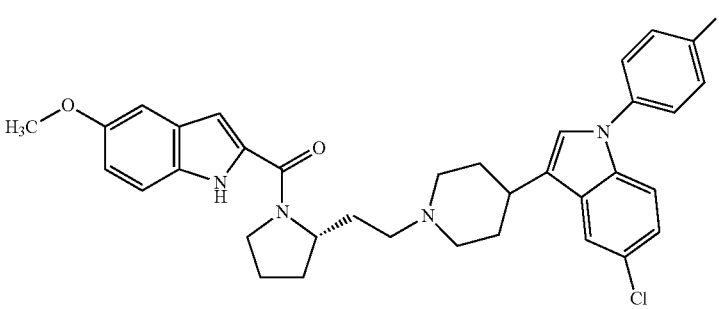 | 599 100% |
TABLE 4
| Ex. No. | STRUCTURE | M + 1 (% Intensity) |
|---|---|---|
| 61 | 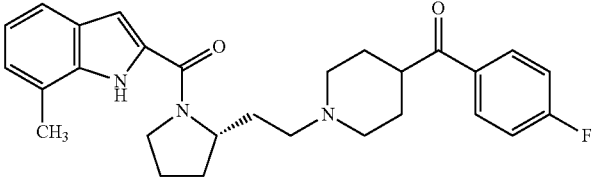 [SMILES: Cc1cccc2cc(C(=O)N3CCC[C@H]3CCN3CCC(C(=O)c4ccc(F)cc4)CC3)[nH]c12] | 462 100% |
| 62 | 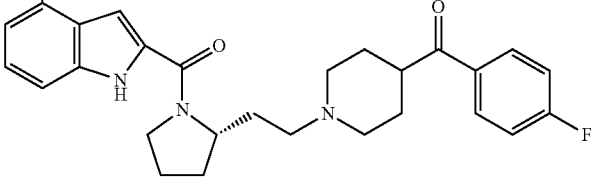 | 466 100% |
| 63 | 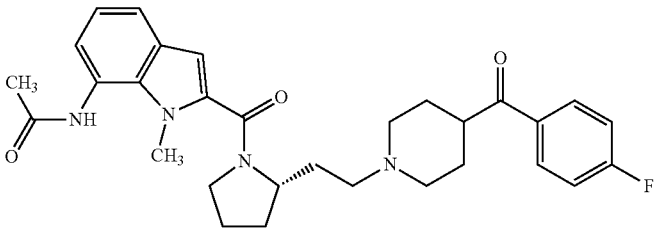 [SMILES: CC(=O)Nc1cccc2cc(C(=O)N3CCC[C@H]3CCN3CCC(C(=O)c4ccc(F)cc4)CC3)n(C)c12] | 519 100% |
| 64 | 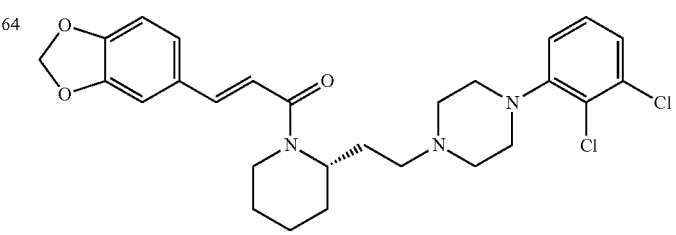 | 517 100% |

TABLE 4-continued

| Ex. No. | STRUCTURE | M + 1 (% Intensity) |
|---|---|---|
| 65 | 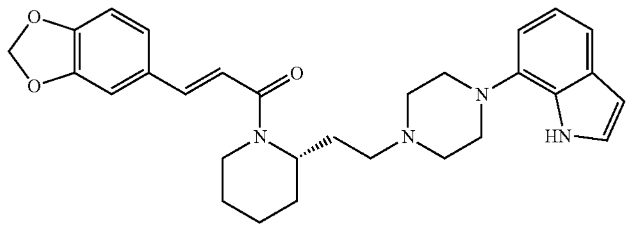 [SMILES: O=C(/C=C/c1ccc2c(c1)OCO2)N1CCCC[C@H]1CCN1CCN(c2cccc3cc[nH]c23)CC1] | 487 100% |
| 66 | 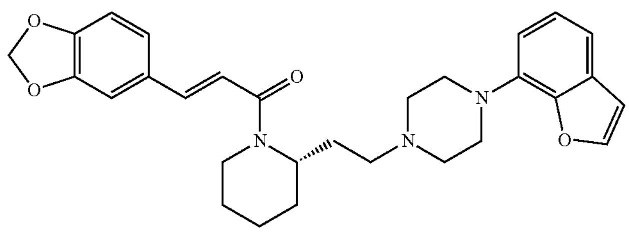 [SMILES: O=C(/C=C/c1ccc2c(c1)OCO2)N1CCCC[C@H]1CCN1CCN(c2cccc3ccoc23)CC1] | 488 100% |
| 67 | 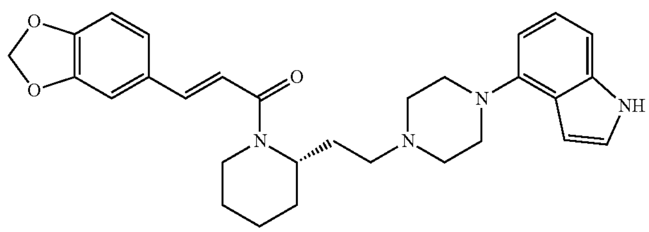 [SMILES: O=C(/C=C/c1ccc2c(c1)OCO2)N1CCCC[C@H]1CCN1CCN(c2cccc3[nH]ccc23)CC1] | 487 100% |
| 68 | 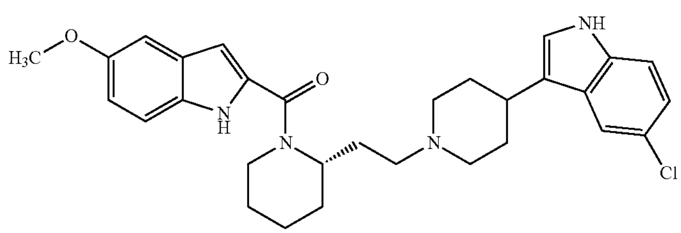 [SMILES: COc1ccc2[nH]c(C(=O)N3CCCC[C@H]3CCN3CCC(c4c[nH]c5ccc(Cl)cc45)CC3)cc2c1] | 520 100% |
| 69 | 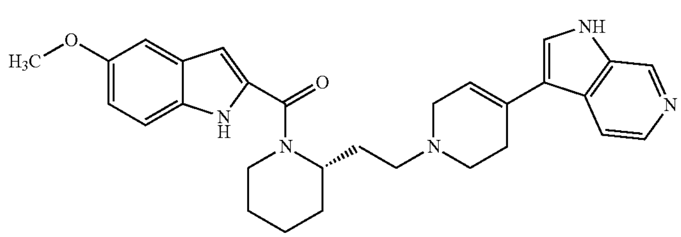 [SMILES: COc1ccc2[nH]c(C(=O)N3CCCC[C@H]3CCN3CC=C(c4c[nH]c5cnccc45)CC3)cc2c1] | 484 100% |
| 70 | 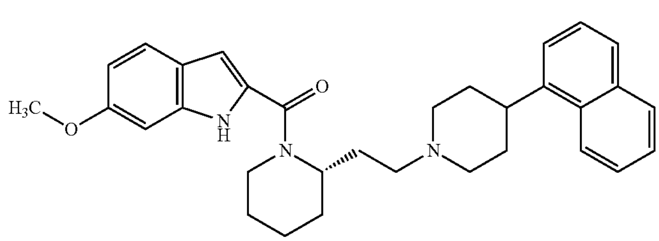 [SMILES: COc1ccc2cc(C(=O)N3CCCC[C@H]3CCN3CCC(c4cccc5ccccc45)CC3)[nH]c2c1] | 496 100% |

TABLE 4-continued
| Ex. No. | STRUCTURE | M + 1 (% Intensity) |
|---|---|---|
| 71 | 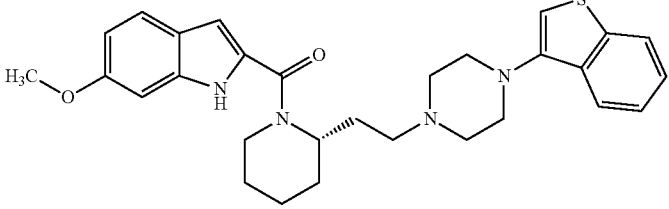 | 503 100% |
| 72 | 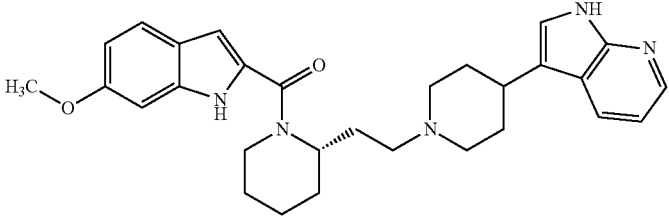 [SMILES: COc1ccc2cc(C(=O)N3CCCC[C@H]3CCN3CCC(c4c[nH]c5ncccc45)CC3)[nH]c2c1] | 486 100% |
| 73 | 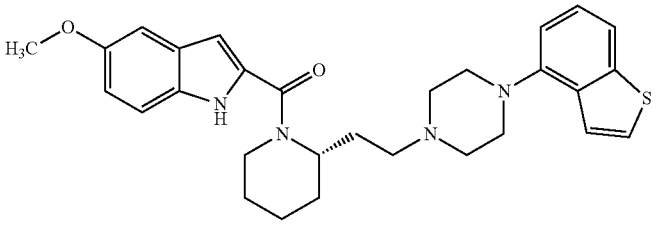 [SMILES: COc1ccc2[nH]c(C(=O)N3CCCC[C@H]3CCN3CCN(c4cccc5sccc45)CC3)cc2c1] | 503 100% |
| 74 | 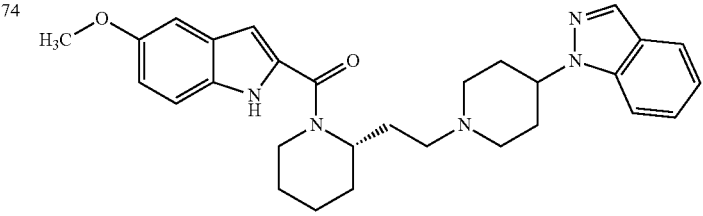 | 486 100% |
| 75 | 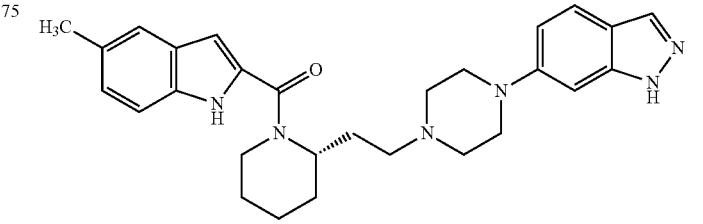 | 471 100% |
| 76 | 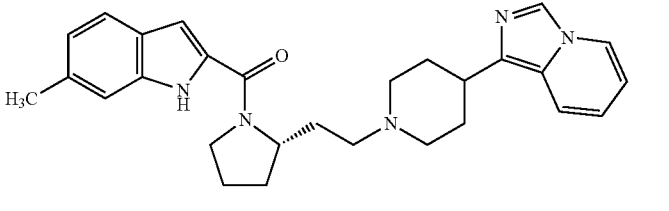 [SMILES: Cc1ccc2cc(C(=O)N3CCC[C@H]3CCN3CCC(c4ncn5ccccc45)CC3)[nH]c2c1] | 456 100% |

TABLE 4-continued

| Ex. No. | STRUCTURE | M + 1 (% Intensity) |
|---|---|---|
| 77 | 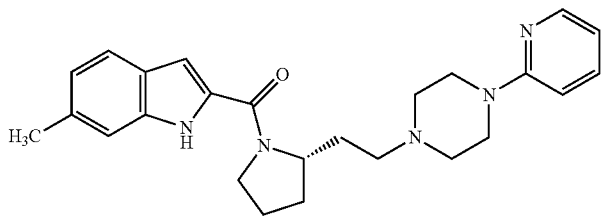 [SMILES: Cc1ccc2cc(C(=O)N3CCC[C@H]3CCN3CCN(c4ccccn4)CC3)[nH]c2c1] | 418 100% |
| 78 | 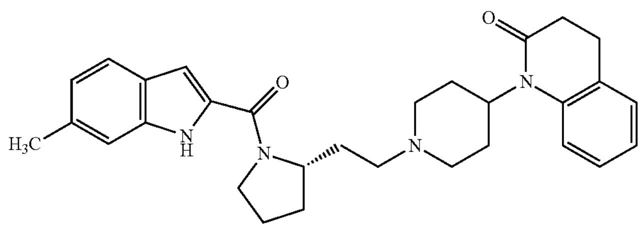 [SMILES: Cc1ccc2cc(C(=O)N3CCC[C@H]3CCN3CCC(N4C(=O)CCc5ccccc54)CC3)[nH]c2c1] | 483 100% |
| 79 | 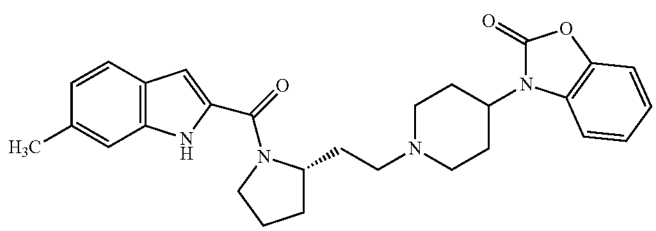 [SMILES: Cc1ccc2cc(C(=O)N3CCC[C@H]3CCN3CCC(n4c(=O)oc5ccccc54)CC3)[nH]c2c1] | 473 100% |
| 80 | 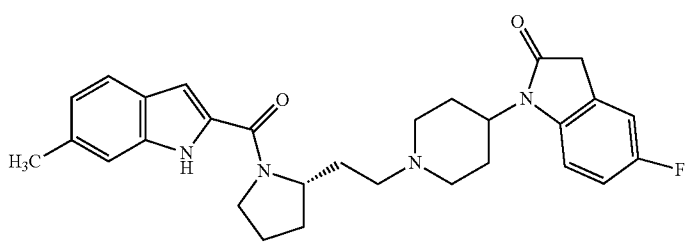 [SMILES: Cc1ccc2cc(C(=O)N3CCC[C@H]3CCN3CCC(N4C(=O)Cc5cc(F)ccc54)CC3)[nH]c2c1] | 490 100% |
| 81 | 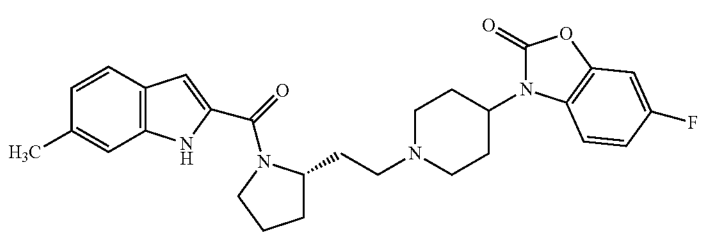 [SMILES: Cc1ccc2cc(C(=O)N3CCC[C@H]3CCN3CCC(n4c(=O)oc5cc(F)ccc54)CC3)[nH]c2c1] | 491 100% |
| 82 | 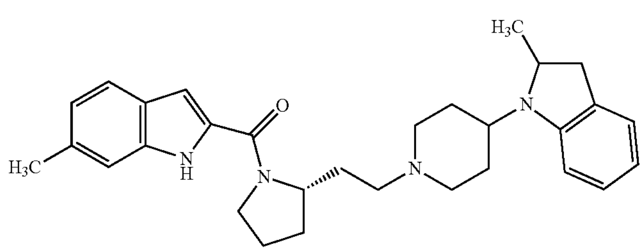 [SMILES: Cc1ccc2cc(C(=O)N3CCC[C@H]3CCN3CCC(N4c5ccccc5CC4C)CC3)[nH]c2c1] | 471 100% |

TABLE 4-continued
| Ex. No. | STRUCTURE | M + 1 (% Intensity) |
|---|---|---|
| 83 | 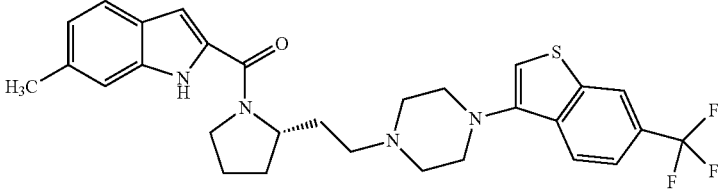 [SMILES: Cc1ccc2cc(C(=O)N3CCC[C@H]3CCN3CCN(c4csc5cc(C(F)(F)F)ccc45)CC3)[nH]c2c1] | 541 100% |
| 84 | 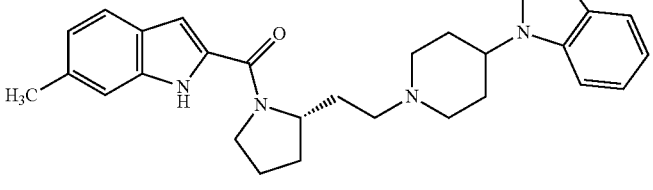 | 456 100% |
| 85 | 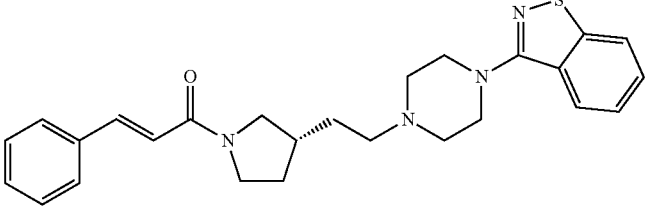 | 447 100% |
| 86 | 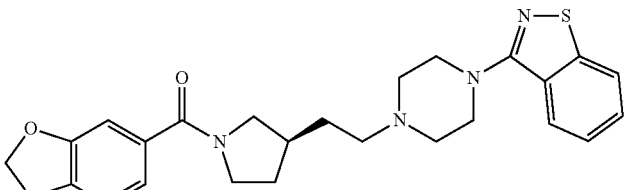 | 465 100% |
TABLE 5
| Ex. No. | STRUCTURE | M + 1 (% Intensity) |
|---|---|---|
| 87 | 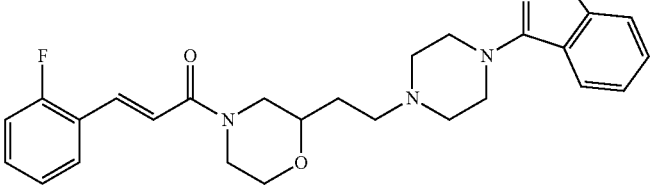 | 481 100% |
| 88 | 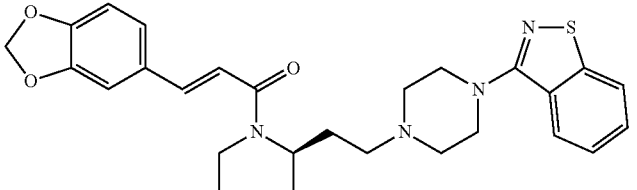 | 505 100% |

TABLE 5-continued

| Ex. No. | STRUCTURE | M + 1 (% Intensity) |
|---|---|---|
| 89 | 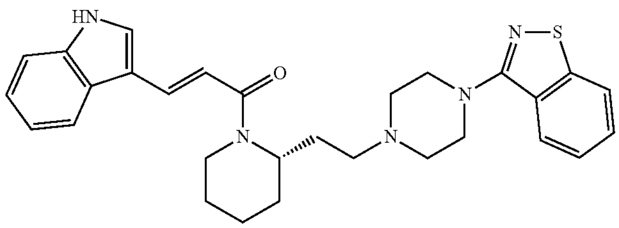 [SMILES: O=C(/C=C/c1c[nH]c2ccccc12)N1CCCC[C@H]1CCN1CCN(c2nsc3ccccc23)CC1] | 500 100% |
| 90 | 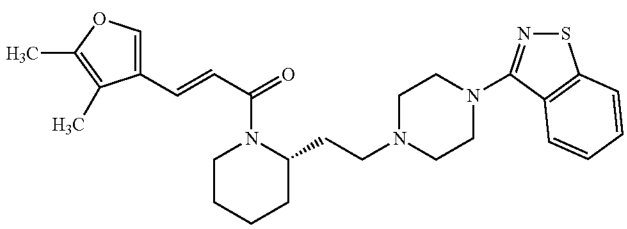 [SMILES: Cc1occ(/C=C/C(=O)N2CCCC[C@H]2CCN2CCN(c3nsc4ccccc34)CC2)c1C] | 479 100% |
| 91 | 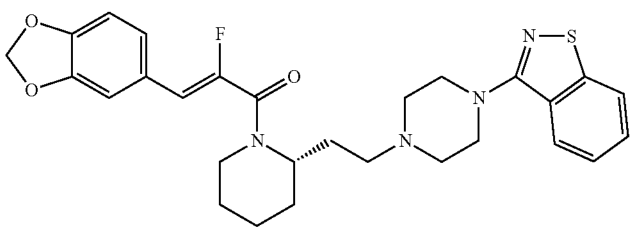 [SMILES: O=C(/C(F)=C/c1ccc2c(c1)OCO2)N1CCCC[C@H]1CCN1CCN(c2nsc3ccccc23)CC1] | 523 100% |
| 92 | 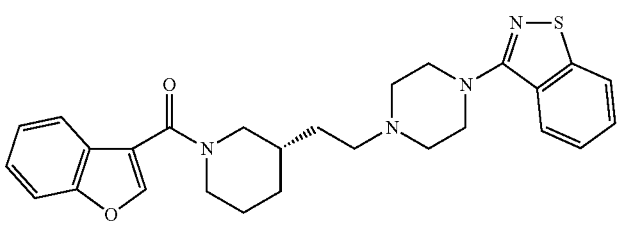 [SMILES: O=C(c1coc2ccccc12)N1CCC[C@@H](CCN2CCN(c3nsc4ccccc34)CC2)C1] | 475 100% |
| 93 | 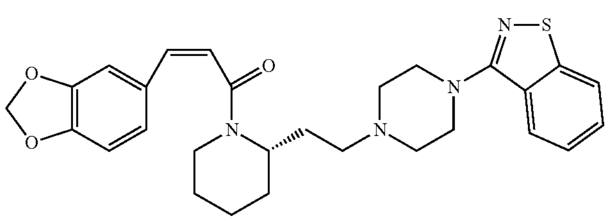 [SMILES: O=C(/C=C\c1ccc2c(c1)OCO2)N1CCCC[C@H]1CCN1CCN(c2nsc3ccccc23)CC1] | 505 100% |
| 94 | 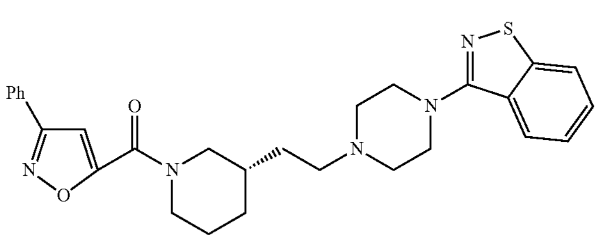 [SMILES: O=C(c1cc(-c2ccccc2)no1)N1CCC[C@@H](CCN2CCN(c3nsc4ccccc34)CC2)C1] | 502 100% |

TABLE 5-continued
| Ex. No. | STRUCTURE | M + 1 (% Intensity) |
|---|---|---|
| 95 | 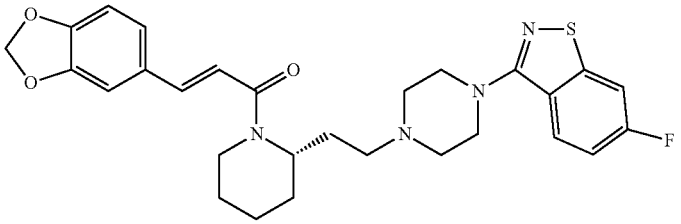 [SMILES: O=C(/C=C/c1ccc2c(c1)OCO2)N1CCCC[C@H]1CCN1CCN(c2nsc3cc(F)ccc23)CC1] | 523 100% |
| 96 | 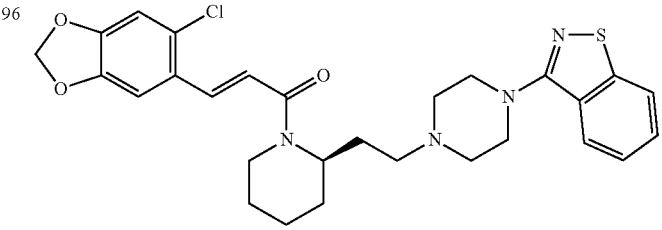 | 539 100% |
| 97 | 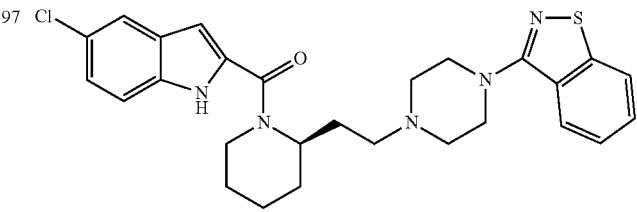 | 508 100% |
| 98 | 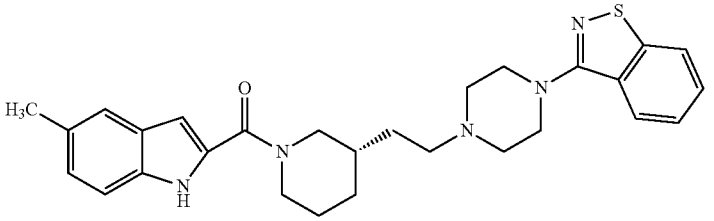 [SMILES: Cc1ccc2[nH]c(C(=O)N3CCC[C@@H](CCN4CCN(c5nsc6ccccc56)CC4)C3)cc2c1] | 488 100% |
| 99 | 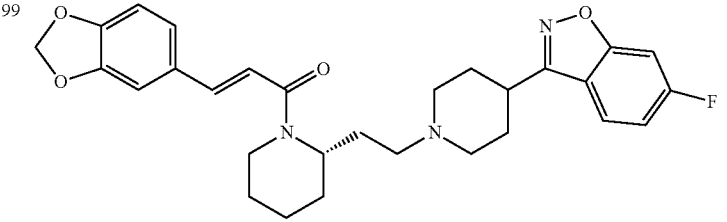 | 506 100% |
| 100 | 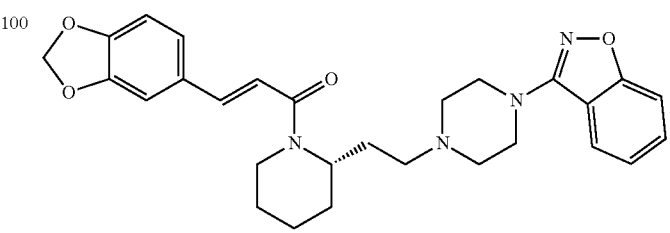 | 489 100% |

TABLE 5-continued

| Ex. No. | STRUCTURE | M + 1 (% Intensity) |
|---|---|---|
| 101 | 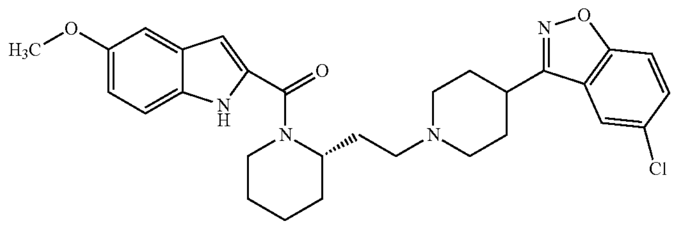 [SMILES: COc1ccc2[nH]c(C(=O)N3CCCC[C@H]3CCN3CCC(c4noc5ccc(Cl)cc45)CC3)cc2c1] | 522 100% |
| 102 | 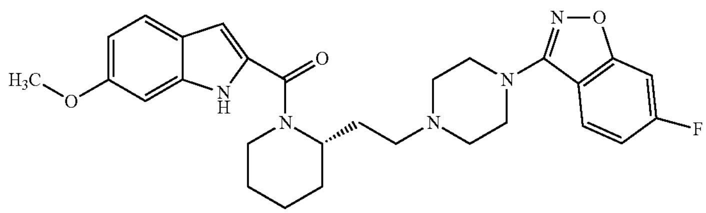 [SMILES: COc1ccc2cc(C(=O)N3CCCC[C@H]3CCN3CCN(c4noc5cc(F)ccc45)CC3)[nH]c2c1] | 506 100% |
| 103 | 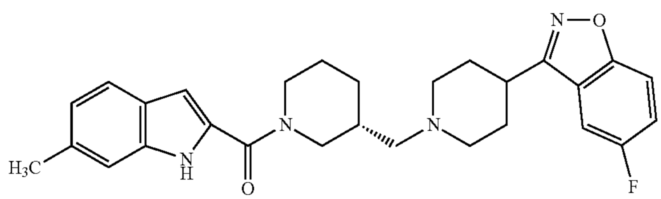 [SMILES: Cc1ccc2cc(C(=O)N3CCC[C@H](CN4CCC(c5noc6ccc(F)cc56)CC4)C3)[nH]c2c1] | 475 100% |
| 104 | 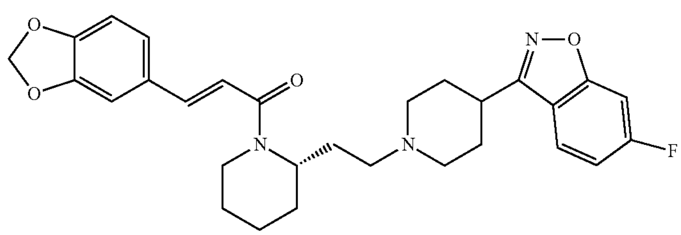 [SMILES: O=C(/C=C/c1ccc2c(c1)OCO2)N1CCCC[C@H]1CCN1CCC(c2noc3cc(F)ccc23)CC1] | 506 100% |
| 105 | 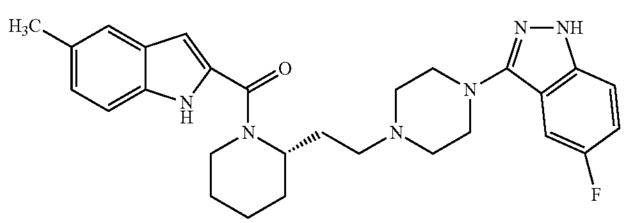 [SMILES: Cc1ccc2[nH]c(C(=O)N3CCCC[C@H]3CCN3CCN(c4n[nH]c5ccc(F)cc45)CC3)cc2c1] | 489 100% |
| 106 | 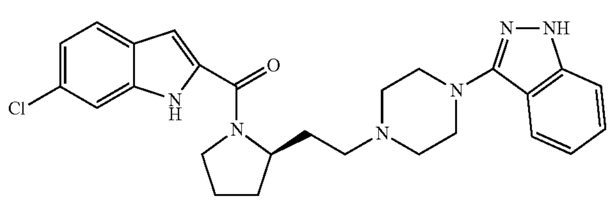 [SMILES: O=C(c1cc2ccc(Cl)cc2[nH]1)N1CCC[C@@H]1CCN1CCN(c2n[nH]c3ccccc23)CC1] | 477 100% |
| 107 | 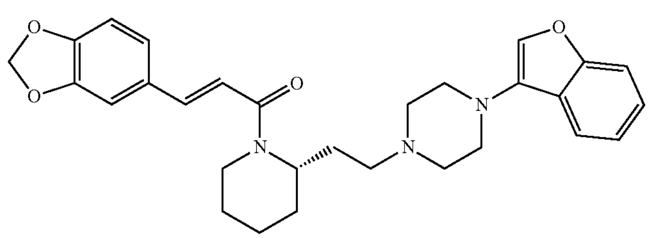 [SMILES: O=C(/C=C/c1ccc2c(c1)OCO2)N1CCCC[C@H]1CCN1CCN(c2coc3ccccc23)CC1] | 488 100% |

TABLE 5-continued

| Ex. No. | STRUCTURE | M + 1 (% Intensity) |
|---|---|---|
| 108 | 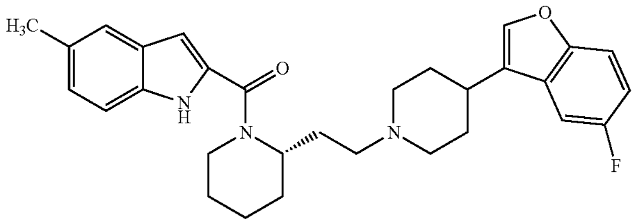 [SMILES: Cc1ccc2[nH]c(C(=O)N3CCCC[C@H]3CCN3CCC(c4coc5ccc(F)cc45)CC3)cc2c1] | 488 100% |
| 109 | 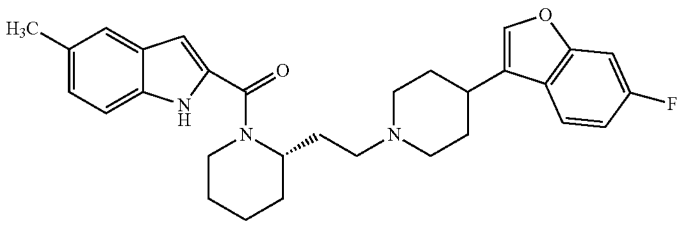 [SMILES: Cc1ccc2[nH]c(C(=O)N3CCCC[C@H]3CCN3CCC(c4coc5cc(F)ccc45)CC3)cc2c1] | 488 100% |
| 110 | 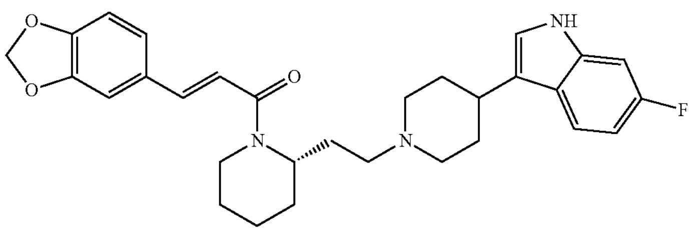 [SMILES: O=C(/C=C/c1ccc2c(c1)OCO2)N1CCCC[C@H]1CCN1CCC(c2c[nH]c3cc(F)ccc23)CC1] | 504 100% |
| 111 | 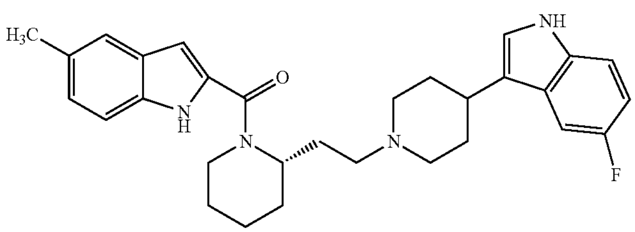 [SMILES: Cc1ccc2[nH]c(C(=O)N3CCCC[C@H]3CCN3CCC(c4c[nH]c5ccc(F)cc45)CC3)cc2c1] | 487 100% |
| 112 | 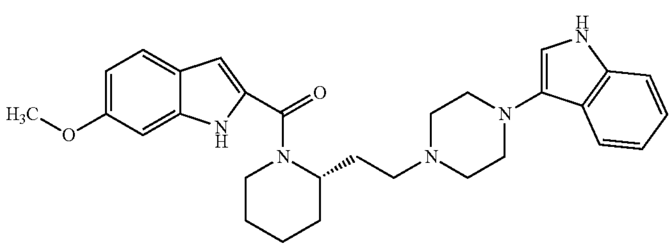 [SMILES: COc1ccc2cc(C(=O)N3CCCC[C@H]3CCN3CCN(c4c[nH]c5ccccc45)CC3)[nH]c2c1] | 486 100% |

TABLE 6

| Ex. No. | STRUCTURE | M + 1 (% Intensity) |
|---|---|---|
| 113 | 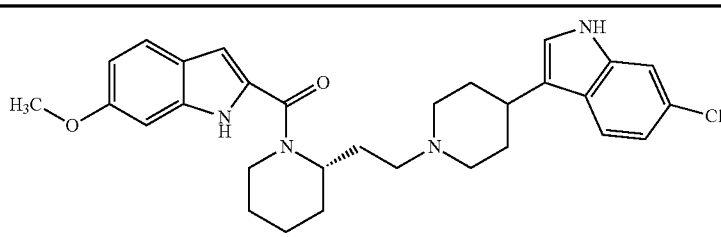 | 519 100% |

TABLE 6-continued

| Ex. No. | STRUCTURE | M + 1 (% Intensity) |
|---|---|---|
| 114 | 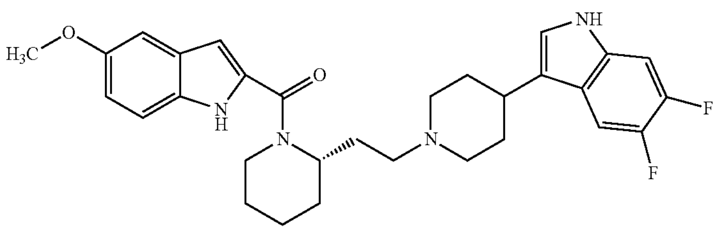 [SMILES: COc1ccc2[nH]c(C(=O)N3CCCC[C@H]3CCN3CCC(c4c[nH]c5cc(F)c(F)cc45)CC3)cc2c1] | 521 100% |
| 115 | 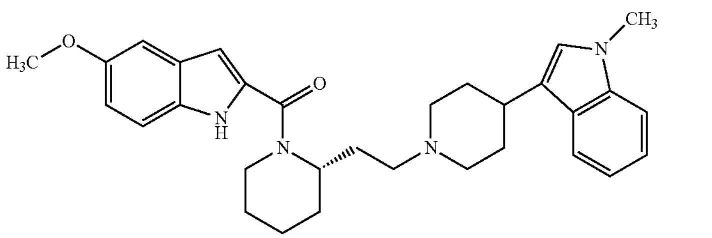 [SMILES: COc1ccc2[nH]c(C(=O)N3CCCC[C@H]3CCN3CCC(c4cn(C)c5ccccc45)CC3)cc2c1] | 499 100% |
| 116 | 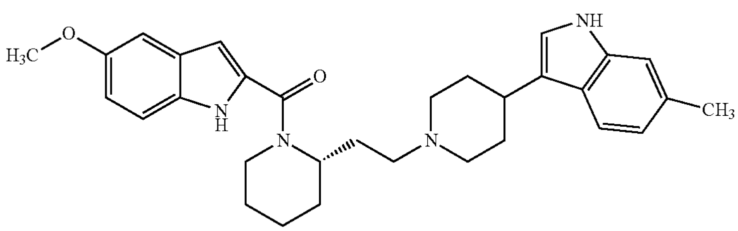 | 499 100% |
| 117 | 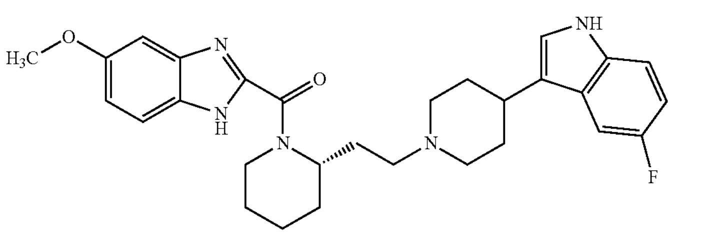 [SMILES: COc1ccc2[nH]c(C(=O)N3CCCC[C@H]3CCN3CCC(c4c[nH]c5ccc(F)cc45)CC3)nc2c1] | 504 100% |
| 118 | 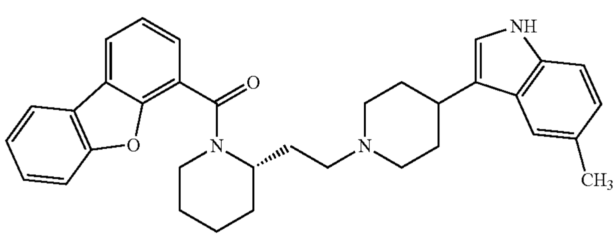 [SMILES: Cc1ccc2[nH]cc(C3CCN(CC[C@@H]4CCCCN4C(=O)c4cccc5c4oc4ccccc45)CC3)c2c1] | 520 100% |
| 119 | 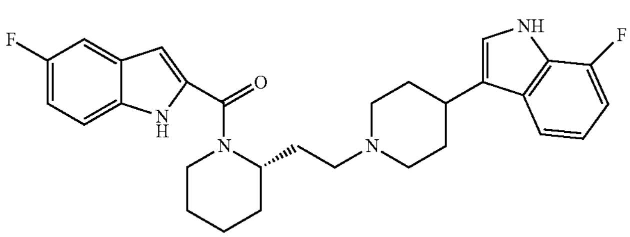 [SMILES: O=C(c1cc2cc(F)ccc2[nH]1)N1CCCC[C@H]1CCN1CCC(c2c[nH]c3c(F)cccc23)CC1] | 491 100% |

TABLE 6-continued

| Ex. No. | STRUCTURE | M + 1 (% Intensity) |
|---|---|---|
| 120 | 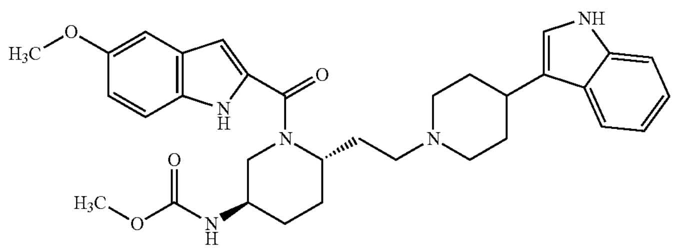 [SMILES: COC(=O)N[C@@H]1CC[C@@H](CCN2CCC(c3c[nH]c4ccccc34)CC2)N(C(=O)c2cc3cc(OC)ccc3[nH]2)C1] | 558 100% |
| 121 | 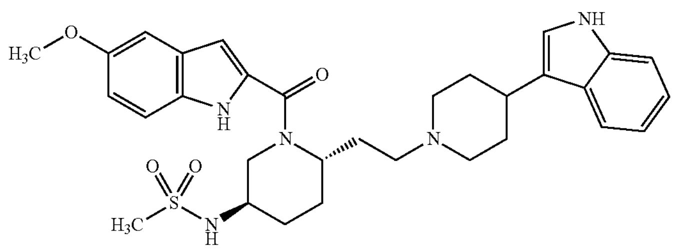 [SMILES: COc1ccc2[nH]c(C(=O)N3C[C@H](NS(C)(=O)=O)CC[C@H]3CCN3CCC(c4c[nH]c5ccccc45)CC3)cc2c1] | 578 100% |
| 122 | 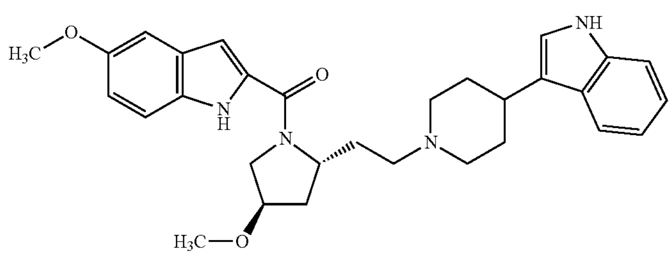 [SMILES: COc1ccc2[nH]c(C(=O)N3C[C@H](OC)C[C@H]3CCN3CCC(c4c[nH]c5ccccc45)CC3)cc2c1] | 501 100% |
| 123 | 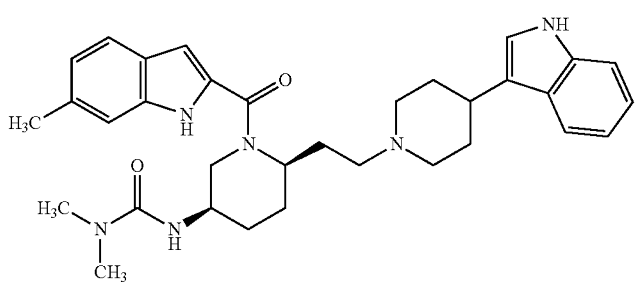 [SMILES: Cc1ccc2cc(C(=O)N3C[C@H](NC(=O)N(C)C)CC[C@@H]3CCN3CCC(c4c[nH]c5ccccc45)CC3)[nH]c2c1] | 555 100% |
| 124 | 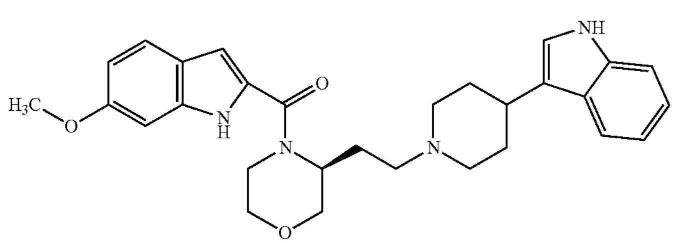 [SMILES: COc1ccc2cc(C(=O)N3CCOC[C@@H]3CCN3CCC(c4c[nH]c5ccccc45)CC3)[nH]c2c1] | 487 100% |
| 125 | 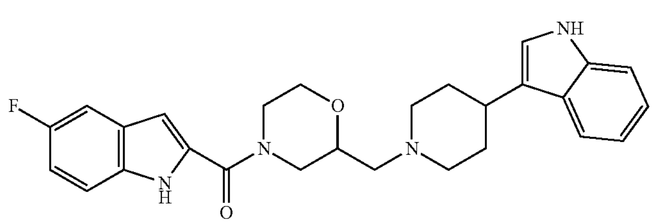 [SMILES: O=C(c1cc2cc(F)ccc2[nH]1)N1CCOC(CN2CCC(c3c[nH]c4ccccc34)CC2)C1] | 461 100% |

TABLE 6-continued

| Ex. No. | STRUCTURE | M + 1 (% Intensity) |
|---|---|---|
| 126 | 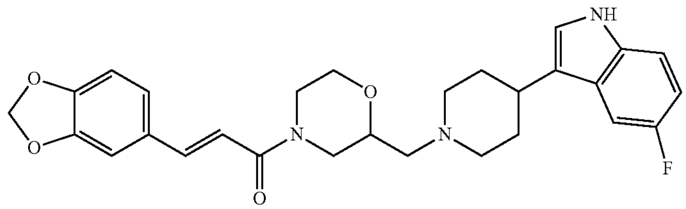 [SMILES: O=C(/C=C/c1ccc2c(c1)OCO2)N1CCOC(CN2CCC(c3c[nH]c4ccc(F)cc34)CC2)C1] | 492 100% |
| 127 | 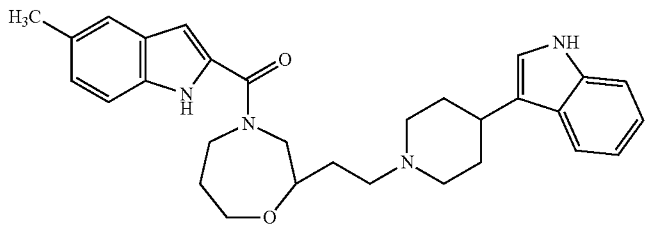 [SMILES: Cc1ccc2[nH]c(C(=O)N3CCCOC(CCN4CCC(c5c[nH]c6ccccc56)CC4)C3)cc2c1] | 485 100% |
| 128 | 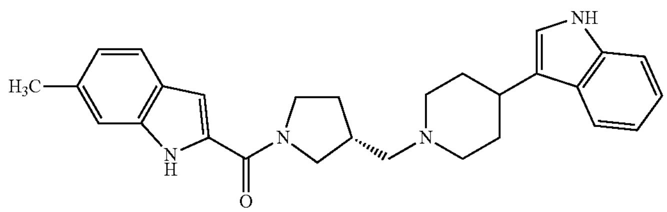 [SMILES: Cc1ccc2cc(C(=O)N3CC[C@H](CN4CCC(c5c[nH]c6ccccc56)CC4)C3)[nH]c2c1] | 485 100% |
| 129 | 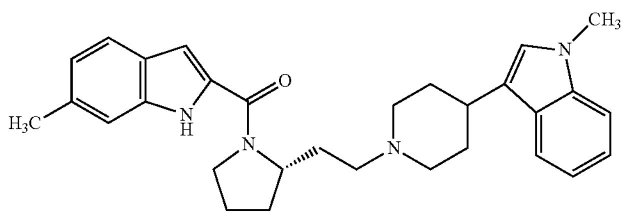 [SMILES: Cc1ccc2cc(C(=O)N3CCC[C@H]3CCN3CCC(c4cn(C)c5ccccc45)CC3)[nH]c2c1] | 469 100% |
| 130 | 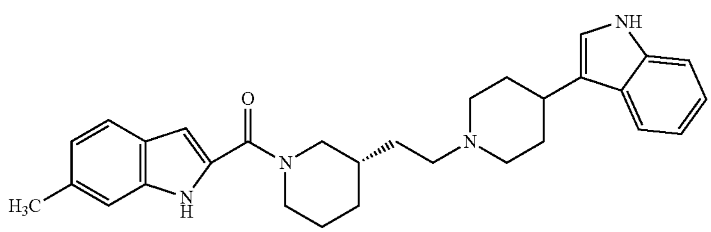 [SMILES: Cc1ccc2cc(C(=O)N3CCC[C@@H](CCN4CCC(c5c[nH]c6ccccc56)CC4)C3)[nH]c2c1] | 469 100% |
| 131 | 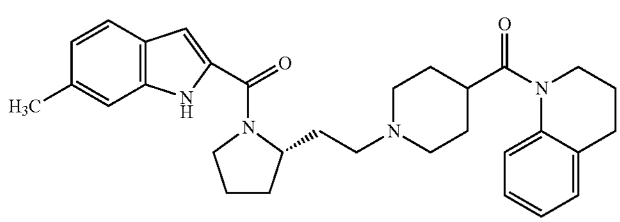 [SMILES: Cc1ccc2cc(C(=O)N3CCC[C@H]3CCN3CCC(C(=O)N4CCCc5ccccc54)CC3)[nH]c2c1] | 499 100% |
| 132 | 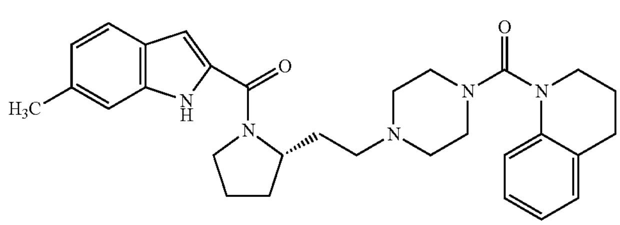 [SMILES: Cc1ccc2cc(C(=O)N3CCC[C@H]3CCN3CCN(C(=O)N4CCCc5ccccc54)CC3)[nH]c2c1] | 500 100% |

TABLE 6-continued

| Ex. No. | STRUCTURE | M + 1 (% Intensity) |
|---|---|---|
| 133 | 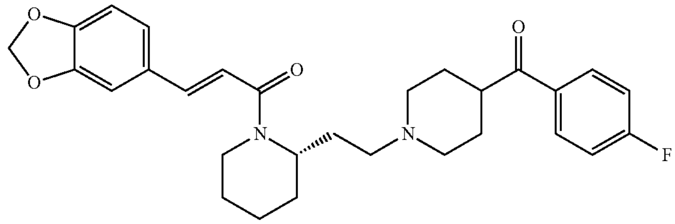 [SMILES: O=C(c1ccc(F)cc1)C1CCN(CC[C@@H]2CCCCN2C(=O)/C=C/c2ccc3c(c2)OCO3)CC1] | 493 100% |
| 134 | 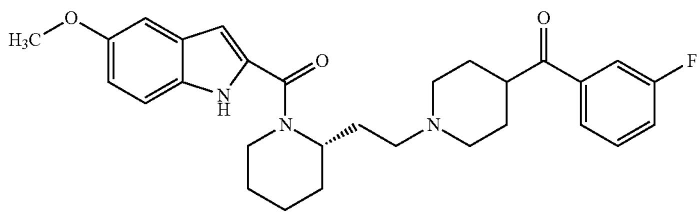 [SMILES: COc1ccc2[nH]c(C(=O)N3CCCC[C@H]3CCN3CCC(C(=O)c4cccc(F)c4)CC3)cc2c1] | 492 100% |
| 135 | 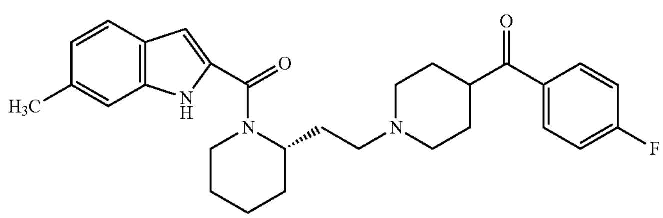 [SMILES: Cc1ccc2cc(C(=O)N3CCCC[C@H]3CCN3CCC(C(=O)c4ccc(F)cc4)CC3)[nH]c2c1] | 476 100% |
| 136 | 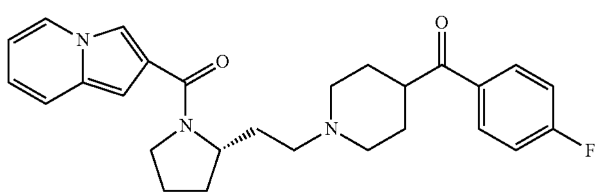 [SMILES: O=C(c1ccc(F)cc1)C1CCN(CC[C@@H]2CCCN2C(=O)c2cc3ccccn3c2)CC1] | 448 100% |
| 137 | 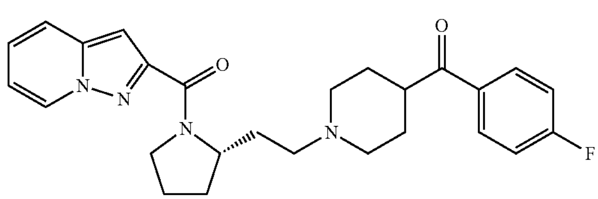 [SMILES: O=C(c1ccc(F)cc1)C1CCN(CC[C@@H]2CCCN2C(=O)c2cc3ccccn3n2)CC1] | 449 100% |
| 138 | 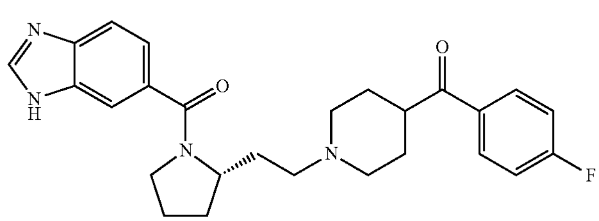 [SMILES: O=C(c1ccc(F)cc1)C1CCN(CC[C@@H]2CCCN2C(=O)c2ccc3nc[nH]c3c2)CC1] | 449 100% |

TABLE 7

| Ex. No. | STRUCTURE | M + 1 (% Intensity) |
|---|---|---|
| 139 | 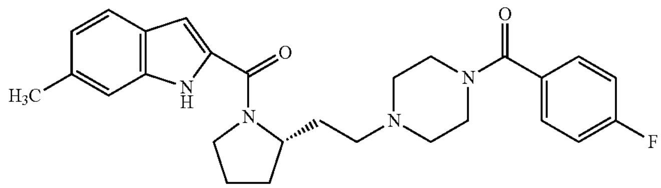 | 463 100% |
| 140 | 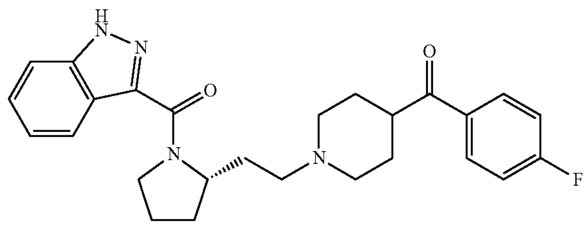 [SMILES: O=C(c1ccc(F)cc1)C1CCN(CC[C@@H]2CCCN2C(=O)c2n[nH]c3ccccc23)CC1] | 449 100% |
| 141 | 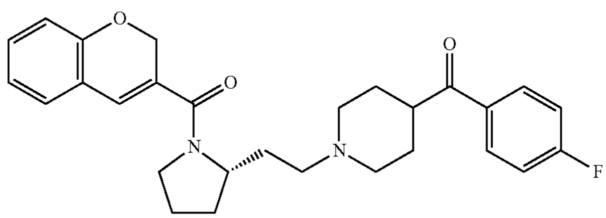 [SMILES: O=C(c1ccc(F)cc1)C1CCN(CC[C@@H]2CCCN2C(=O)C2=Cc3ccccc3OC2)CC1] | 463 100% |
| 142 | 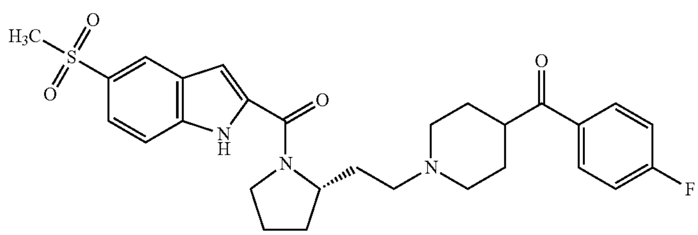 [SMILES: CS(=O)(=O)c1ccc2[nH]c(C(=O)N3CCC[C@H]3CCN3CCC(C(=O)c4ccc(F)cc4)CC3)cc2c1] | 526 70% |
| 143 | 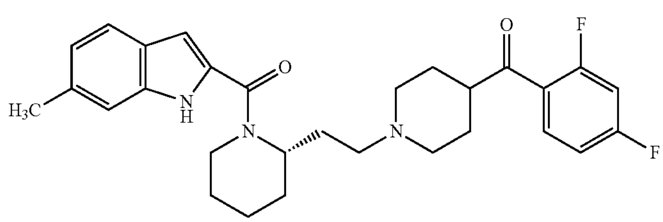 [SMILES: Cc1ccc2cc(C(=O)N3CCCC[C@H]3CCN3CCC(C(=O)c4ccc(F)cc4F)CC3)[nH]c2c1] | 494 100% |
| 144 | 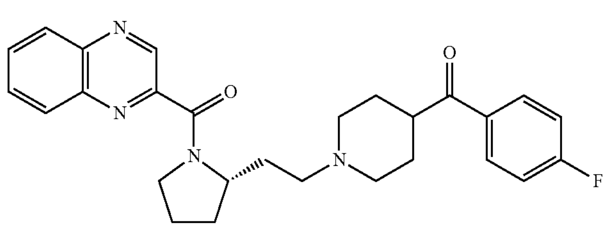 [SMILES: O=C(c1ccc(F)cc1)C1CCN(CC[C@@H]2CCCN2C(=O)c2cnc3ccccc3n2)CC1] | 461 100% |

TABLE 7-continued
| Ex. No. | STRUCTURE | M + 1 (% Intensity) |
|---|---|---|
| 145 | 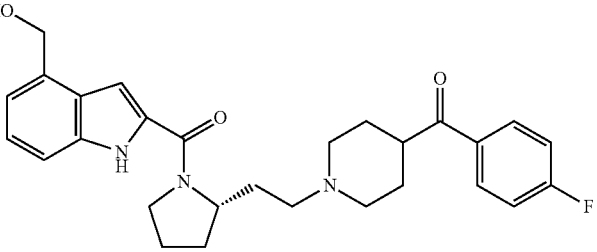 | 478 100% |
| 146 | 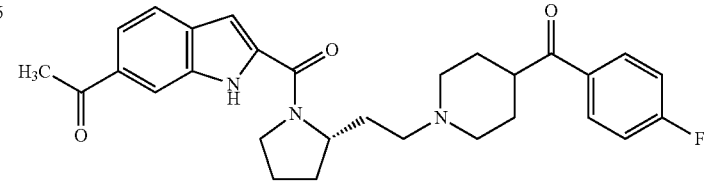 | 490 100% |
| 147 | 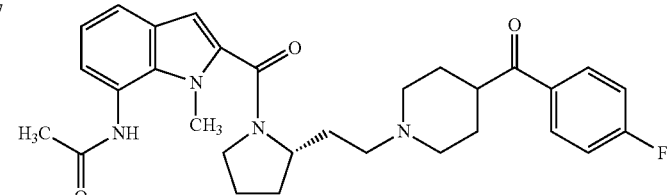 | 519 100% |
| 148 | 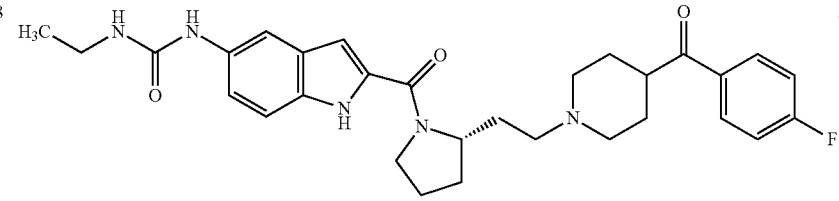 | 534 100% |
| 149 | 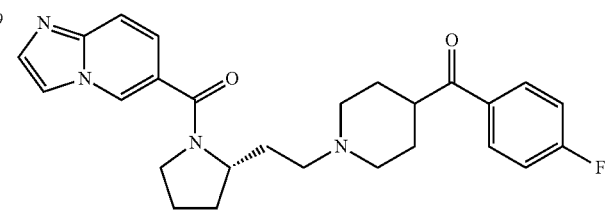 | 449 80% |
| 150 | 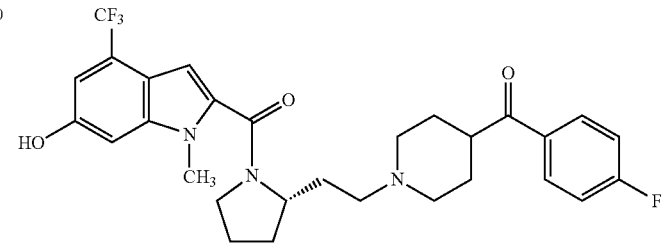 | 545 100% |
| 151 | 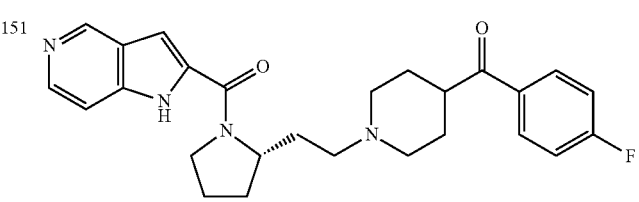 | 449 100% |

TABLE 7-continued
| Ex. No. | STRUCTURE | M + 1 (% Intensity) |
|---|---|---|
| 152 | 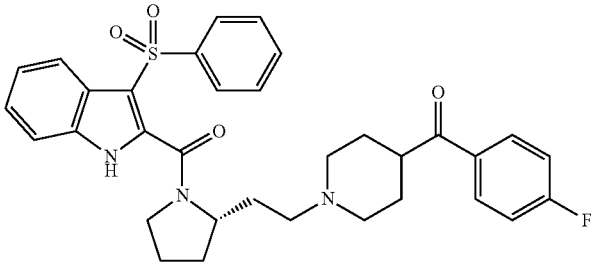 [SMILES: O=C(c1ccc(F)cc1)C1CCN(CC[C@@H]2CCCN2C(=O)c2[nH]c3ccccc3c2S(=O)(=O)c2ccccc2)CC1] | 588 100% |
| 153 | 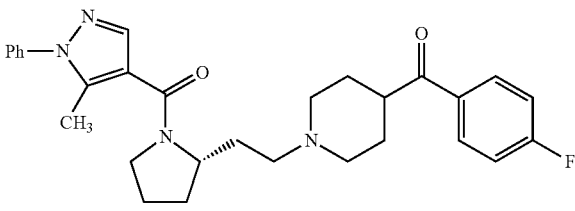 [SMILES: Cc1c(C(=O)N2CCC[C@H]2CCN2CCC(C(=O)c3ccc(F)cc3)CC2)cnn1-c1ccccc1] | 489 100% |
| 154 | 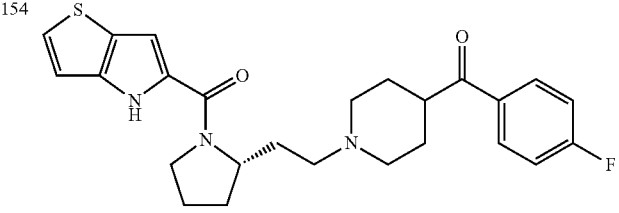 | 454 100% |
| 155 | 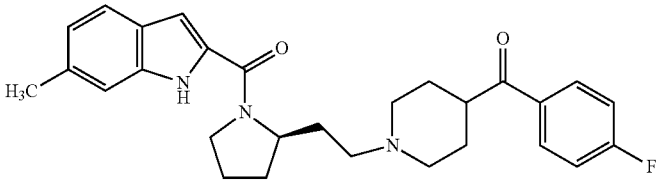 [SMILES: Cc1ccc2cc(C(=O)N3CCC[C@@H]3CCN3CCC(C(=O)c4ccc(F)cc4)CC3)[nH]c2c1] | 462 100% |
| 156 | 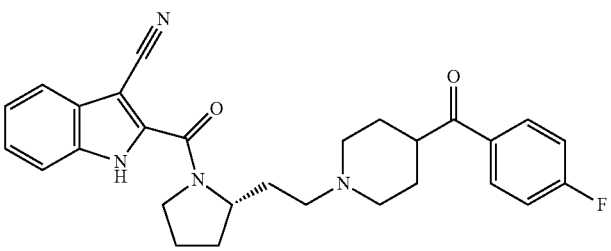 [SMILES: N#Cc1c(C(=O)N2CCC[C@H]2CCN2CCC(C(=O)c3ccc(F)cc3)CC2)[nH]c2ccccc12] | 473 70% |
| 157 | 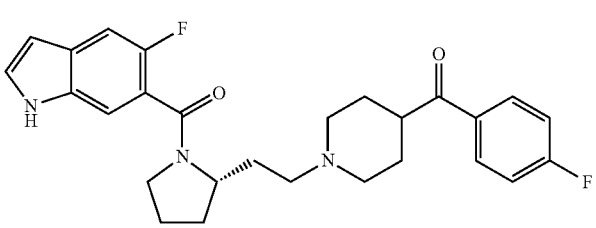 [SMILES: O=C(c1ccc(F)cc1)C1CCN(CC[C@@H]2CCCN2C(=O)c2cc3[nH]ccc3cc2F)CC1] | 466 100% |

TABLE 7-continued

| Ex. No. | STRUCTURE | M + 1 (% Intensity) |
|---|---|---|
| 158 | H₃C-pyridine-C(O)-N-pyrrolidine-CH₂CH₂-N-piperidine-C(O)-C₆H₄-F | 424 100% |

Example 159

(S)-(6-Fluoro-1H-indol-2-yl)(2-(2-(4-(4-fluorobenzoyl)piperidin-1-yl)ethyl)pyrrolidin-1-yl)-methanone

[Chemical Formula 113]

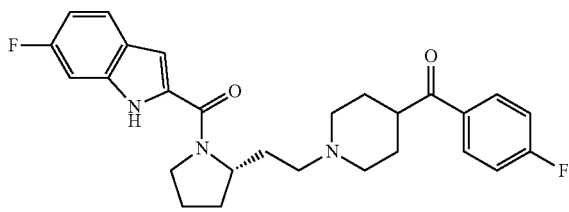

The title compound was obtained by the same procedure as Example 1 using intermediate 1 and commercially available materials.

¹H-NMR (300 MHz, CDCl₃) δ 9.53-9.64 (m, 1H), 7.96 (dd, 2H, J=8.4 Hz, 5.5 Hz), 7.57-7.69 (m, 1H), 7.08-7.16 (m, 3H), 6.86-6.94 (m, 2H), 4.42-4.57 (m, 1H), 3.84-3.98 (m, 2H), 3.18-3.28 (m, 1H), 3.03-3.12 (m, 2H), 2.51-2.53 (m, 2H), 2.01-2.22 (m, 6H), 1.60-1.88 (m, 6H).

Example 160

(S)-(2-(2-(4-(4-Fluorobenzoyl)piperidin-1-yl)ethyl)pyrrolidin-1-yl)(6-(trifluoromethoxy)-1H-indol-2-yl)methanone

[Chemical Formula 114]

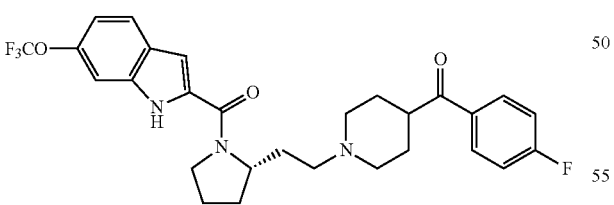

The title compound was obtained by the same procedure as Example 1 using intermediate 1 and commercially available materials.

¹H-NMR (300 MHz, CDCl₃) δ 1.58-1.75 (m, 3H), 1.78-2.08 (m, 6H), 2.10-2.30 (m, 4H), 2.52 (br, 2H), 3.00-3.14 (m, 2H), 3.13-3.25 (m, 1H), 4.33-4.72 (m, 2H), 7.02 (d, J=8.0 Hz, 1H), 7.14 (t, J=8.0 Hz, 2H), 7.35 (br, 1H), 7.61-7.83 (m, 1H), 7.90-8.10 (br, 1H), 10.40 (br, 1H).

MS (ESI+) 532 (M⁺+1, 100%)

Example 161

(S)-(2-(2-(4-(4-Fluorobenzoyl)piperidin-1-yl)ethyl)pyrrolidin-1-yl)(6-isopropyl-1H-indol-2-yl)methanone

[Chemical Formula 115]

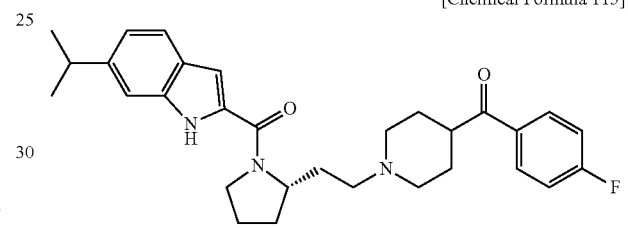

The title compound was obtained by the same procedure as Example 1 using intermediate 1 and commercially available materials.

¹H-NMR (300 MHz, CDCl₃) δ 1.32 (d, J=7.0 Hz, 6H), 1.80-1.88 (m, 2H), 1.88-2.22 (m, 8H), 2.29-2.36 (m, 2H), 3.02 (septet, J=7.0 Hz, 1H), 3.07-3.20 (m, 2H), 3.45-3.52 (m, 1H), 3.84-3.99 (m, 2H), 4.38-4.47 (m, 1H), 6.84 (s, 1H), 7.05 (dd, J=8.3 Hz, J=1.2 Hz, 1H), 7.14 (dd, J=8.7 Hz, J=8.7 Hz, 2H), 7.25 (s, 1H), 7.58 (d, J=8.5 Hz, 1H), 7.94 (dd, J=8.2 Hz, J=5.7 Hz, 2H), 9.16 (s, 1H)

MS (ESI+) 491 (M⁺+1, 41%)

Example 162

(S)-(5-Fluoro-4-methoxy-1H-indol-2-yl)(2-(2-(4-(4-fluorobenzoyl)piperidin-1-yl)ethyl)pyrrolidin-1-yl)methanone

[Chemical Formula 116]

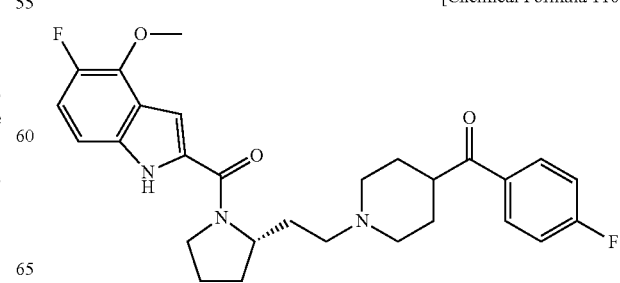

The title compound was obtained by the same procedure as Example 1 using intermediate 1 and intermediate 68.

$^1$H-NMR (300 MHz, CDCl$_3$) δ 1.82-1.84 (m, 5H), 2.02-2.13 (m, 6H), 2.24-2.26 (m, 1H), 2.46-2.49 (m, 2H), 3.00-3.02 (m, 1H), 3.08-3.11 (m, 1H), 3.16-3.18 (m, 1H), 3.90-3.99 (m, 2H), 4.42 (br, 1H), 6.96-7.08 (m, 3H), 7.10-7.15 (m, 2H), 7.93-7.98 (m, 2H), 9.43 (br, 1H).

MS (ESI+) 496 (M$^+$+1, 100%)

Example 163

(S)-(3,6-Difluoro-1H-indol-2-yl)(2-(2-(4-(4-fluorobenzoyl)piperidin-1-yl)ethyl)pyrrolidin-1-yl)methanone

[Chemical Formula 117]

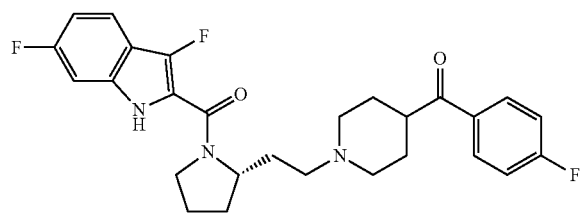

The title compound was obtained by the same procedure as Example 1 using intermediate 1 and intermediate 67.

$^1$H-NMR (300 MHz, CDCl$_3$) δ 9.34 (brs, 1H), 7.95 (dd, J=8.9 Hz, 5.4 Hz, 2H), 7.57 (dd, J=8.9 Hz, 5.2 Hz, 1H), 7.13 (t, J=8.6 Hz, 2H), 6.99-7.02 (m, 1H), 6.90 (dt, J=2.1 Hz, 9.2 Hz, 1H), 4.38 (brs, 1H), 3.80 (brs, 2H), 3.01-3.18 (m, 3H), 2.00-2.51 (m, 7H), 1.65-1.83 (m, 7H). MS (ESI+) 484 (M$^+$+1, 100%)

Example 164

(S)-(3-Fluoro-6-(trifluoromethoxy)-1H-indol-2-yl)(2-(2-(4-(4-fluorobenzoyl)piperidin-1-yl)ethyl)pyrrolidin-1-yl)methanone

[Chemical Formula 118]

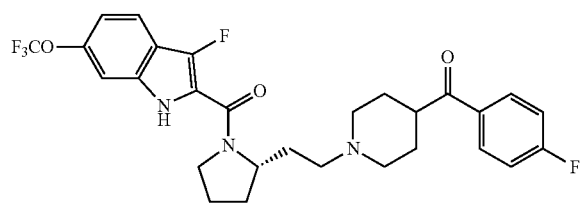

The title compound was obtained by the same procedure as Example 1 using intermediate 1 and intermediate 69.

$^1$H-NMR (300 MHz, CDCl$_3$) δ 9.73-9.83 (m, 1H), 7.95 (dd, J=8.8 Hz, 5.5 Hz, 2H), 7.63 (d, J=8.8 Hz, 1H), 7.21 (s, 1H), 7.10-7.16 (m, 2H), 7.01 (d, J=8.8 Hz, 1H), 4.41 (brs, 1H), 3.80 (brs, 2H), 3.00-3.18 (m, 3H), 2.01-2.54 (m, 7H), 1.67-1.84 (m, 7H). MS (ESI+) 550 (M$^+$+1, 100%)

Example 165

(S)-(3-Fluoro-1H-indol-2-yl)(2-(2-(4-(4-fluorobenzoyl)piperidin-1-yl)ethyl)pyrrolidin-1-yl)methanone

[Chemical Formula 119]

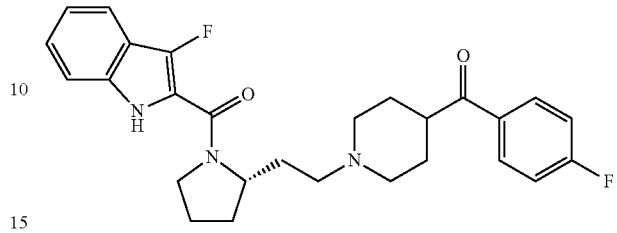

The title compound was obtained by the same procedure as Example 1 using intermediate 1 and intermediate 70.

$^1$H-NMR (300 MHz, CDCl$_3$) δ 8.93 (brs, 1H), 7.95 (dd, J=8.8 Hz, 5.6 Hz, 2H) 7.63 (d, J=8.0 Hz, 1H), 7.28-7.34 (m, 2H), 7.10-7.15 (m, 3H), 4.38 (brs, 1H), 3.81 (brs, 2H), 3.01-3.18 (m, 3H), 2.48 (m, 2H), 1.83-2.31 (m, 12H). MS (ESI+) 466 (M$^+$+1, 100%)

Example 166

((2S,5S)-2-(2-(4-(4-Fluorobenzoyl)piperidin-1-yl)ethyl)-5-methylpyrrolidin-1-yl)(6-methyl-1H-indol-2-yl)methanone

[Chemical Formula 120]

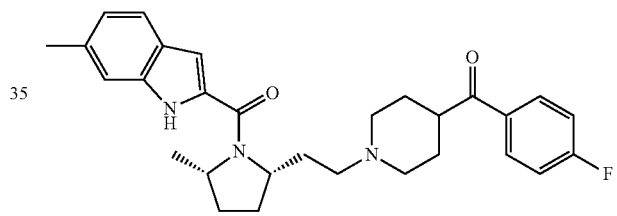

The title compound was obtained by the same procedure as Example 1 using intermediate 71 and commercially available materials.

$^1$H-NMR (300 MHz, CDCl$_3$) δ 1.44 (d, J=4.0 Hz, 3H), 1.53-2.08 (m, 8H), 2.04-2.22 (m, 2H), 2.45 (s, 3H), 2.44-2.53 (m, 2H), 2.57-2.77 (m, 1H), 3.03-3.12 (m, 2H), 3.16-3.29 (m, 2H), 4.20-4.55 (m, 2H), 6.90-6.99 (m, 1H), 7.09-7.18 (m, 3H), 7.30-7.36 (m, 1H), 7.92-8.03 (m, 2H), 9.70 (br, 1H). MS (ESI+) 476 (M$^+$+1, 100%)

Example 167

((2S,5S)-2-(2-(4-(4-Fluorobenzoyl)piperidin-1-yl)ethyl)-5-methylpyrrolidin-1-yl)(6-(trifluoromethyl)-1H-indol-2-yl)methanone

[Chemical Formula 121]

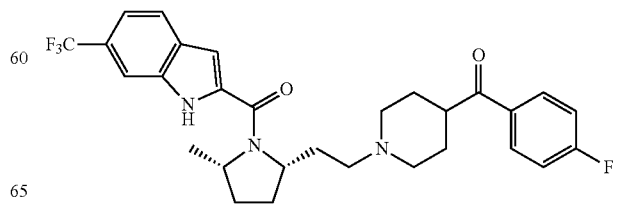

The title compound was obtained by the same procedure as Example 1 using intermediate 71 and commercially available materials.

¹H-NMR (300 MHz, DMSO d₆) δ 1.36 (d, J=4.0 Hz, 3H), 1.30-1.40 (m, 12H), 2.94-3.30 (m, 5H), 3.50-3.76 (m, 1H), 4.18-4.40 (m, 1H), 7.07 (br, 1H), 7.30-7.43 (m, 3H), 7.73-7.84 (m, 2H), 8.05-8.13 (m, 2H), 12.02 (br, 1H). MS (ESI+) 530 (M⁺+1, 100%)

Example 168

((2S,5S)-2-(2-(4-(4-Fluorobenzoyl)piperidin-1-yl)ethyl)-5-methylpyrrolidin-1-yl)(6-(trifluoromethylthio)-1H-indol-2-yl)methanone

[Chemical Formula 122]

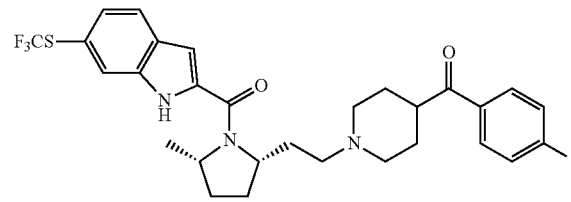

The title compound was obtained by the same procedure as Example 1 using intermediate 71 and commercially available materials.

¹H-NMR (300 MHz, DMSO d₆) δ 1.36 (d, J=8.0 Hz, 3H), 1.60-1.80 (m, 1H), 2.02-2.23 (m, 10H), 2.24-2.40 (m, 1H), 2.97-3.23 (m, 5H), 3.02-3.73 (m, 1H), 4.19-4.25 (m, 1H), 7.04 (br, 1H), 7.31 (d, J=8.0 Hz, 1H), 7.33-7.42 (m, 2H), 7.79-7.84 (m, 2H), 8.04-8.12 (2H, m), 11.96 (br, 1H). MS (ESI+) 562 (M⁺+1, 100%)

Example 169

(S)-(2-(2-(4-(4-Fluorobenzoyl)piperidin-1-yl)ethyl)pyrrolidin-1-yl)(1-methyl-1H-indol-5-yl)methanone

[Chemical Formula 123]

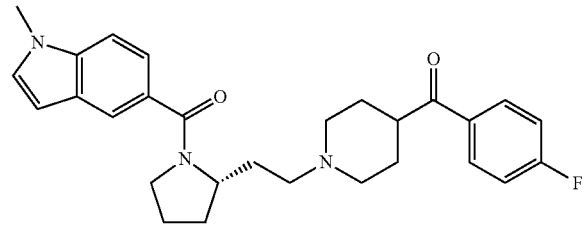

The title compound was obtained by the same procedure as Example 1 using intermediate 1 and commercially available materials.

¹H-NMR (300 MHz, CDCl₃) δ 7.96 (brs, 2H), 7.82 (brs, 1H), 7.42-7.45 (m, 1H), 7.31 (d, J=8.3 Hz, 1H), 7.09-7.17 (m, 3H), 6.52 (d, J=2.4 Hz, 1H), 4.17-4.40 (m, 1H), 3.81 (s, 3H), 3.51-3.59 (m, 2H), 3.04-3.20 (m, 2H), 2.13-2.53 (m, 3H), 1.66-1.86 (m, 12H). MS (ESI+) 462 (M⁺+1, 95%)

Example 170

(S)-(2-(2-(4-(6-Fluorobenzo[d]isoxazol-3-yl)piperidin-1-yl)ethyl)pyrrolidin-1-yl)(3-phenyl-1H-pyrazol-5-yl)methanone hydrochloride

[Chemical Formula 124]

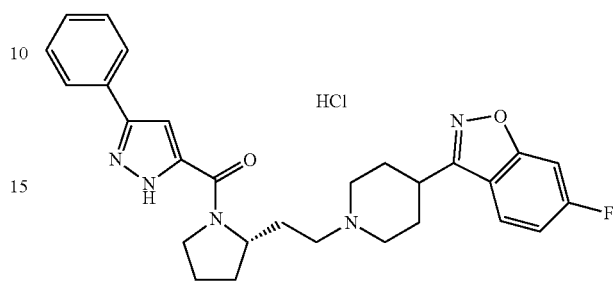

The title compound was obtained by treating a compound obtained by the same procedure as Example 1 using intermediate 1 and commercially available materials in the similar manner to Example 172.

¹H-NMR (300 MHz, DMSO d₆) δ 1.90-2.01 (m, 4H), 2.18-2.37 (m, 5H), 3.11-3.17 (m, 4H), 3.36-3.51 (m, 2H), 3.62-3.77 (m, 2H), 3.80-3.95 (m, 2H), 4.24-4.32 (m, 1H), 7.13 (s, 1H), 7.32-7.36 (m, 2H), 7.42-7.46 (m, 2H), 7.73 (dd, J=9.0 Hz, J=2.2 Hz, 1H), 7.82-7.84 (m, 2H), 8.14-8.21 (m, 1H), 10.2-10.7 (br, 1H)

MS (ESI+) 488 (M⁺+1, 100%)

Example 171

(S)-(3-Fluoro-1H-indol-2-yl)(2-(2-(4-(4-fluorobenzoyl)piperidin-1-yl)ethyl)pyrrolidin-1-yl)methanone hydrobromide

[Chemical Formula 125]

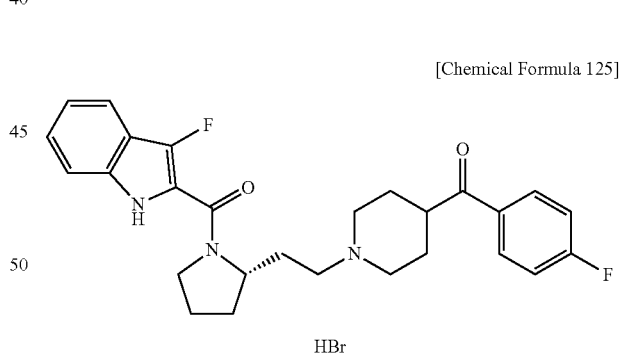

To a suspension of the compound obtained in Example 165 (2.99 g, 6.43 mmol) in methanol (30 mL) was added dropwise 48% aqueous hydrobromic acid solution (0.69 mL, 6.10 mmol), and the obtained solution was concentrated under reduced pressure. To the residue was added a mixed solvent of ethanol/ethyl acetate, and the precipitated crystal was filtered to give the title compound (3.19 g, 5.84 mmol, 96%).

¹H-NMR (300 MHz, DMSO-d₆) δ 11.39 (s, 1H), 9.14 (brs, 1H), 8.09 (dd, J=8.7 Hz, 5.6 Hz, 2H), 7.59 (d, J=8.1 Hz, 1H), 7.36-7.42 (m, 3H), 7.26 (t, J=7.7 Hz, 1H), 7.10 (t, J=7.4 Hz, 1H), 4.23-4.28 (m, 1H), 3.61-3.74 (m, 5H), 3.05-3.21 (m, 3H), 1.76-2.26 (m, 11H).

Example 172

(S)-(3-Fluoro-1H-indol-2-yl)(2-(2-(4-(4-fluorobenzoyl)piperidin-1-yl)ethyl)pyrrolidin-1-yl)methanone hydrochloride

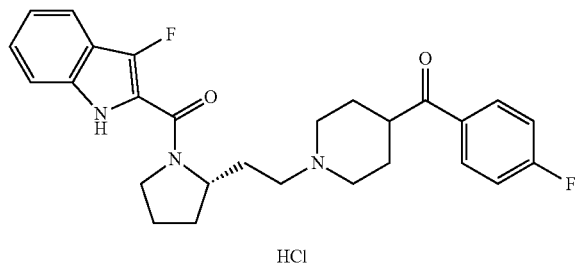

[Chemical Formula 126]

HCl

To a solution of the compound obtained in Example 165 (20 mg, 0.043 mmol) in ethyl acetate (2 mL) was added 4N hydrochloric acid/ethyl acetate (500 μL), and the mixture was stirred, and then ethyl acetate was removed under reduced pressure. The residue was dried under reduced pressure to give the title compound (20 mg).

$^1$H-NMR (DMSO-$d_6$) δ 1.69-1.79 (m, 2H), 1.88-2.00 (m, 6H), 2.10-2.16 (m, 1H), 2.24-2.32 (m, 1H), 3.03-3.18 (m, 4H), 3.57-3.69 (m, 5H), 4.23-4.29 (m, 1H), 7.10 (dd, J=7.6 Hz, J=7.6 Hz, 1H), 7.23-7.27 (m, 1H), 7.37-7.41 (m, 3H), 7.59 (d, J=8.0 Hz, 1H), 8.08 (dd, J=8.5 Hz, J=5.4 Hz, 2H), 10.13 (bs, 1H), 11.42 (s, 1H).

Experimental Example

Experimental Procedure (1) Dopamine $D_{2L}$ Receptor Binding Assay $D_{2L}$ receptor binding assay was performed in reference to a method described by Hirose et al. (Japan. J. Pharmacol., 53, 321-329, 1990). After a reaction in a total volume of 200 μL of 50 mM Tris-HCl (pH=7.6) buffer solution containing 50 μL of [$^3$H]-spiperone (final concentration 0.5 nM), 1 μL of test drug in DMSO, and 149 μL of human $D_{2L}$ receptor-expressing CHO cell membrane sample, human $D_{2L}$ receptor binding activity of [$^3$H]-spiperone was measured. The reaction solution let stand for 60 minutes at room temperature, and then it was quickly added on a glass fiber filter plate (Multiscreen FB, Millipore inc.) coated with 0.3% polyethyleneimine (PEI) and filtered under reduced pressure. The glass fiber filter was washed with 200 μL of ice-cooled 50 mM Tris-HCl (pH=7.6) twice, repeatedly filtered under reduced pressure, and then transferred to a vial containing 4 mL of Ecoscint A (National Diagnostics inc.). The residual radioactivity on the glass fiber filter was measured by a liquid scintillation counter. Nonspecific binding was measured in the presence of 10 μM of spiperone, and [$^3$H]-spiperone binding inhibition rate in the presence of 10 nM of test drug was determined. The larger binding inhibition rate (%) means that test drug has the higher binding affinity for human $D_{2L}$ receptor. The results are shown in Tables 8 to 13.

(2) Serotonin 5-HT$_{2A}$ Receptor Binding Assay

5-HT$_{2A}$ receptor binding assay was performed in reference to a method described by Hirose et al. (Japan. J. Pharmacol., 53, 321-329, 1990). After a reaction in a total volume of 200 μL of 50 mM Tris-HCl (pH=7.6) buffer solution containing 50 μL of [$^3$H]-ketanserin (final concentration 1 nM), 1 μL of test drug in DMSO, and 149 μL of human 5-HT$_{2A}$ receptor-expressing CHO cell membrane sample, human 5-HT$_{2A}$ receptor binding activity of [$^3$H]-ketanserin was measured. The reaction solution let stand for 15 minutes at 37° C., and then it was quickly added on a glass fiber filter plate (Multiscreen FB, Millipore inc.) coated with 0.05% Brij 35 and filtered under reduced pressure. The glass fiber filter was washed with 200 μL of ice-cooled 50 mM Tris-HCl (pH=7.6) twice, repeatedly filtered under reduced pressure, and then transferred to a vial containing 4 mL of Ecoscint A (National Diagnostics inc.). The residual radioactivity on the glass fiber filter was measured by a liquid scintillation counter. Nonspecific binding was measured in the presence of 10 μM of MDL-100907, and [$^3$H]-ketanserin binding inhibition rate in the presence of 1 nM or 10 nM of test drug was determined. The results are shown in Tables 8 to 13.

(3) Serotonin 5-HT$_6$ Receptor Binding Assay

After a reaction in a total volume of 200 μL of 50 mM Tris-HCl (pH=7.6), 4 mM CaCl$_2$, and 0.5 mM EDTA buffer solution containing 50 μL of [$^3$H]-clozapine (final concentration 2 nM), 1 μL of test drug in DMSO, and 149 μL of human 5-HT$_6$ receptor-expressing CHO cell membrane sample, human 5-HT$_6$ receptor binding activity of [$^3$H]-clozapine was measured. The reaction solution let stand for 40 minutes at room temperature, and then it was quickly added on a glass fiber filter plate (Multiscreen FB, Millipore inc.) coated with 0.3% polyethyleneimine (PEI) and filtered under reduced pressure. The glass fiber filter was washed with 200 μL of ice-cooled 50 mM Tris-HCl (pH=7.6) twice, repeatedly filtered under reduced pressure, and then transferred to a vial containing 4 mL of Ecoscint A (National Diagnostics inc.). The residual radioactivity on the glass fiber filter was measured by a liquid scintillation counter. Nonspecific binding was measured in the presence of 10 μM of SB-258585, and [$^3$H]-clozapine binding inhibition rate in the presence of 100 nM of test drug was determined. The results are shown in Tables 8 to 13.

(4) Adrenaline $α_{1D}$ Receptor Binding Assay

After a reaction in a total volume of 200 μL of 50 mM Tris-HCl (pH=7.6) buffer solution containing 50 μL of [$^3$H]-prazosin (final concentration 0.6 nM), 1 μL of test drug in DMSO, and 149 μL of human $α_{1D}$ receptor-expressing CHO cell membrane sample, human $α_{1D}$ receptor binding activity of [$^3$H]-prazosin was measured. The reaction solution let stand for 30 minutes at room temperature, and then it was quickly added on a glass fiber filter plate (Multiscreen FB, Millipore inc.) coated with 0.3% polyethyleneimine (PEI) and filtered under reduced pressure. The glass fiber filter was washed with 200 μL of ice-cooled 50 mM Tris-HCl (pH=7.6) twice, repeatedly filtered under reduced pressure, and then transferred to a vial containing 4 mL of Ecoscint A (National Diagnostics inc.). The residual radioactivity on the glass fiber filter was measured by a liquid scintillation counter. Nonspecific binding was measured in the presence of 1 μM of prazosin, and [$^3$H]-prazosin binding inhibition rate in the presence of 100 nM of test drug was determined. The results are shown in Tables 8 to 13.

TABLE 8

| Ex. No. | STRUCTURE | BINDING INHIBITION RATE (%) | | | | |
|---|---|---|---|---|---|---|
| | | $D_{2L}$ | 5HT2A | | 5HT6 | $\alpha_{1D}$ |
| | | 10 nM | 1 nM | 10 nM | 100 nM | 100 nM |
| 1 | 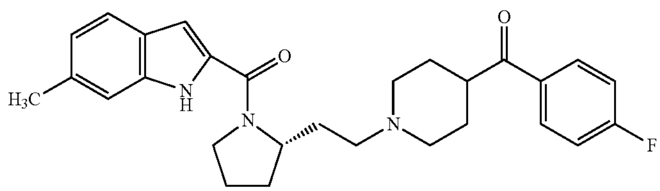 | 91 | 73 | | 96 | 68 |
| 2 | 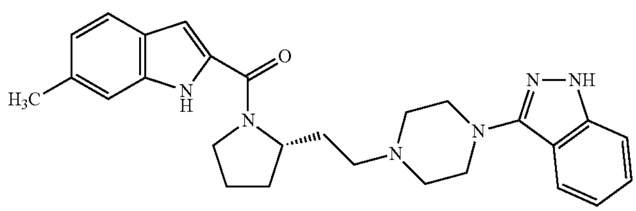 [SMILES: Cc1ccc2cc(C(=O)N3CCC[C@H]3CCN3CCN(c4n[nH]c5ccccc45)CC3)[nH]c2c1] | 73 | 65 | | 95 | 63 |
| 3 | 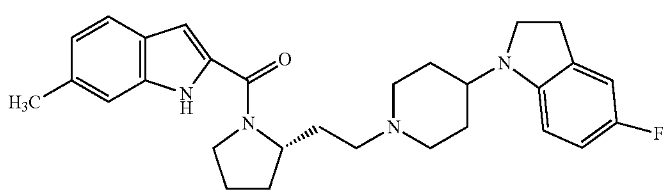 [SMILES: Cc1ccc2cc(C(=O)N3CCC[C@H]3CCN3CCC(N4CCc5cc(F)ccc54)CC3)[nH]c2c1] | 80 | 65 | | 94 | 74 |
| 4 | 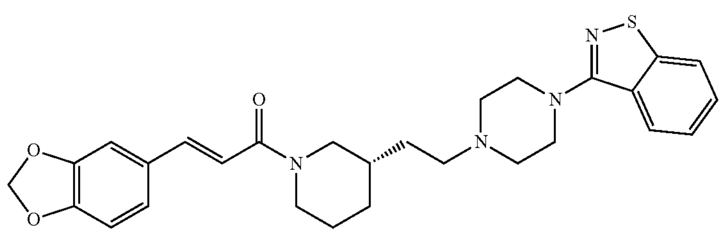 [SMILES: O=C(/C=C/c1ccc2c(c1)OCO2)N1CCC[C@@H](CCN2CCN(c3nsc4ccccc34)CC2)C1] | 73 | | 96 | 65 | 30 |
| 5 | 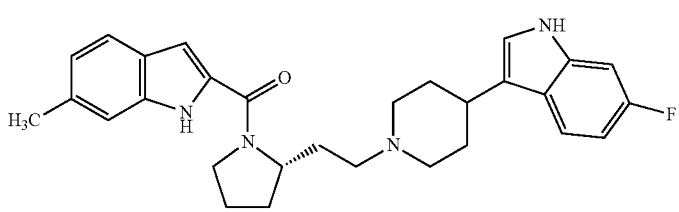 [SMILES: Cc1ccc2cc(C(=O)N3CCC[C@H]3CCN3CCC(c4c[nH]c5cc(F)ccc45)CC3)[nH]c2c1] | 83 | 72 | | 98 | 70 |
| 6 | 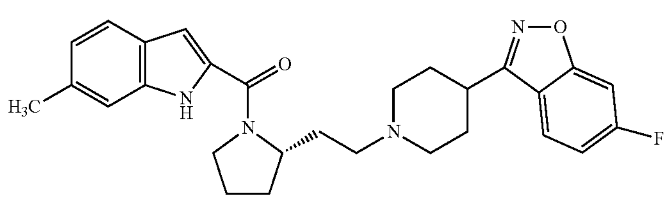 [SMILES: Cc1ccc2cc(C(=O)N3CCC[C@H]3CCN3CCC(c4noc5cc(F)ccc45)CC3)[nH]c2c1] | 91 | 61 | | 94 | 71 |
| 7 | 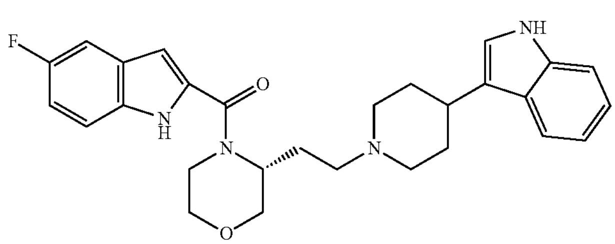 [SMILES: O=C(c1cc2cc(F)ccc2[nH]1)N1CCOC[C@H]1CCN1CCC(c2c[nH]c3ccccc23)CC1] | 85 | | 100 | 97 | 86 |

TABLE 8-continued
| Ex. No. | STRUCTURE | BINDING INHIBITION RATE (%) | | | | |
|---|---|---|---|---|---|---|
| | | $D_{2L}$ | 5HT2A | | 5HT6 | $\alpha_{1D}$ |
| | | 10 nM | 1 nM | 10 nM | 100 nM | 100 nM |
| 8 | 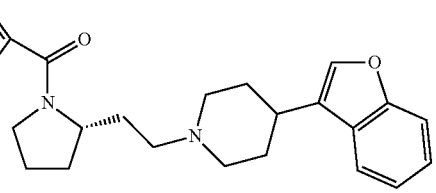 | 76 | | 92 | 93 | 62 |
| 9 | 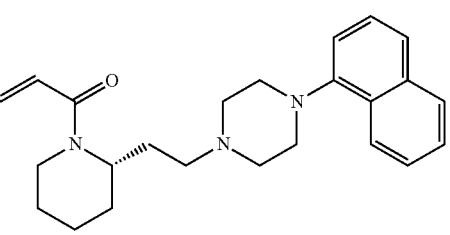 | 32 | | 94 | 61 | 5 |
| 10 | 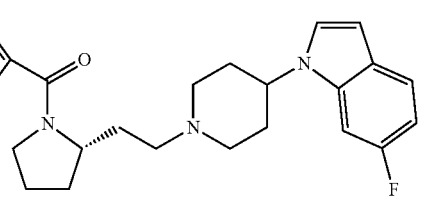 | 52 | 37 | | 74 | 12 |
| 11 | 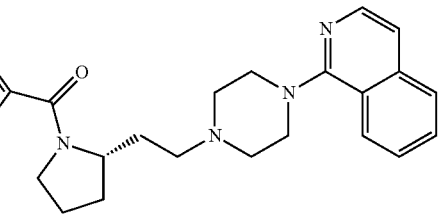 | 69 | 64 | | 86 | 5 |
| 12 | 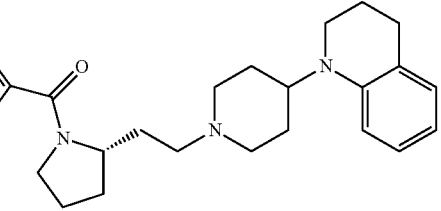 | 59 | 28 | | 84 | 43 |
| 13 | 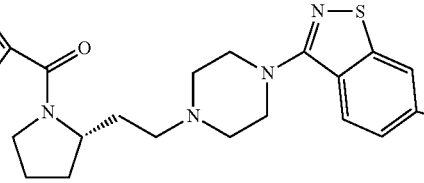 | 72 | 34 | | 93 | 60 |

TABLE 9

| Ex. No. | STRUCTURE | BINDING INHIBITION RATE (%) | | | | |
|---|---|---|---|---|---|---|
| | | D$_{2L}$ | 5HT2A | | 5HT6 | α$_{1D}$ |
| | | 10 nM | 1 nM | 10 nM | 100 nM | 100 nM |
| 14 | 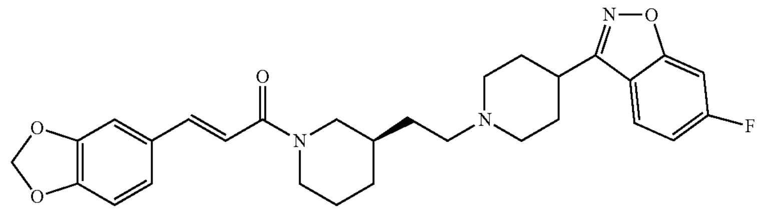 [SMILES: O=C(/C=C/c1ccc2c(c1)OCO2)N1CCC[C@H](CCN2CCC(c3noc4cc(F)ccc34)CC2)C1] | 75 | | | 92 | 89 |
| 15 | 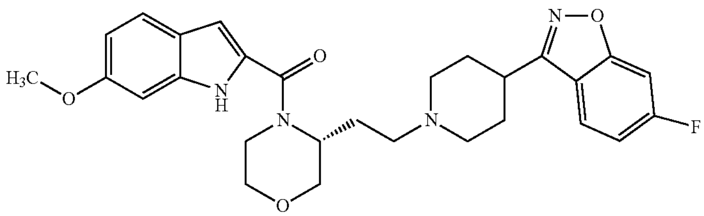 [SMILES: COc1ccc2cc(C(=O)N3CCOC[C@H]3CCN3CCC(c4noc5cc(F)ccc45)CC3)[nH]c2c1] | 84 | 76 | 94 | 79 | 74 |
| 16 | 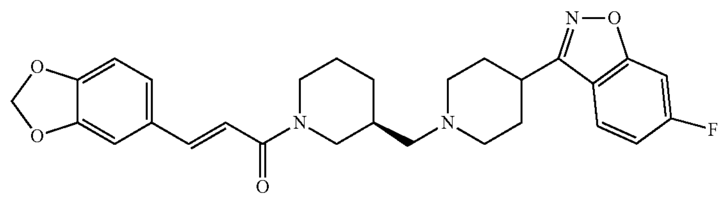 [SMILES: O=C(/C=C/c1ccc2c(c1)OCO2)N1CCC[C@@H](CN2CCC(c3noc4cc(F)ccc34)CC2)C1] | 97 | | 93 | 87 | 91 |
| 17 | 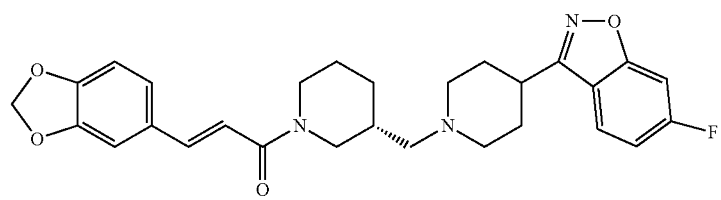 [SMILES: O=C(/C=C/c1ccc2c(c1)OCO2)N1CCC[C@H](CN2CCC(c3noc4cc(F)ccc34)CC2)C1] | 84 | | 99 | 93 | 92 |
| 18 | 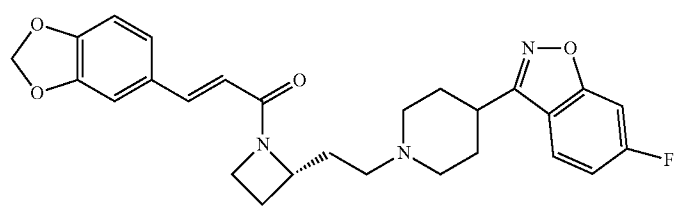 [SMILES: O=C(/C=C/c1ccc2c(c1)OCO2)N1CC[C@H]1CCN1CCC(c2noc3cc(F)ccc23)CC1] | 54 | | 100 | 74 | 102 |
| 19 | 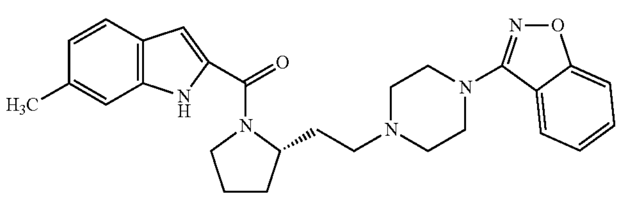 [SMILES: Cc1ccc2cc(C(=O)N3CCC[C@H]3CCN3CCN(c4noc5ccccc45)CC3)[nH]c2c1] | 88 | | 84 | 92 | 51 |
| 20 | 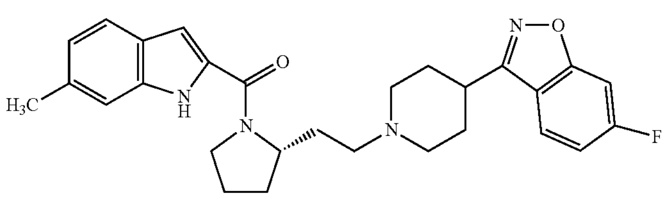 [SMILES: Cc1ccc2cc(C(=O)N3CCC[C@H]3CCN3CCC(c4noc5cc(F)ccc45)CC3)[nH]c2c1] | 91 | | | 94 | 71 |

TABLE 9-continued

| Ex. No. | STRUCTURE | BINDING INHIBITION RATE (%) | | | | |
|---|---|---|---|---|---|---|
| | | D$_{2L}$ | 5HT2A | | 5HT6 | α$_{1D}$ |
| | | 10 nM | 1 nM | 10 nM | 100 nM | 100 nM |
| 21 | 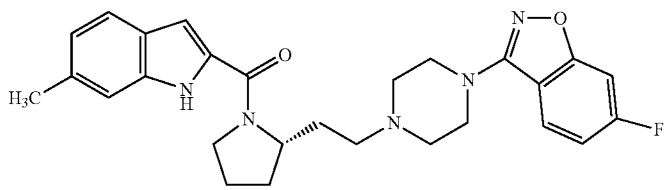 [SMILES: Cc1ccc2cc(C(=O)N3CCC[C@H]3CCN3CCN(c4noc5cc(F)ccc45)CC3)[nH]c2c1] | 73 | 41 | | 94 | 55 |
| 22 | 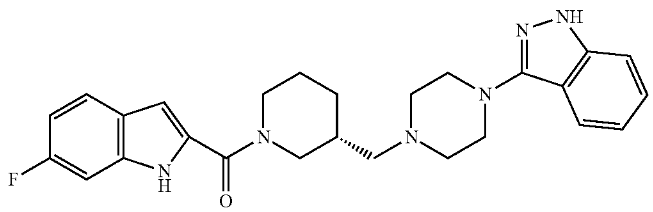 [SMILES: O=C(c1cc2ccc(F)cc2[nH]1)N1CCC[C@H](CN2CCN(c3n[nH]c4ccccc34)CC2)C1] | 26 | | | 85 | |
| 23 | 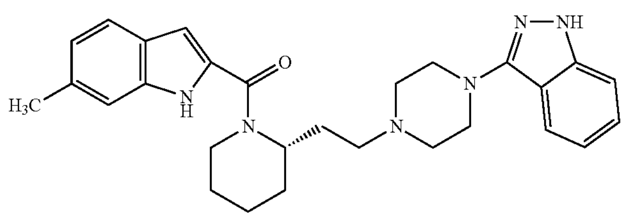 [SMILES: Cc1ccc2cc(C(=O)N3CCCC[C@H]3CCN3CCN(c4n[nH]c5ccccc45)CC3)[nH]c2c1] | 62 | 34 | | 75 | 34 |
| 24 | 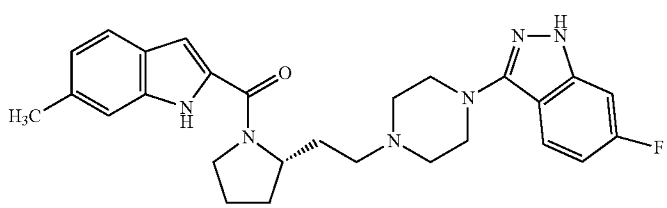 [SMILES: Cc1ccc2cc(C(=O)N3CCC[C@H]3CCN3CCN(c4n[nH]c5cc(F)ccc45)CC3)[nH]c2c1] | 88 | | | 98 | 64 |
| 25 | 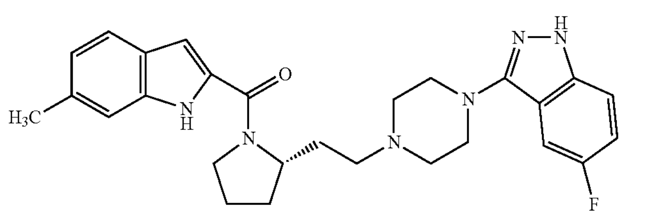 [SMILES: Cc1ccc2cc(C(=O)N3CCC[C@H]3CCN3CCN(c4n[nH]c5ccc(F)cc45)CC3)[nH]c2c1] | 28 | | | 82 | |
| 26 | 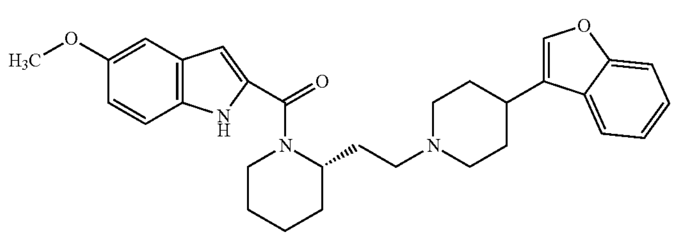 [SMILES: COc1ccc2[nH]c(C(=O)N3CCCC[C@H]3CCN3CCC(c4coc5ccccc45)CC3)cc2c1] | 77 | 77 | 98 | 65 | 67 |

TABLE 10

| Ex. No. | STRUCTURE | BINDING INHIBITION RATE (%) | | | | |
|---|---|---|---|---|---|---|
| | | D$_{2L}$ | 5HT2A | | 5HT6 | α$_{1D}$ |
| | | 10 nM | 1 nM | 10 nM | 100 nM | 100 nM |
| 27 | 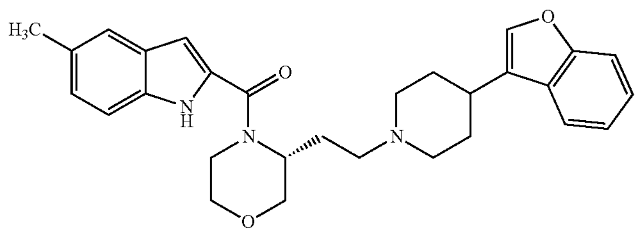 [SMILES: Cc1ccc2[nH]c(C(=O)N3CCOC[C@H]3CCN3CCC(c4coc5ccccc45)CC3)cc2c1] | 87 | | 93 | 85 | 97 |
| 28 | 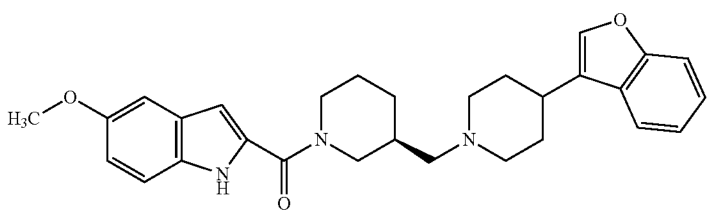 [SMILES: COc1ccc2[nH]c(C(=O)N3CCC[C@@H](CN4CCC(c5coc6ccccc56)CC4)C3)cc2c1] | 96 | | | 83 | 97 |
| 29 | 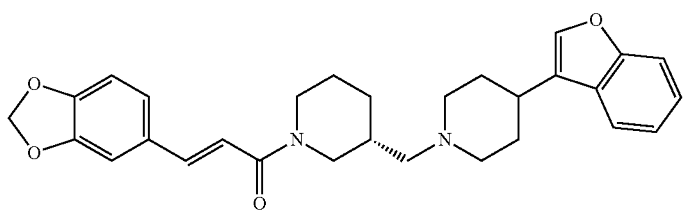 [SMILES: O=C(/C=C/c1ccc2c(c1)OCO2)N1CCC[C@H](CN2CCC(c3coc4ccccc34)CC2)C1] | 80 | | 100 | 85 | 92 |
| 30 | 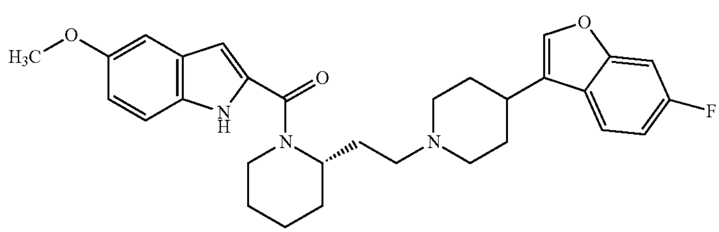 [SMILES: COc1ccc2[nH]c(C(=O)N3CCCC[C@H]3CCN3CCC(c4coc5cc(F)ccc45)CC3)cc2c1] | 92 | | 95 | 65 | |
| 31 | 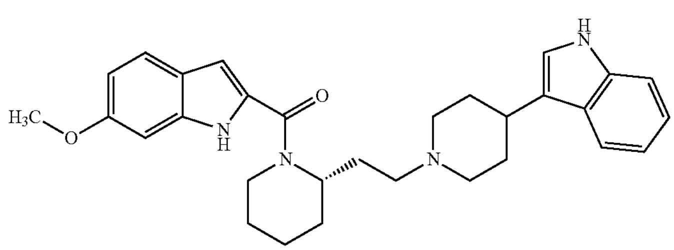 | 78 | | 96 | 88 | 54 |
| 32 | 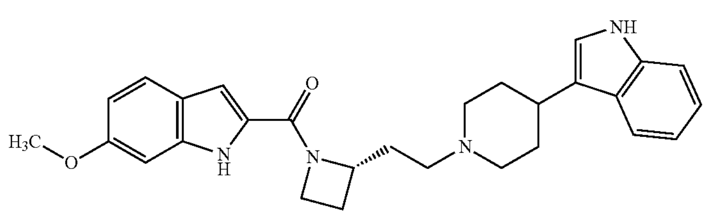 [SMILES: COc1ccc2cc(C(=O)N3CC[C@H]3CCN3CCC(c4c[nH]c5ccccc45)CC3)[nH]c2c1] | 36 | | 95 | 97 | 68 |

TABLE 10-continued

| Ex. No. | STRUCTURE | BINDING INHIBITION RATE (%) | | | | |
|---|---|---|---|---|---|---|
| | | $D_{2L}$ | 5HT2A | | 5HT6 | $\alpha_{1D}$ |
| | | 10 nM | 1 nM | 10 nM | 100 nM | 100 nM |
| 33 | 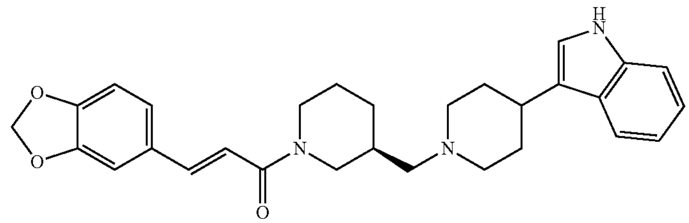 [SMILES: O=C(/C=C/c1ccc2c(c1)OCO2)N1CCC[C@@H](CN2CCC(c3c[nH]c4ccccc34)CC2)C1] | 95 | | | 92 | 73 |
| 34 | 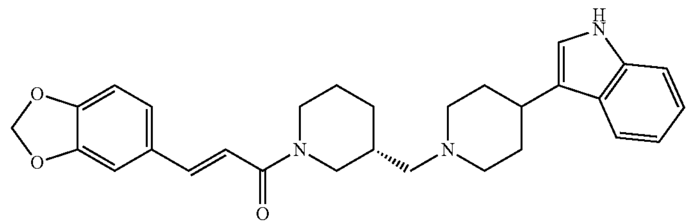 [SMILES: O=C(/C=C/c1ccc2c(c1)OCO2)N1CCC[C@H](CN2CCC(c3c[nH]c4ccccc34)CC2)C1] | 75 | 98 | | 86 | 93 |
| 35 | 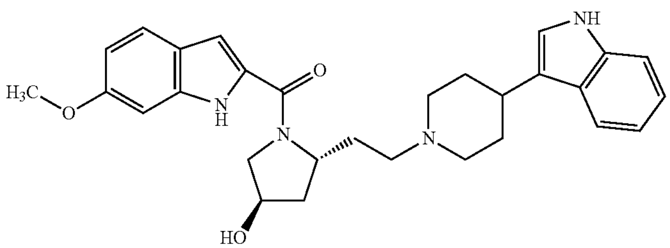 [SMILES: COc1ccc2cc(C(=O)N3C[C@H](O)C[C@H]3CCN3CCC(c4c[nH]c5ccccc45)CC3)[nH]c2c1] | 37 | 89 | | 79 | 81 |
| 36 | 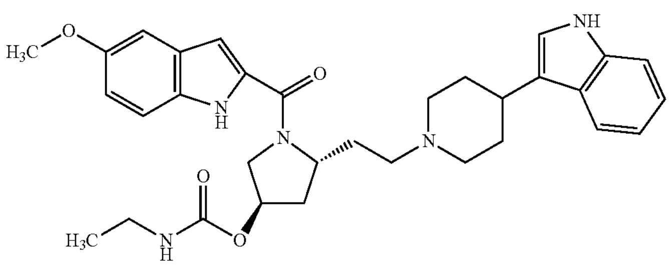 [SMILES: CCNC(=O)O[C@@H]1C[C@@H](CCN2CCC(c3c[nH]c4ccccc34)CC2)N(C(=O)c2cc3cc(OC)ccc3[nH]2)C1] | 48 | 87 | | 86 | 75 |
| 37 | 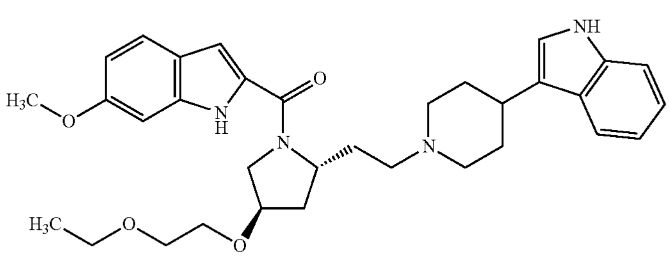 [SMILES: CCOCCO[C@@H]1C[C@@H](CCN2CCC(c3c[nH]c4ccccc34)CC2)N(C(=O)c2cc3ccc(OC)cc3[nH]2)C1] | 0 | 91 | | 78 | |
| 38 | 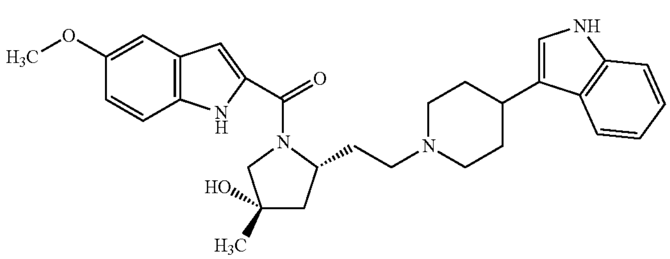 [SMILES: COc1ccc2[nH]c(C(=O)N3C[C@@](C)(O)C[C@H]3CCN3CCC(c4c[nH]c5ccccc45)CC3)cc2c1] | 72 | 97 | | 86 | 67 |

TABLE 10-continued

| Ex. No. | STRUCTURE | BINDING INHIBITION RATE (%) | | | |
|---|---|---|---|---|---|
| | | $D_{2L}$ | 5HT2A | 5HT6 | $\alpha_{1D}$ |
| | | 10 nM | 1 nM / 10 nM | 100 nM | 100 nM |
| 39 | (structure) | 77 | 70 / — | 86 | 69 |

Note: Ex. 39 5HT2A values: 77 at 10 nM column shown as D2L; 5HT2A 1 nM = 70, 10 nM empty.

TABLE 11

| Ex. No. | STRUCTURE | BINDING INHIBITION RATE (%) | | | | |
|---|---|---|---|---|---|---|
| | | $D_{2L}$ | 5HT2A | | 5HT6 | $\alpha_{1D}$ |
| | | 10 nM | 1 nM | 10 nM | 100 nM | 100 nM |
| 40 | (structure) | 78 | 73 | 99 | 88 | 50 |
| 41 | (structure) | 85 | | | 78 | 81 |
| 42 | (structure) | 57 | | | 85 | 70 |
| 43 | (structure) | 74 | 77 | | 83 | 82 |

TABLE 11-continued
| Ex. No. | STRUCTURE | BINDING INHIBITION RATE (%) | | | | |
|---|---|---|---|---|---|---|
| | | $D_{2L}$ 10 nM | 5HT2A 1 nM | 5HT2A 10 nM | 5HT6 100 nM | $\alpha_{1D}$ 100 nM |
| 44 | 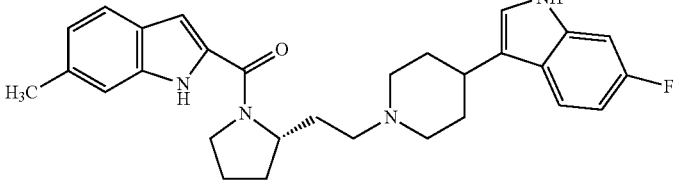 | 83 | | | 98 | 70 |
| 45 | 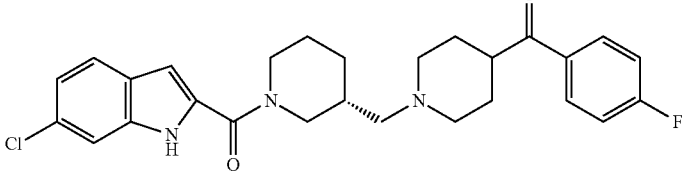 | 82 | 84 | | 97 | 46 |
| 46 | 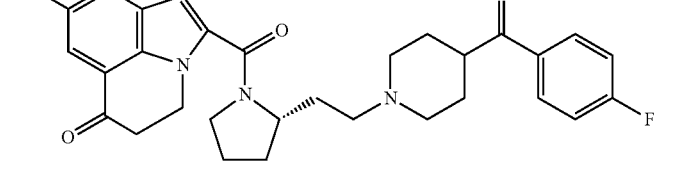 | 58 | 48 | | 82 | 54 |
| 47 | 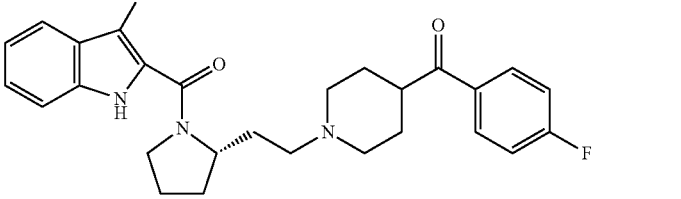 | 72 | | | 94 | 85 |
| 48 | 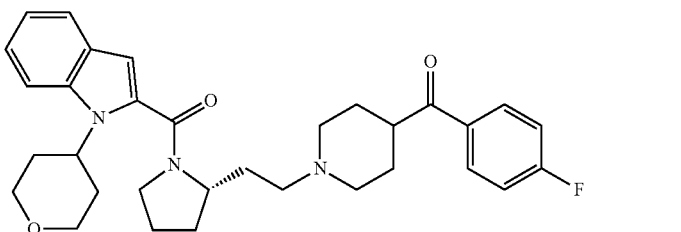 | 82 | | | 97 | 40 |
| 49 | 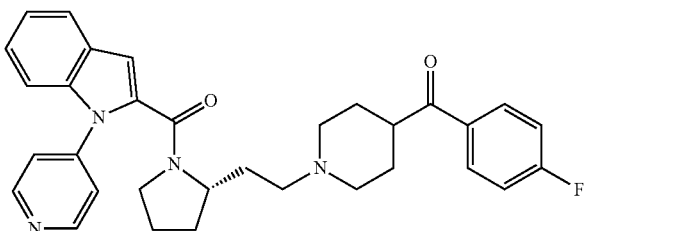 | 83 | | | 75 | 30 |
| 50 | 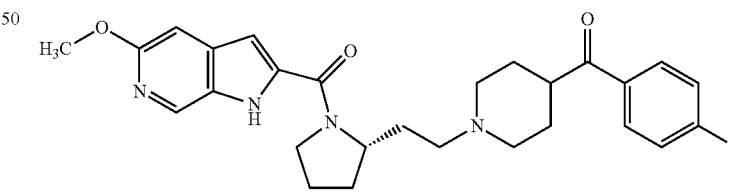 | 71 | 66 | | 88 | 43 |

TABLE 11-continued

| Ex. No. | STRUCTURE | BINDING INHIBITION RATE (%) | | | |
|---|---|---|---|---|---|
| | | D$_{2L}$ | 5HT2A | | 5HT6 | α$_{1D}$ |
| | | 10 nM | 1 nM | 10 nM | 100 nM | 100 nM |
| 51 | [structure] | 81 | 76 | | 95 | 51 |
| 52 | [structure] | 86 | 43 | | 95 | 64 |

TABLE 12

| Ex. No. | STRUCTURE | BINDING INHIBITION RATE (%) | | | |
|---|---|---|---|---|---|
| | | D$_{2L}$ | 5HT2A | | 5HT6 | α$_{1D}$ |
| | | 10 nM | 1 nM | 10 nM | 100 nM | 100 nM |
| 53 | [structure] | 89 | | | 94 | 48 |
| 54 | [structure] | 71 | 7 | | 81 | 63 |
| 55 | [structure] | 83 | | | 100 | |

TABLE 12-continued
| Ex. No. | STRUCTURE | BINDING INHIBITION RATE (%) | | | | |
|---|---|---|---|---|---|---|
| | | $D_{2L}$ | 5HT2A | | 5HT6 | $\alpha_{1D}$ |
| | | 10 nM | 1 nM | 10 nM | 100 nM | 100 nM |
| 56 | 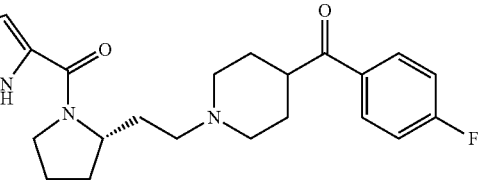 | 84 | 70 | | 91 | 70 |
| 57 | 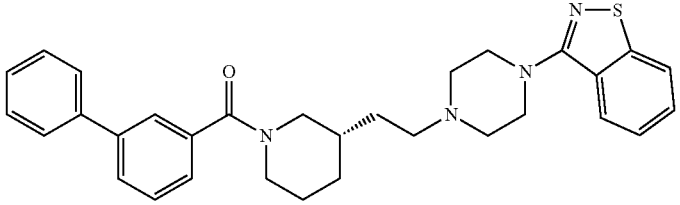 [SMILES: O=C(c1cccc(-c2ccccc2)c1)N1CCC[C@@H](CCN2CCN(c3nsc4ccccc34)CC2)C1] | 69 | | | 86 | 76 |
| 58 | 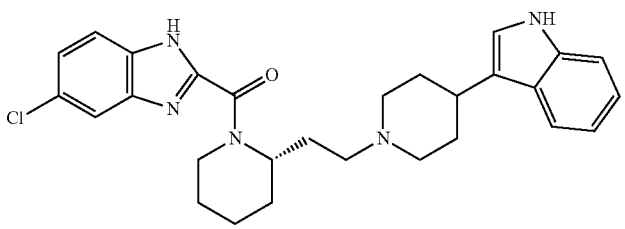 [SMILES: O=C(c1nc2cc(Cl)ccc2[nH]1)N1CCCC[C@H]1CCN1CCC(c2c[nH]c3ccccc23)CC1] | 57 | 74 | 91 | 98 | 97 |
| 59 | 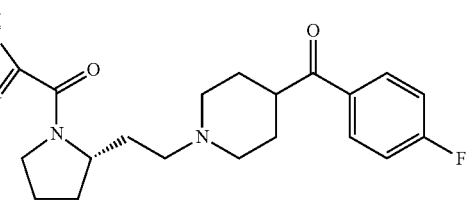 | 91 | 58 | | 87 | 95 |
| 60 | 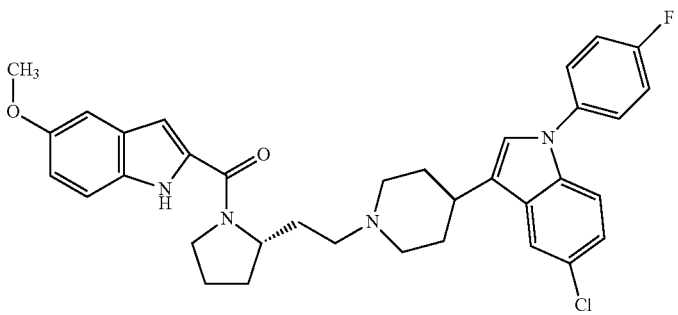 [SMILES: COc1ccc2[nH]c(C(=O)N3CCC[C@H]3CCN3CCC(c4cn(-c5ccc(F)cc5)c5ccc(Cl)cc45)CC3)cc2c1] | 76 | | 78 | 97 | 76 |
| 61 | 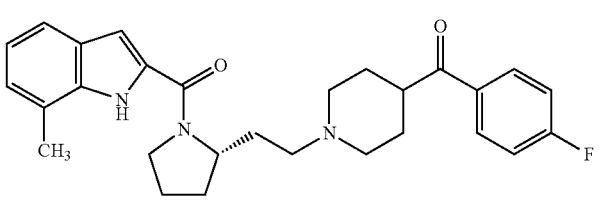 [SMILES: Cc1cccc2cc(C(=O)N3CCC[C@H]3CCN3CCC(C(=O)c4ccc(F)cc4)CC3)[nH]c12] | 69 | 46 | | 82 | 29 |

TABLE 12-continued
| Ex. No. | STRUCTURE | BINDING INHIBITION RATE (%) | | | | |
| --- | --- | --- | --- | --- | --- | --- |
| | | $D_{2L}$ | 5HT2A | | 5HT6 | $\alpha_{1D}$ |
| | | 10 nM | 1 nM | 10 nM | 100 nM | 100 nM |
| 62 | 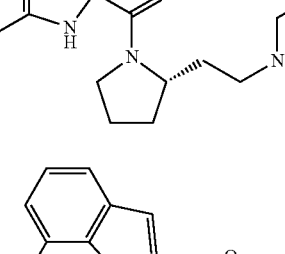 | 81 | 61 | | 87 | 43 |
| 63 | 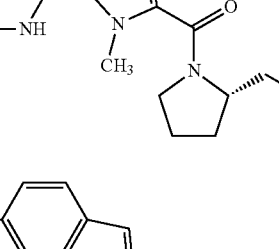 | 0 | | | 17 | |
| 159 | 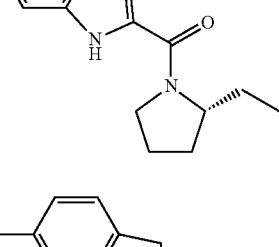 | 93 | 78 | | 96 | 71 |
| 160 | 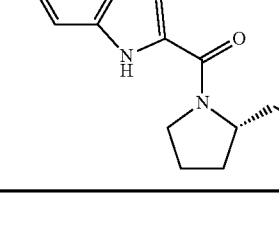 | 90 | 72 | | 98 | 53 |
TABLE 13
| Ex. No. | STRUCTURE | BINDING INHIBITION RATE (%) | | | | |
| --- | --- | --- | --- | --- | --- | --- |
| | | $D_{2L}$ | 5HT2A | | 5HT6 | $\alpha_{1D}$ |
| | | 10 nM | 1 nM | 10 nM | 100 nM | 100 nM |
| 161 | 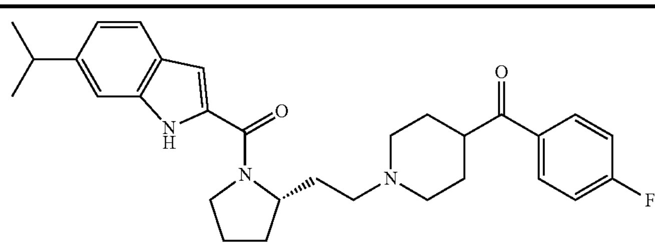 | 49 | 69 | | 97 | 66 |

TABLE 13-continued
| Ex. No. | Structure | D$_{2L}$ 10 nM | 5HT2A 1 nM | 5HT2A 10 nM | 5HT6 100 nM | α$_{1D}$ 100 nM |
|---|---|---|---|---|---|---|
| 162 | 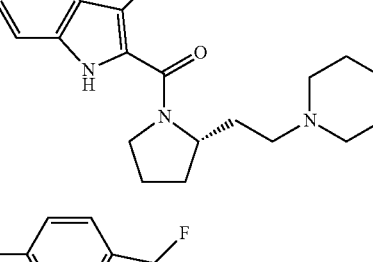 | 86 | 84 | | 93 | 79 |
| 163 | 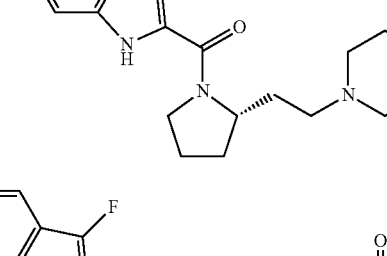 | 88 | 75 | | 95 | 48 |
| 164 | 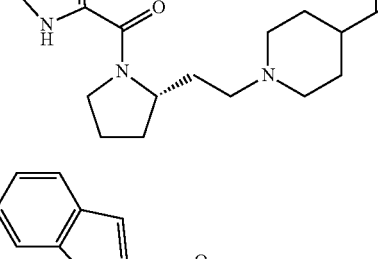 | 79 | 56 | | 99 | 43 |
| 165 | 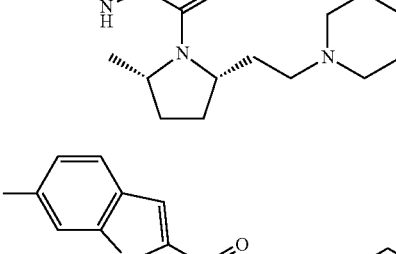 | 90 | 74 | | 90 | 53 |
| 166 | 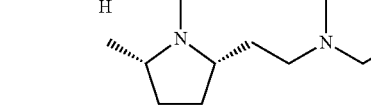 | 88 | | | 97 | 62 |
| 167 | 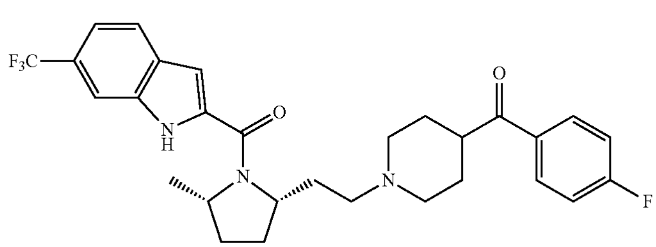 [SMILES: C[C@H]1CC[C@@H](CCN2CCC(C(=O)c3ccc(F)cc3)CC2)N1C(=O)c1cc2ccc(C(F)(F)F)cc2[nH]1] | 75 | | | 95 | 33 |

TABLE 13-continued

| | BINDING INHIBITION RATE (%) | | | |
|---|---|---|---|---|
| | $D_{2L}$ | 5HT2A | | 5HT6 | $\alpha_{1D}$ |
| Ex. No. STRUCTURE | 10 nM | 1 nM | 10 nM | 100 nM | 100 nM |
| 168 | 81 | | | 94 | 61 |
| 169 | 81 | 47 | | 73 | 49 |
| 170 | 87 | | | 95 | 83 |

INDUSTRIAL APPLICABILITY

N-Acyl cyclic amine derivatives or pharmaceutically acceptable salts thereof of the present invention show high effectiveness against positive symptoms, negative symptoms and cognitive dysfunction in schizophrenia, and are useful as a therapeutic agent reducing side-effects risks as seen in a conventional therapeutic agent for schizophrenia as well as having remarkable effects for central neurological diseases associated with cognitive dysfunction other than schizophrenia.

The invention claimed is:

1. A compound of the following formula (1):

[Chemical Formula 1]

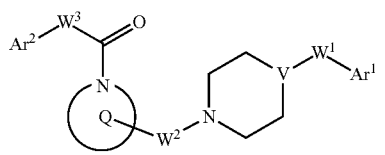

(1)

wherein $Ar^1$ and $Ar^2$ are each independently optionally substituted $C_{6-10}$ aryl or optionally substituted heteroaryl;

V is $CR^3$, in which $R^3$ is hydrogen, hydroxyl, halogen, cyano, or optionally substituted $C_{1-6}$ alkyl;

$W^1$ is a single bond, oxygen, sulfur, —C(O)— or —$NR^2$—, in which $R^2$ is hydrogen or optionally substituted $C_{1-6}$ alkyl, piperidine ring in case that V is $CR^3$ may be each independently optionally substituted by one or more and same or different groups selected from the group consisting of hydroxyl, halogen, cyano, $C_{1-6}$ alkyl and $C_{1-6}$ alkoxy on any substituent positions;

$W^2$ is optionally substituted ethylene;

$W^3$ is a single bond, oxygen, sulfur, —NH—, optionally substituted methylene, optionally substituted ethylene, or —$CR^4$=$CR^5$—, in which $R^4$ and $R^5$ are each independently hydrogen, halogen or optionally substituted $C_{1-6}$ alkyl;

Ring Q is a group of the following formula (a):

[Chemical Formula 2]

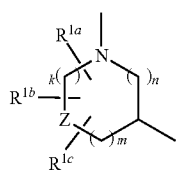

(a)

in which n is 0;

m is 0, 1 or 2;

k is 1, 2 or 3;

Z is a single bond, methylene, oxygen, sulfur, —S(O)—, —S(O)$_2$— or —NR$^{21}$—, in which R$^{21}$ is hydrogen or optionally substituted C$_{1-6}$ alkyl;

R$^{1a}$, R$^{1b}$ and R$^{1c}$ are each, same or different, hydrogen, hydroxyl, halogen, cyano, carboxyl, optionally substituted amino, optionally substituted C$_{1-6}$ alkyl, optionally substituted C$_{3-7}$ cycloalkyl, optionally substituted C$_{3-7}$ cycloalkyl-C$_{1-4}$ alkyl, optionally substituted C$_{7-14}$ aralkyl, optionally substituted heteroaryl-C$_{1-4}$ alkyl, optionally substituted saturated heterocyclic C$_{1-4}$ alkyl, optionally substituted C$_{6-10}$ aryl, optionally substituted heteroaryl, optionally substituted saturated heterocycle, optionally substituted C$_{1-6}$ alkoxy, optionally substituted C$_{3-7}$ cycloalkoxy, optionally substituted C$_{6-10}$ aryloxy, optionally substituted heteroaryloxy, optionally substituted saturated heterocyclic oxy, optionally substituted C$_{7-14}$ aralkyloxy, optionally substituted C$_{1-6}$ alkylcarbonylamino, optionally substituted C$_{3-7}$ cycloalkylcarbonylamino, optionally substituted C$_{6-10}$ arylcarbonylamino, optionally substituted saturated heterocyclic carbonylamino, optionally substituted heteroarylcarbonylamino, optionally substituted C$_{1-6}$ alkylcarbonyloxy, optionally substituted aminocarbonyloxy, optionally substituted C$_{1-6}$ alkoxycarbonylamino, optionally substituted C$_{3-7}$ cycloalkoxycarbonylamino, optionally substituted saturated heterocyclic oxycarbonylamino, optionally substituted aminocarbonylamino, optionally substituted aminosulfonylamino, optionally substituted C$_{1-6}$ alkylsulfonylamino, optionally substituted C$_{3-7}$ cycloalkylsulfonylamino, optionally substituted C$_{6-10}$ arylsulfonylamino, optionally substituted saturated heterocyclic sulfonylamino, or optionally substituted heteroarylsulfonylamino, alternatively, R$^{1a}$ and R$^{1b}$ may combine each other together with the carbon atom to which they bind to form C$_{3-7}$ cycloalkyl ring, or saturated heterocycle, in which the C$_{3-7}$ cycloalkyl ring and the saturated heterocycle may be optionally substituted by one or more and same or different groups selected from the group consisting of hydroxyl, halogen, cyano, C$_{1-6}$ alkyl, C$_{1-6}$ alkoxy, C$_{6-10}$ aryl, heteroaryl and 4- to 7-membered saturated heterocycle; or a pharmaceutically acceptable salt thereof.

2. The compound of claim 1, represented by the following formula (2):

[Chemical Formula 3]

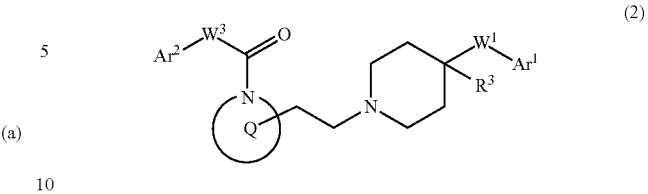

(2)

wherein Ar$^1$ and Ar$^2$ are each independently optionally substituted C$_{6-10}$ aryl or optionally substituted heteroaryl;

W$^1$ is a single bond or —C(O)—;

W$^3$ is a single bond, optionally substituted methylene, optionally substituted ethylene, or —CR$^4$=CR$^5$—, in which R$^4$ and R$^5$ are each independently hydrogen, halogen or optionally substituted C$_{1-6}$ alkyl;

R$^3$ is hydrogen, hydroxyl, halogen or cyano;

Ring Q is a group of the following formula (a-1):

[Chemical Formula 4]

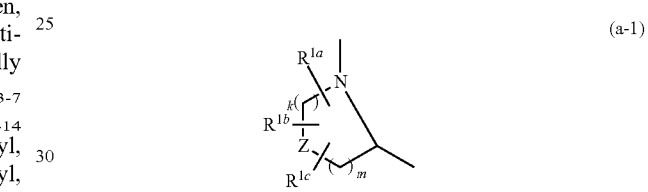

(a-1)

in which m is 0, 1 or 2;

k is 1, 2 or 3;

Z is a single bond, methylene, oxygen, or —NR$^{21}$—, in which R$^{21}$ is hydrogen or optionally substituted C$_{1-6}$ alkyl;

R$^{1a}$, R$^{1b}$ and R$^{1c}$ have the same meanings as defined in claim 1; or a pharmaceutically acceptable salt thereof.

3. The compound of claim 1, wherein Ar$^1$ is any one of groups of the following formulae (b-1) to (b-17):

[Chemical Formula 5]

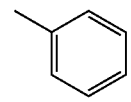

(b-1)

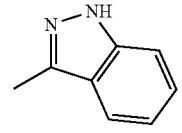

(b-2)

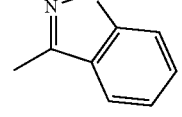

(b-3)

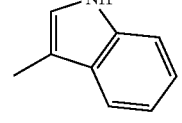

(b-4)

in which carbon atoms in the groups of the formulae (b-1) to (b-17) may be optionally substituted by one or more and same or different groups selected from the group consisting of halogen, hydroxyl, cyano, $C_{1-6}$ alkyl and $C_{1-6}$ alkoxy; or a pharmaceutically acceptable salt thereof.

4. The compound of claim 1, wherein $Ar^2$ is any one of groups of the following formulae (c-1) to (c-19):

[Chemical Formula 6]

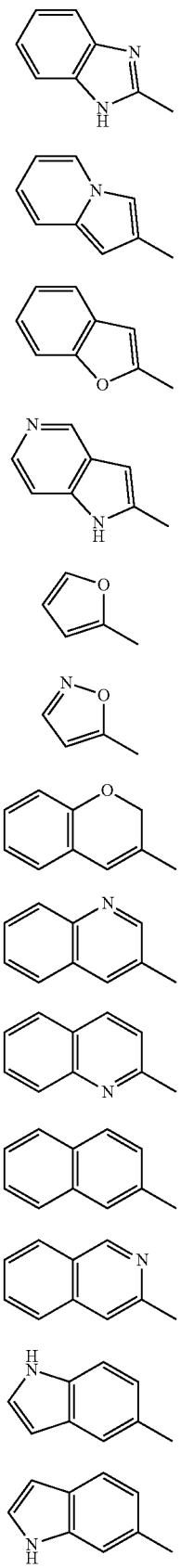

in which carbon atoms in the groups of the formulae (c-1) to (c-19) may be optionally substituted by one or more and same or different groups selected from the group consisting of hydroxyl, halogen, cyano, carboxyl, optionally substituted amino, optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkoxy, optionally substituted $C_{1-6}$ alkylthio, optionally substituted $C_{3-7}$ cycloalkoxy, optionally substituted $C_{6-10}$ aryloxy, optionally substituted heteroaryloxy, optionally substituted saturated heterocyclic oxy, optionally substituted $C_{1-6}$ alkylcarbonylamino, optionally substituted $C_{3-7}$ cycloalkylcarbonylamino, optionally substituted $C_{6-10}$ arylcarbonylamino, optionally substituted heteroarylcarbonylamino, optionally substituted saturated heterocyclic carbonylamino, optionally substituted $C_{1-6}$ alkoxycarbonylamino, optionally substituted $C_{3-7}$ cycloalkoxycarbonylamino, optionally substituted saturated heterocyclic oxycarbonylamino, optionally substituted aminocarbonylamino, optionally substituted aminosulfonylamino, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{6-10}$ arylcarbonyl, optionally substituted heteroarylcarbonyl, optionally substituted saturated heterocyclic carbonyl, optionally substituted $C_{1-6}$ alkoxycarbonyl, optionally substituted $C_{3-7}$ cycloalkoxycarbonyl, optionally substituted saturated heterocyclic oxycarbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl;

NH in the groups of the formulae (c-1) to (c-19) may be optionally substituted by one or more and same or different groups selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{1-6}$ alkoxycarbonyl, optionally substituted $C_{3-7}$ cycloalkoxycarbonyl, optionally substituted saturated heterocyclic oxycarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl; or a pharmaceutically acceptable salt thereof.

5. The compound of claim 4, wherein carbon atoms in the groups of the formulae (c-1) to (c-19) may be optionally substituted by one or more and same or different groups selected from the group consisting of hydroxyl, halogen, cyano, optionally substituted $C_{1-6}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{1-6}$ alkoxy, optionally substituted $C_{1-6}$ alkylthio, optionally substituted saturated heterocyclic oxy, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl;

NH in the groups of the formulae (c-1) to (c-19) may be optionally substituted by one or more and same or different groups selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{1-6}$ alkoxycarbonyl, optionally substituted $C_{3-7}$ cycloalkoxycarbonyl, optionally substituted saturated heterocyclic oxycarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl; or a pharmaceutically acceptable salt thereof.

6. The compound of claim 1, wherein $R^{1a}$, $R^{1b}$ and $R^{1c}$ are each, same or different, hydrogen, hydroxyl, halogen, cyano, optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkoxy, optionally substituted $C_{3-7}$ cycloalkoxy, optionally substituted $C_{6-10}$ aryloxy, optionally substituted heteroaryloxy, optionally substituted saturated heterocyclic oxy, optionally substituted $C_{7-14}$ aralkyloxy, optionally substituted $C_{1-6}$ alkylcarbonyloxy, or optionally substituted aminocarbonyloxy, alternatively, $R^{1a}$ and $R^{1b}$ may combine each other together with the carbon atom to which they bind to form $C_{3-7}$ cycloalkyl ring, or saturated heterocycle, in which the $C_{3-7}$ cycloalkyl ring and the saturated heterocycle may be optionally substituted by one or more and same or different groups selected from the group consisting of hydroxyl, halogen and cyano; or a pharmaceutically acceptable salt thereof.

7. The compound of claim 1, wherein Ring Q is any one of rings of the following formulae (a-2) to (a-7):

[Chemical Formula 7]

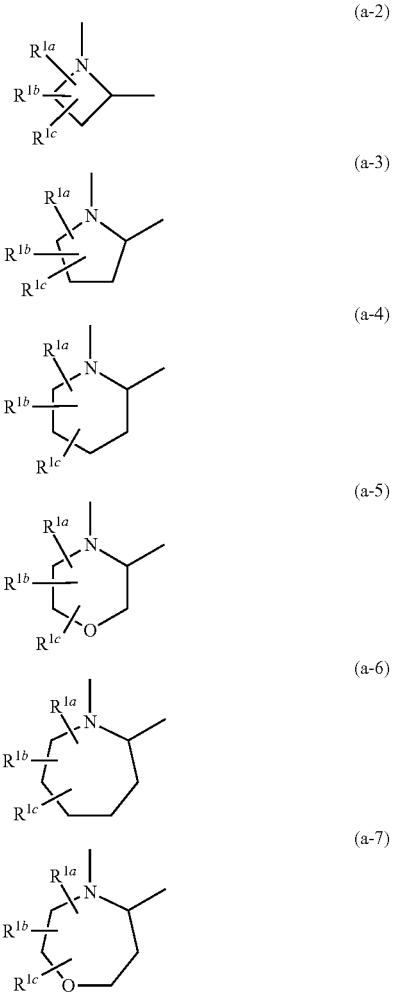

in which $R^{1a}$, $R^{1b}$ and $R^{1c}$ are each, same or different, hydrogen, hydroxyl, halogen, cyano, optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkoxy, optionally substituted $C_{3-7}$ cycloalkoxy, optionally substituted $C_{6-10}$ aryloxy, optionally substituted heteroaryloxy, optionally substituted saturated heterocyclic oxy, optionally substituted $C_{7-14}$ aralkyloxy, optionally substituted $C_{1-6}$ alkylcarbonyloxy, or optionally substituted aminocarbonyloxy, alternatively, $R^{1a}$ and $R^{1b}$ may combine each other together with the carbon atom to which they bind to form $C_{3-7}$ cycloalkyl ring, or saturated heterocycle, in which the $C_{3-7}$ cycloalkyl ring and the saturated heterocycle may be optionally substituted by one or more and same or different groups selected from the group consisting of hydroxyl, halogen and cyano; or a pharmaceutically acceptable salt thereof.

8. The compound of claim 1, wherein $Ar^1$ is any one of groups of the following formulae (b-1) to (b-4):

[Chemical Formula 8]

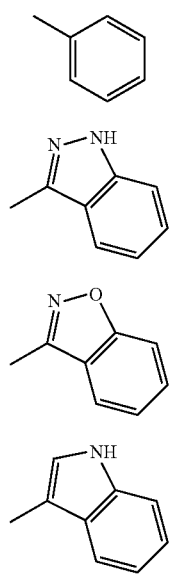

(b-1)
(b-2)
(b-3)
(b-4)

in which carbon atoms in the groups of the formulae may be optionally substituted by one or more and same or different groups selected from the group consisting of halogen, hydroxyl, cyano, $C_{1-6}$ alkyl and $C_{1-6}$ alkoxy; or a pharmaceutically acceptable salt thereof.

9. The compound of claim 1, wherein $Ar^2$ is any one of groups of the following formulae (c-1) to (c-3):

[Chemical Formula 9]

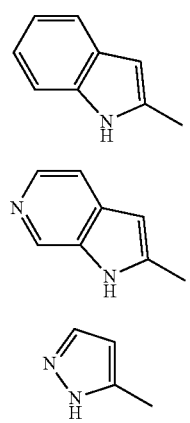

(c-1)
(c-2)
(c-3)

in which carbon atoms in the groups may be optionally substituted by one or more and same or different groups selected from the group consisting of hydroxyl, halogen, cyano, optionally substituted $C_{1-6}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{1-6}$ alkoxy, optionally substituted $C_{1-6}$ alkylthio, optionally substituted saturated heterocyclic oxy, optionally substituted $C_{6-10}$ aryl, optionally substituted heteroaryl, optionally substituted saturated heterocycle, optionally substituted $C_{1-6}$ alkyl-carbonyl, optionally substituted $C_{3-7}$ cycloalkylcarbonyl, optionally substituted $C_{3-7}$ cycloalkyl-$C_{1-4}$alkylcarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl;

and in which the NH in the groups may be optionally substituted by one or more and same or different groups selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{1-6}$ alkoxycarbonyl, optionally substituted $C_{3-7}$ cycloalkoxycarbonyl, optionally substituted saturated heterocyclic oxycarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyland; or a pharmaceutically acceptable salt thereof.

10. The compound of claim 7, wherein Ring Q is a group of formula (a-3) of claim 7, or a pharmaceutically acceptable salt thereof.

11. The compound of claim 1, wherein $W^3$ is a single bond, V is CH, or a pharmaceutically acceptable salt thereof.

12. The compound of claim 1, represented by the following formula (3):

[Chemical Formula 10]

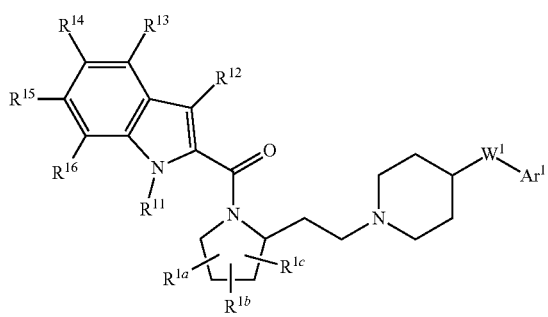

(3)

wherein Ar¹ is any one of groups of the following formulae (b-1'), (b-2'), (b-3') or (b-4'):

[Chemical Formula 11]

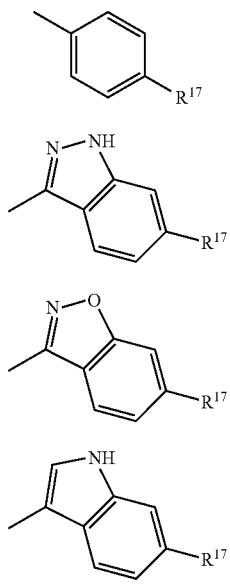

(b-1')

(b-2')

(b-3')

(b-4')

in which $R^{17}$ is hydrogen or halogen;

$W^1$ is a single bond or —C(O)—;

$R^{1a}$, $R^{1b}$ and $R^{1c}$ are each, same or different, hydrogen, hydroxyl, halogen, cyano, optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkoxy, optionally substituted $C_{3-7}$ cycloalkoxy, optionally substituted $C_{6-10}$ aryloxy, optionally substituted heteroaryloxy, optionally substituted saturated heterocyclic oxy, optionally substituted $C_{7-14}$ aralkyloxy, optionally substituted $C_{1-6}$ alkylcarbonyloxy, or optionally substituted aminocarbonyloxy, alternatively, $R^{1a}$ and $R^{1b}$ may combine each other together with the carbon atom to which they bind to form $C_{3-7}$ cycloalkyl ring, or saturated heterocycle, in which the $C_{3-7}$ cycloalkyl ring and the saturated heterocycle may be optionally substituted by one or more and same or different groups selected from the group consisting of hydroxyl, halogen and cyano;

$R^{11}$ is selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{1-6}$ alkoxycarbonyl, optionally substituted $C_{3-7}$ cycloalkoxycarbonyl, optionally substituted saturated heterocyclic oxycarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl;

$R^{12}$, $R^{13}$, $R^{14}$, $R^{15}$ and $R^{16}$ are the same or different groups selected from the group consisting of hydroxyl, halogen, cyano, optionally substituted $C_{1-6}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{1-6}$ alkoxy, optionally substituted $C_{1-6}$ alkylthio, optionally substituted saturated heterocyclic oxy, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl; or a pharmaceutically acceptable salt thereof.

13. The compound of claim 1, represented by the following formula (4):

[Chemical Formula 12]

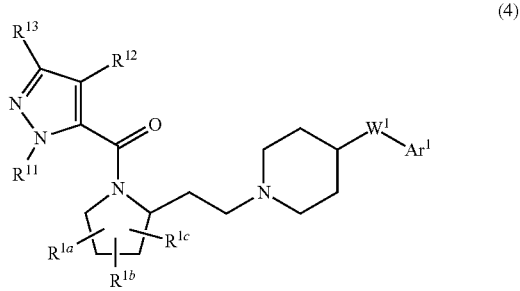

(4)

wherein Ar¹ is any one of groups of the formulae (b-1'), (b-2'), (b-3') or (b-4'):

[Chemical Formula 11]

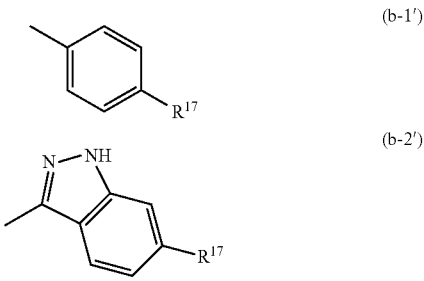

(b-1')

(b-2')

-continued

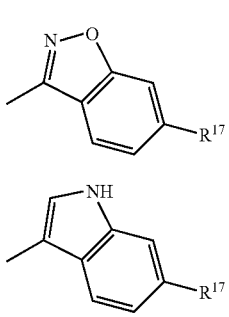

(b-3')

(b-4')

in which $R^{17}$ is hydrogen or halogen;

$W^1$ is a single bond or —C(O)—;

$R^{1a}$, $R^{1b}$ and $R^{1c}$ are each, same or different, hydrogen, hydroxyl, halogen, cyano, optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkoxy, optionally substituted $C_{3-7}$ cycloalkoxy, optionally substituted $C_{6-10}$ aryloxy, optionally substituted heteroaryloxy, optionally substituted saturated heterocyclic oxy, optionally substituted $C_{7-14}$ aralkyloxy, optionally substituted $C_{1-6}$ alkylcarbonyloxy, or optionally substituted aminocarbonyloxy, alternatively, $R^{1a}$ and $R^{1b}$ may combine each other together with the carbon atom to which they bind to form $C_{3-7}$ cycloalkyl ring, or saturated heterocycle, in which the $C_{3-7}$ cycloalkyl ring and the saturated heterocycle may be optionally substituted by one or more and same or different groups selected from the group consisting of hydroxyl, halogen and cyano;

$R^{11}$ is selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{1-6}$ alkoxycarbonyl, optionally substituted $C_{3-7}$ cycloalkoxycarbonyl, optionally substituted saturated heterocyclic oxycarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl;

$R^{12}$ and $R^{13}$ are the same or different groups selected from the group consisting of hydroxyl, halogen, cyano, optionally substituted $C_{1-6}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{1-6}$ alkoxy, optionally substituted $C_{1-6}$ alkylthio, optionally substituted saturated heterocyclic oxy, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl; or a pharmaceutically acceptable salt thereof.

14. The compound of claim 1, represented by the following formula (5):

[Chemical Formula 13]

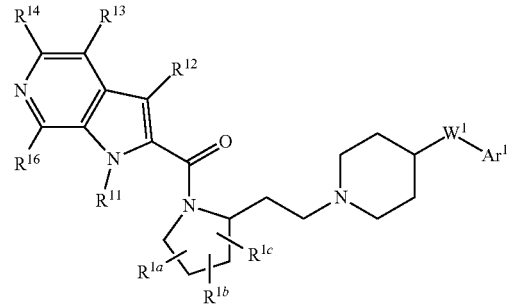

(5)

wherein $Ar^1$ is any one of the formulae (b-1'), (b-2'), (b-3') or (b-4'):

[Chemical Formula 11]

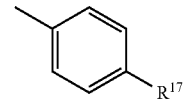

(b-1')

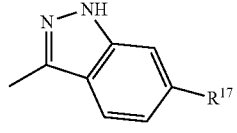

(b-2')

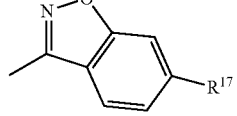

(b-3')

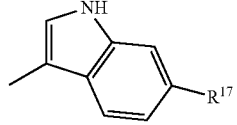

(b-4')

in which $R^{17}$ is hydrogen or halogen;

$W^1$ is a single bond or —C(O)—;

$R^{1a}$, $R^{1b}$ and $R^{1c}$ are each, same or different, hydrogen, hydroxyl, halogen, cyano, optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkoxy, optionally substituted $C_{3-7}$ cycloalkoxy, optionally substituted $C_{6-10}$ aryloxy, optionally substituted heteroaryloxy, optionally substituted saturated heterocyclic oxy, optionally substituted $C_{7-14}$ aralkyloxy, optionally substituted $C_{1-6}$ alkylcarbonyloxy, or optionally substituted aminocarbonyloxy, alternatively, $R^{1a}$ and $R^{1b}$ may combine each other together with the carbon atom to which they bind to form $C_{3-7}$ cycloalkyl ring, or saturated heterocycle, in which the $C_{3-7}$ cycloalkyl ring and the saturated heterocycle may be optionally substituted by one or more and same or different groups selected from the group consisting of hydroxyl, halogen and cyano;

$R^{11}$ is selected from the group consisting of optionally substituted $C_{1-6}$ alkyl, optionally substituted $C_{3-7}$ cycloalkyl, optionally substituted $C_{3-7}$ cycloalkyl-$C_{1-4}$ alkyl, optionally substituted saturated heterocyclic $C_{1-4}$ alkyl, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{1-6}$ alkoxycarbonyl, optionally substituted $C_{3-7}$ cycloalkoxycarbonyl, optionally substituted saturated heterocyclic oxycarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl;

$R^{12}$, $R^{13}$, $R^{14}$, and $R^{16}$ are the same or different groups selected from the group consisting of hydroxyl, halogen, cyano, optionally substituted $C_{1-6}$ alkyl, optionally substituted $C_{7-14}$ aralkyl, optionally substituted heteroaryl-$C_{1-4}$ alkyl, optionally substituted saturated heterocyclic $C_{1-4}$ alkyl, optionally substituted $C_{1-6}$ alkoxy, optionally substituted $C_{1-6}$ alkylthio, optionally substituted saturated heterocyclic oxy, optionally substituted $C_{6-10}$ aryl, optionally substituted heteroaryl, optionally substituted saturated heterocycle, optionally substituted $C_{1-6}$ alkylcarbonyl, optionally substituted $C_{3-7}$ cycloalkylcarbonyl, optionally substituted $C_{3-7}$ cycloalkyl-$C_{1-4}$ alkylcarbonyl, optionally substituted $C_{6-10}$ arylcarbonyl, optionally substituted heteroarylcarbonyl, optionally substituted saturated heterocyclic carbonyl, optionally substituted aminocarbonyl, optionally substituted $C_{1-6}$ alkylsulfonyl, optionally substituted $C_{3-7}$ cycloalkylsulfonyl, optionally substituted $C_{6-10}$ arylsulfonyl, optionally substituted heteroarylsulfonyl, optionally substituted saturated heterocyclic sulfonyl and optionally substituted aminosulfonyl; or a pharmaceutically acceptable salt thereof.

15. The compound of claim 1, selected from the group consisting of:
(S)-(2-(2-(4-(4-fluorobenzoyl)piperidin-1-yl)ethyl)pyrrolidin-1-yl)(6-methyl-1H-indol-2-yl)methanone;
(S)-(6-fluoro-1H-indol-2-yl)(2-(2-(4-(4-fluorobenzoyl)piperidin-1-yl)ethyl)pyrrolidin-1-yl)methanone;
(S)-(2-(2-(4-(4-fluorobenzoyl)piperidin-1-yl)ethyl)pyrrolidin-1-yl)(6-(trifluoromethoxy)-1H-indol-2-yl)methanone;
(S)-(2-(2-(4-(4-fluorobenzoyl)piperidin-1-yl)ethyl)pyrrolidin-1-yl)(6-isopropyl-1H-indol-2-yl)methanone;
(S)-(5-fluoro-4-methoxy-1H-indol-2-yl)(2-(2-(4-(4-fluorobenzoyl)piperidin-1-yl)ethyl)-pyrrolidin-1-yl)methanone;
(S)-(3,6-difluoro-1H-indol-2-yl)(2-(2-(4-(4-fluorobenzoyl)piperidin-1-yl)ethyl)pyrrolidin-1-yl)methanone;
(S)-(3-fluoro-6-(trifluoromethoxy)-1H-indol-2-yl)(2-(2-(4-(4-fluorobenzoyl)piperidin-1-yl)ethyl)pyrrolidin-1-yl)methanone;
(S)-(3-fluoro-1H-indol-2-yl)(2-(2-(4-(4-fluorobenzoyl)piperidin-1-yl)ethyl)pyrrolidin-1-yl)methanone;
((2S,5S)-2-(2-(4-(4-fluorobenzoyl)piperidin-1-yl)ethyl)-5-methylpyrrolidin-1-yl)(6-methyl-1H-indol-2-yl)methanone;
((2S,5S)-2-(2-(4-(4-fluorobenzoyl)piperidin-1-yl)ethyl)-5-methylpyrrolidin-1-yl)(6-(trifluoro-methyl)-1H-indol-2-yl)methanone;
((2S,5S)-2-(2-(4-(4-fluorobenzoyl)piperidin-1-yl)ethyl)-5-methylpyrrolidin-1-yl)(6-(trifluoro-methylthio)-1H-indol-2-yl)methanone;
(S)-(2-(2-(4-(4-fluorobenzoyl)piperidin-1-yl)ethyl)pyrrolidin-1-yl)(1-methyl-1H-indol-5-yl)methanone and
(S)-(2-(2-(4-(6-fluorobenzo[d]isoxazol-3-yl)piperidin-1-yl)ethyl)pyrrolidin-1-yl)(3-phenyl-1H-pyrazol-5-yl) methanone; or a pharmaceutically acceptable salt thereof.

16. (S)-(2-(2-(4-(4-Fluorobenzoyl)piperidin-1-yl)ethyl)pyrrolidin-1-yl)(6-methyl-1H-indol-2-yl)methanone.

17. (S)-(6-Fluoro-1H-indol-2-yl)(2-(2-(4-(4-fluorobenzoyl)piperidin-1-yl)ethyl)pyrrolidin-1-yl)methanone.

18. (S)-(5-Fluoro-4-methoxy-1H-indol-2-yl)(2-(2-(4-(4-fluorobenzoyl)piperidin-1-yl)ethyl)pyrrolidin-1-yl)methanone.

19. (S)-(3,6-Difluoro-1H-indol-2-yl)(2-(2-(4-(4-fluorobenzoyl)piperidin-1-yl)ethyl)pyrrolidin-1-yl)methanone.

20. (S)-(3-Fluoro-6-(trifluoromethoxy)-1H-indol-2-yl)(2-(2-(4-(4-fluorobenzoyl)piperidin-1-yl)ethyl)pyrrolidin-1-yl) methanone.

21. (S)-(3-Fluoro-1H-indol-2-yl)(2-(2-(4-(4-fluorobenzoyl)piperidin-1-yl)ethyl)pyrrolidin-1-yl)methanone hydrochloride.

22. A therapeutic agent for schizophrenia, comprising a compound of claim 1 or a pharmaceutically acceptable salt thereof.

23. A method for treating schizophrenia, comprising administering a therapeutically effective amount of a compound of claim 1 or a pharmaceutically acceptable salt thereof to a mammal in need thereof.

* * * * *